(12) United States Patent
Lanza et al.

(10) Patent No.: US 9,849,201 B2
(45) Date of Patent: Dec. 26, 2017

(54) HOMING AGENTS

(71) Applicant: The Washington University, St. Louis, MO (US)

(72) Inventors: Gregory M Lanza, St. Louis, MO (US); Samuel A. Achilefu, St. Louis, MO (US); Grace Hufang Cui, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 561 days.

(21) Appl. No.: 14/270,061

(22) Filed: May 5, 2014

(65) Prior Publication Data

US 2015/0023872 A1    Jan. 22, 2015

Related U.S. Application Data

(60) Provisional application No. 61/819,432, filed on May 3, 2013, provisional application No. 61/902,630, filed on Nov. 11, 2013.

(51) Int. Cl.

| | |
|---|---|
| *A61K 51/00* | (2006.01) |
| *A61M 36/14* | (2006.01) |
| *A61K 51/08* | (2006.01) |
| *C07K 7/06* | (2006.01) |
| *A61K 49/00* | (2006.01) |
| *A61K 49/08* | (2006.01) |
| *A61K 49/12* | (2006.01) |
| *A61K 49/14* | (2006.01) |
| *A61K 51/06* | (2006.01) |

(52) U.S. Cl.
CPC ........ *A61K 51/088* (2013.01); *A61K 49/0002* (2013.01); *A61K 49/0032* (2013.01); *A61K 49/0054* (2013.01); *A61K 49/0056* (2013.01); *A61K 49/085* (2013.01); *A61K 49/124* (2013.01); *A61K 49/14* (2013.01); *A61K 51/065* (2013.01); *C07K 7/06* (2013.01)

(58) Field of Classification Search
CPC .... A61K 38/00; A61K 49/00; A61K 49/0002; A61K 49/0032; A61K 49/0054; A61K 49/0056; A61K 49/085; A61K 49/124; A61K 49/14; A61K 51/00; A61K 51/065; A61K 51/08; A61K 51/088; C07K 7/06
USPC .......... 424/1.11, 1.49, 1.65, 1.69, 1.81, 1.85, 424/1.89, 9.1, 9.2, 9.3, 9.4, 9.5, 9.6; 514/1, 1.1; 534/7, 10–16; 530/300; 206/223, 569, 570
See application file for complete search history.

(56) References Cited

U.S. PATENT DOCUMENTS

| | | | |
|---|---|---|---|
| 6,652,835 B1 | 11/2003 | Lauffer et al. | |
| 6,984,373 B2 | 1/2006 | Wescott et al. | |
| 6,991,775 B2 | 1/2006 | Koerner et al. | |
| 7,238,341 B2 | 7/2007 | Zhang et al. | |
| 7,412,279 B2 | 8/2008 | Weisskoff et al. | |
| 7,465,434 B2 | 12/2008 | Benford | |
| 8,278,274 B2 | 10/2012 | Bussat et al. | |
| 2005/0271663 A1* | 12/2005 | Ignatovich | A61K 47/48676 424/145.1 |
| 2015/0361402 A1* | 12/2015 | Steinmetz | C07K 14/005 424/93.6 |

OTHER PUBLICATIONS

Alba et al., "Cost-Effectiveness of Ventricular Assist Device Therapy as a Bridge to Transplantation Compared with Nonbridged Cardiac Recipients", Circulation, 2013, pp. 2424-2435, vol. 127.
Angelides et. al., "Detection of malignant tumors using Tc-99m labeled Fab' fragments from a monoclonal antibody with specificity for D-dimer of cross-linked fibrin", Clinical Nuclear Medicine, 1996, pp. 242-244, vol. 21, No. 3, Abstract only.
Annis et al., "Novel Solid-Phase Reagents for Facile Formation of Intermolecular Disulfide Bridges in Peptides under Mild Conditions", J Am Chem Soc., 1998, pp. 7226-7238, vol. 120, No. 29.
Bates et al., "Imaging Characteristics of a Novel Technetium Tc 99m-Labeled Platelet Glycoprotein IIb/IIIa Receptor Antagonist in Patients With Acute Deep Vein Thrombosis or a History of Deep Vein Thrombosis", Arch Intern Med., 2003, pp. 452-456, vol. 163.
Bautovich et al., "Detection of Deep Venous Thrombi and Pulmonary Embolus with Technetium-99m-DD-3B6/22 Anti-fibrin Monoclonal Antibody Fab Fragment", The Journal of Nuclear Medicine, 1994, pp. 195-203, vol. 35.
Bigott-Hennkens et al., "Labeling, Stability and Biodistribution Studies of 99m Tc-cyclized Tyr3-octreotate Derivatives", Nucl Med Biol., 2011, pp. 549-555, vol. 38.
Birschmann et al., "Ambient hemolysis and activation of coagulation is different between HeartMate II and HeartWare left ventricular assist devices", The Journal of Heart and Lung Transplantation, 2014, pp. 80-87, vol. 33.
Ciesienski et al., "Fibrin-Targeted PET Probes for the Detection of Thrombi", Molecular Pharmaceutics, 2013, pp. 1100-1110, vol. 10.
Cowger et al., "Hemolysis: A harbinger of adverse outcome after left ventricular assist device implant", The Journal of Heart and Lung Transplantation, 2014, pp. 35-43, vol. 33.
Crow et al., "Acquired von Willebrand Syndrome in Continuous-Flow Ventricular Assist Device Recipients", Ann Thoracic Surgeons, 2010, pp. 1263-1269, vol. 90.
Debakey et al., "Left Ventricular Bypass Pump for Cardiac Assistance", Clinical Experience, 1971, pp. 3-11, vol. 27.
Fang et al., "Heart Failure-Related Hospitalization in the U.S., 1979 to 2004", Journal of the American College of Cardiology, 2008, pp. 428-434, vol. 52, No. 6.
Go et al., "Heart Disease and Stroke Statistics—2014 Update: A Report From the American Heart Association", Circulation, 2014, pp. e28-e292, vol. 129.
Hasin et al., "Readmissions After Implantation of Axial Flow Left Ventricular Assist Device", Journal of the American College of Cardiology, 2013, pp. 153-163, vol. 61.

(Continued)

Primary Examiner — D L Jones
(74) Attorney, Agent, or Firm — Polsinelli PC

(57) ABSTRACT

The present disclosure provides peptide constructs for diagnostic imaging and therapeutic applications, using pegylated peptides which exhibit specific binding for a target molecule of interest, such as a biomarker of a disease or disorder.

17 Claims, 100 Drawing Sheets
(19 of 100 Drawing Sheet(s) Filed in Color)

(56) References Cited

OTHER PUBLICATIONS

Heidt et al., "Activated Platelets in Carotid Artery Thrombosis in Mice Can be Selectively Targeted with a Radiolabeled Single-Chain Antibody", PLos ONE, 2011, pp. 1-9, vol. 6.

Kiernan et al., "Management of HeartWare left ventricular assist device thrombosis using intracavitary thrombolytics", The Journal of Thoracic and Cardiovascular Surgery, 2011, pp. 712-714, vol. 142.

Kirklin et al., "The Fourth INTERMACS Annual Report: 4,000 implants and counting", The Journal of Heart and Lung Transplantation, 2012, pp. 117-126, vol. 31.

Kirklin et al., "Interagency Registry for Mechanically Assisted Circulatory Support (INTERMACS) analysis of pump thrombosis in the HeartMate II left ventricular assist device", The Journal of Heart and Lung Transplantation, 2014, pp. 12-22, vol. 33.

Klink et al., "Arteriosclerosis, Thrombosis, and Vascular Biology", American Heart Association, 2010, pp. 403-410, vol. 30.

Knight et al., "Tc-99m Antifibrin Fab' Fragments for Imaging Venous Thrombi: Evaluation in a Canine Model 1" Radiology, 1989, pp. 163-169, vol. 173.

Kolodziej et al., "Fibrin Specific Peptides Derived by Phage Display: Characterization of Peptides and Conjugates for Imaging", Bioconjug Chem., 2012, pp. 548-556, vol. 23, No. 3.

Kudryk et al., "Monoclonal Antibody Designated T2G1 Reacts with Human Fibrin Chain but Not with the Corresponding Chain from Mouse Fibrin", Arteriosclerosis, Thrombosis, and Vascular Biology, 2000, pp. 1848-1849, vol. 20.

Lloyd-Jones et al., "Executive Summary:Heart Disease and Stroke Statistics—2010 Update: A Report From the American Heart Association", Circulation, 2010, pp. e46-e215.

Lund et al., "Patient selection for left ventricular assist devices", European Journal of Heart Failure, 2010, pp. 434-443, vol. 12.

May-Newman et al., "Thromboembolism Is Linked to Intraventricular Flow Stasis in a Patient Supported with a Left Ventricle Assist Device", ASAIO Journal, 2000, pp. 452-455, vol. 59.

Mehra et al., "The vexing problem of thrombosis in long-term mechanical circulatory support", The Journal of Heart and Lung Transplantation, 2014, pp. 1-11, vol. 33.

Mishra et al., "Hospital costs fell as numbers of LVADs were increasing: experiences from Oslo University Hospital", Journal of Cardiothoracic Surgery, 2012, pp. 1-7, vol. 7.

Morris et al., "SPECT Imaging of Pulmonary Emboli with Radiolabeled Thrombus-Specific Imaging Agents", Seminars in Nuclear Medicine, 2010, pp. 474-479, vol. 40.

Morris et al., "Pulmonary Emboli Imaging with 99m Tc-labelled Anti-D-dimer (DI-80B3) Fab Followed by SPECT", Heart Lung Circ., 2011, pp. 503-511, vol. 20.

Mousa et al., "In Vivo Models for the Evaluation of Antithrombotics and Thrombolytics", Methods Mol Biol., 2010, pp. 2-107, vol. 663.

Nair et al., "Monovalent and Bivalent Fibrin-specific MRI Contrast Agents for Detection of Thrombus", Angew Chem Int Ed Engl., 2008, pp. 4918-4921, No. 26.

Najjar et al., "An analysis of pump thrombus events in patients in the HeartWare Advance bridge to transplant and continued access protocol trial", The Journal of Heart and Lung Transplantation, 2014, pp. 23-34, vol. 33.

Overoye-Chan et al., "EP-2104R: A Fibrin-Specific Gadolinium-Based MRI Contrast Agent for Detection of Thrombus", J Am Chem Soc., 2008, pp. 6025-6039, vol. 130 No. 18.

Popova et al., "Clinical Experience With HeartWare Left Ventricular Assist Device in Patients with End-Stage Heart Failure", The Society of Thoracic Surgeons, 2012, pp. 810-815, vol. 93.

Rosebrough et al., "Thrombus Imaging with Indium-111 and Iodine-131-Labeled Fibrin-Specific Monoclonal Antibody and Its F(ab') 2 and Fab Fragments", The Journal of Nuclear Medicine, 1988, pp. 1212-1222, vol. 29.

Rosebrough et al., "Thrombus Imaging: A comparison of Radiolabeled GC4 and T2G1s Fibrin-Specific Monoclonal Antibodies", The Journal of Nuclear Medicine, 1990, pp. 1048-1054, vol. 31.

Rothenburger et al., "Treatment of Thrombus Formation Associated With the MicroMed DeBakey VAD Using Recombinant Tissue Plasminogen Activator", Circulation Journal of the American Heart Association, 2002, pp. 189-192, vol. 106.

Shah et al., "Continuous flow left ventricular assist device related aortic root thrombosis complicated by left main coronary artery occlusion", Journal of Heart and Lung Transplant, 2014, pp. 119-120, vol. 33.

Sheikh et al., "HeartMate II continuous-flow left ventricular assist system", Expert Rev Med Devices, 2011, pp. 11-21, vol. 8.

Starling et al., "Unexpected Abrupt Increase in Left Ventricular Assist Device Thrombosis", The New England Journal of Medicine, 2014, pp. 33-40, vol. 370.

Stulak et al., "Gastrointestinal bleeding and subsequent risk of thromboembolic events during support with a left ventricular assist device", The Journal of Heart and Lung Transplantation, 2014, pp. 60-64, vol. 33.

Tang et al., "Failed Repeated Thrombolysis Requiring Left Ventricular Assist Device Pump Exchange", Catheterization and Cardiovascular Interventions, 2013, pp. 1072-1074, vol. 81.

Taylor et al., "Registry of the International Society for Heart and Lung Transplantation: Twenty-sixth Official Adult Heart Transplant Report—2009", J Heart Lung Transplant, 2009, pp. 1007-1022, vol. 28.

Tellor et al., "The use of eptifibatide for suspected pump thrombus or thrombosis in patients with left ventricular assist devices", The Journal of Heart and Lung Transplantation, 2014, pp. 94-101, vol. 33.

Uppal et al., "Bimodal Thrombus Imaging: Simultaneous PET/MR Imaging with a Fibrin-targeted Dual PET/MR Probe-Feasibility Study in Rat Model 1", Radiology, 2011, pp. 812-820, vol. 258.

Uppal et al., "Molecular imaging of fibrin in a breast cancer xenograft mouse model", National Institute of Health, 2012, pp. 553-558, vol. 47.

Vicente et al., "Antithrombotic activity of dermatan sulfate in heparin cofactor II-deficient mice", Blood, 2004, pp. 3965-3970, vol. 104.

Von Zur et al., "Magnetic Resonance Imaging Contrast Agent Targeted Toward Activated Platelets Allows In Vivo Detection of Thrombosis and Monitoring of Thrombolysis", Circulation, 2008, pp. 258-267, vol. 118.

Vymazal et al., "Thrombus Imaging with Fibrin-Specific Gadolinium-Based MR Contrast Agent EP-2104R", Results of a phase II clinical study of feasibility, 2009, pp. 697-704, vol. 44, No. 11.

Westrick et al., "Murine Models of Vascular Thrombosis", Arterioscler Thromb Vasc Biol., 2007, pp. 2079-2093, vol. 27.

Yancy et al., "2013 ACCF/AHA Guideline for the Management of Heart Failure", Journal of the American College of Cardiology, 2013, pp. e147-e239, vol. 62.

Yuan et al., "The Spectrum of Complications Following Left Ventricular Assist Device Placement", Transplantation and Medical Support, 2012, pp. 630-638, vol. 27.

Delgado et al., "Direct Thrombolytic Therapy for Intraventricular Thrombosis in Patients With the Jarvik 2000 Left Ventricular Assist Device", The Journal of Heart and Lung Transplantation, 2005, pp. 231-233, vol. 24, No. 2.

* cited by examiner

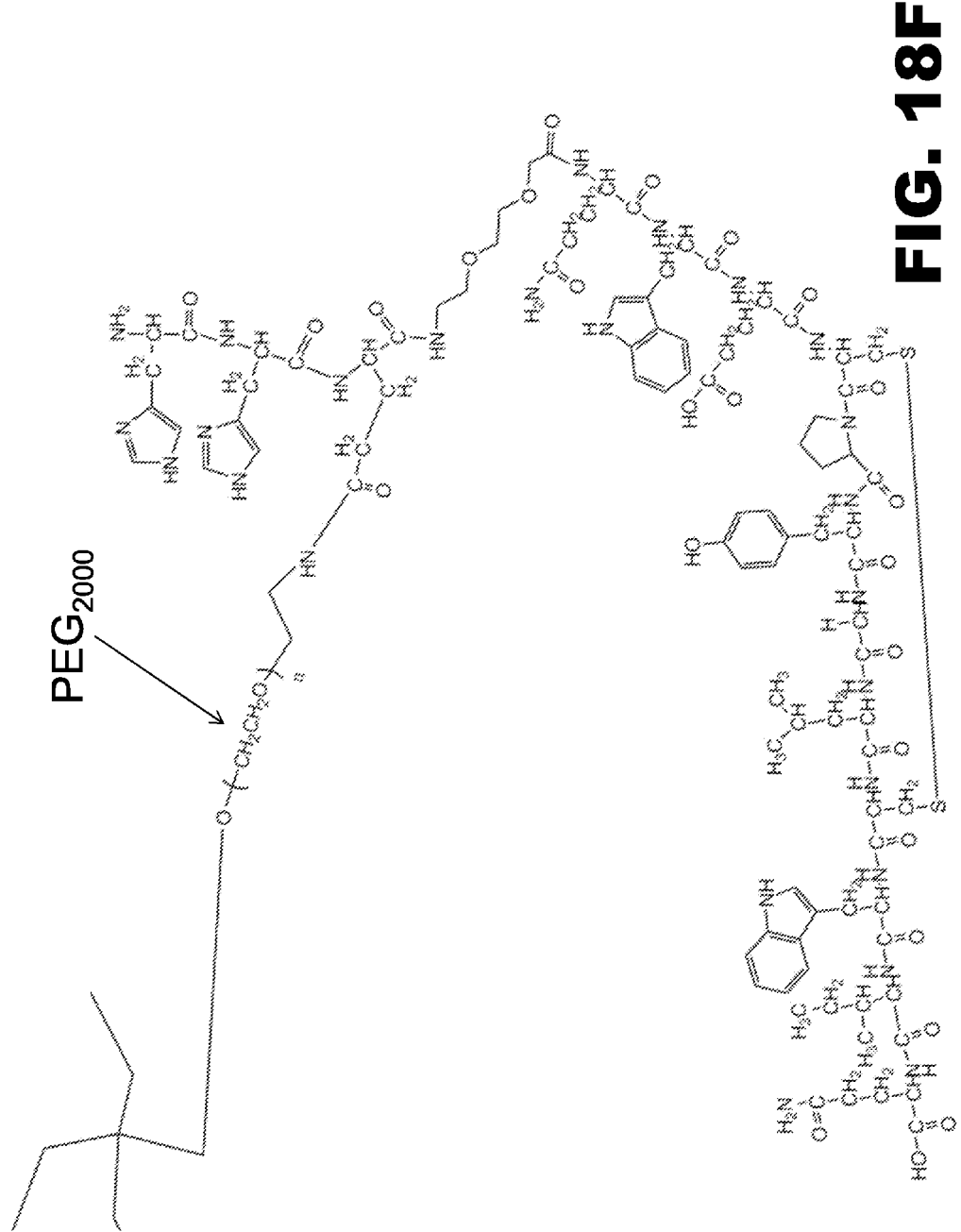

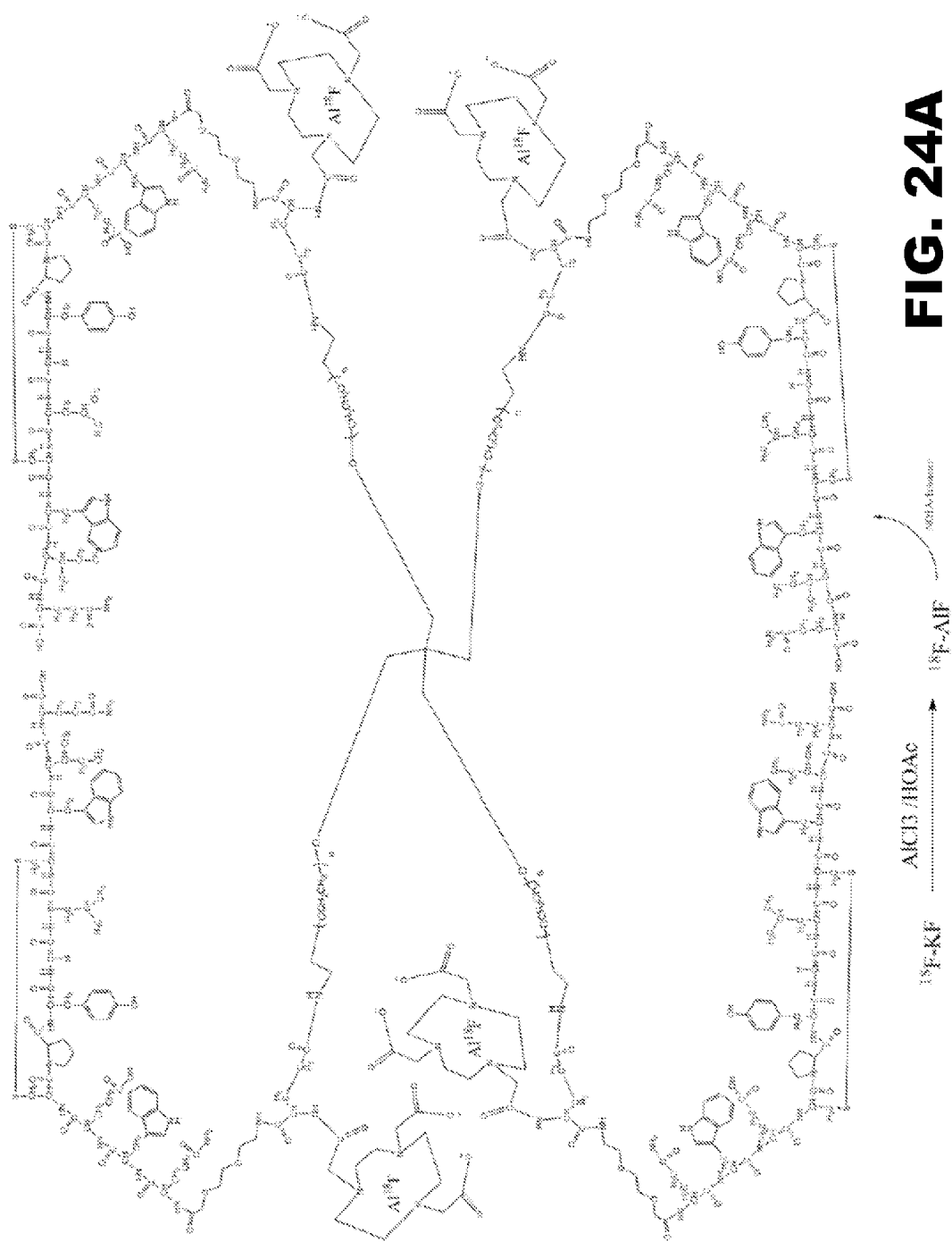

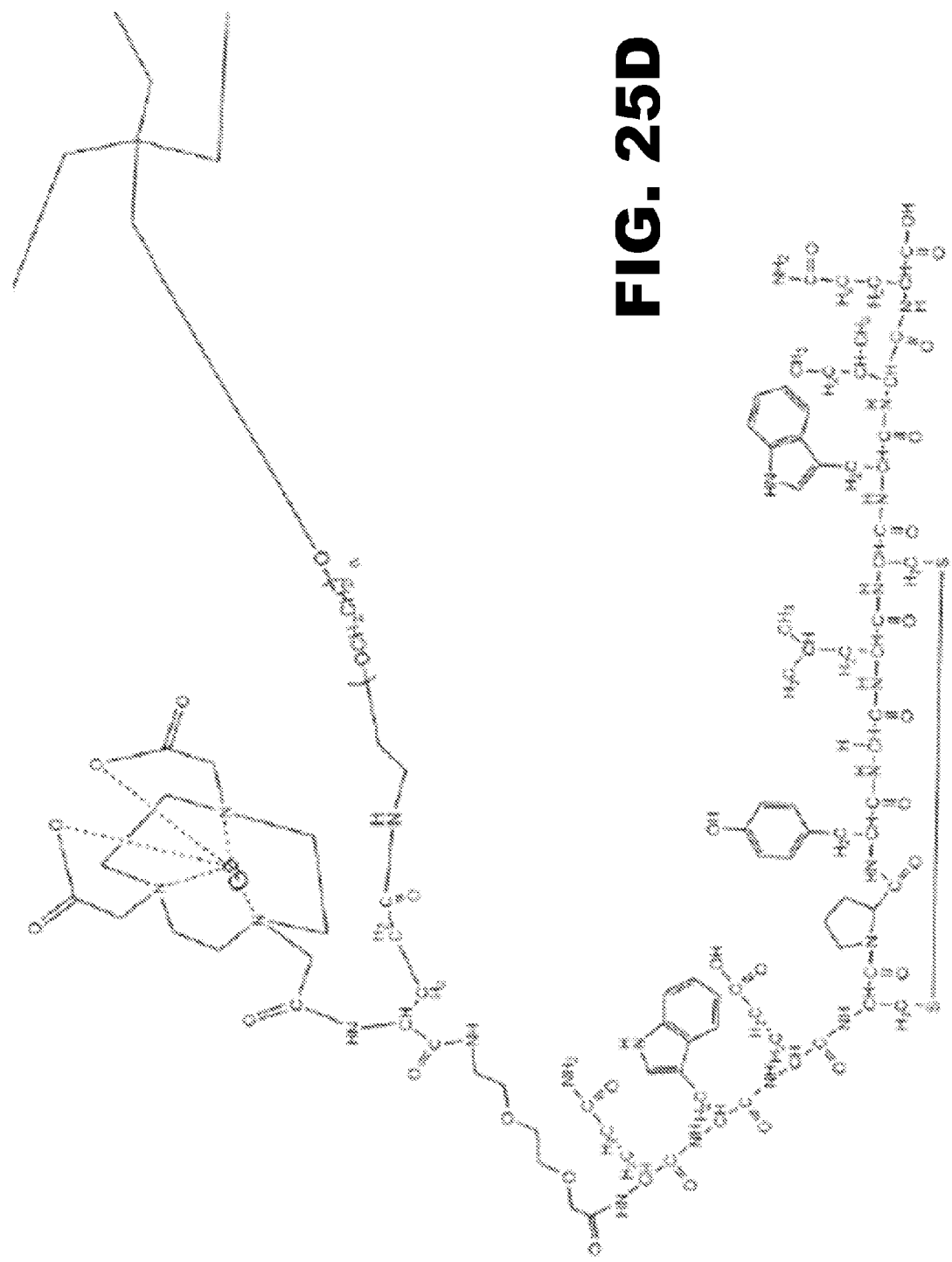

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 1

Gln Trp Glu Cys Pro Tyr Gly Leu Cys Trp Ile Gln
1               5                   10

HOMING AGENTS

CROSS REFERENCE TO RELATED APPLICATIONS

This application claims the priority of U.S. provisional application No. 61/819,432, filed May 3, 2013 and U.S. provisional application No. 61/902,630 filed Nov. 11, 2013, each of which is hereby incorporated by reference in its entirety.

GOVERNMENTAL RIGHTS

This invention was made with government support under NS059302 and STTR grant R42HL112518 awarded by the National Institutes of Health. The government has certain right in the invention

FIELD OF THE INVENTION

The disclosure relates to peptide constructs and compositions for targeted diagnostic and therapeutic applications, and related methods.

BACKGROUND OF THE INVENTION

Heart failure (HF) is at epidemic proportions, affecting 5 to 6 million patients in the US. Despite the myriad of major advances in cardiology, the prognosis for patients with severe, medically refractive HF is exceedingly poor. Approximately 250,000 deaths occur annually with the majority of these individuals enduring an increasingly impaired quality of life accompanied by significant economic and personal losses due to recurrent hospitalizations. Because the number of available heart donors (~2,200/year) has not increased over the last decade, there is an enormous and expanding gap between the medical need for transplant and a woefully low supply.

Left ventricular assist devices (LVAD), mechanical circulatory support systems, have developed tremendously from the large pulsatile devices of the last decade to the third generation continuous flow devices of today. The reduced size and power requirements of today's axial-flow instruments has allowed LVADs to become a therapeutic option for patients with intractable HF, whether as a bridge to transplantation (BTT) or a destination therapy (DT). According to the INTERMAS 4th Annual report for reporting US institutions, the number of LVADs placed as a BTT or DT increased from 61 in 2006 to 906 in 2010, and the number continues to increase. While LVAD placement offers considerable hope and benefit to many patients with severe HF, their successful clinical implementation remains a learning process, even regarding patient selection. Moreover, LVADs are associated with well known complications, including gastrointestinal bleeding, driveline infections, and thrombosis. Although GI bleeding and infection can be readily diagnosed and treated, intra-pump thrombosis cannot be easily diagnosed, and treatment approaches are too risky to administer to patients without a clear diagnostic mechanism to rely upon. For instance, the use of antiplatelet agents or thrombolytics for suspected intra-pump thrombosis is associated with very high risks of death with reports of up to 50% death in patients treated with fibrinolytics. Similarly, removal of LVADs in this cardiovascularly comprised population is associated with a 30 to 50% risk of death in one year. As such, the lack of an easy and reliable diagnostic tool capable of detecting intra-pump thrombosis has so far limited the wider adoption of these devices.

Therefore, there is a need for a rapid, easy, and quantitative method of assessing intra-pump thrombosis.

SUMMARY OF THE INVENTION

In one aspect, the present disclosure provides a homing agent comprising a p-armed peptide construct comprising n PEG monomers covalently bound together to form a p-armed PEG multimer wherein p is at least 3; p linkers; and p homing molecules, wherein each homing molecule is linked to an arm of the PEG multimer by one of the linkers, the homing agent is capable of selectively binding to a target molecule; and at least one diagnostic and/or therapeutic agent linked to an N-terminus of at least one homing molecule.

In another aspect, the present disclosure provides a radiopharmaceutical composition comprising any homing agent as described herein, together with a pharmaceutically-acceptable carrier.

In still another aspect, the present disclosure provides a method for detecting intradevice thrombus in a subject having an implanted mechanical circulation assist device. The method comprises: a) administering into the bloodstream of the subject an effective amount a homing agent comprising a p-armed peptide construct comprising n PEG monomers covalently bound together to form a p-armed PEG multimer wherein p is at least 3; p linkers; and p homing molecules, wherein each homing molecule is linked to an arm of the PEG multimer by one of the linkers, the homing agent is capable of selectively binding to fibrin; and at least one imaging agent linked to an N-terminus of at least one homing molecule, b) waiting a time sufficient for binding of the homing agent to thrombus to occur; and c) detecting a signal from the imaging agent localized at a site of thrombus.

In another aspect, the present disclosure provides a kit for detecting or quantifying an intradevice thrombus in a subject having an implanted mechanical circulation assist device, the kit comprising: an amount of a thrombus imaging agent comprising: a p-armed peptide construct comprising n PEG monomers covalently bound together to form a p-armed PEG multimer wherein p is at least 3; p linkers; and p homing molecules, wherein each homing molecule is linked to an arm of the PEG multimer by one of the linkers, the homing molecules capable of selectively binding a target molecule; and a imaging agent linked to an N-terminus of at least one homing molecule; and an amount of at least one additional reagent selected from a reducing agent, a coordinating ligand, an adjuvant, an antioxidant, a buffer, and a chelating agent.

BRIEF DESCRIPTION OF THE FIGURES

The application file contains at least one photograph executed in color. Copies of this patent application publication with color photographs will be provided by the Office upon request and payment of the necessary fee.

Activity injected for each probe was 0.5 mCi. *p<0.05, n=3/group, each point is an independent experimental replicate.

Figure 22:
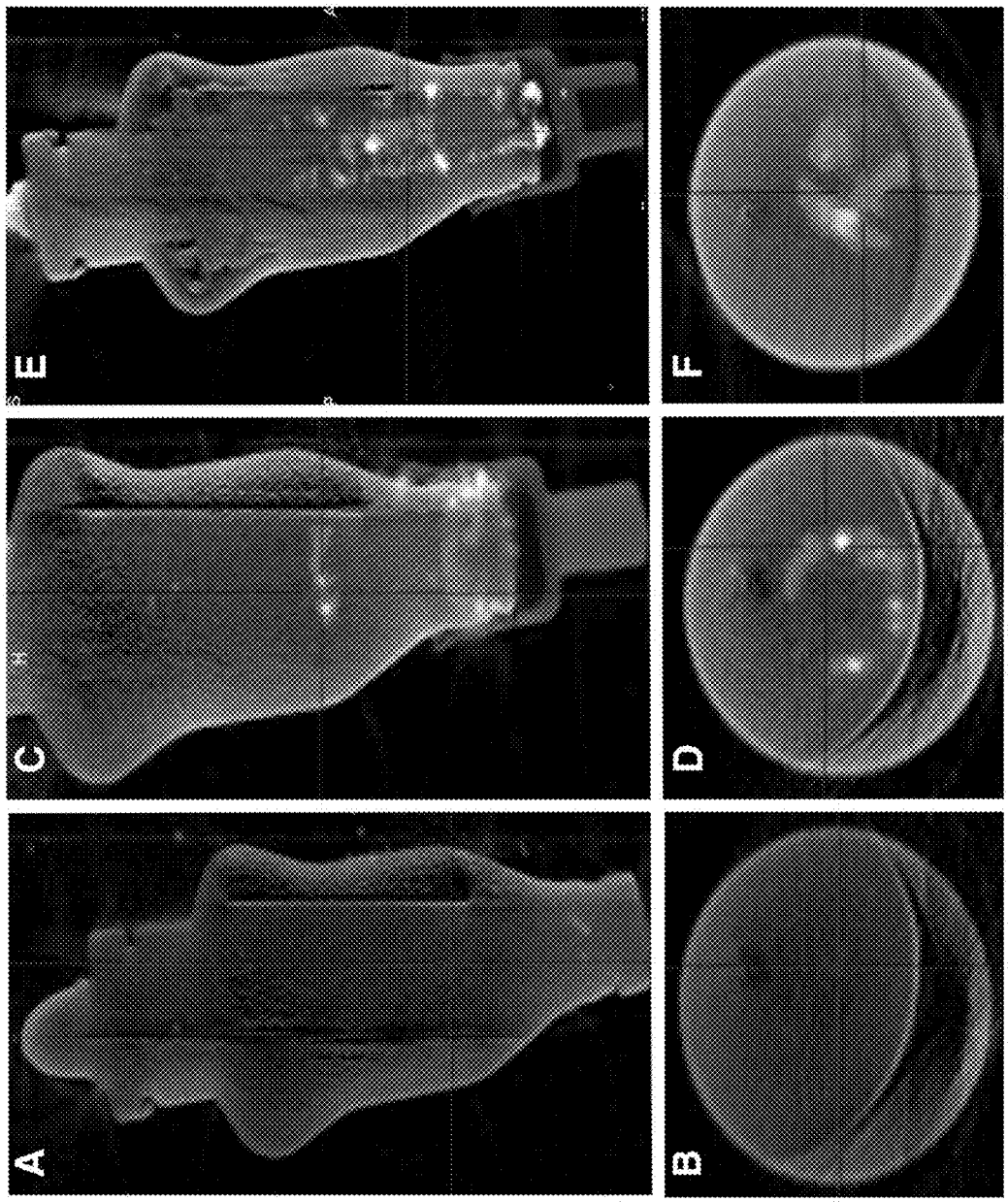
Figure 23A:
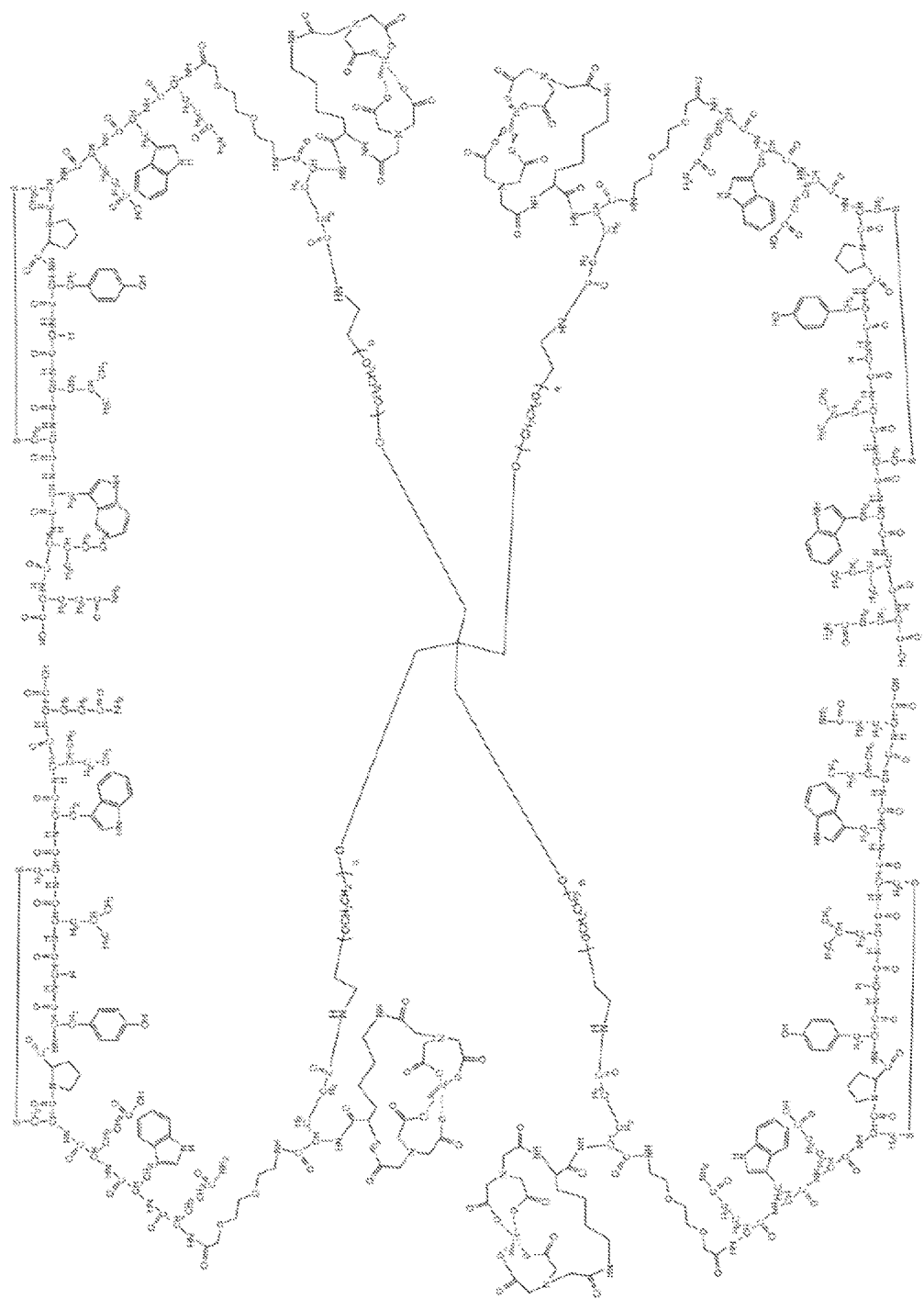
Figure 23B:
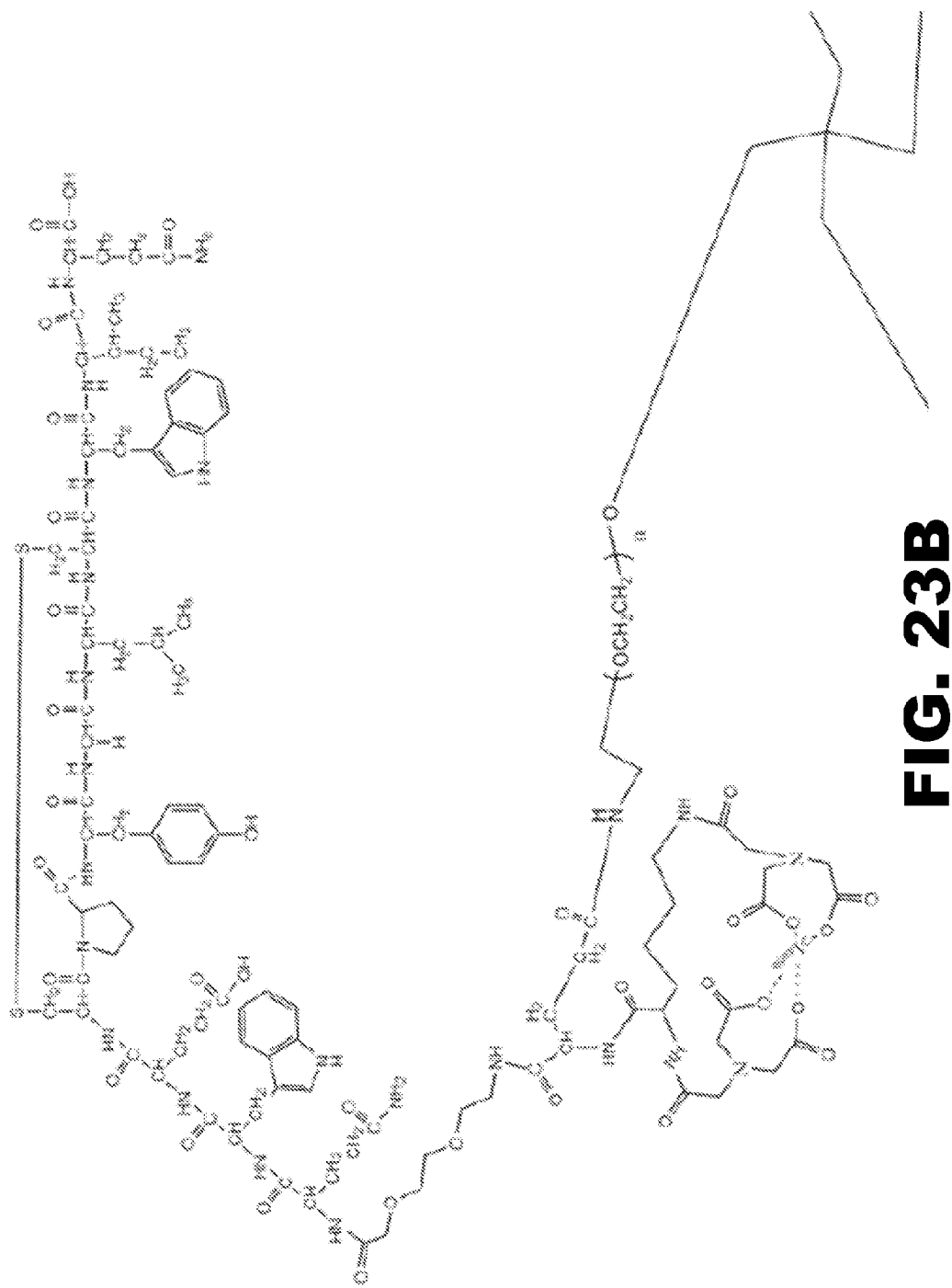
Figure 23C:
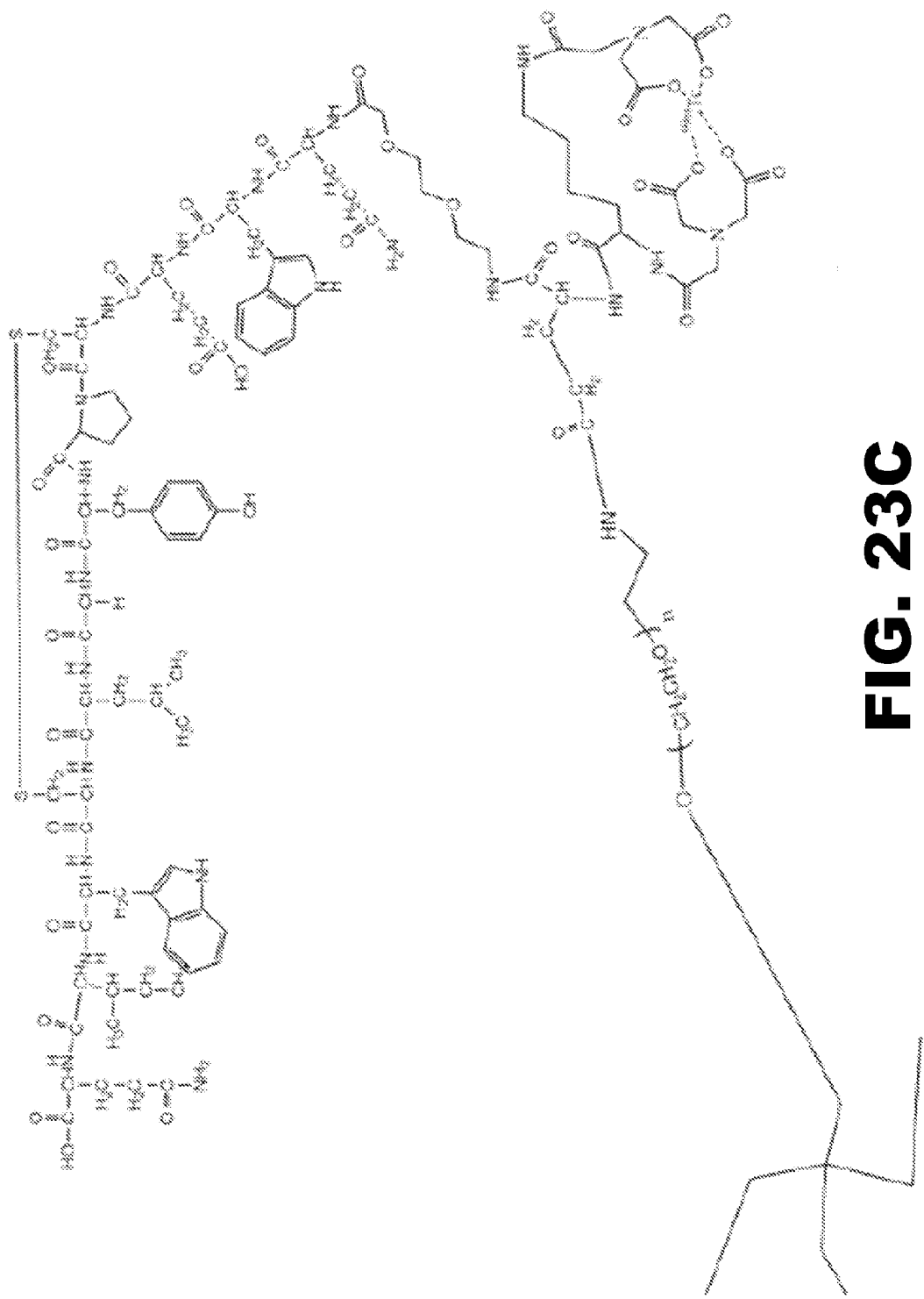
Figure 23D:
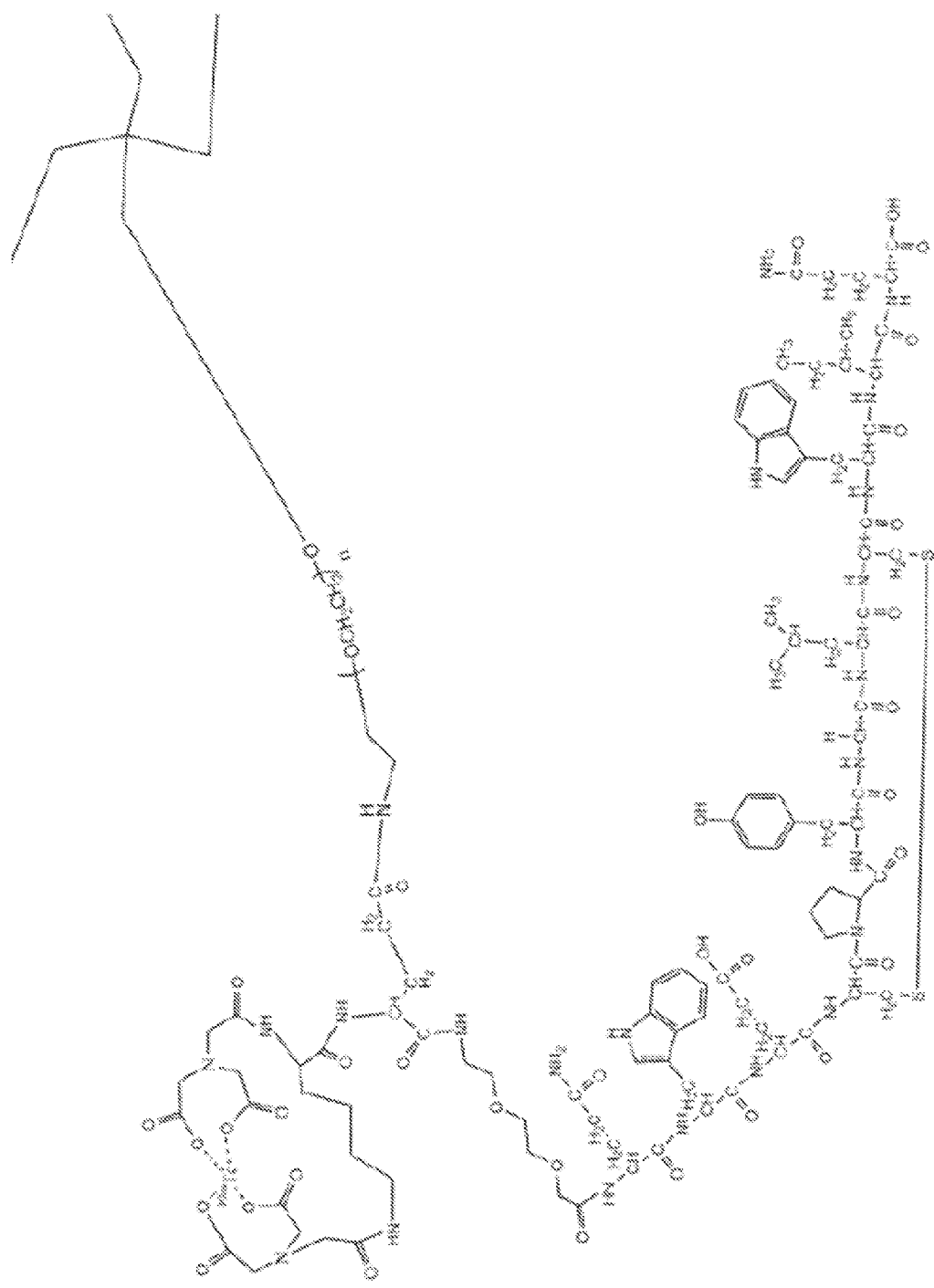
Figure 23E:
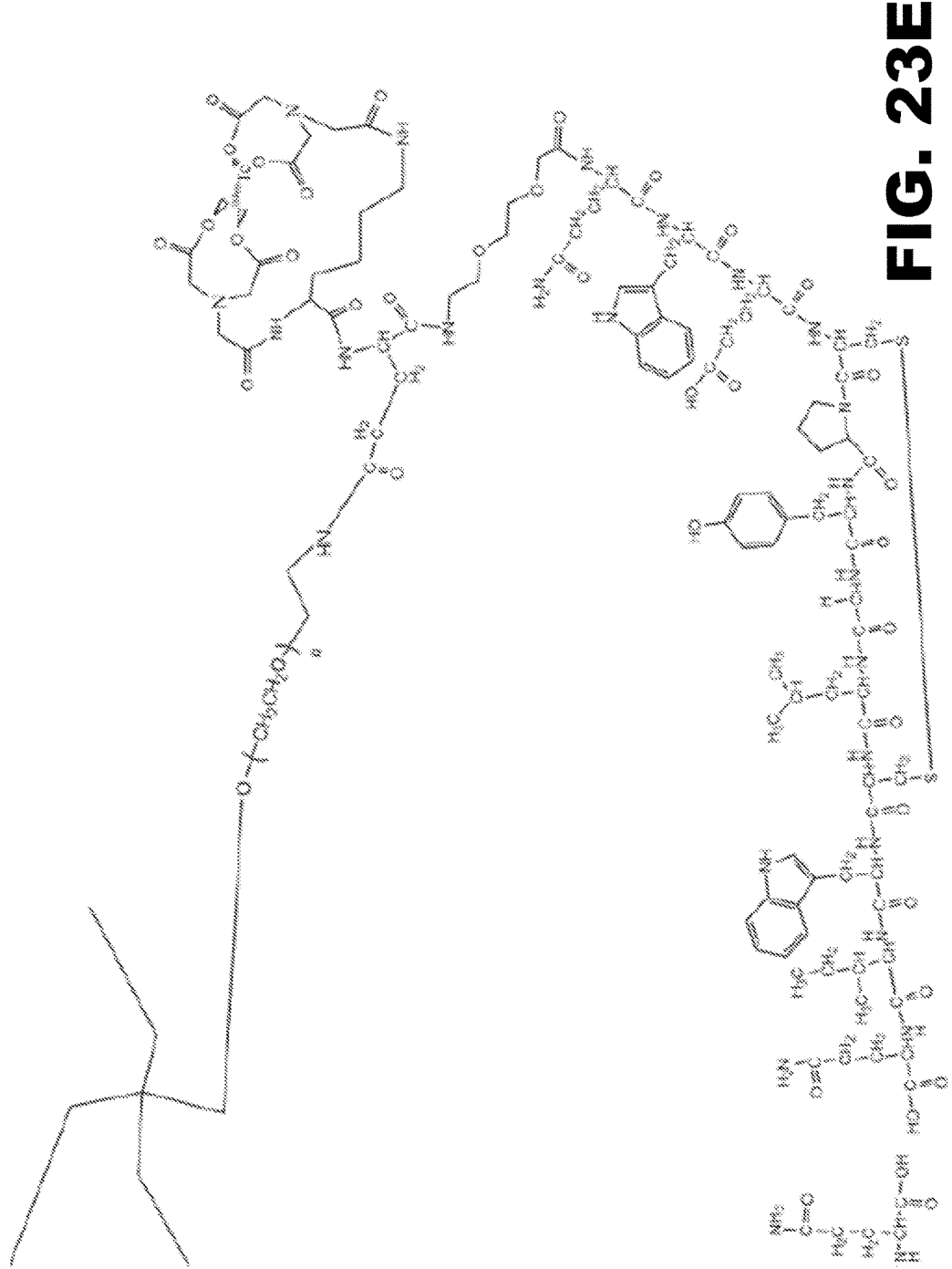
Figure 24B:
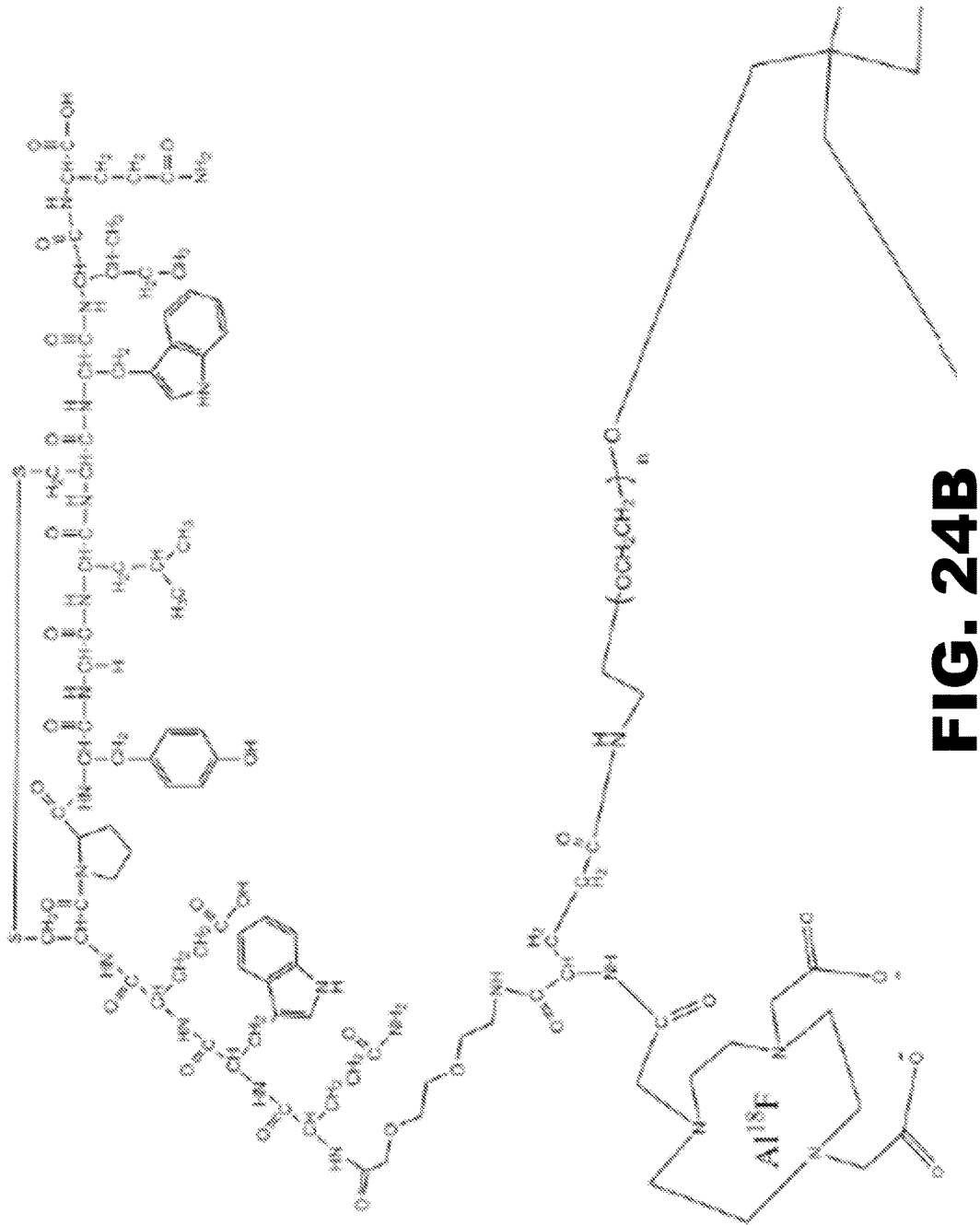
Figure 24C:
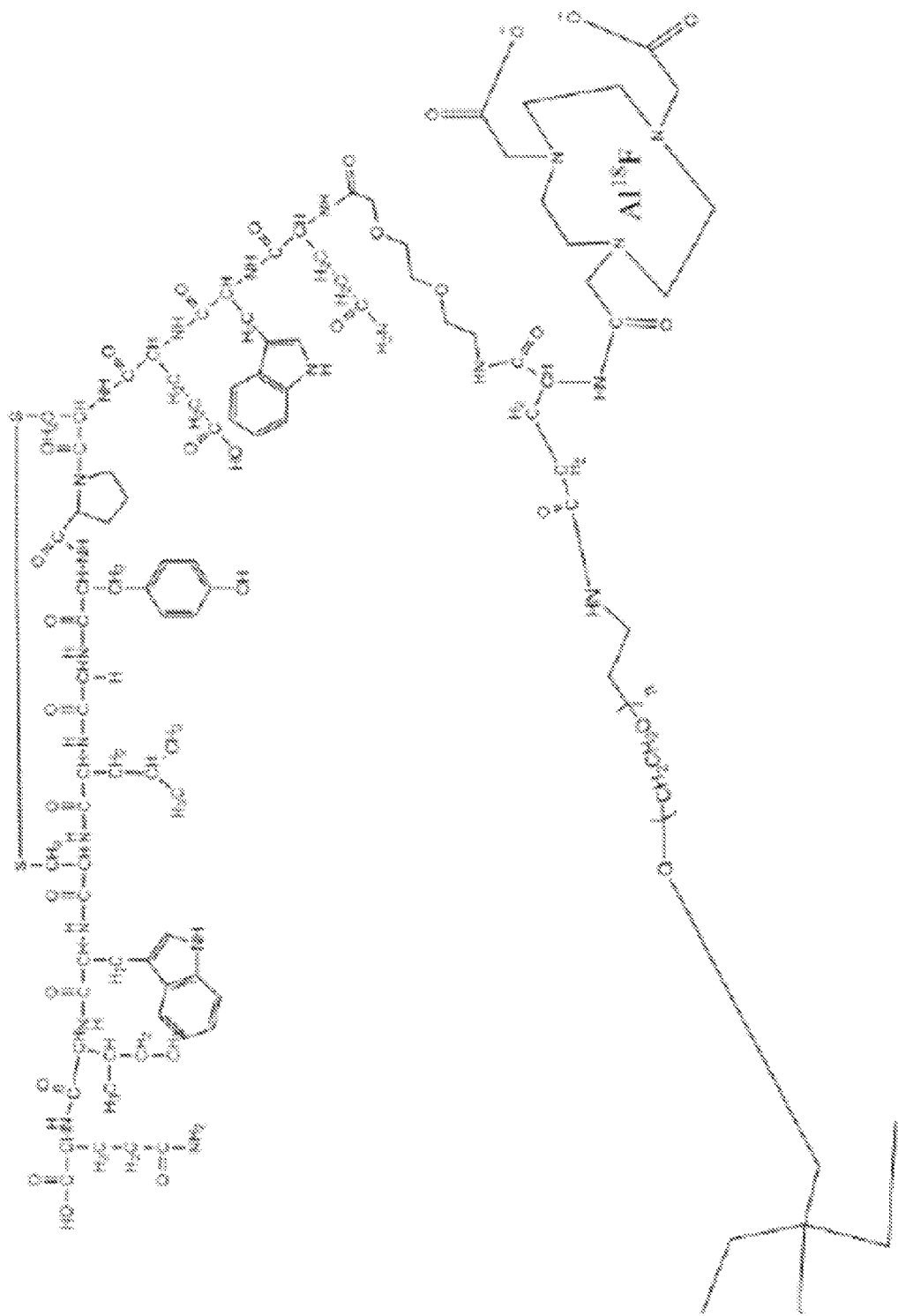
Figure 24D:
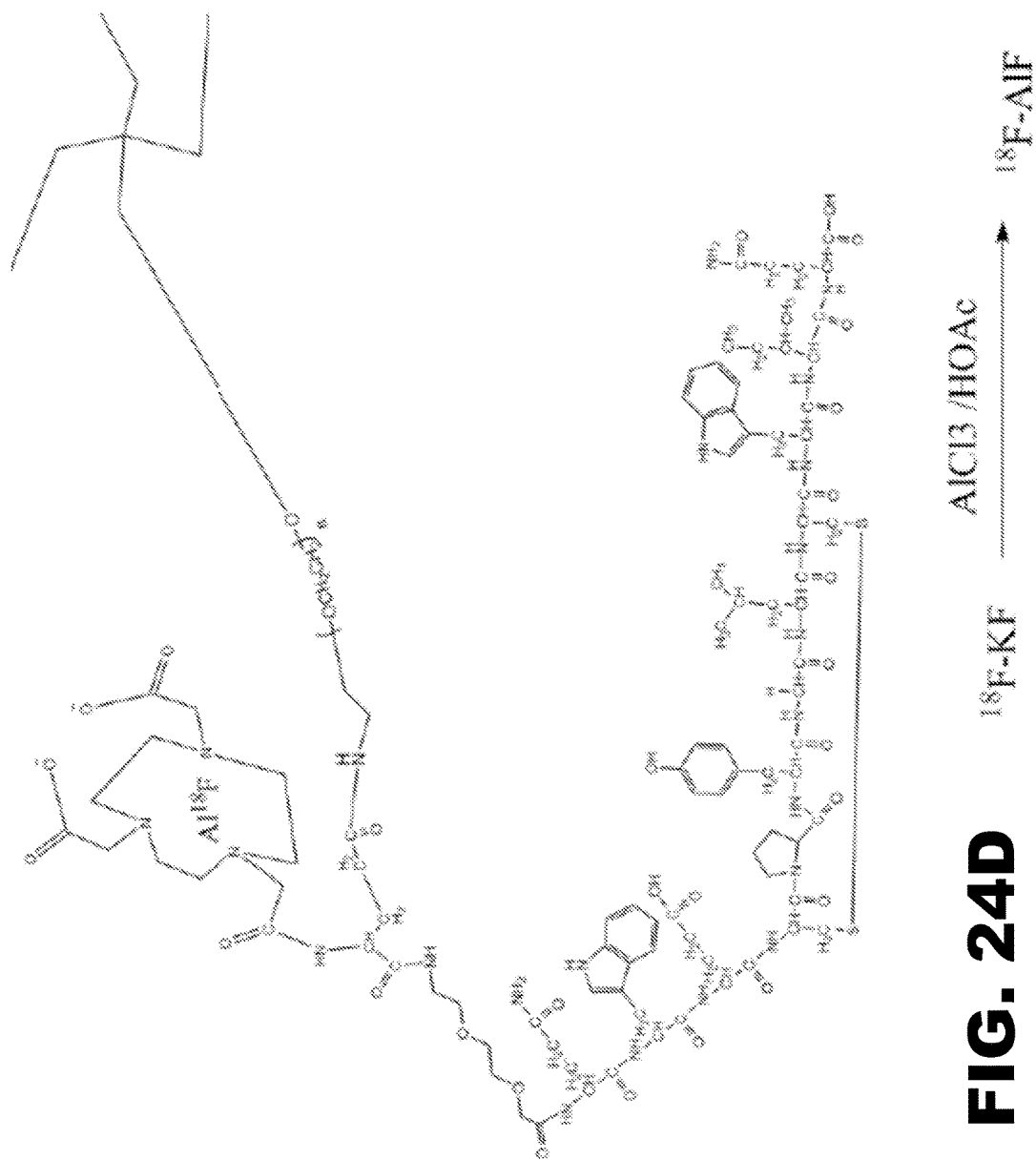
Figure 24E:
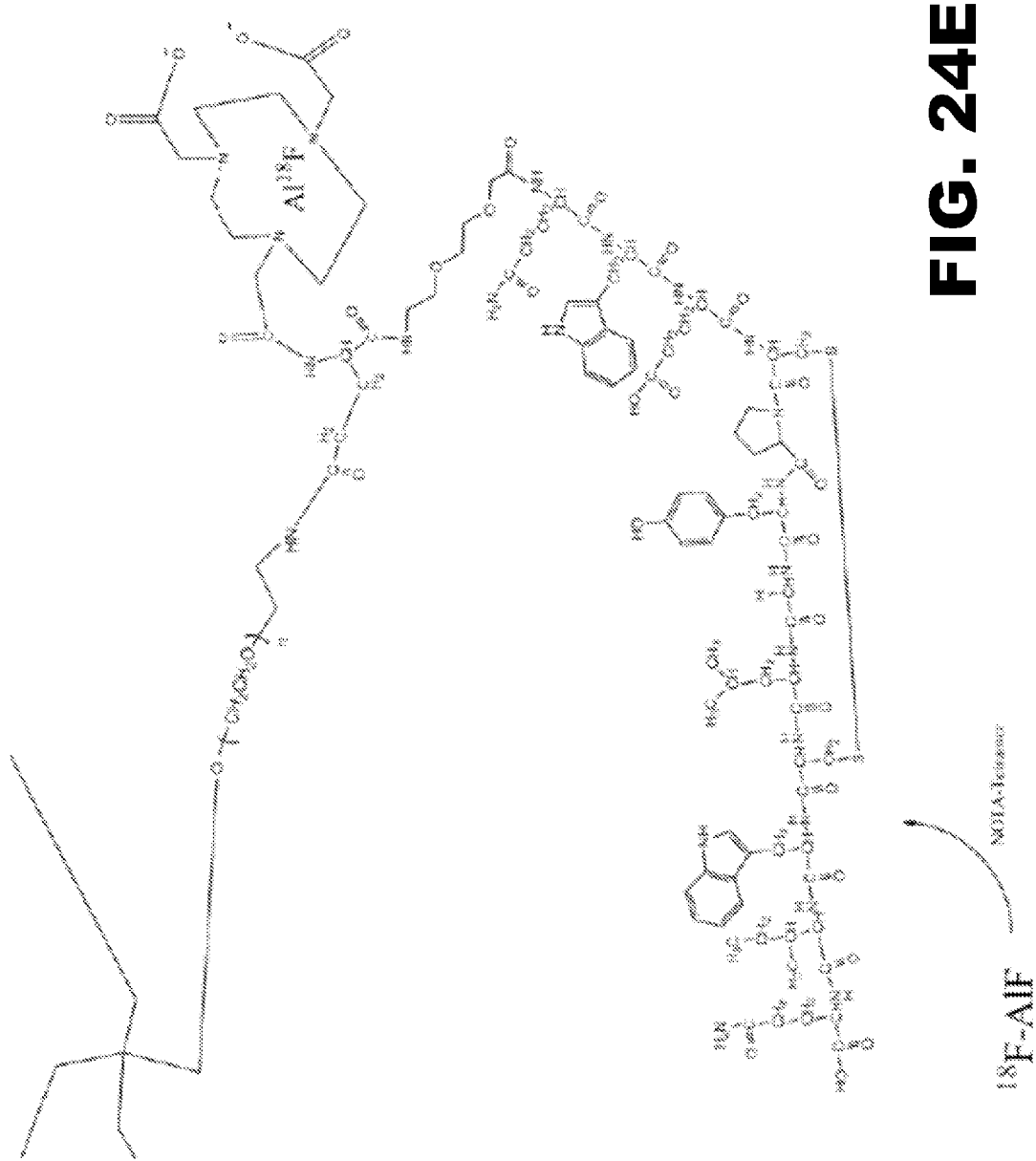
Figure 25A:
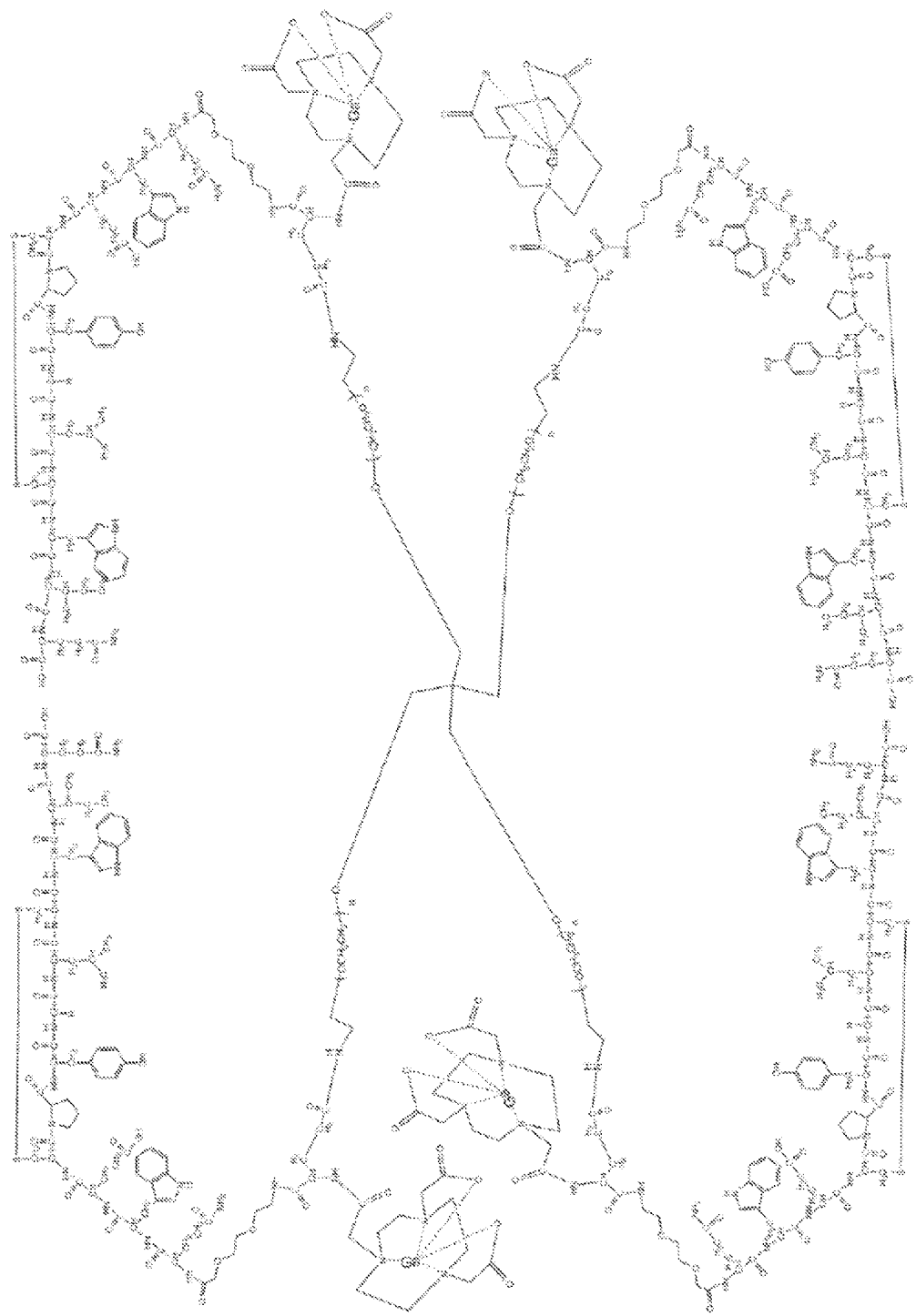
Figure 25B:
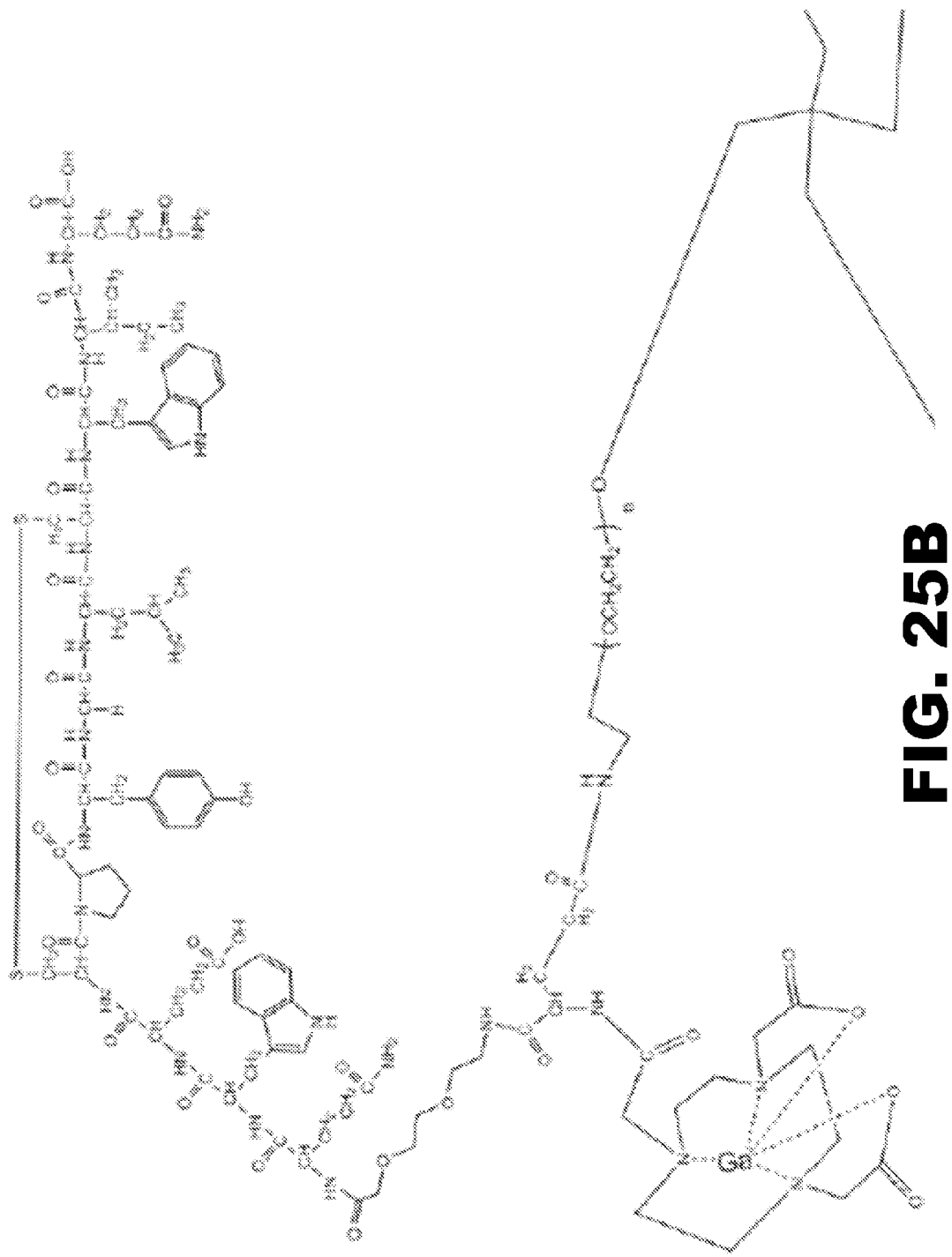
Figure 25C:
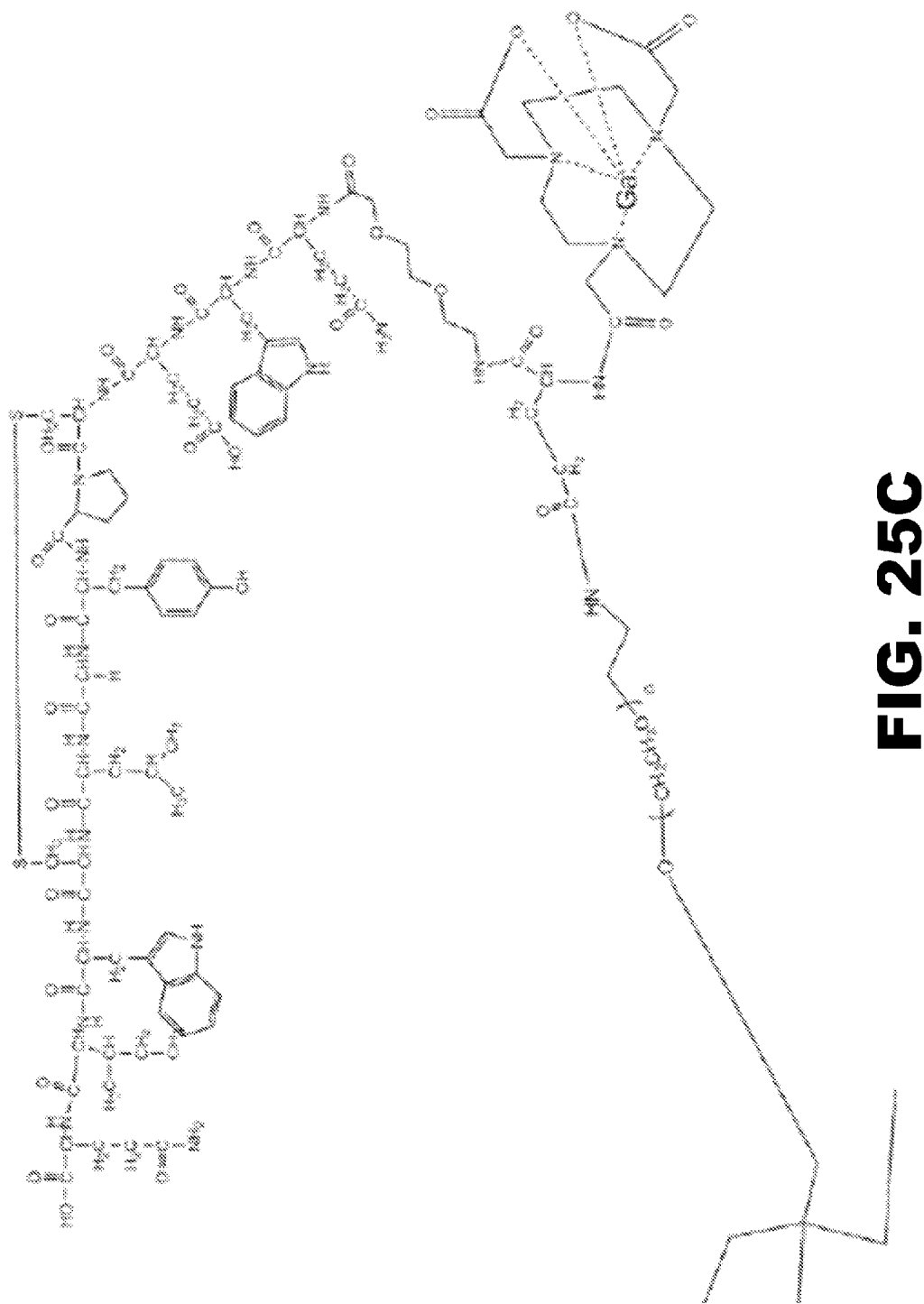
Figure 25E:
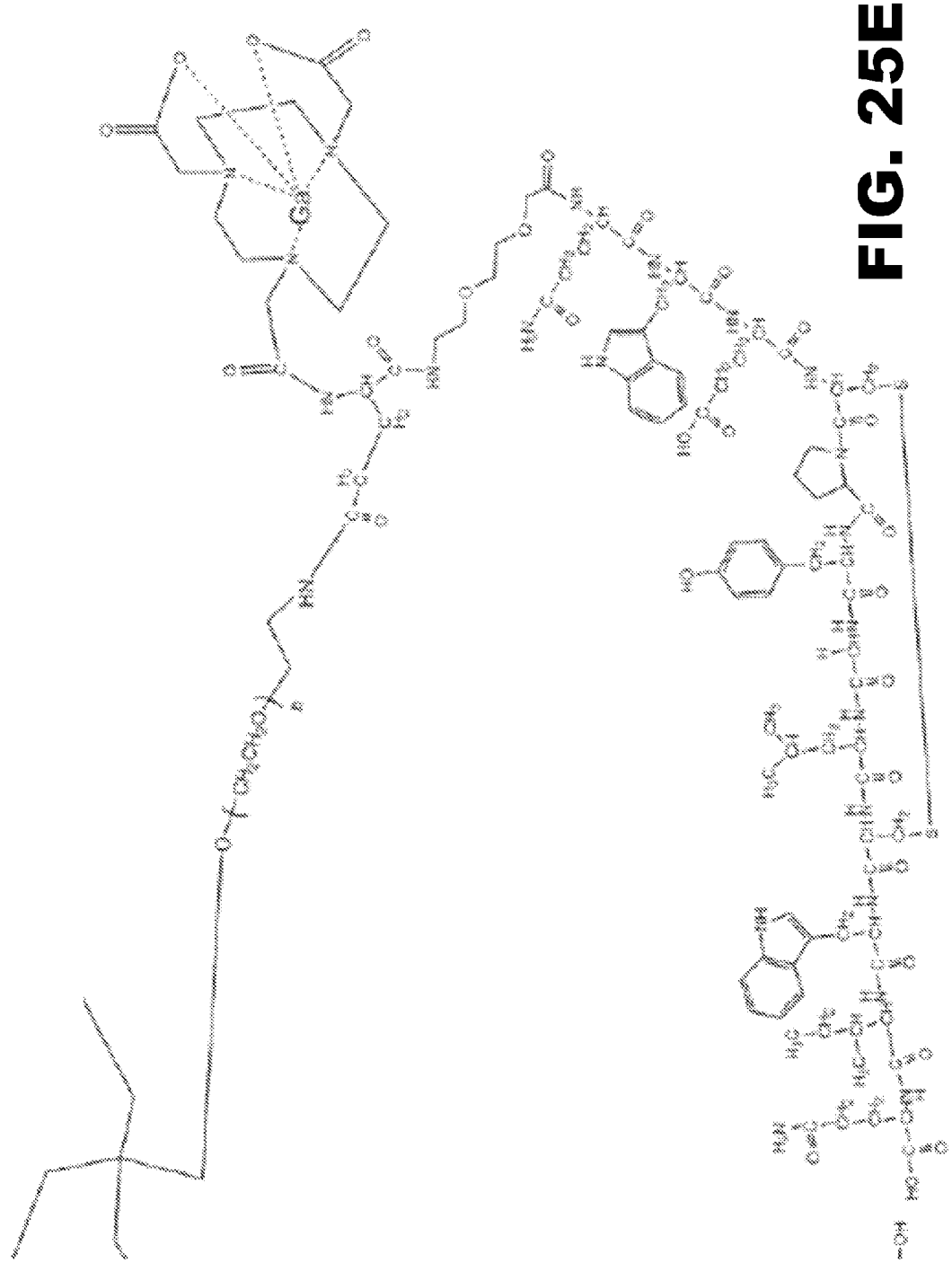
Figure 26A:
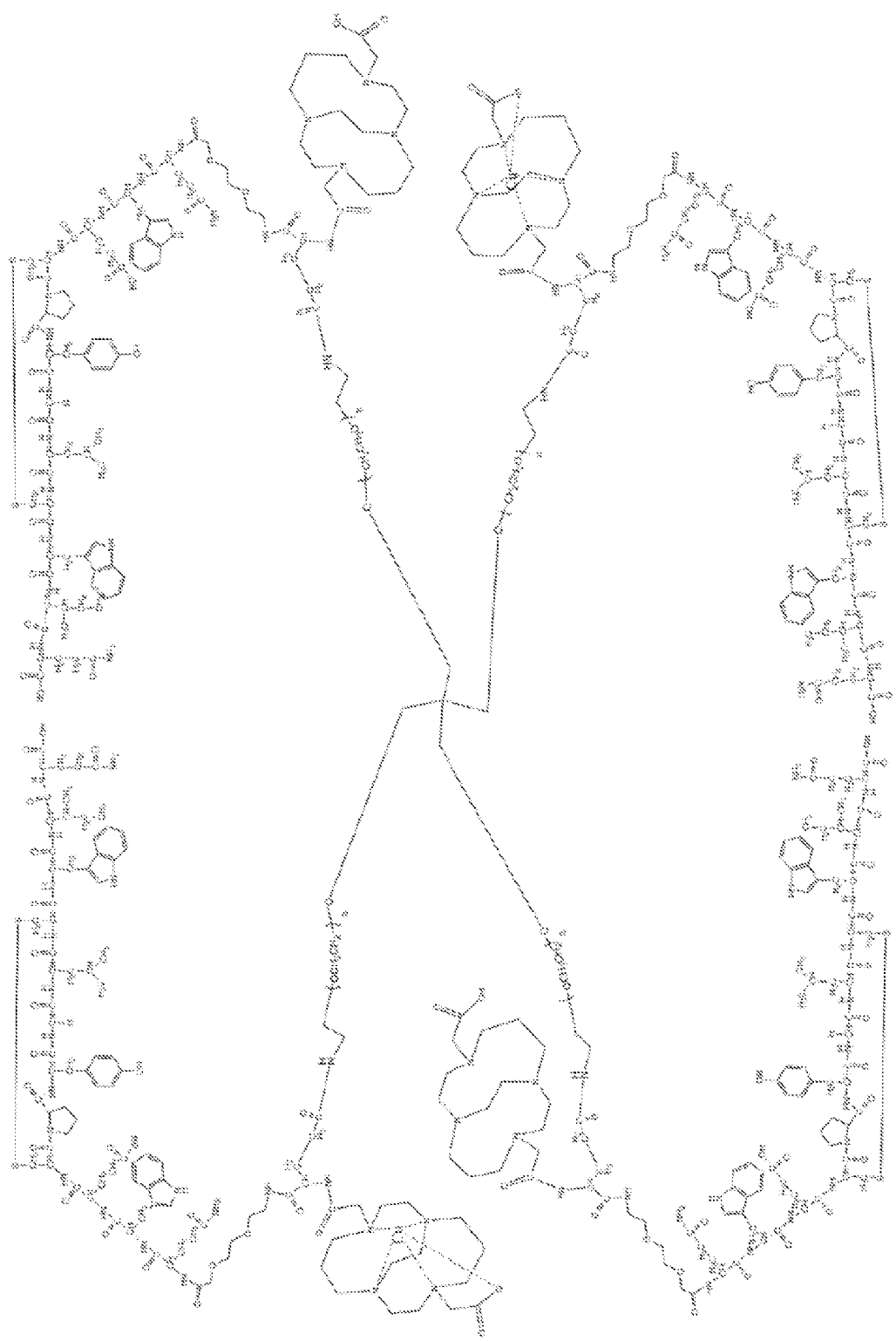
Figure 26B:
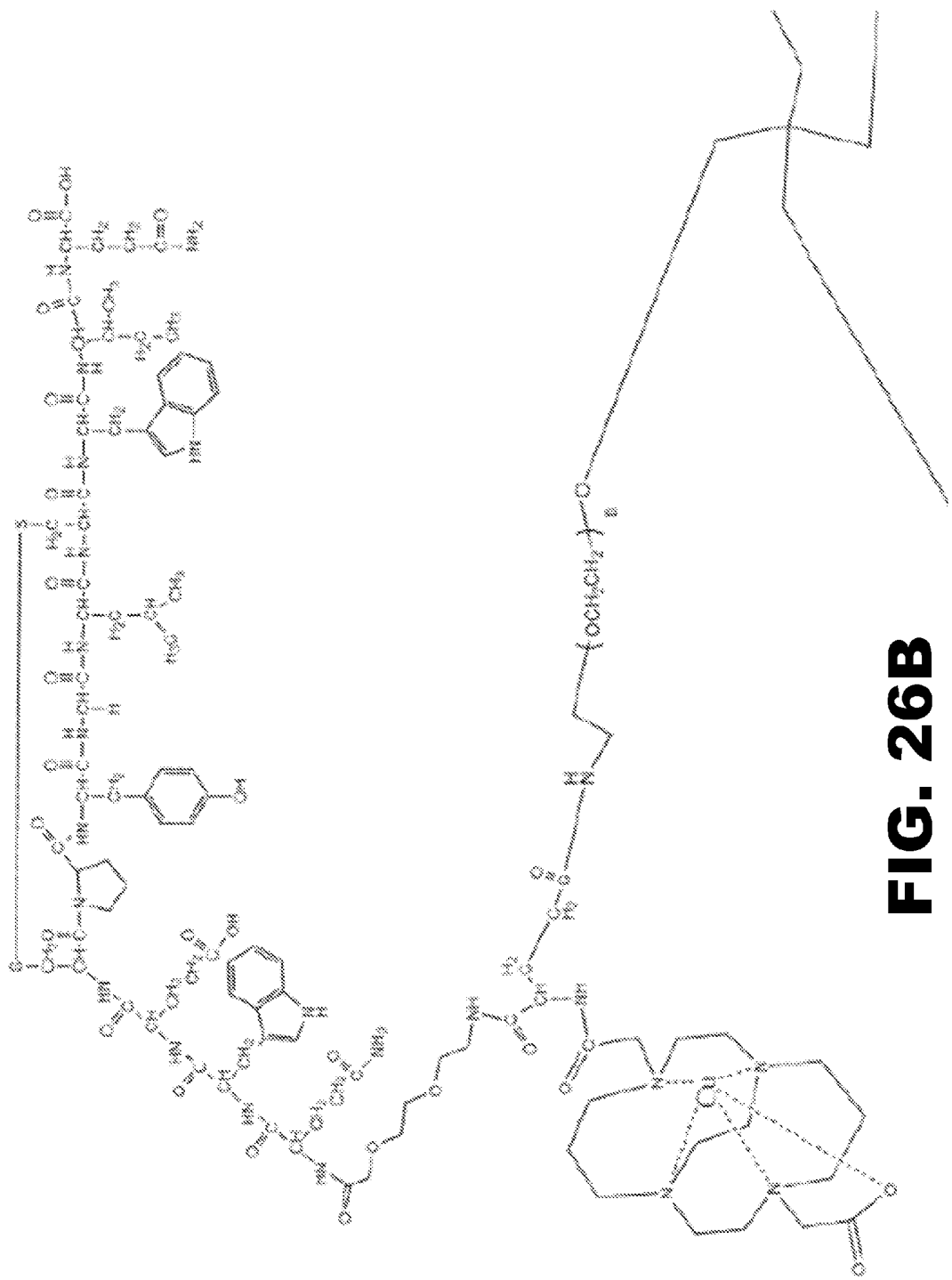
Figure 26C:
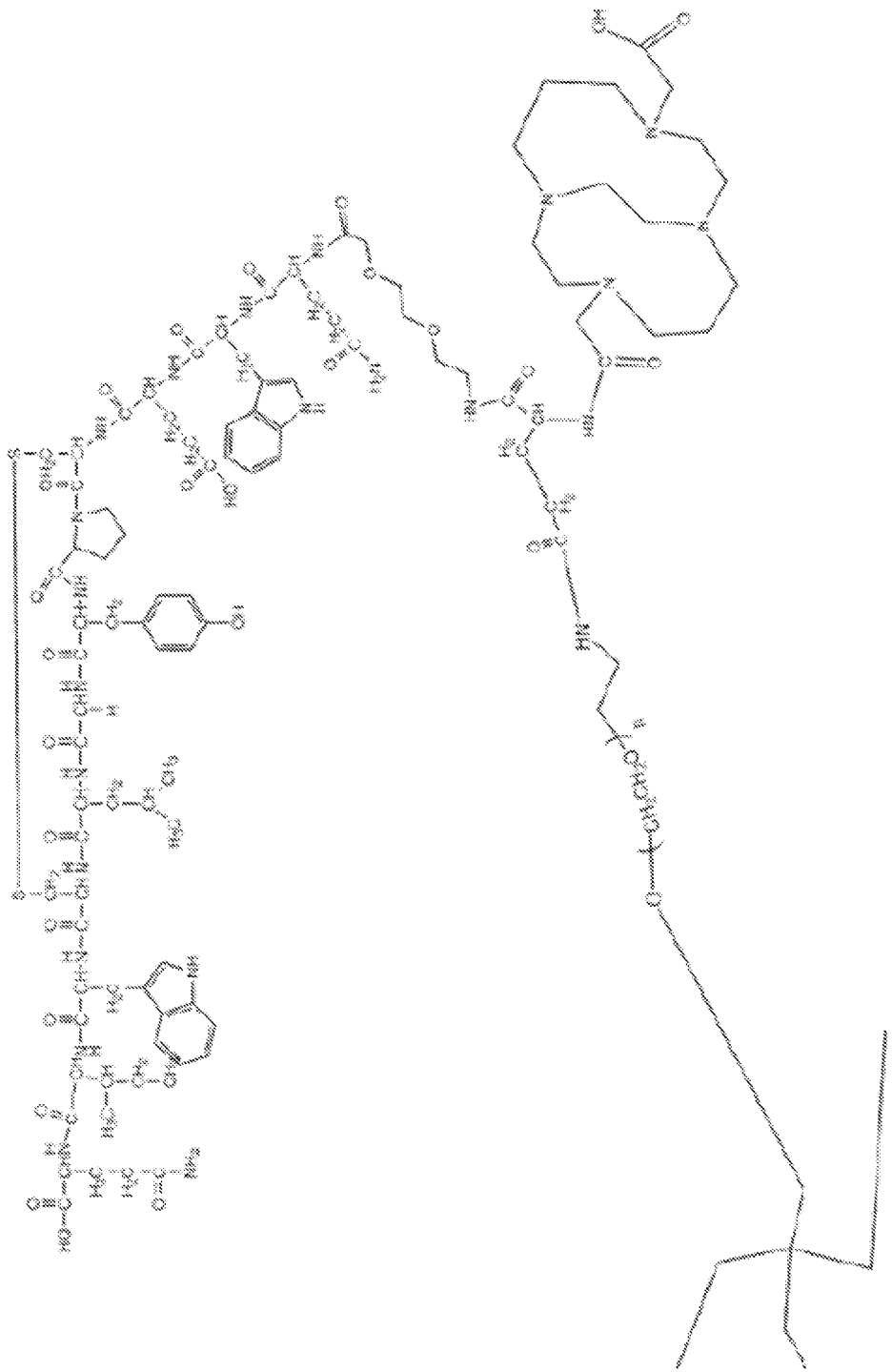
Figure 26D:
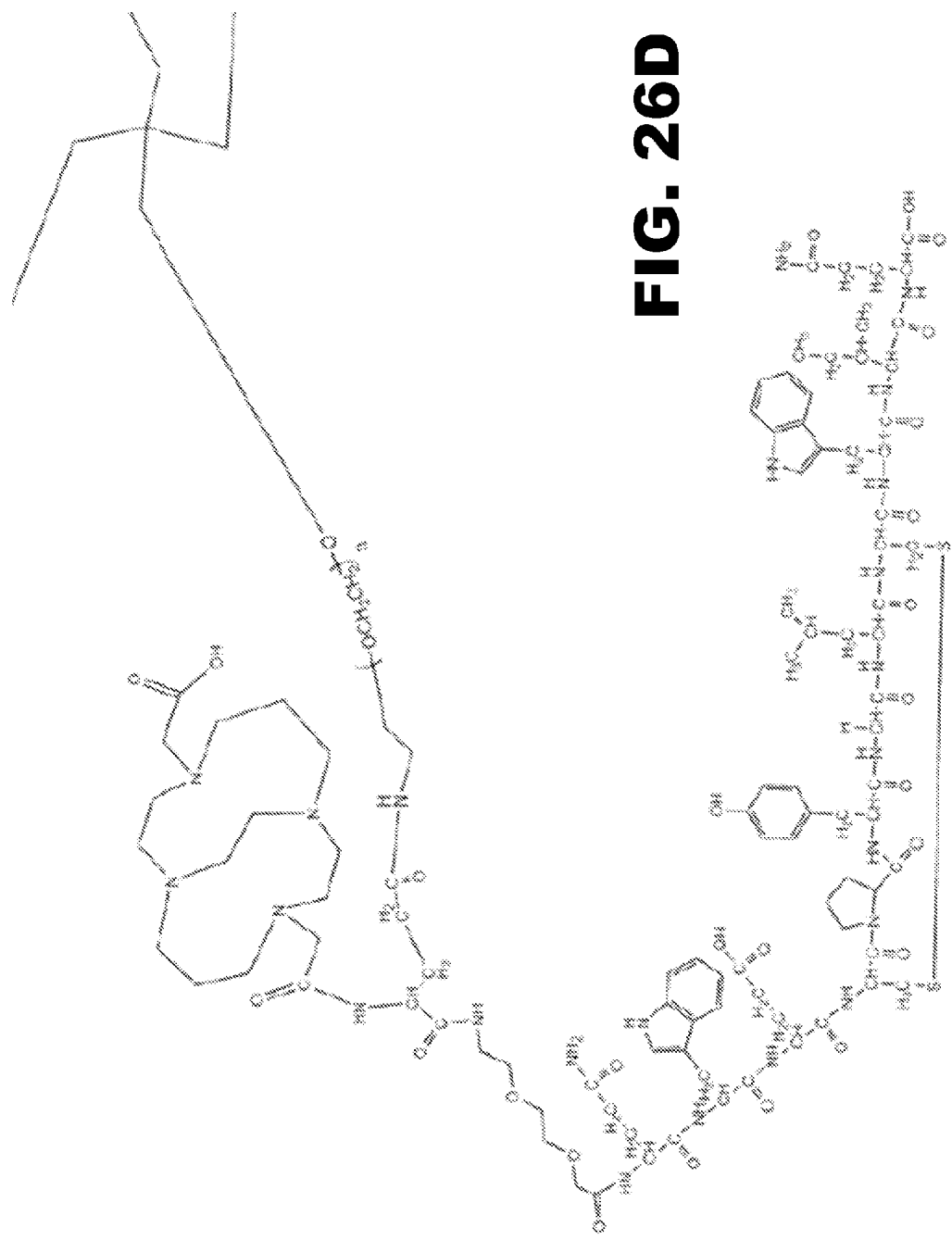
Figure 26E:
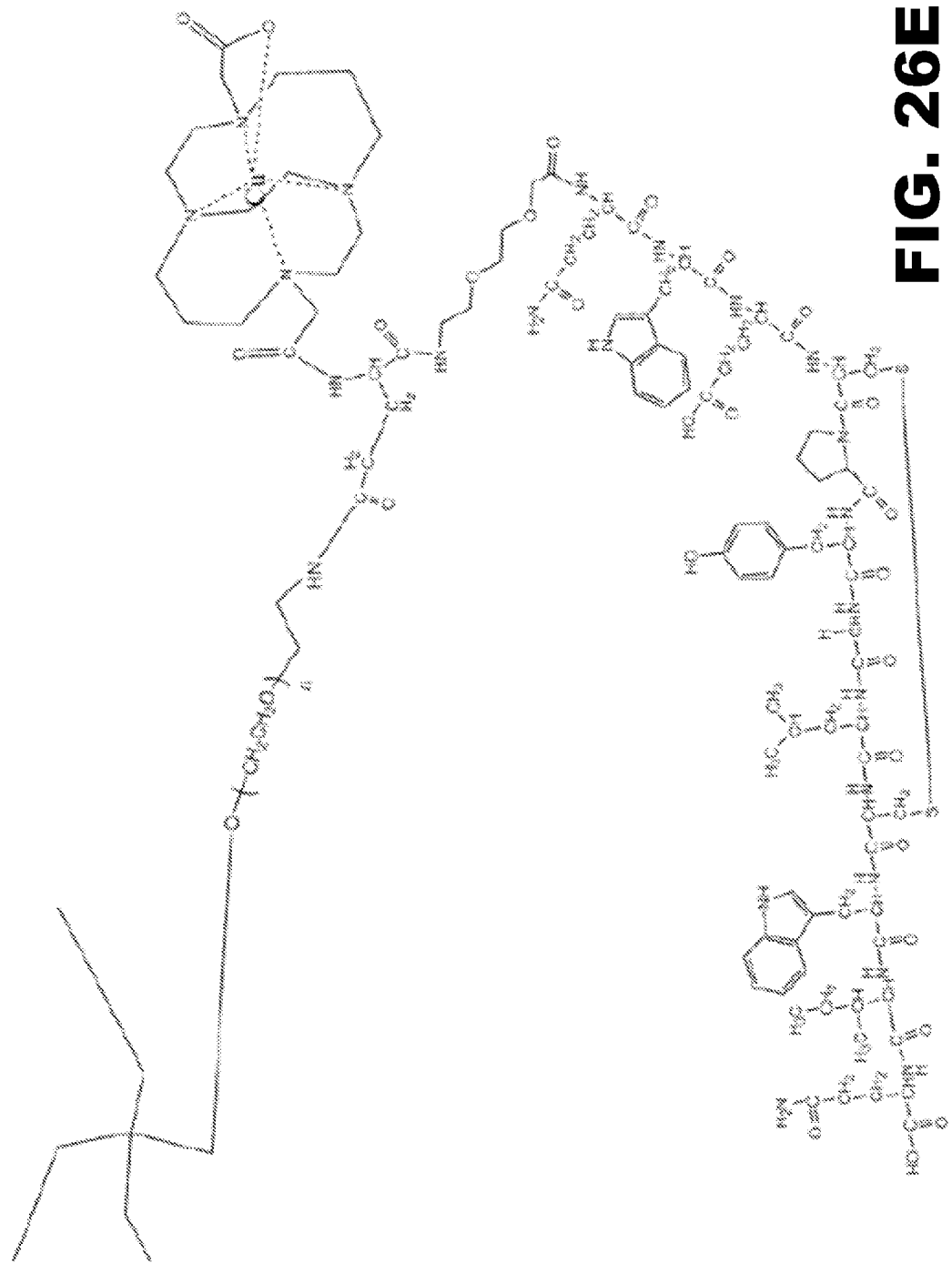
Figure 27A:
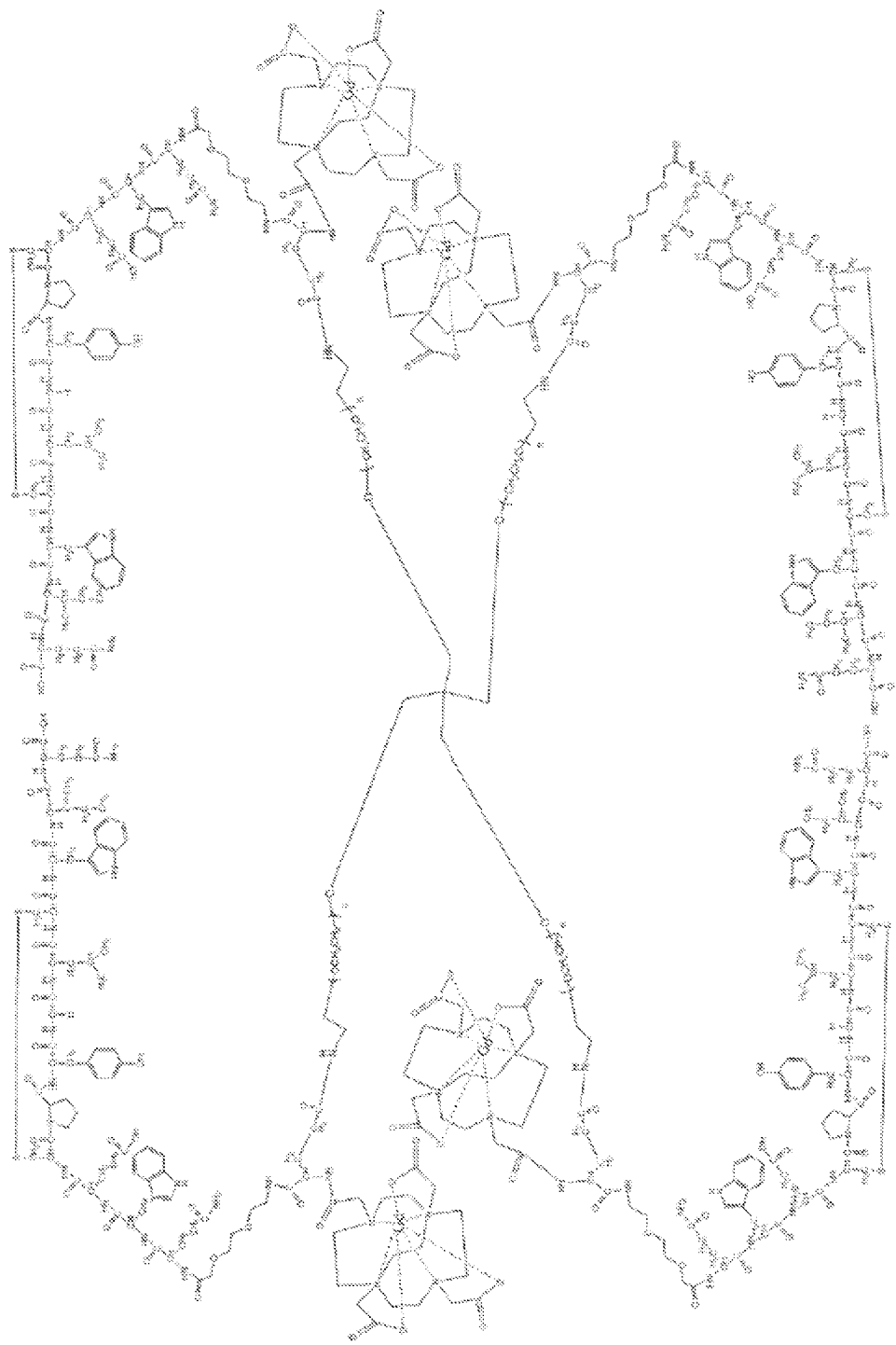
Figure 27B:
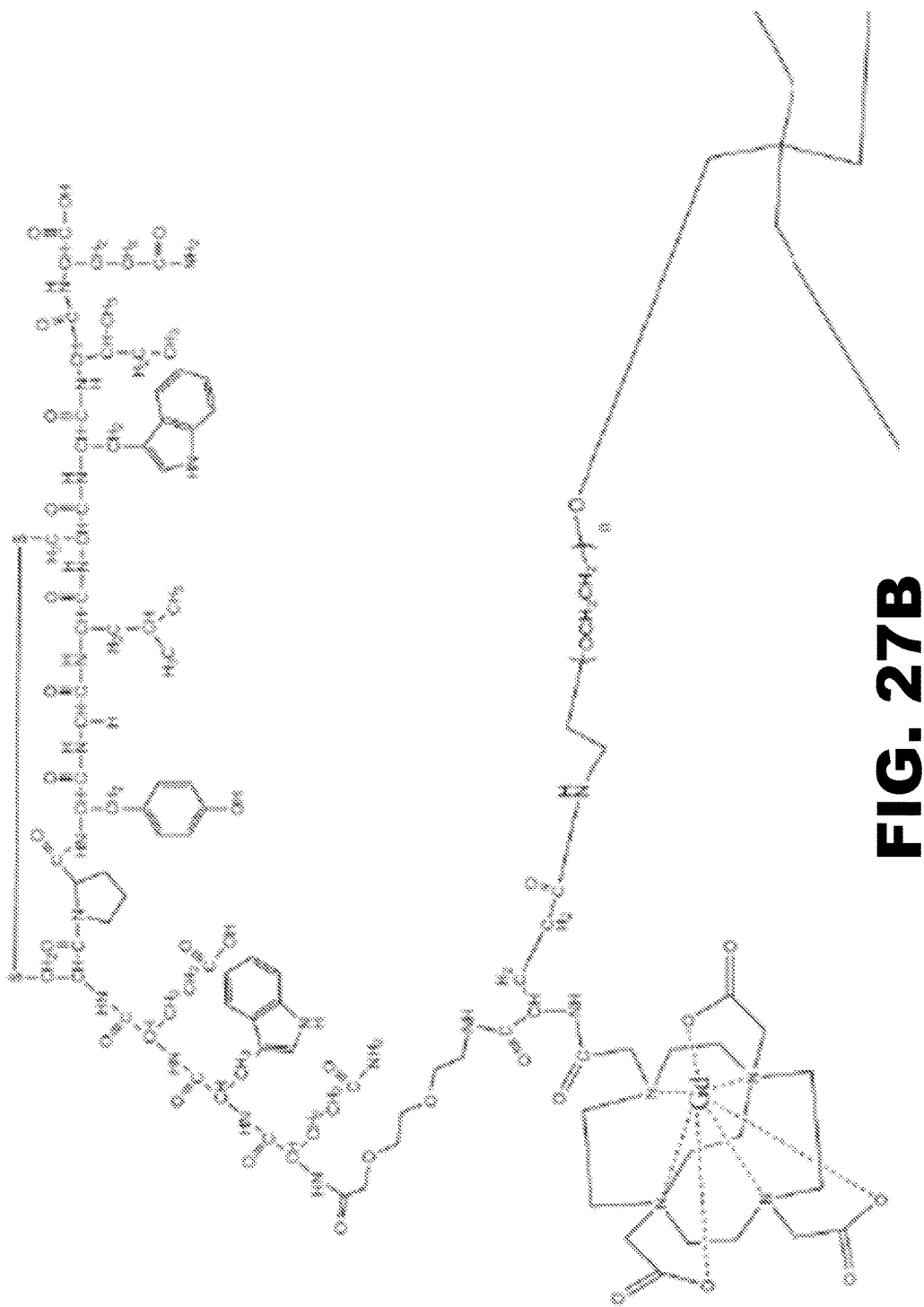
Figure 27C:
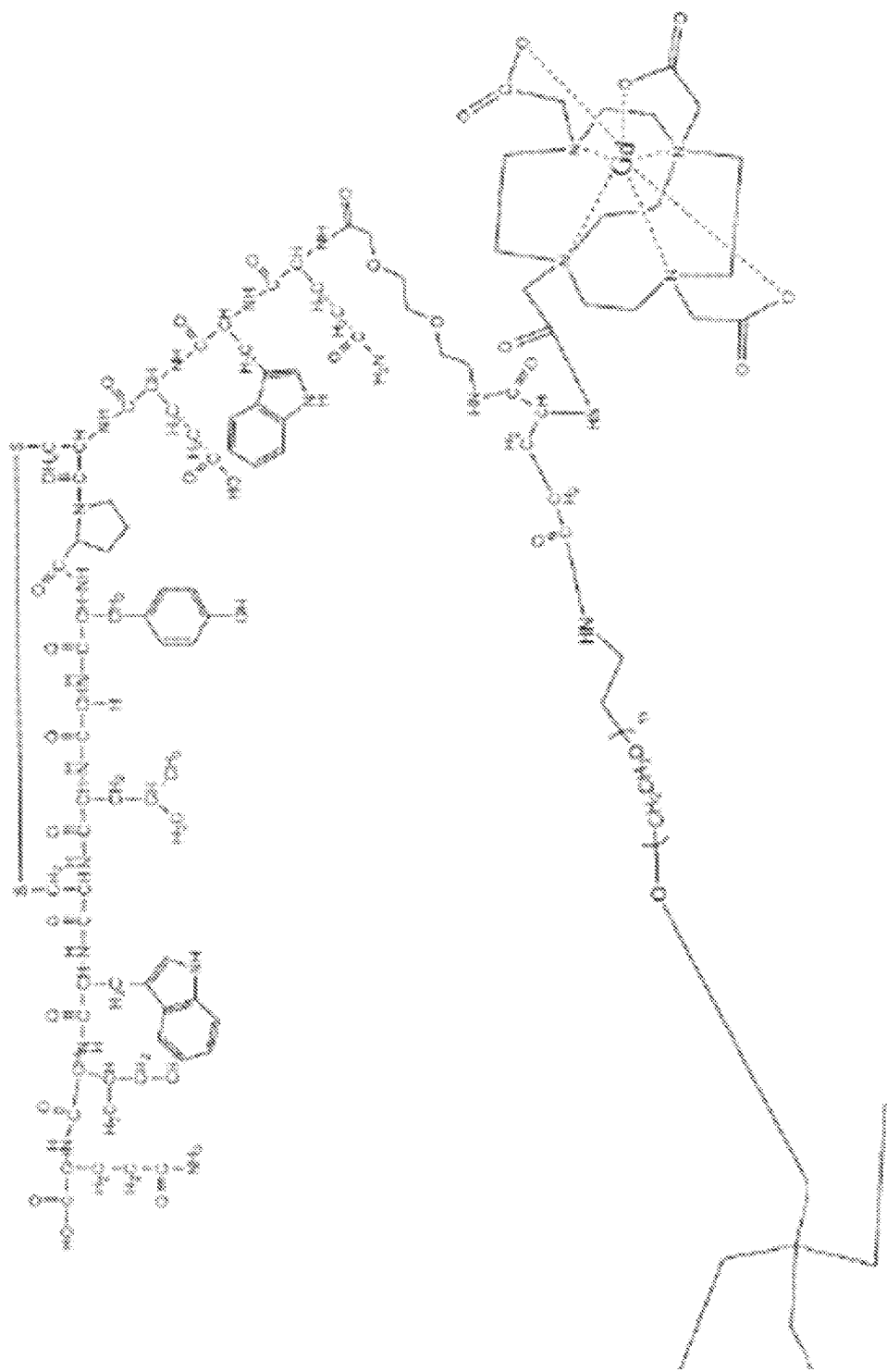
Figure 27D:
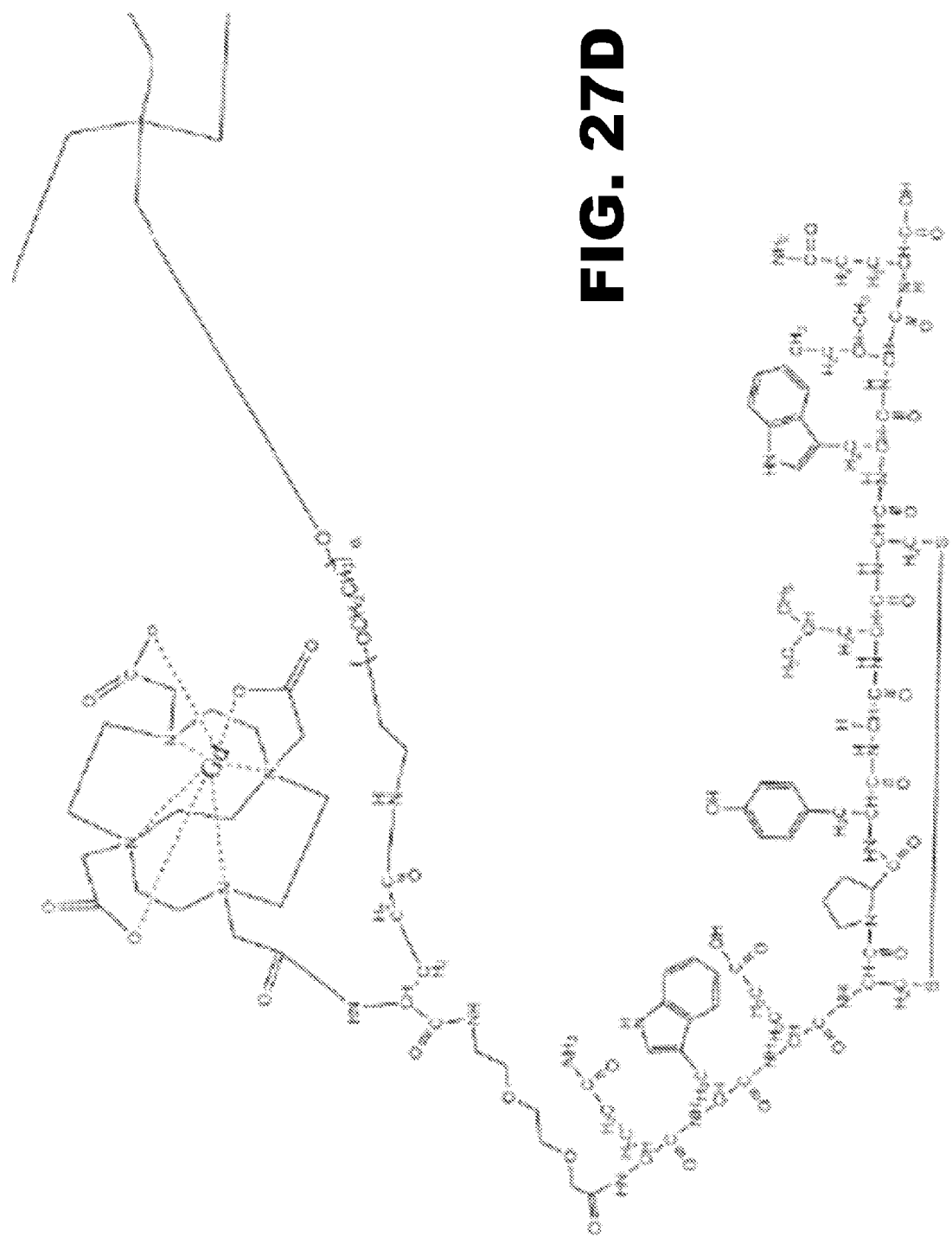
Figure 27E:
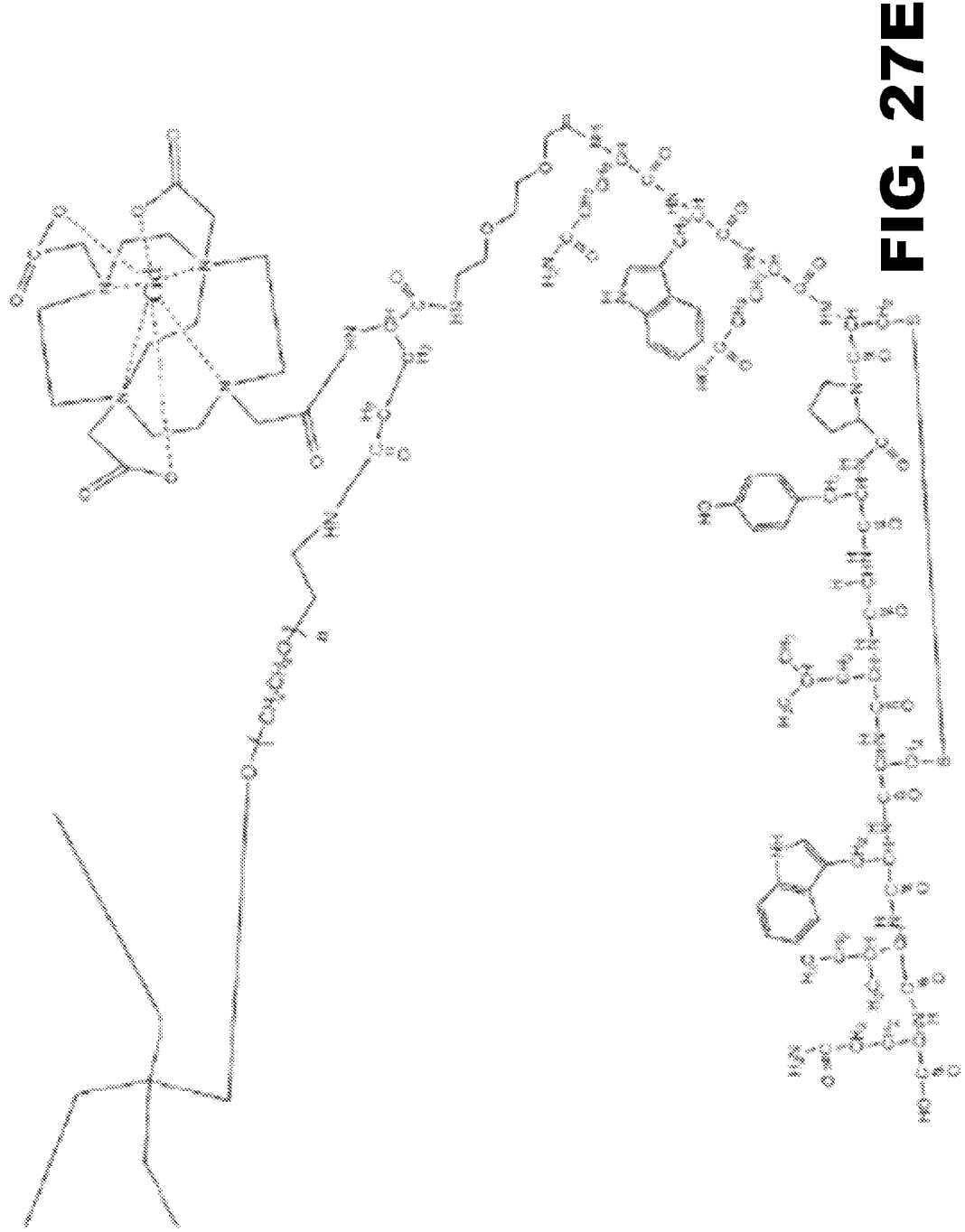
Figure 28A:
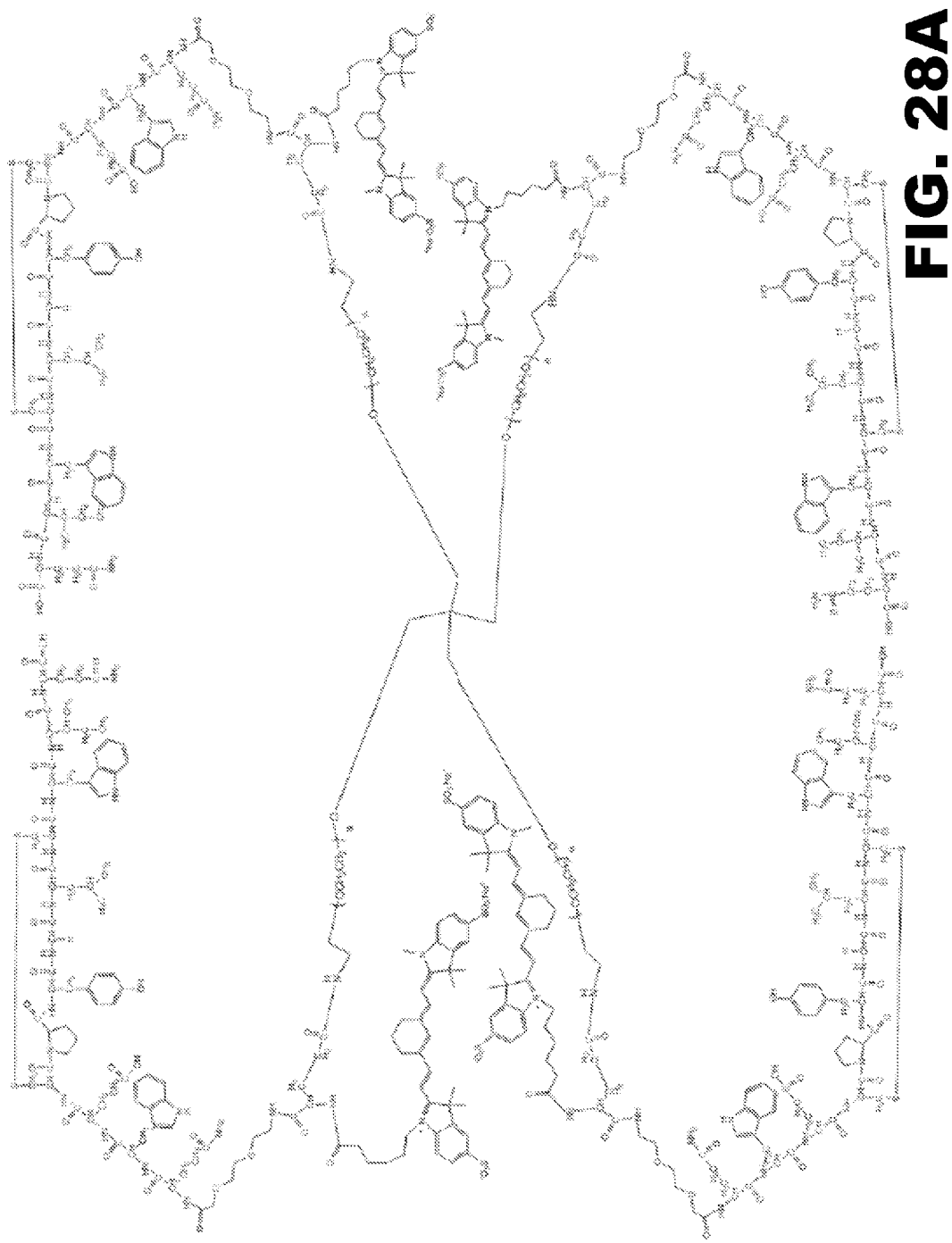
Figure 28B:
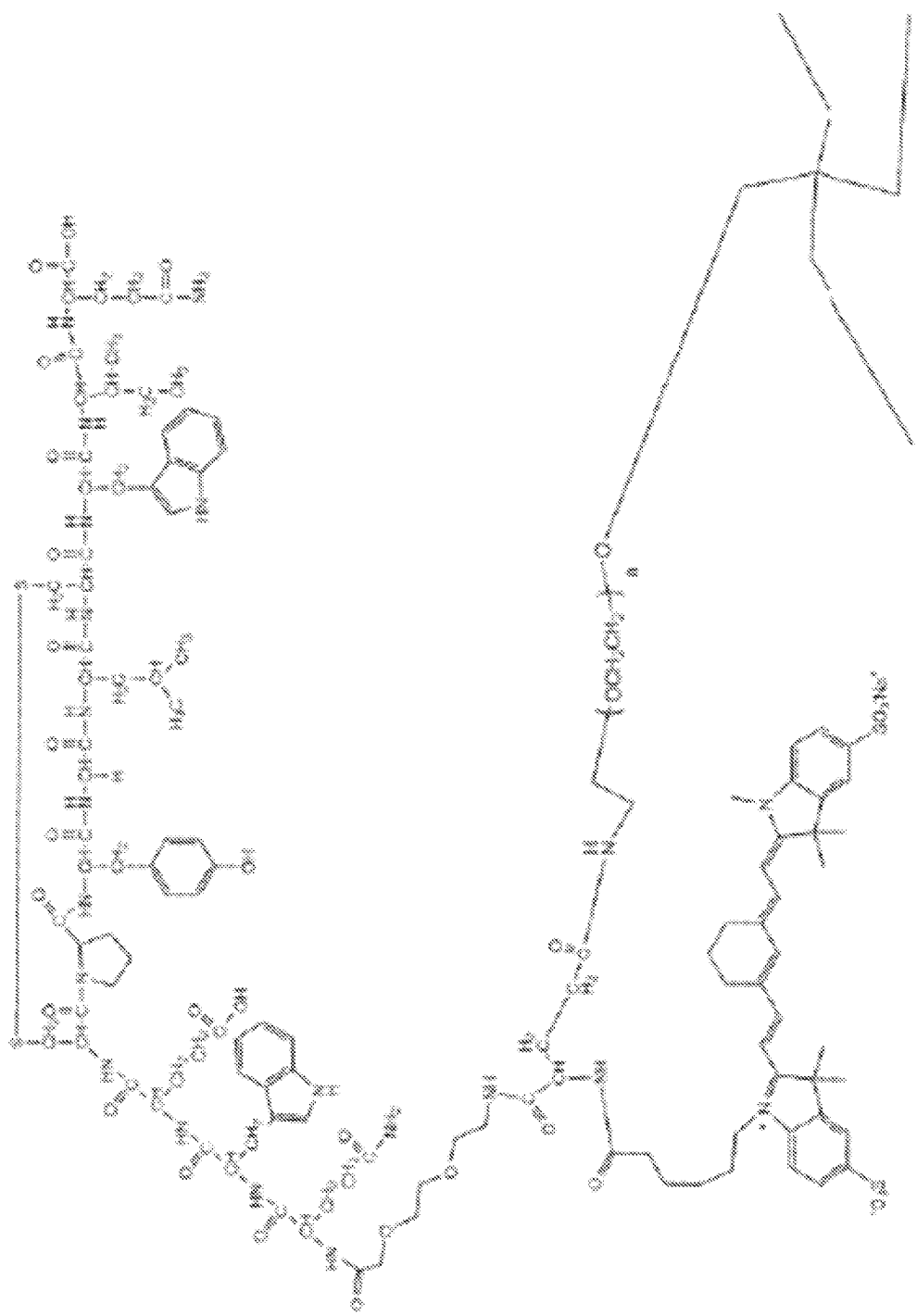
Figure 28C:
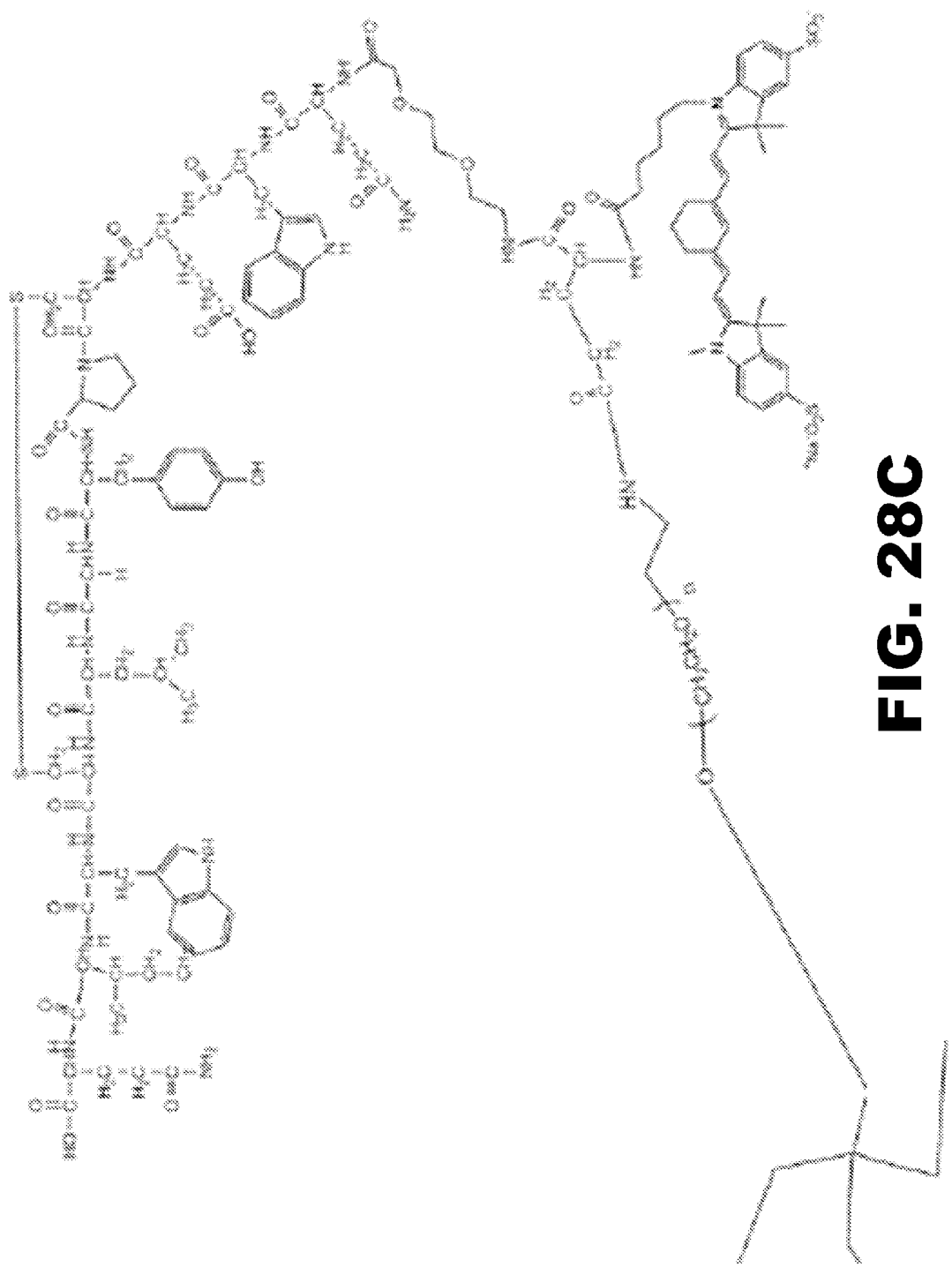
Figure 28D:
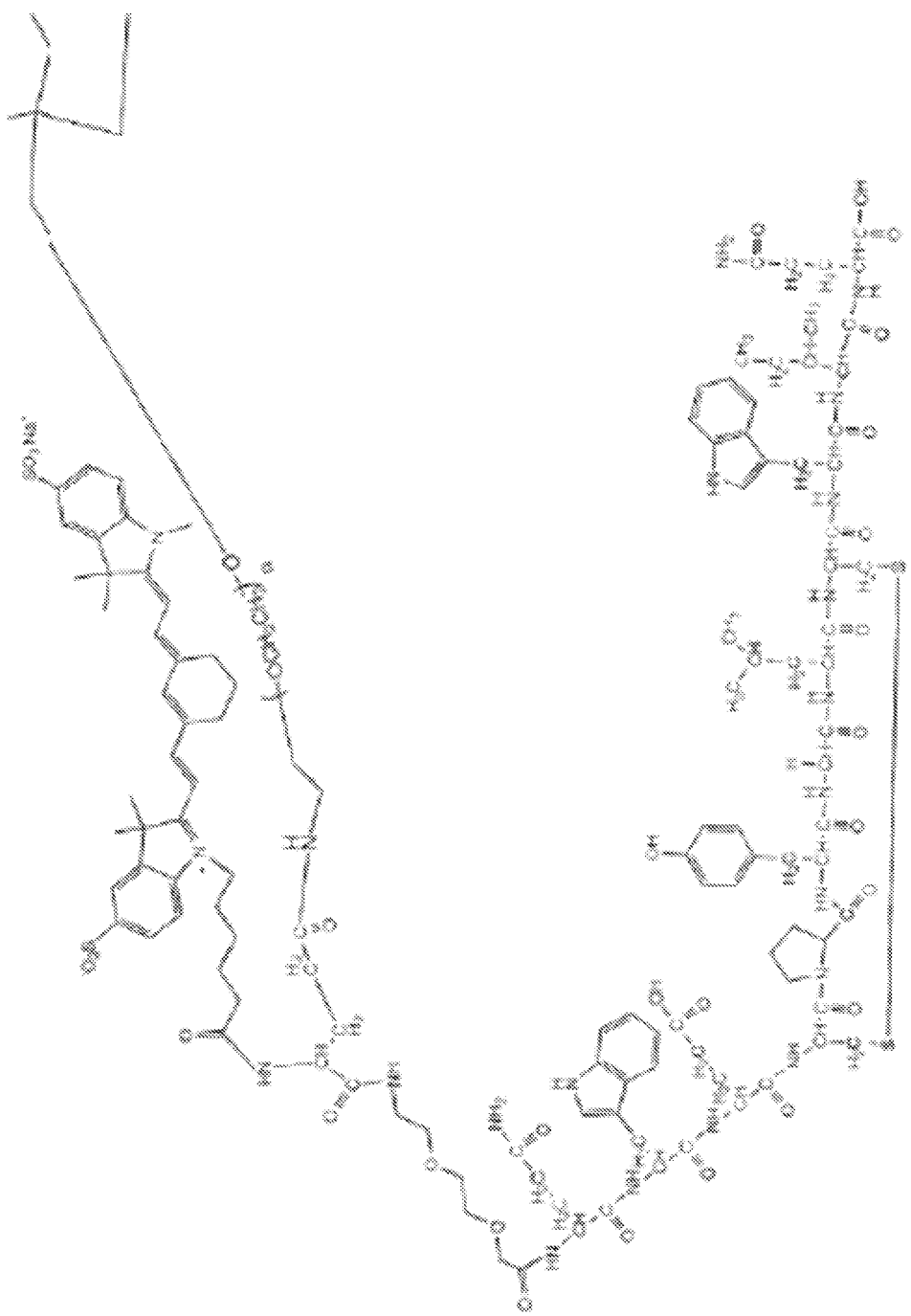
Figure 28E:
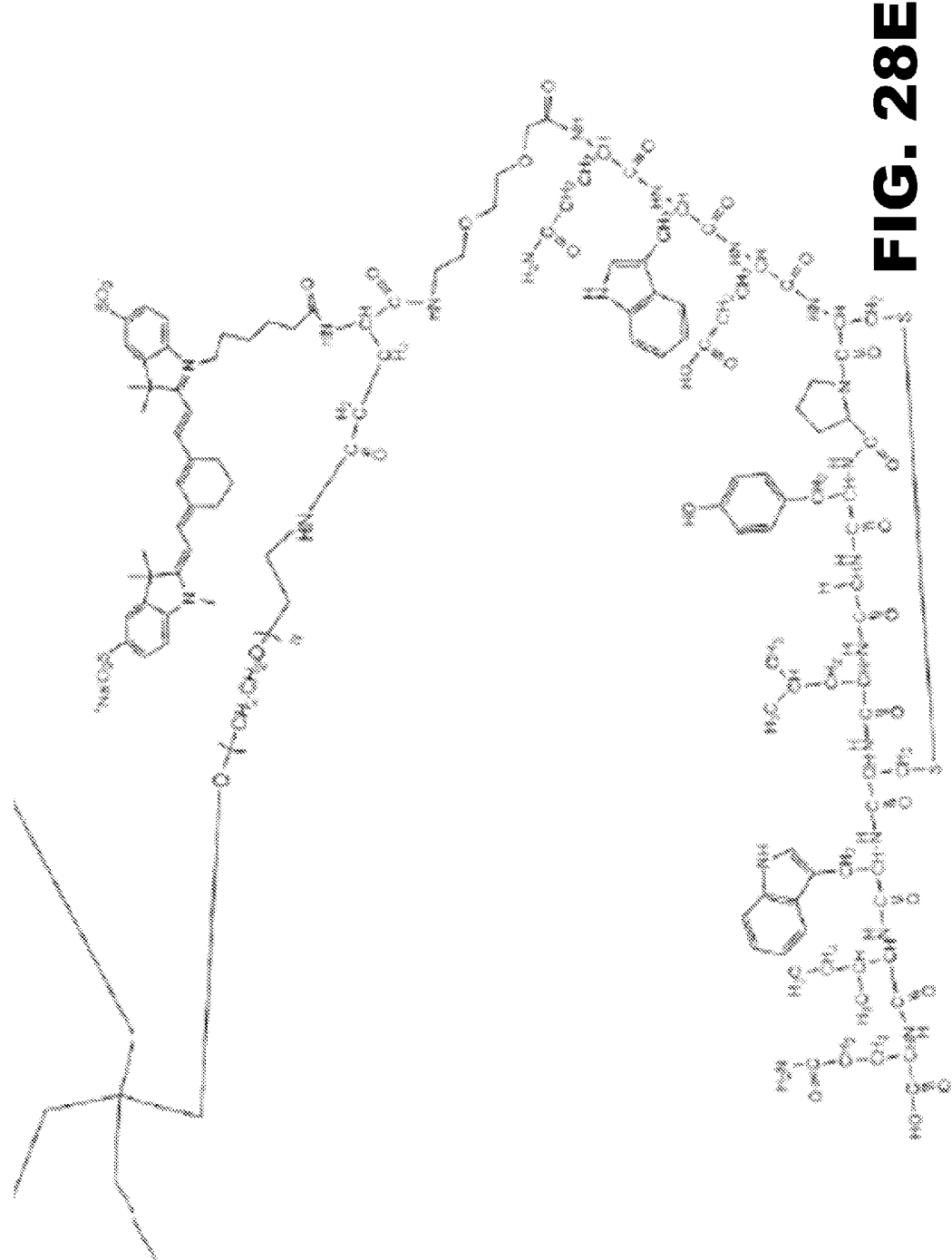
Figure 29A:
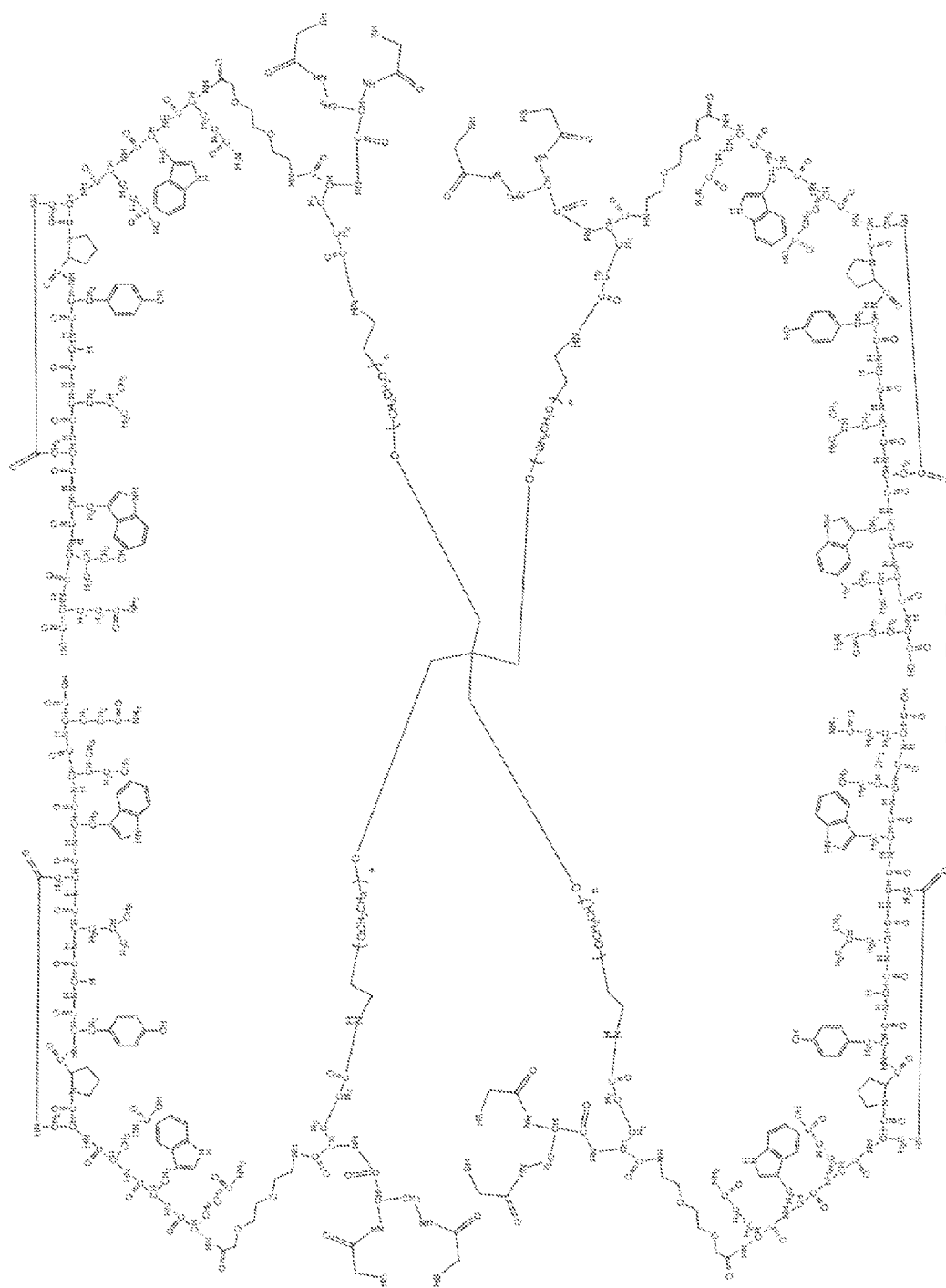
Figure 29B:
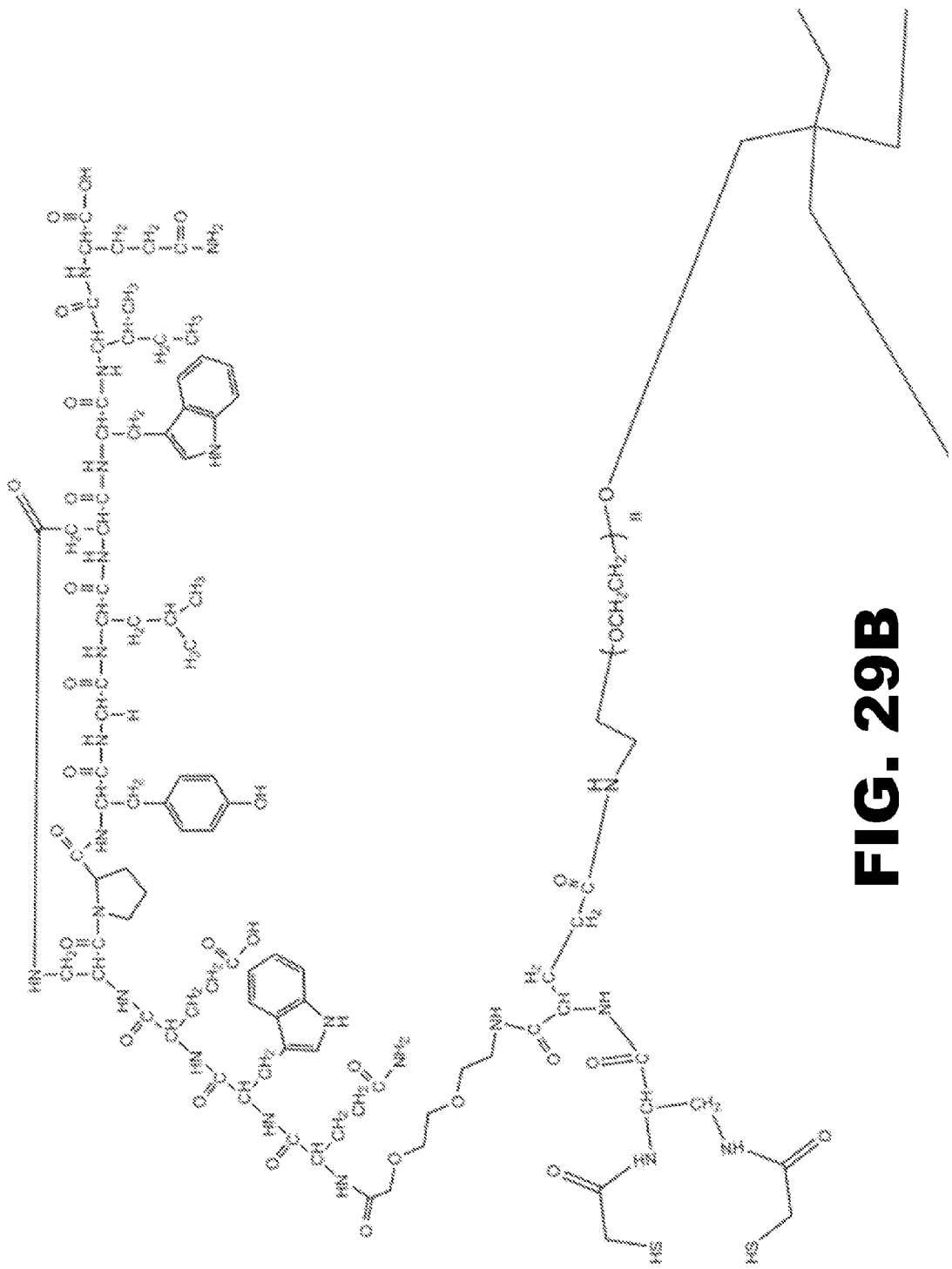
Figure 29C:
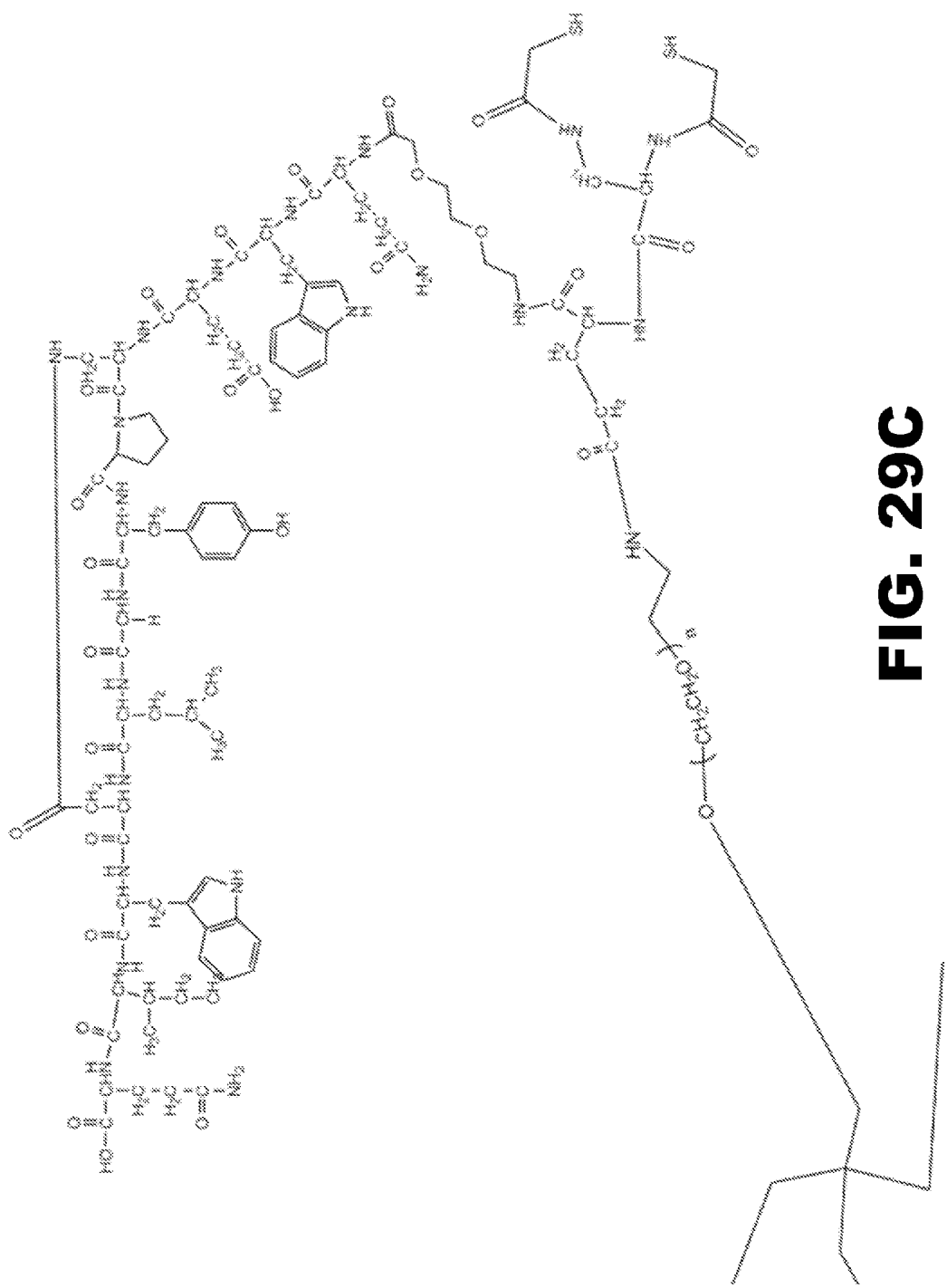
Figure 29D:
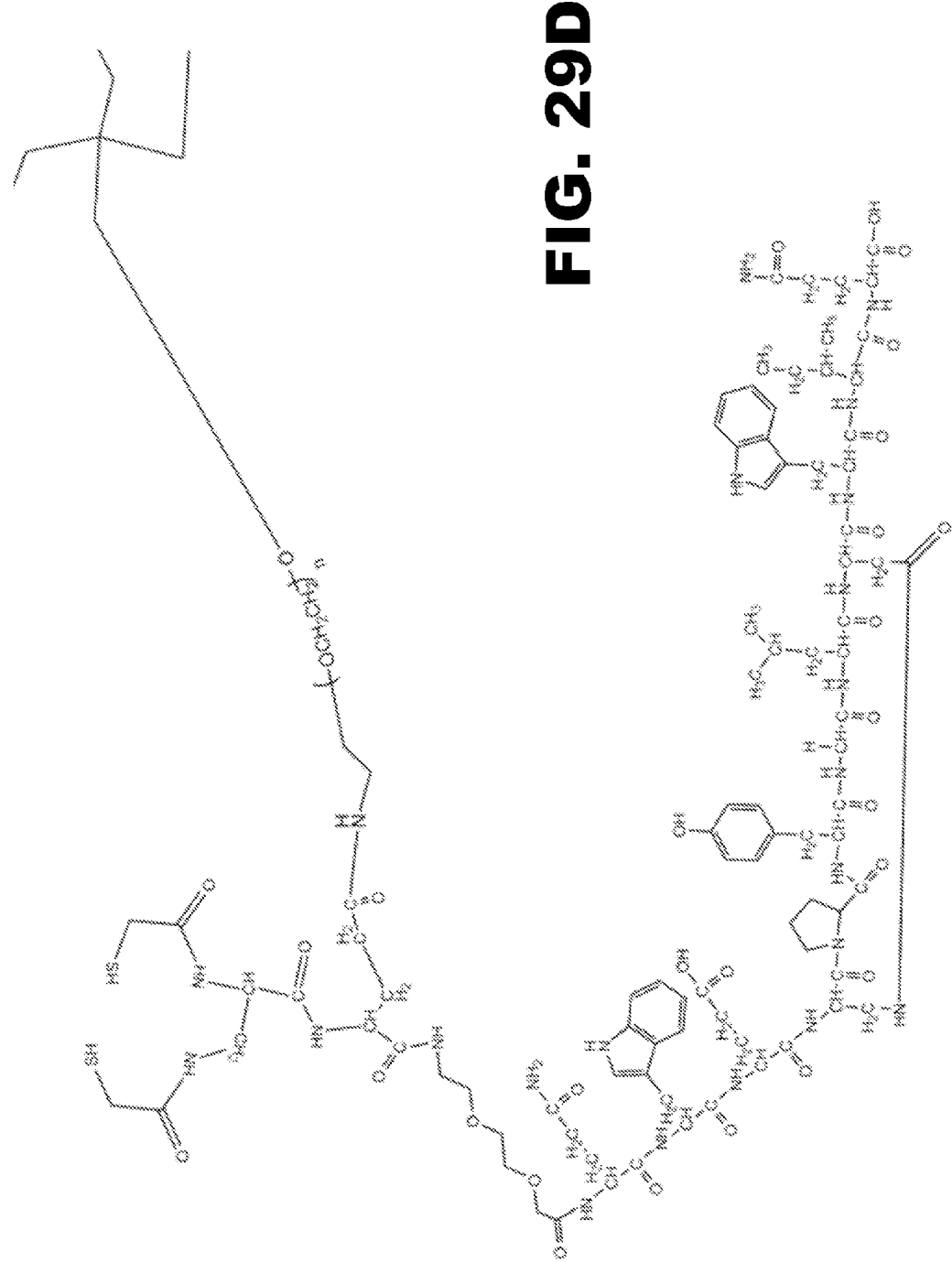
Figure 29E:
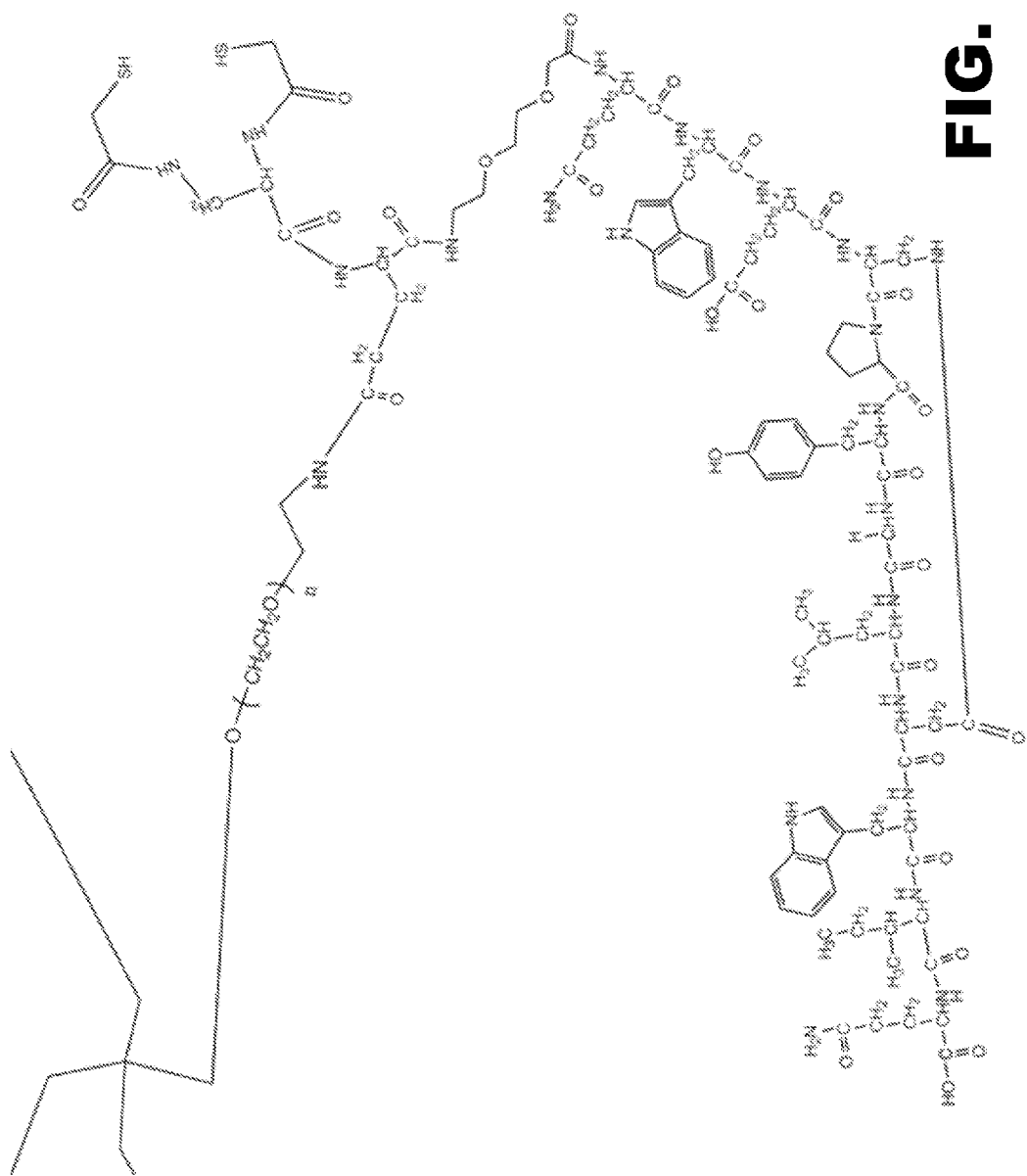
Figure 30A:
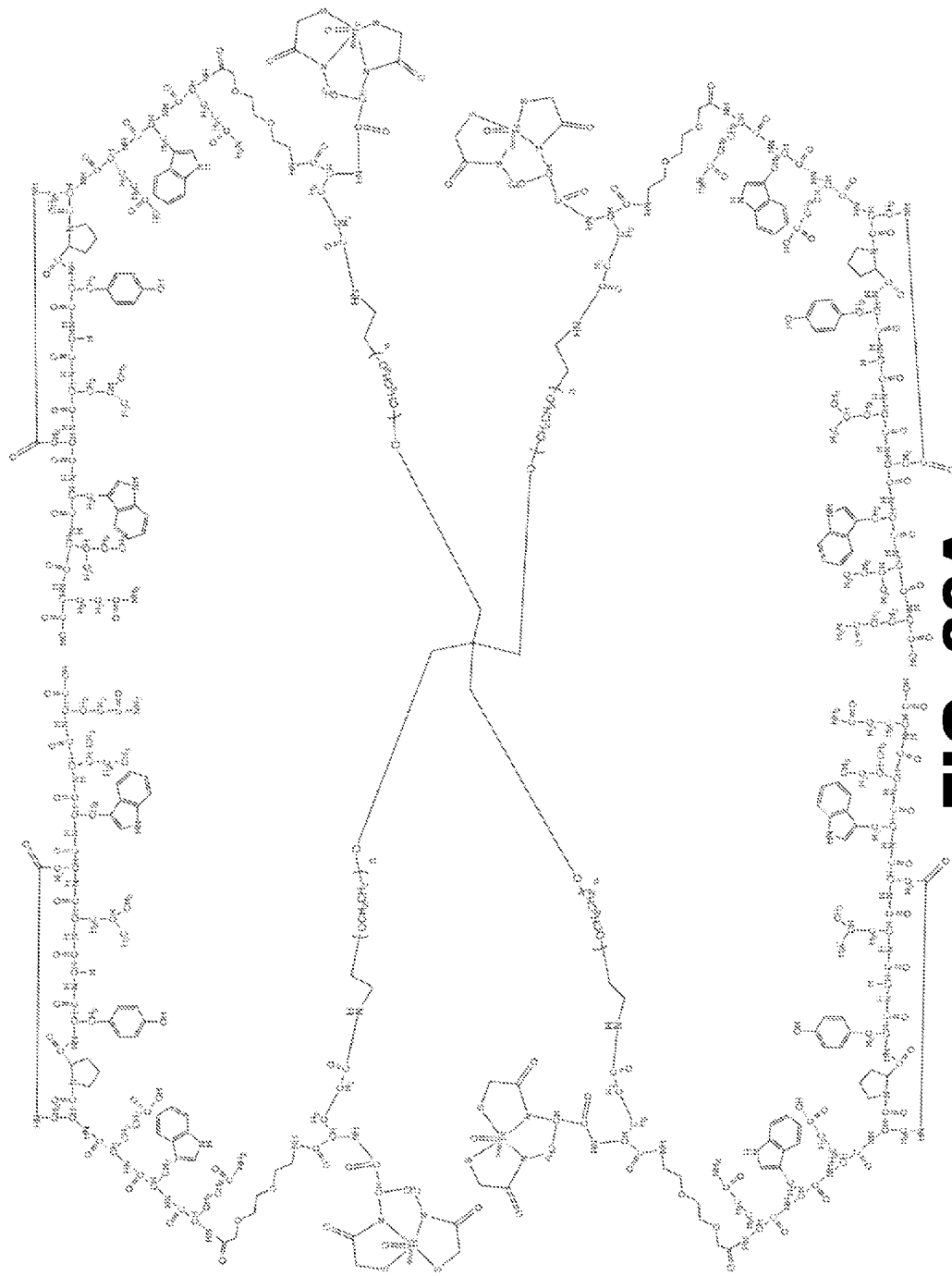
Figure 30B:
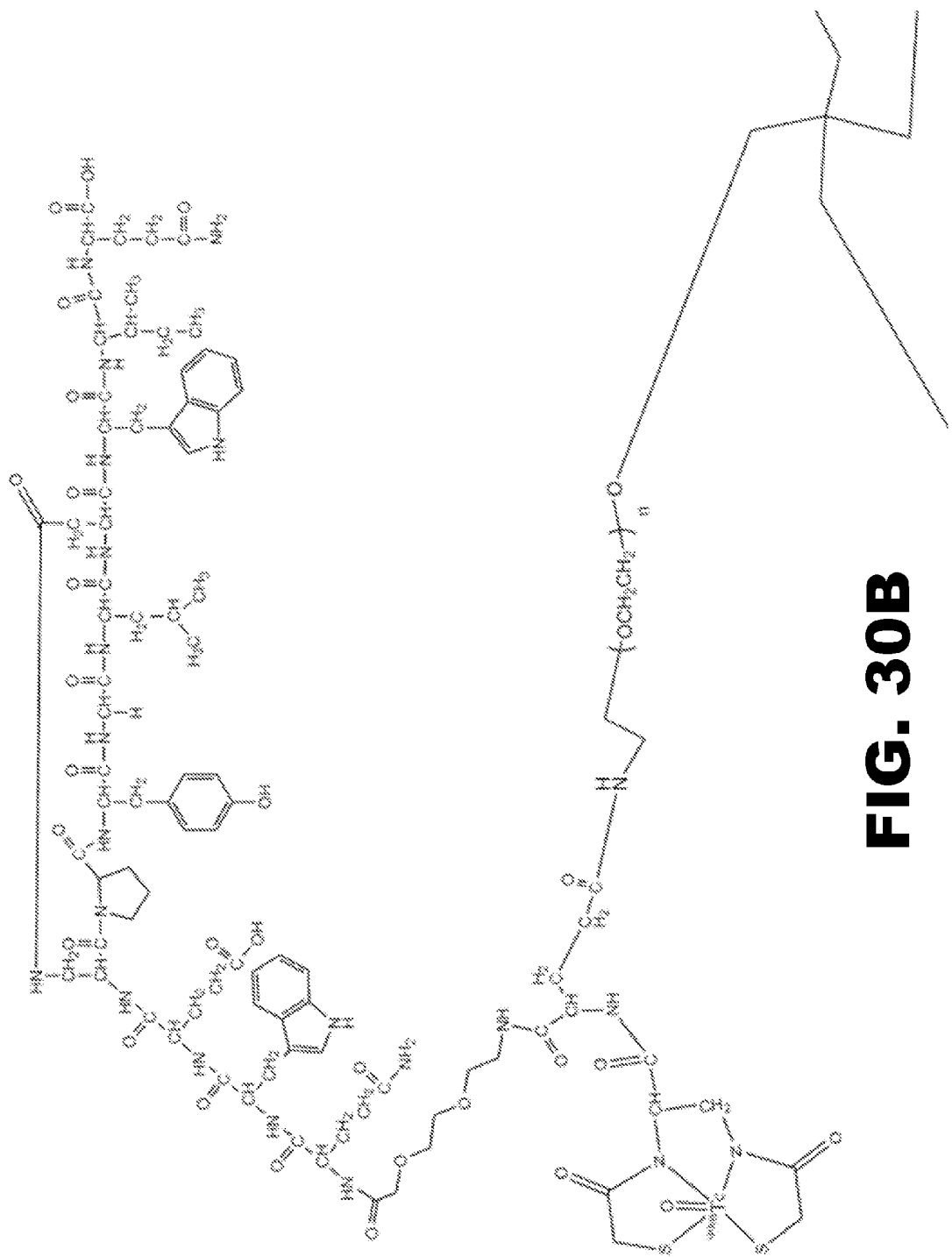
Figure 30C:
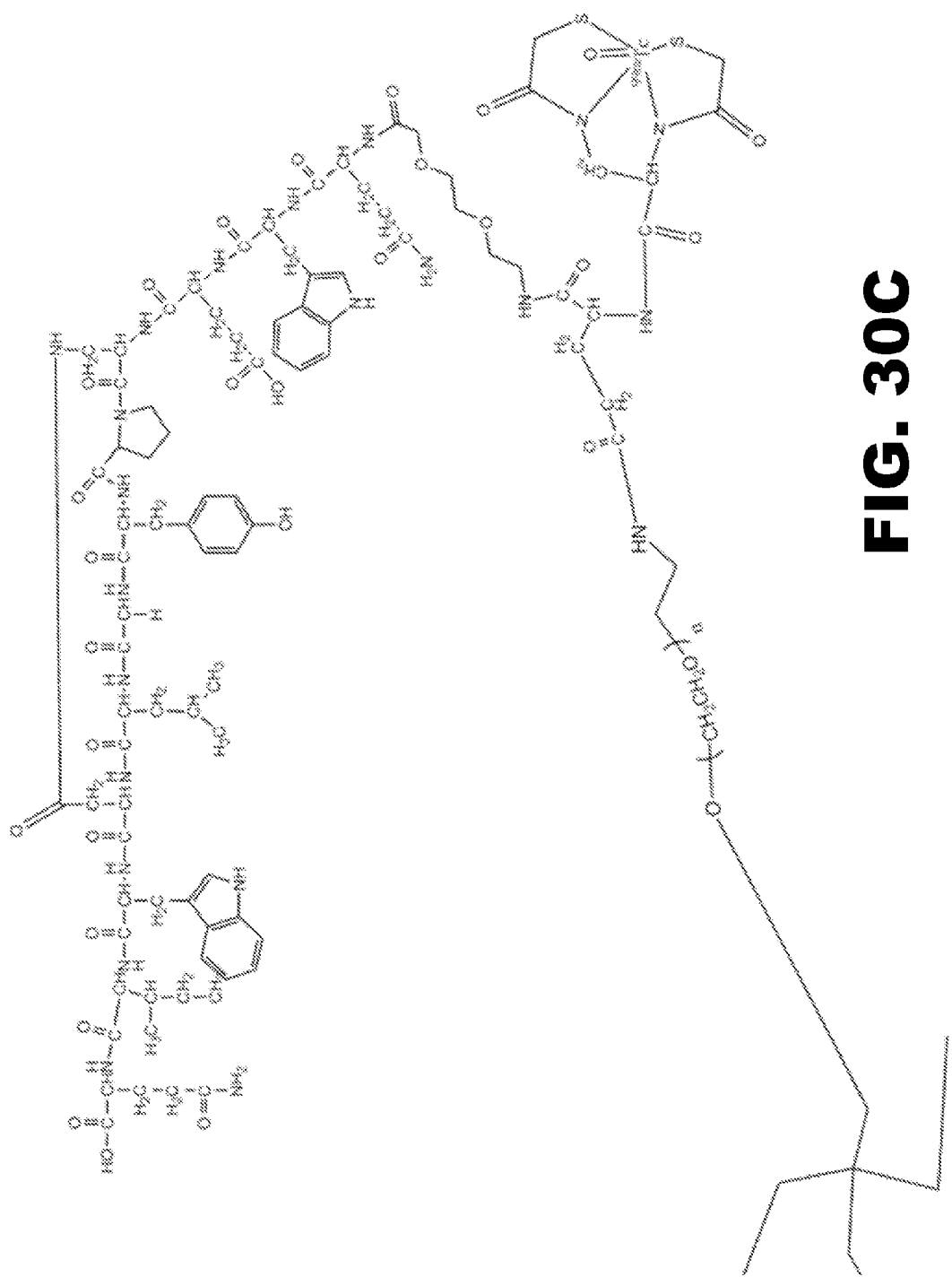
Figure 30D:
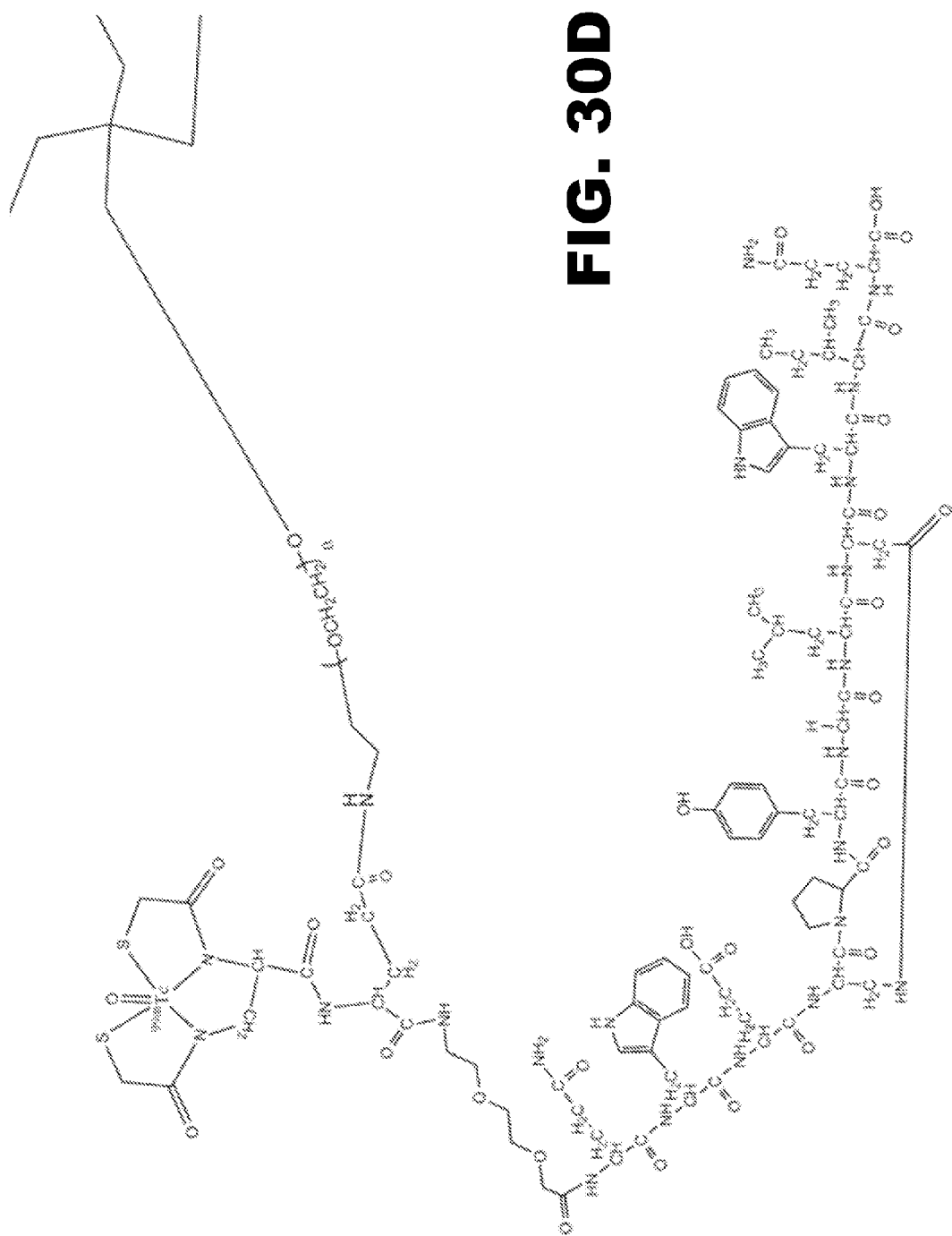
Figure 30E:
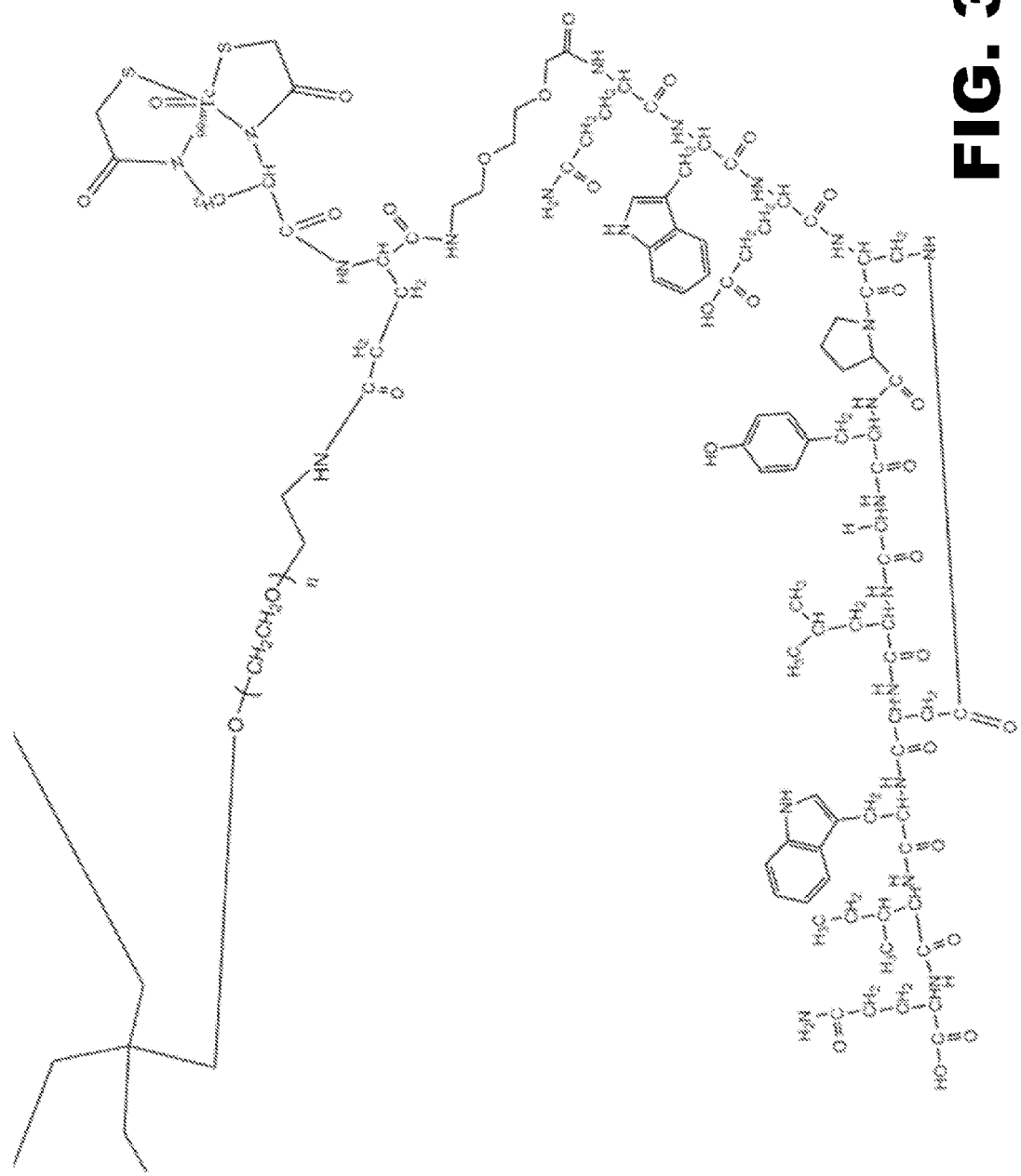
Figure 31A:
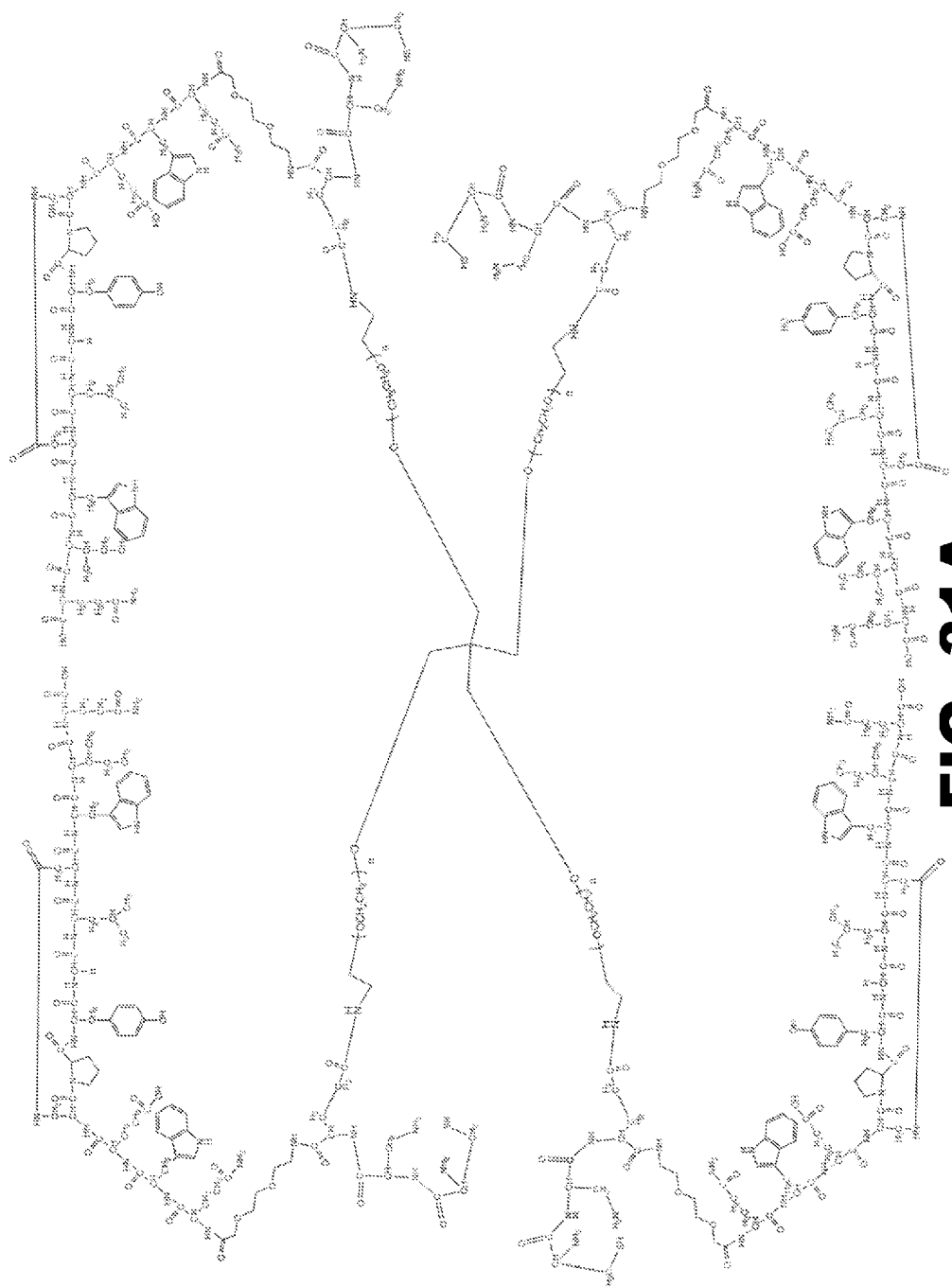
Figure 31B:
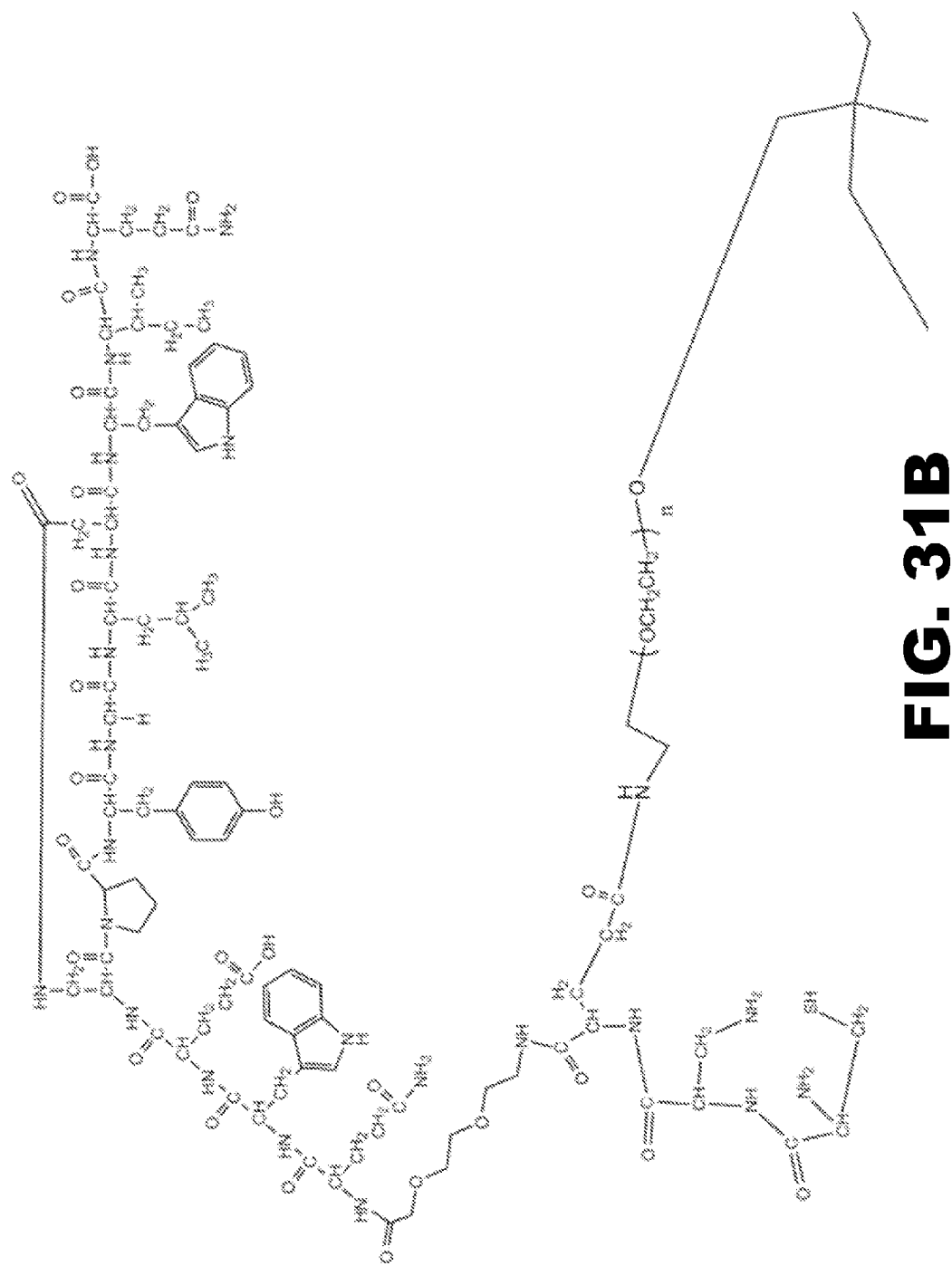
Figure 31C:
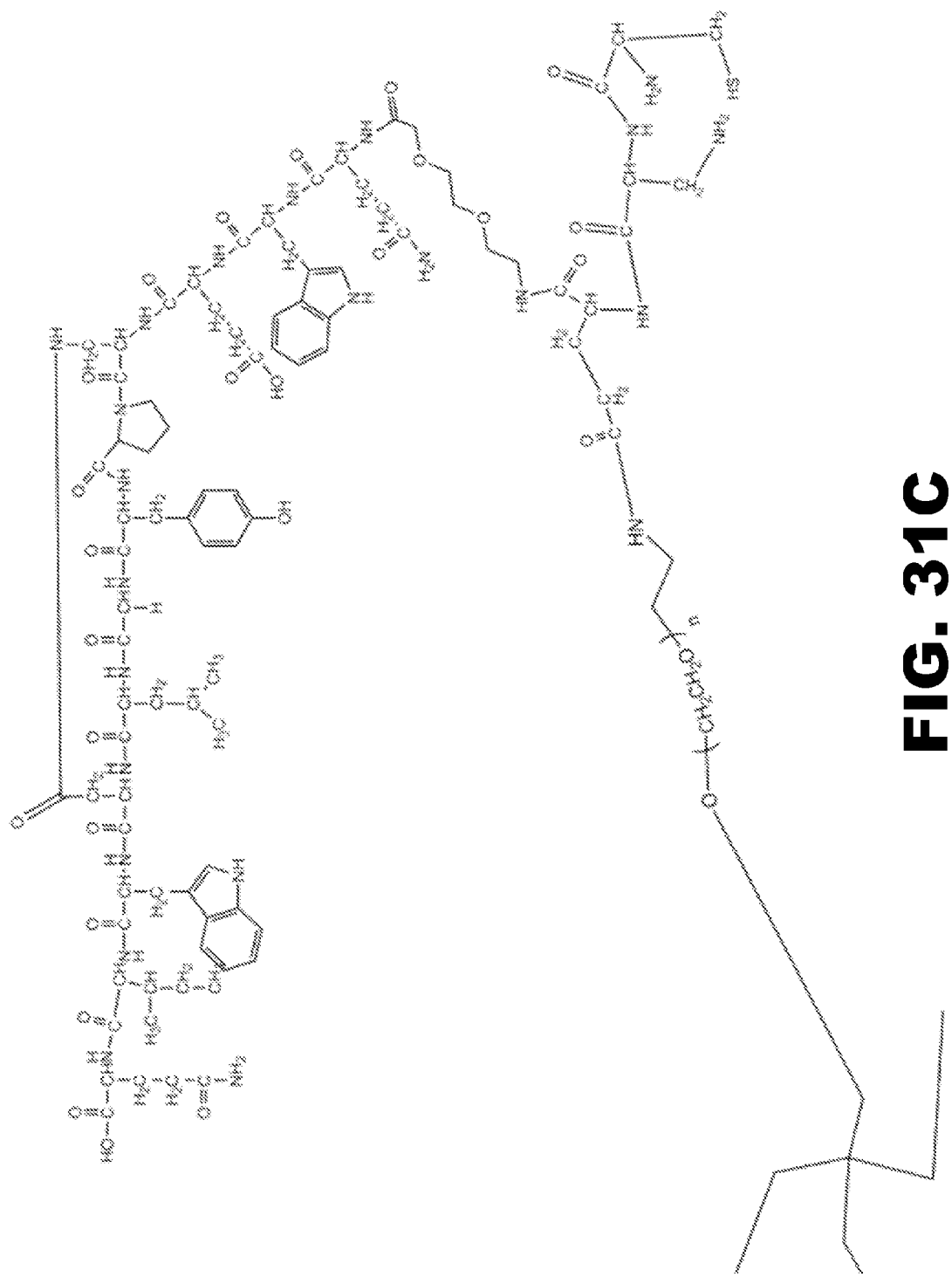
Figure 31D:
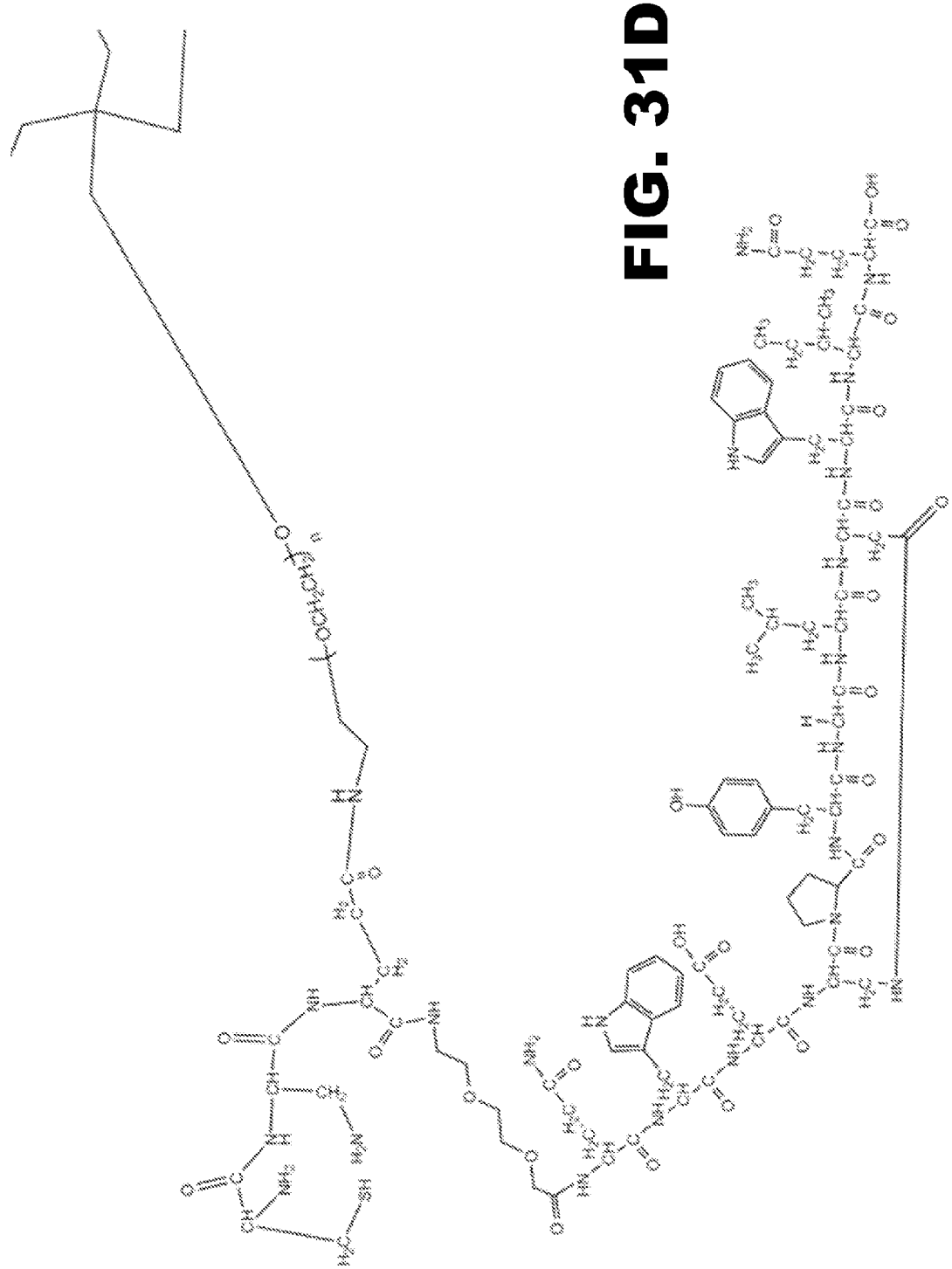
Figure 31E:
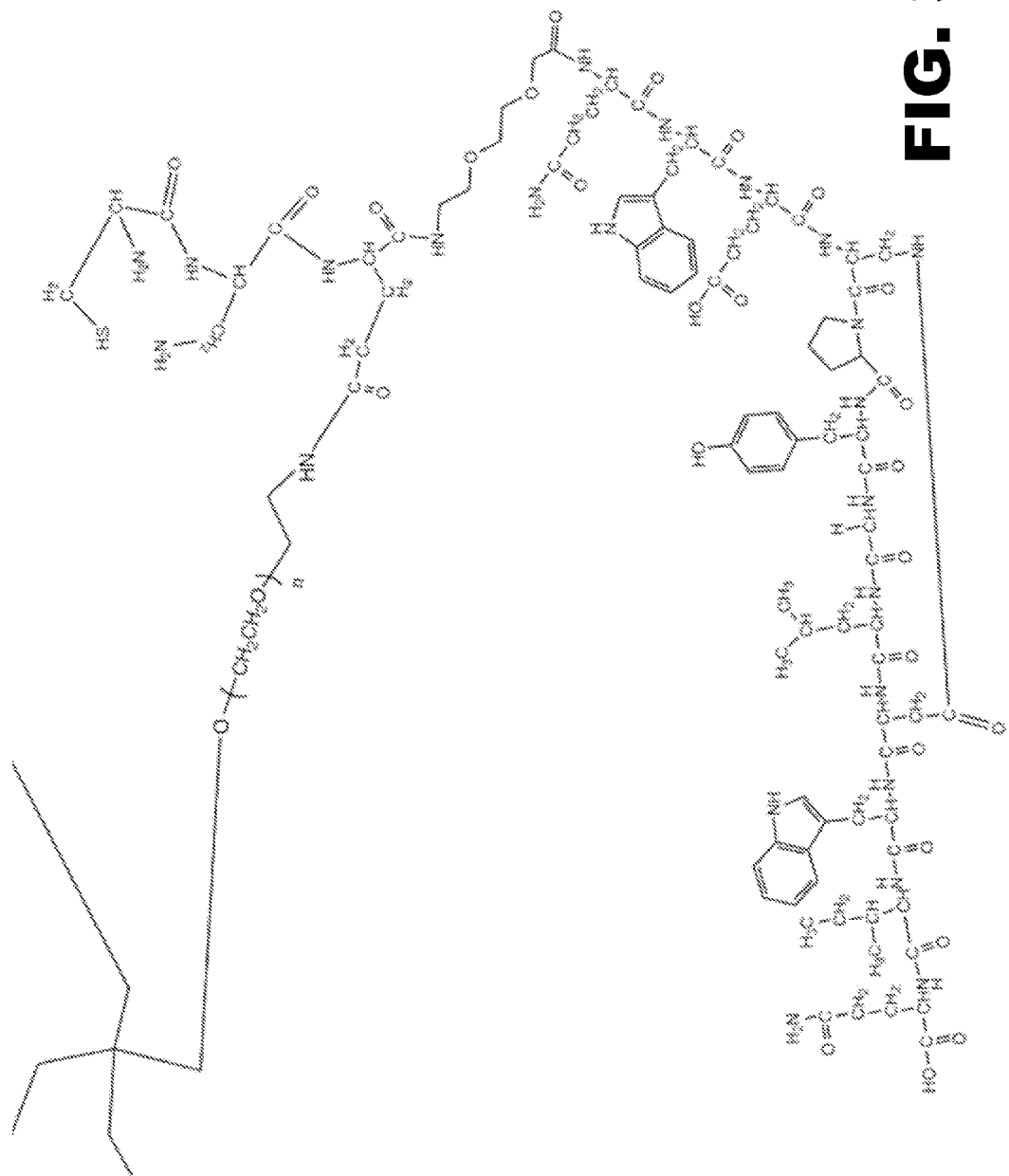
Figure 32A:
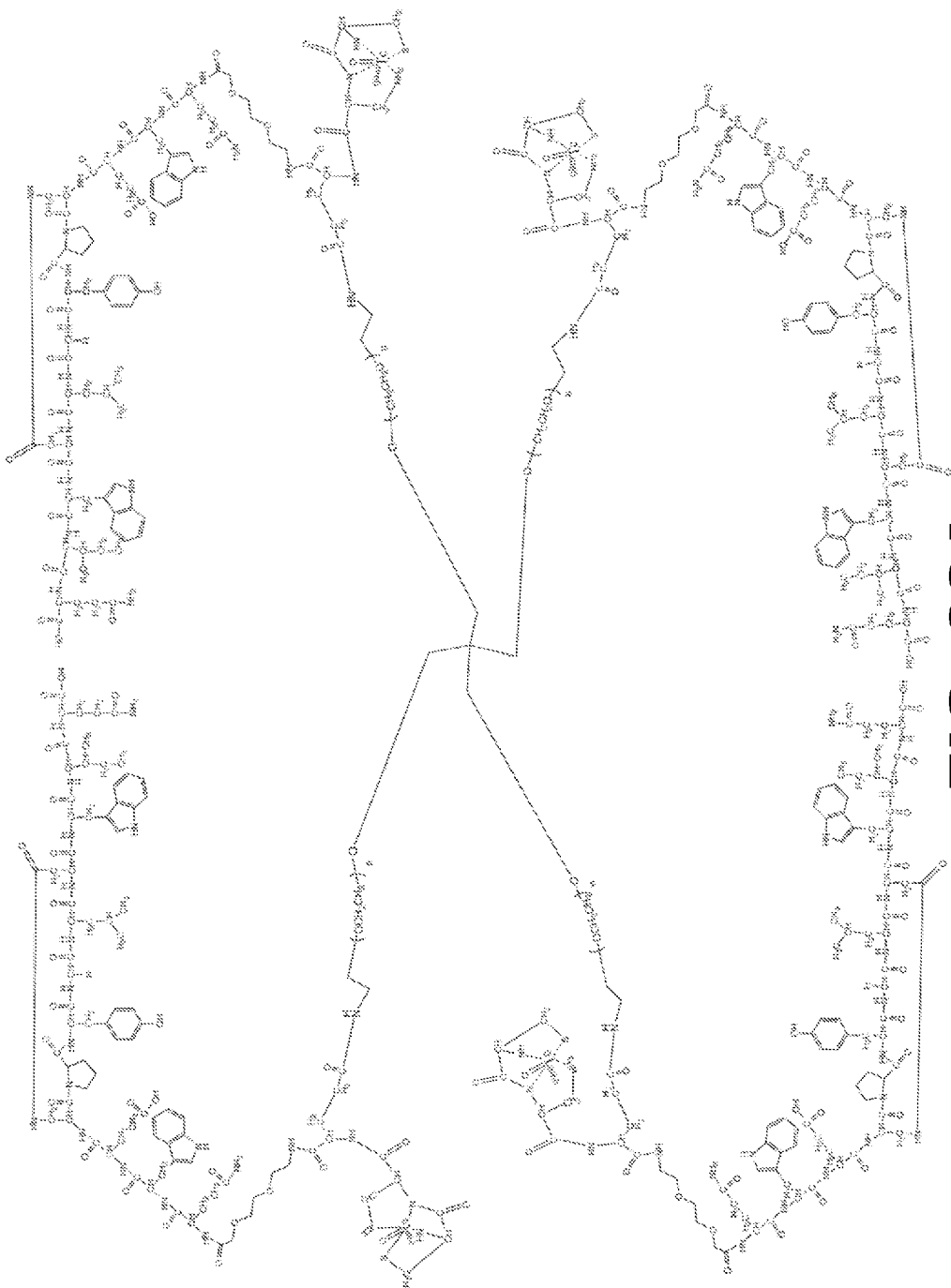
Figure 32B:
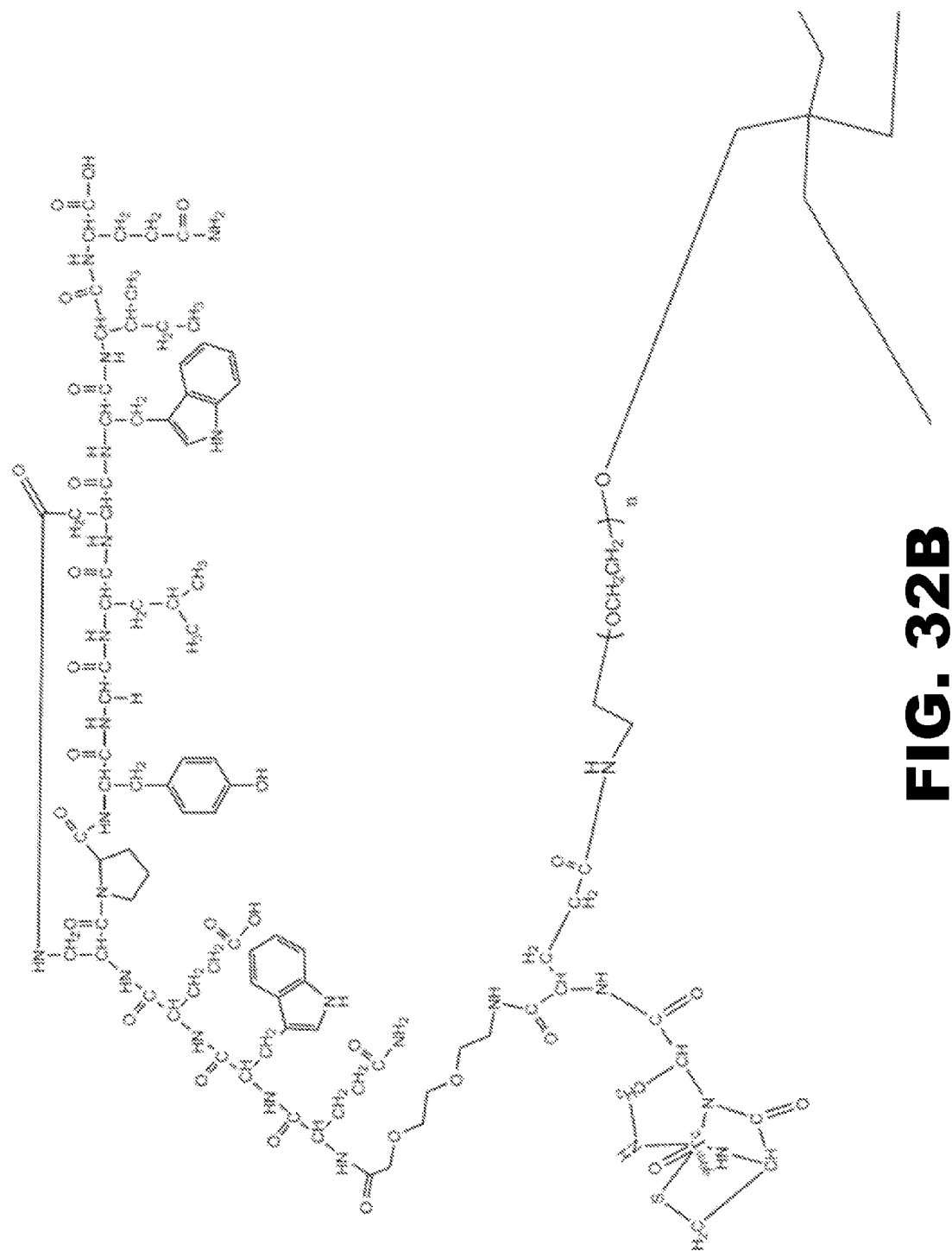
Figure 32C:
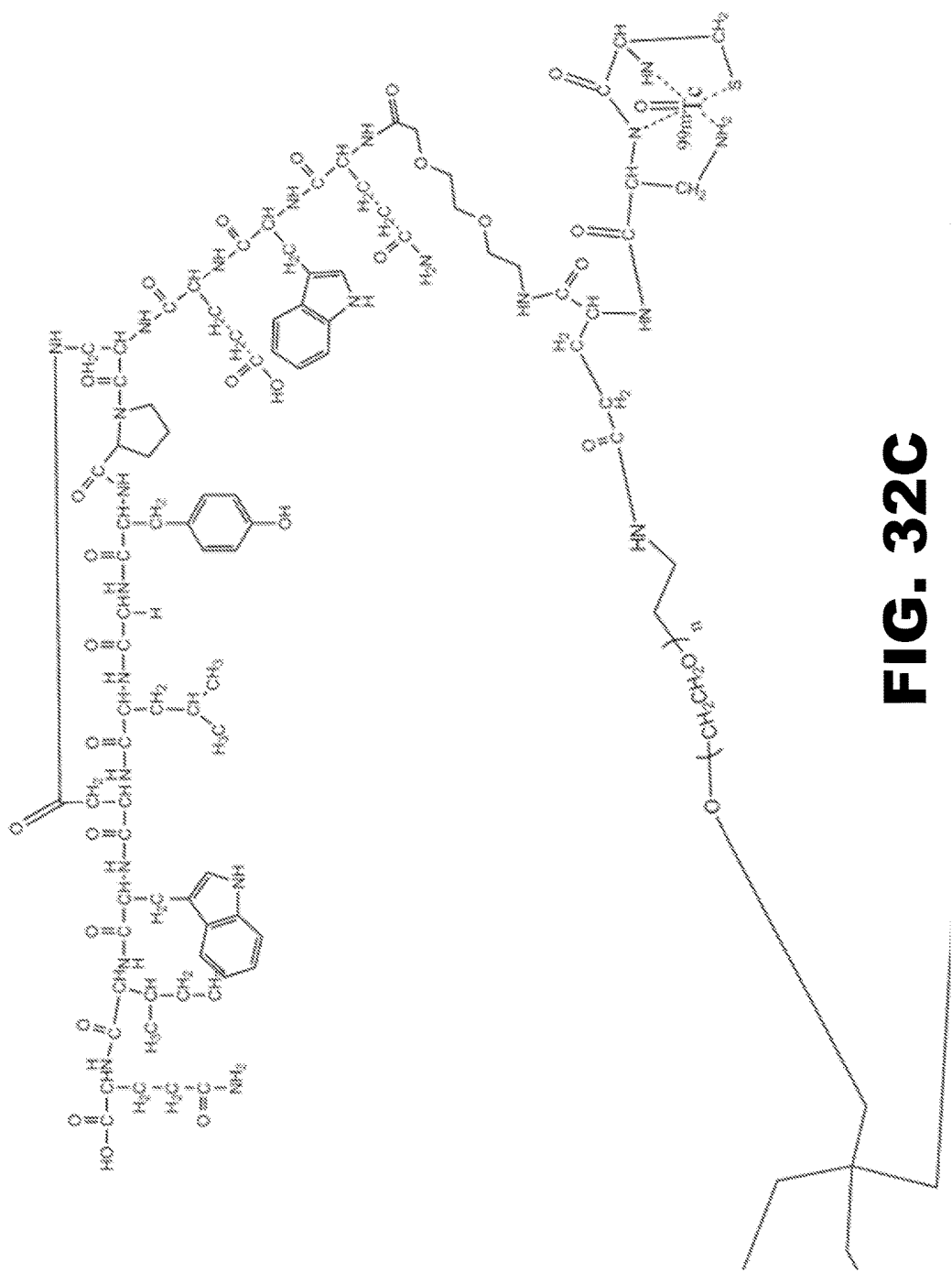
Figure 32D:
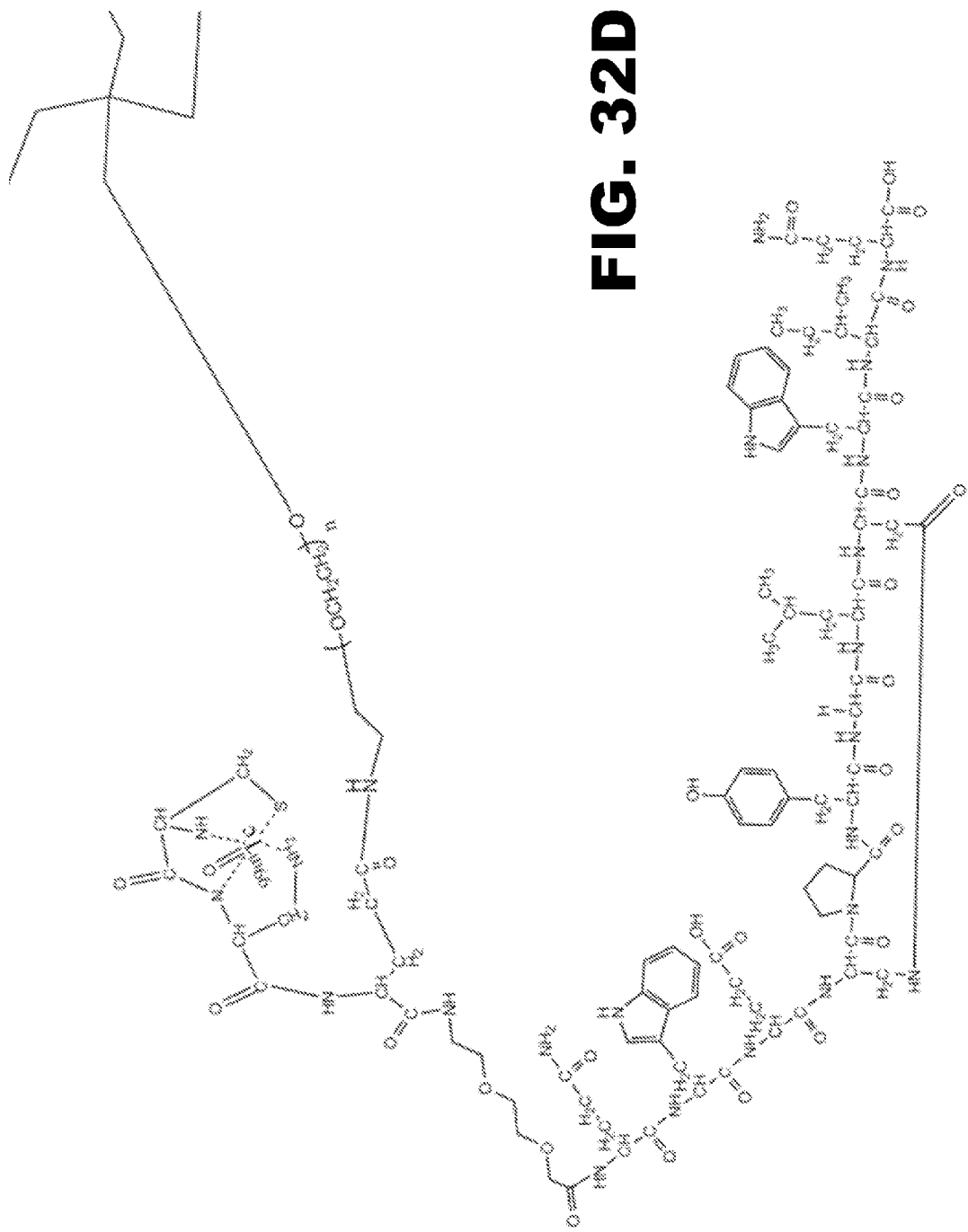
Figure 32E:
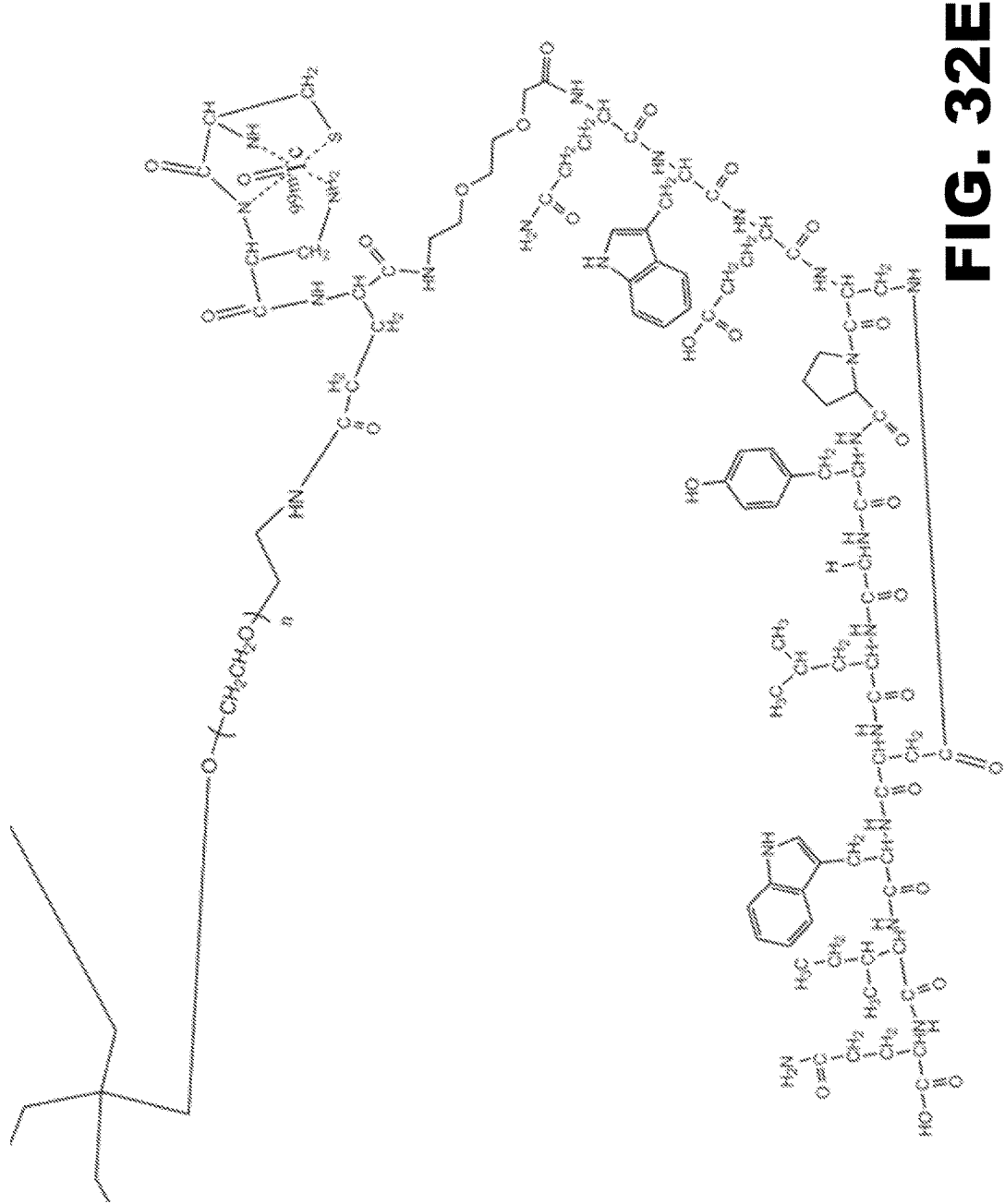
Figure 33A:
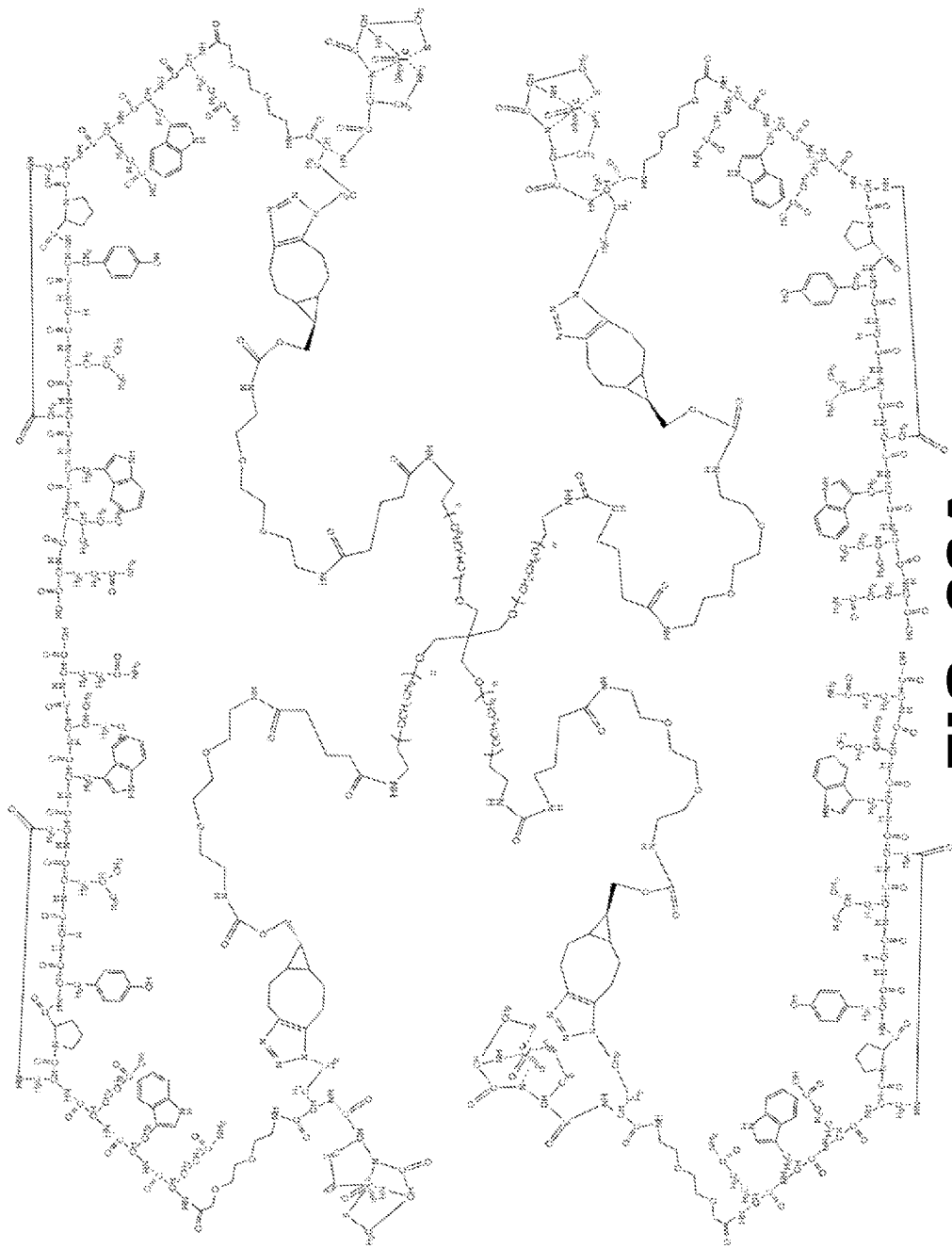
Figure 33B:
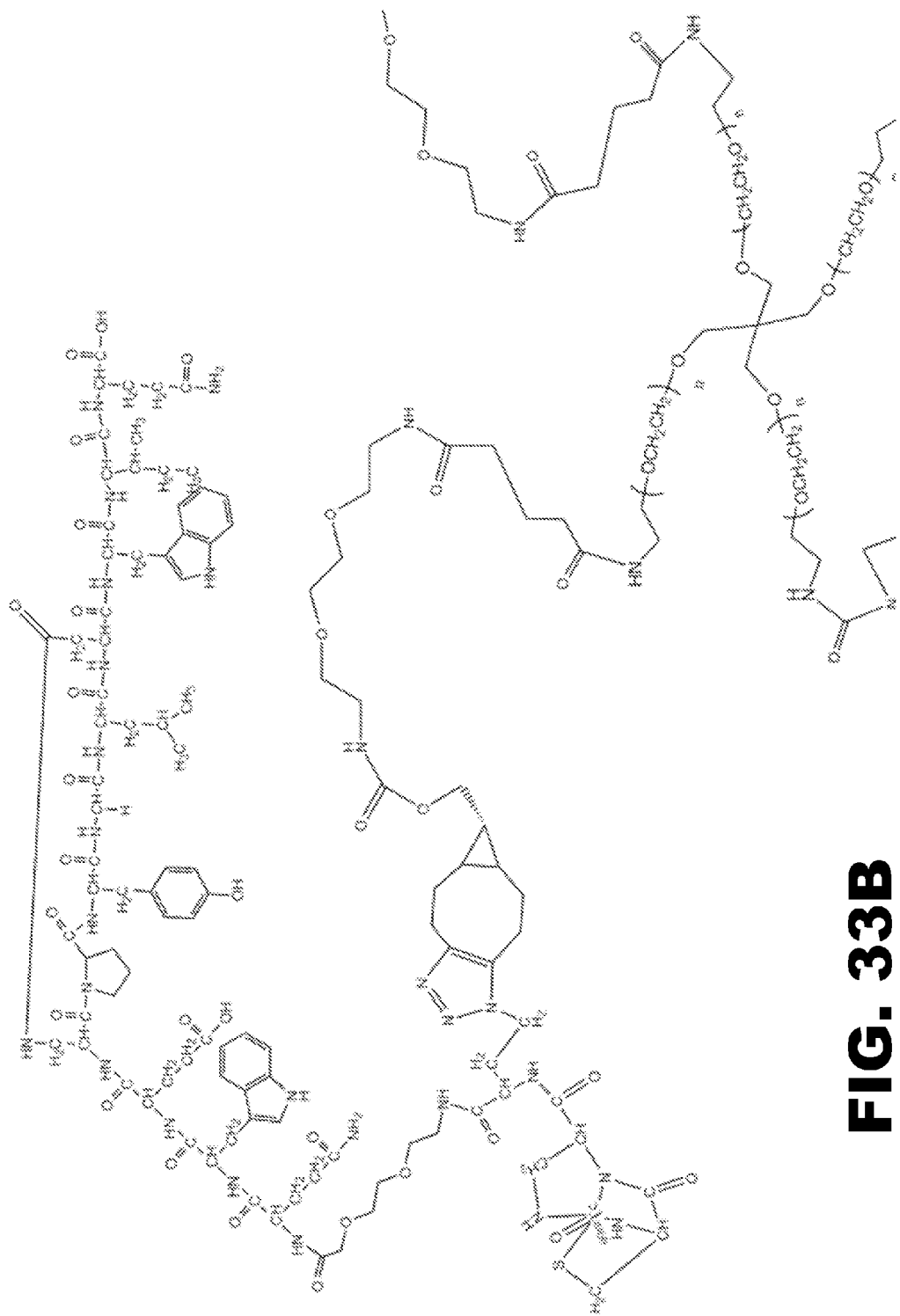
Figure 33C:
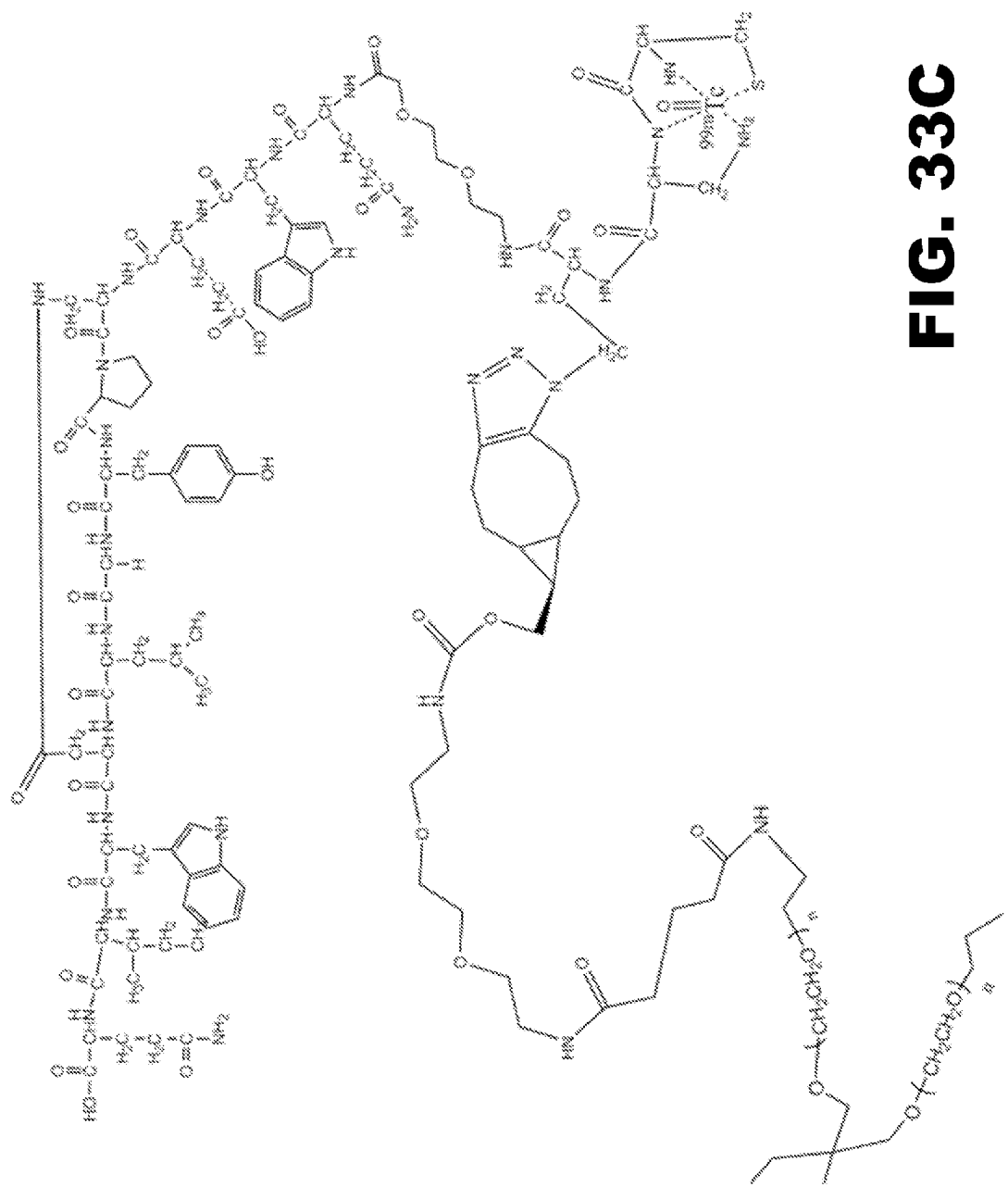
Figure 33D:
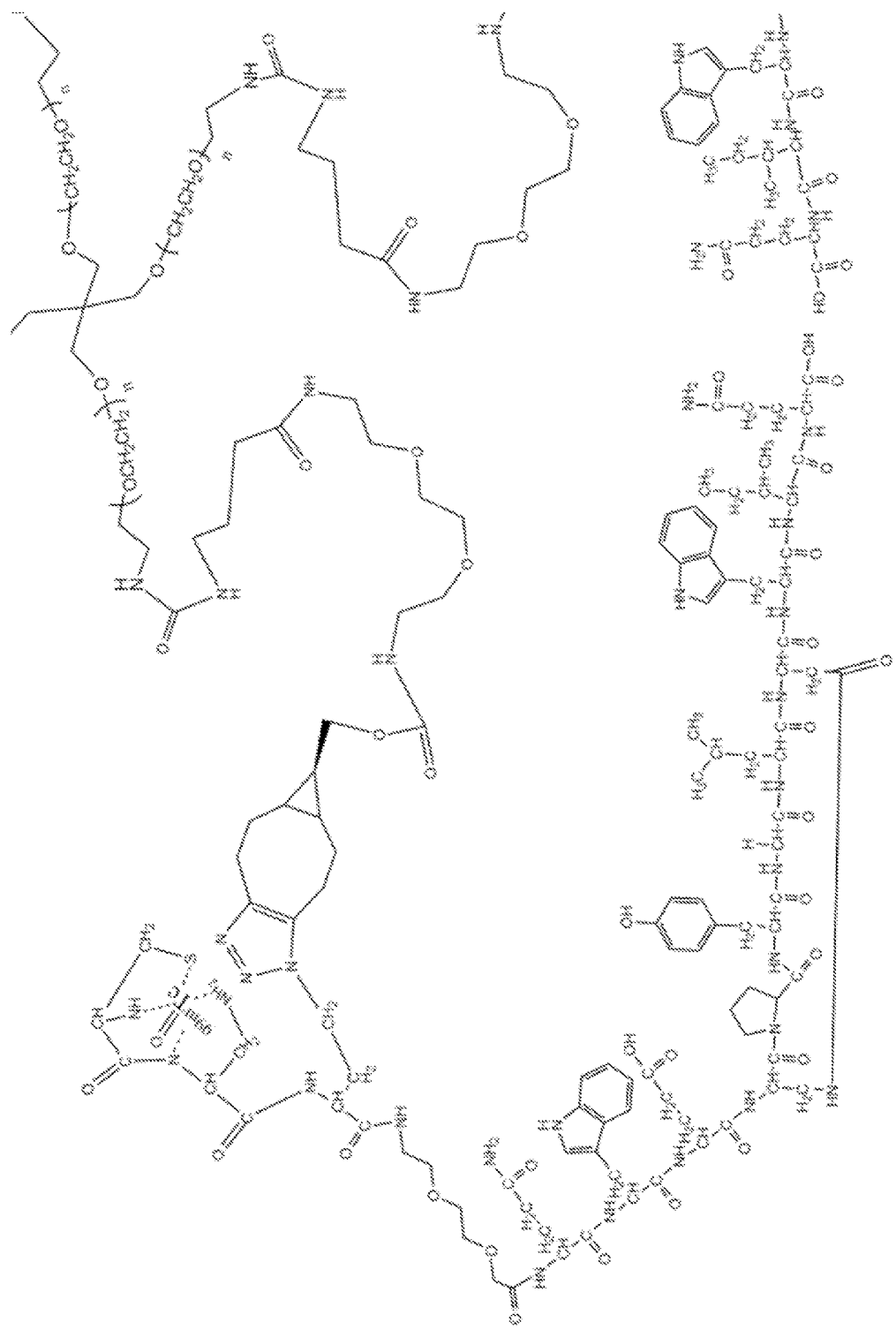
Figure 33E:
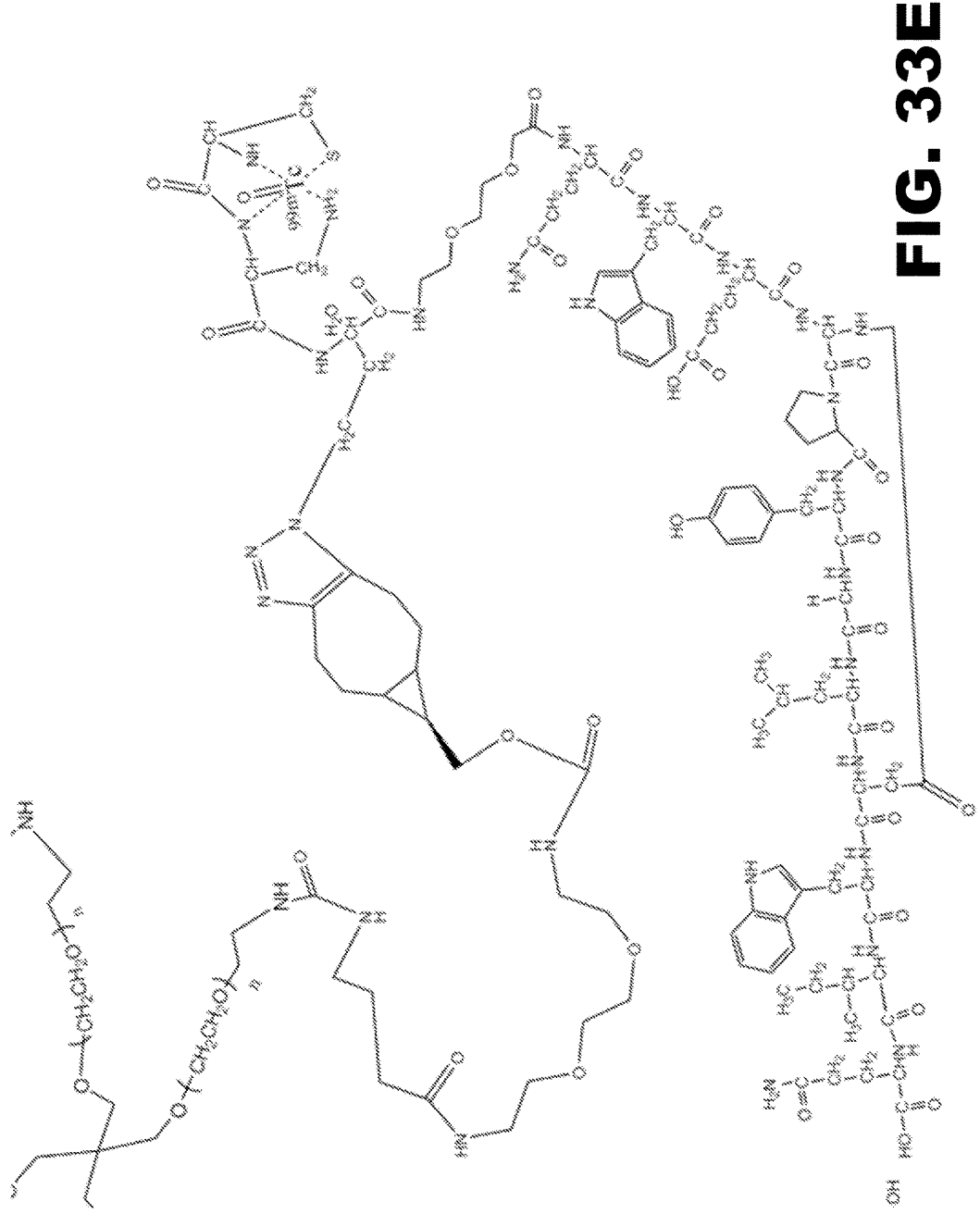
Figure 34A:
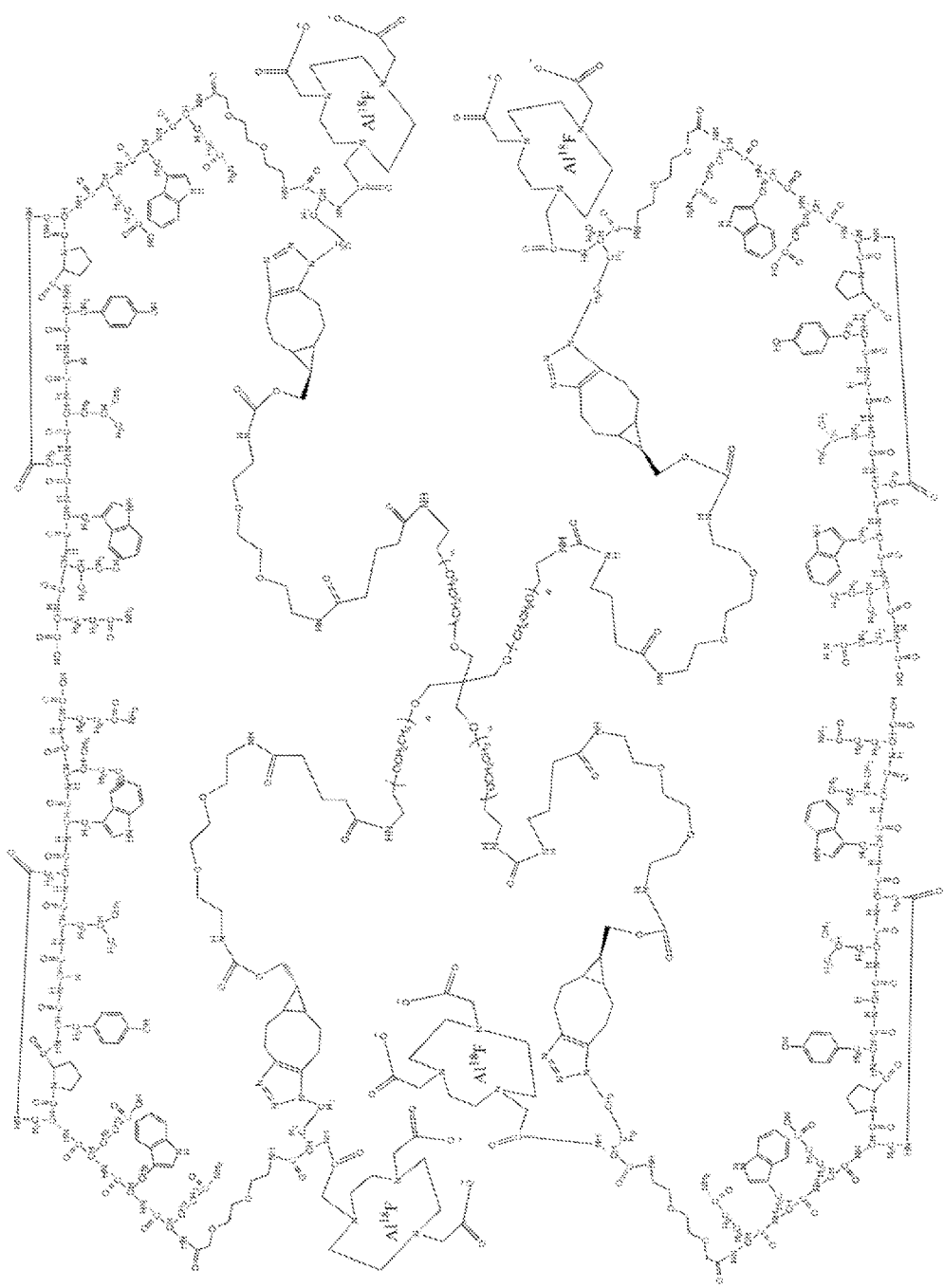
Figure 34B:
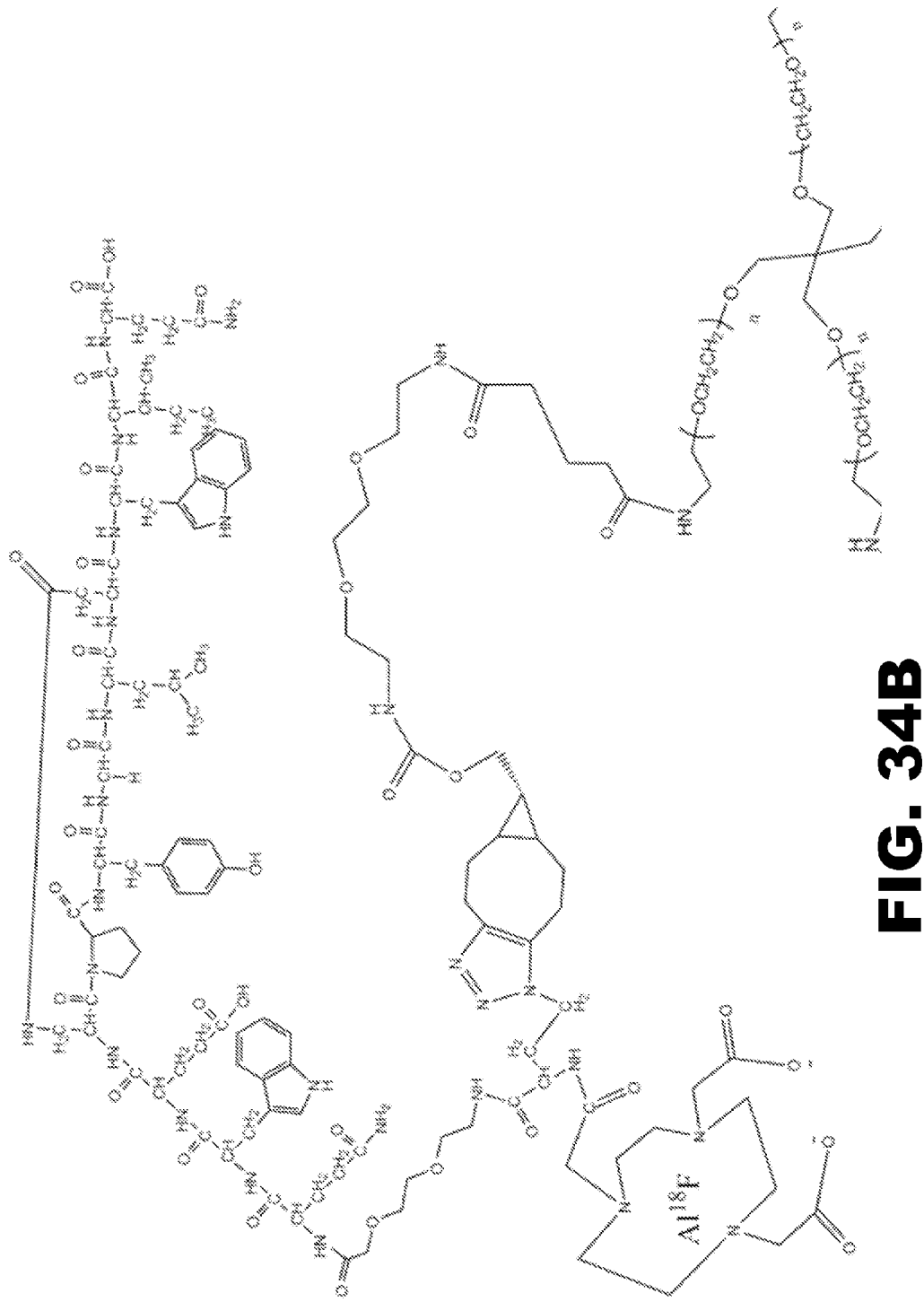
Figure 34C:
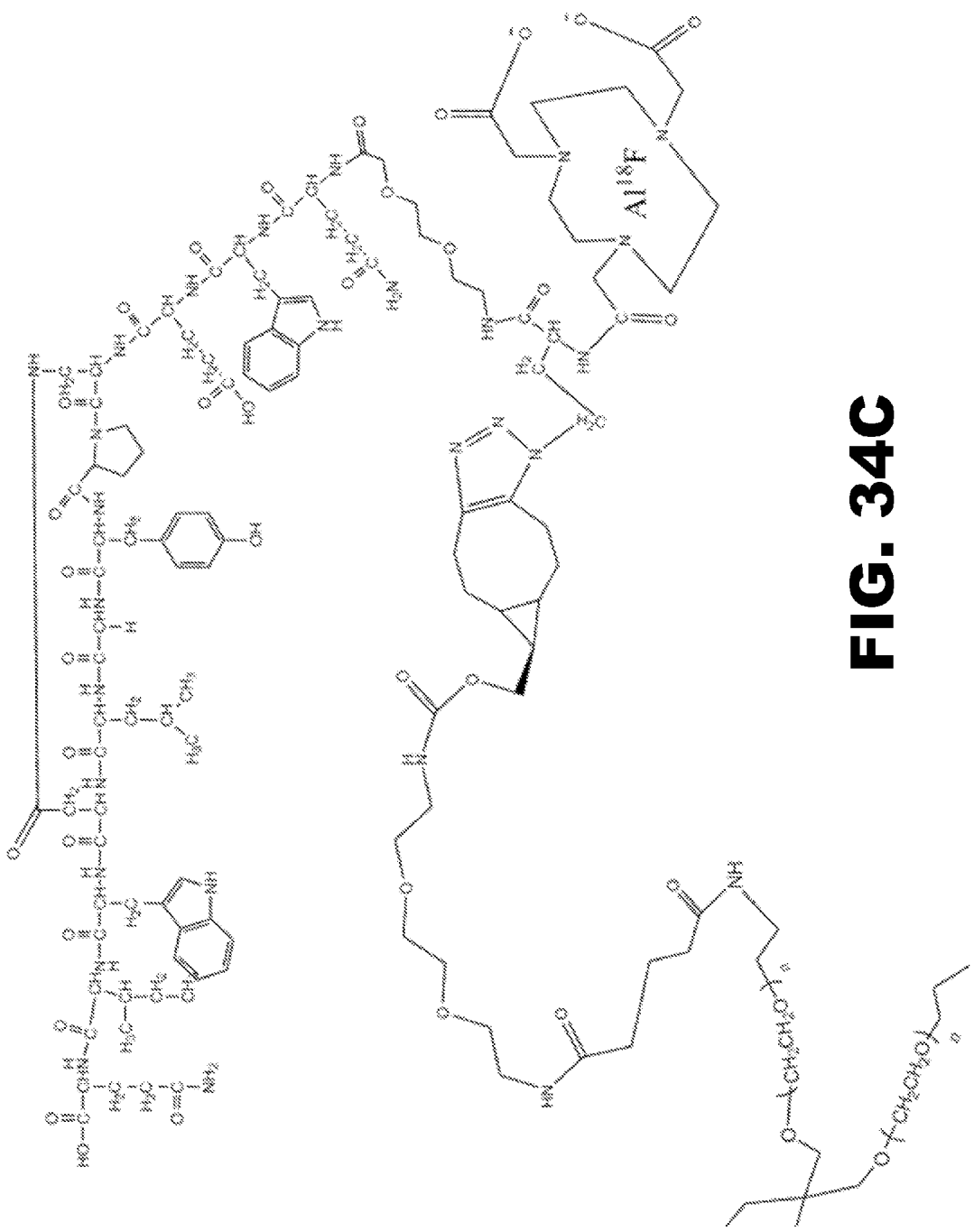
Figure 34D:
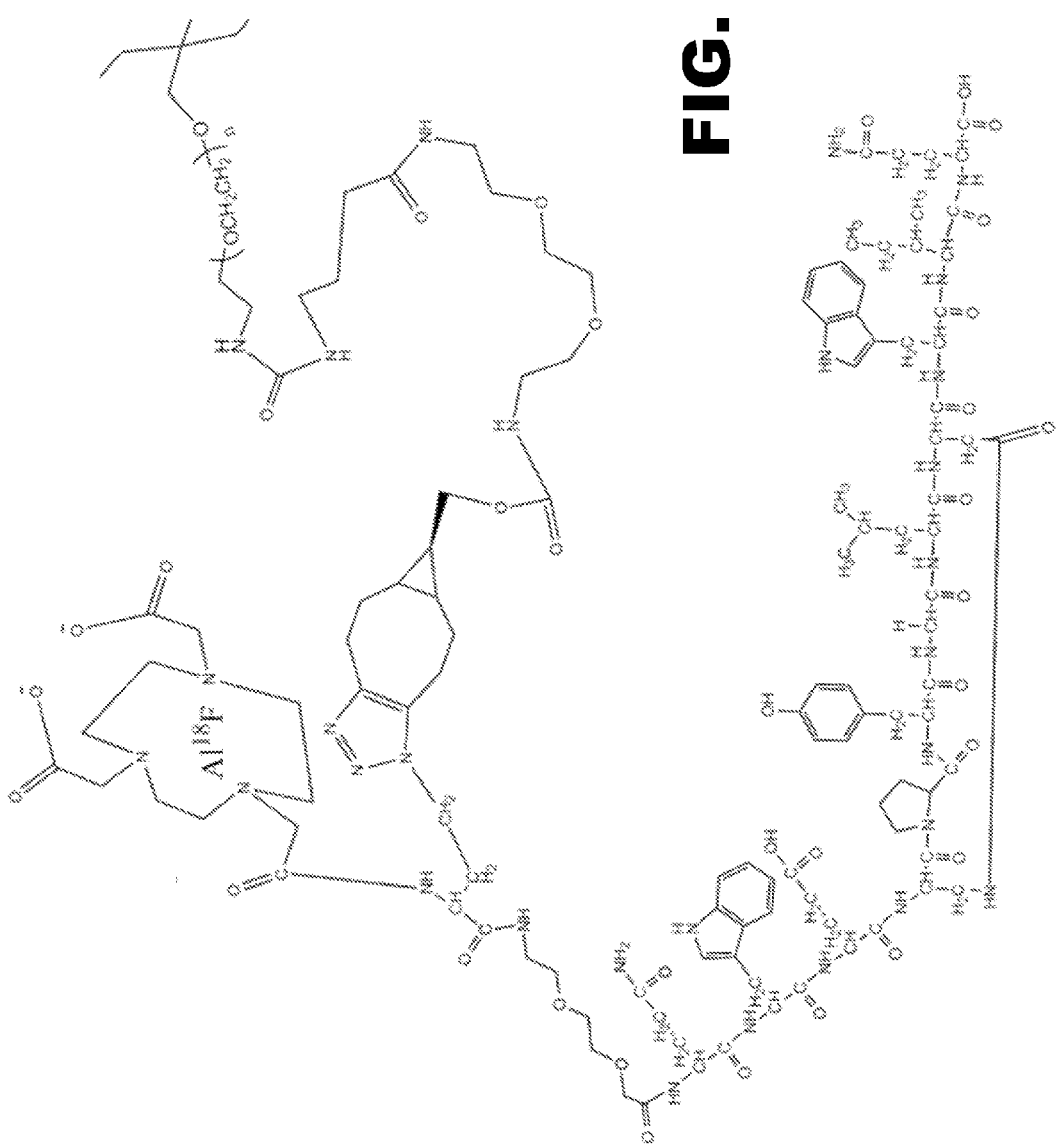
Figure 34E:
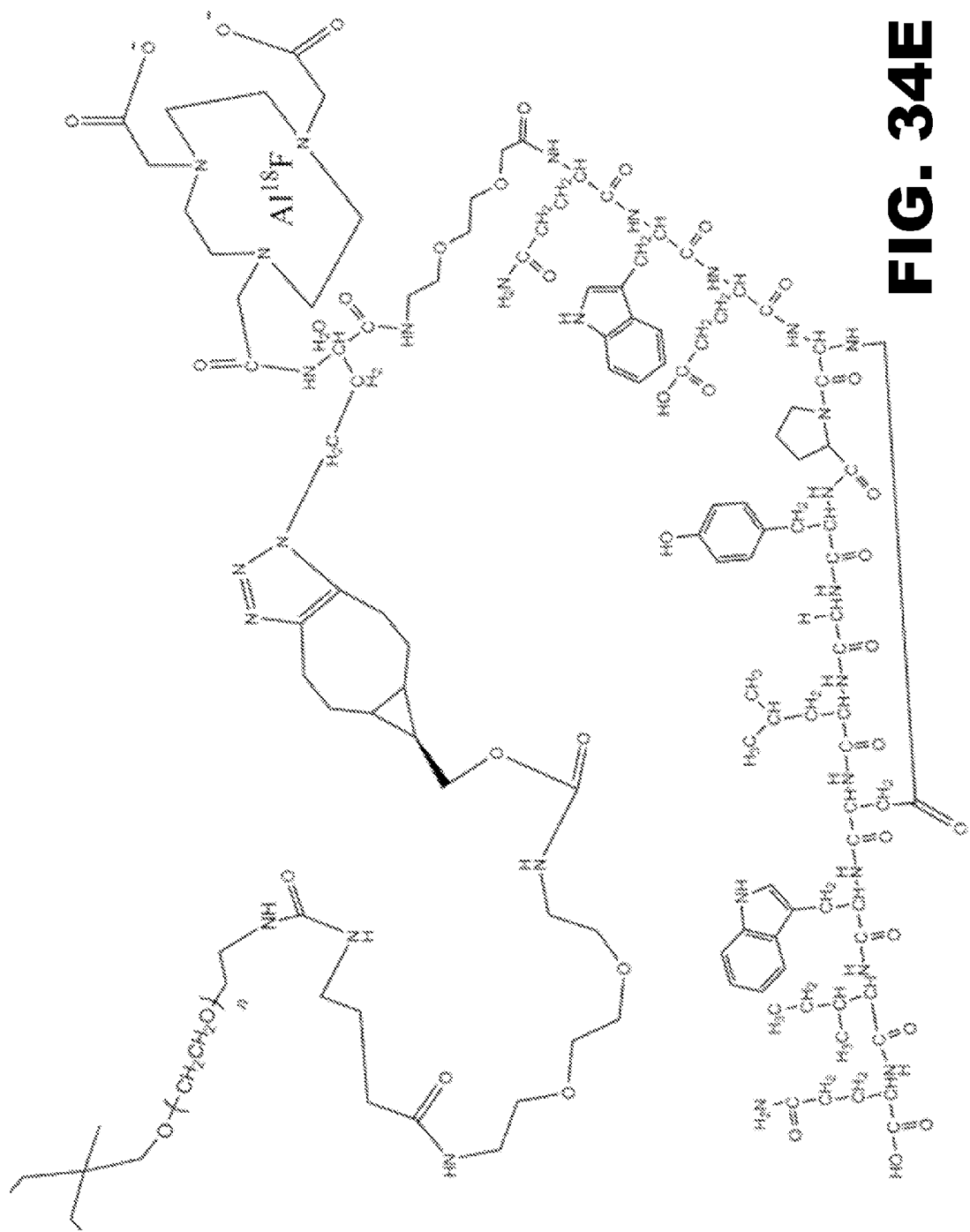
Figure 35A:
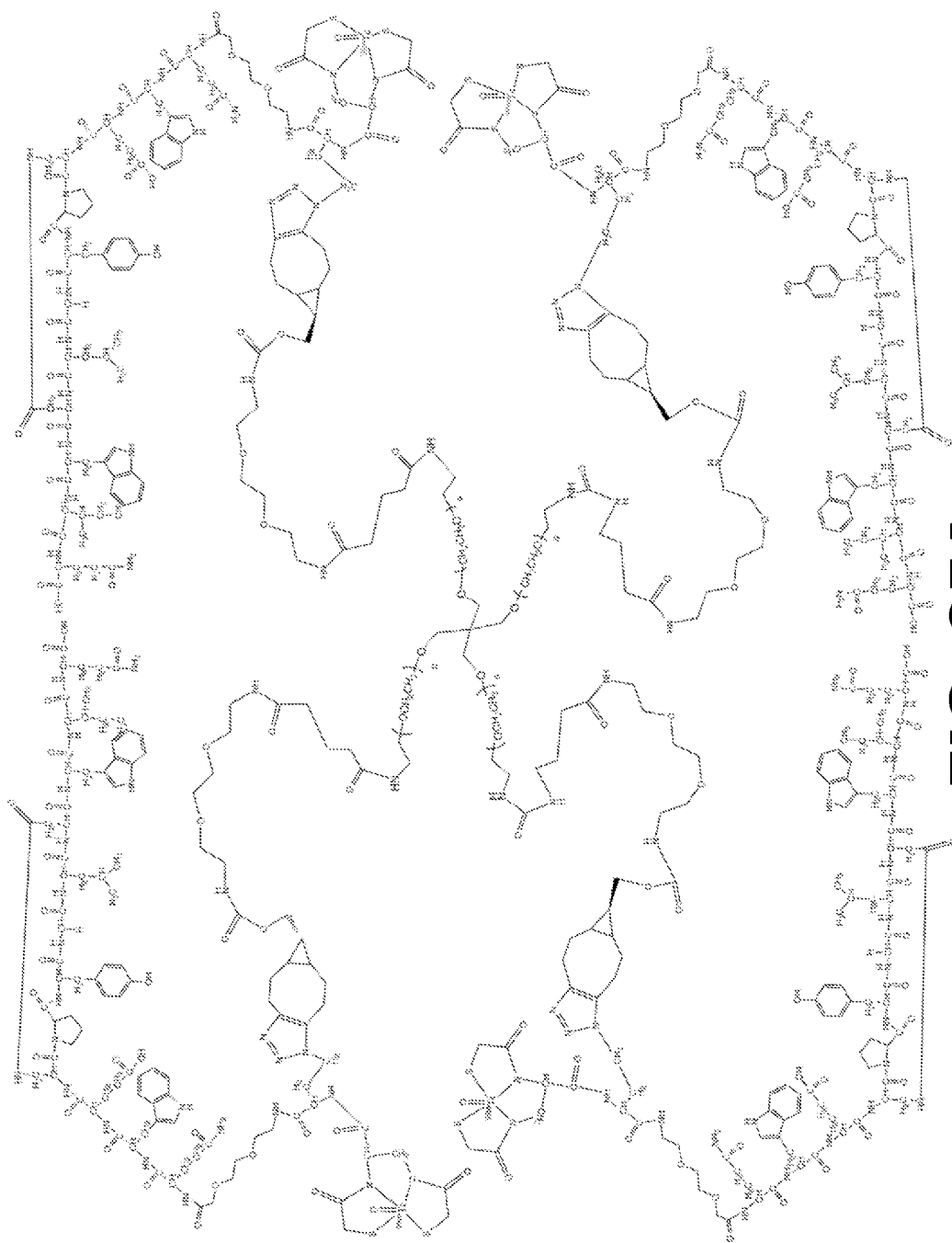
Figure 35B:
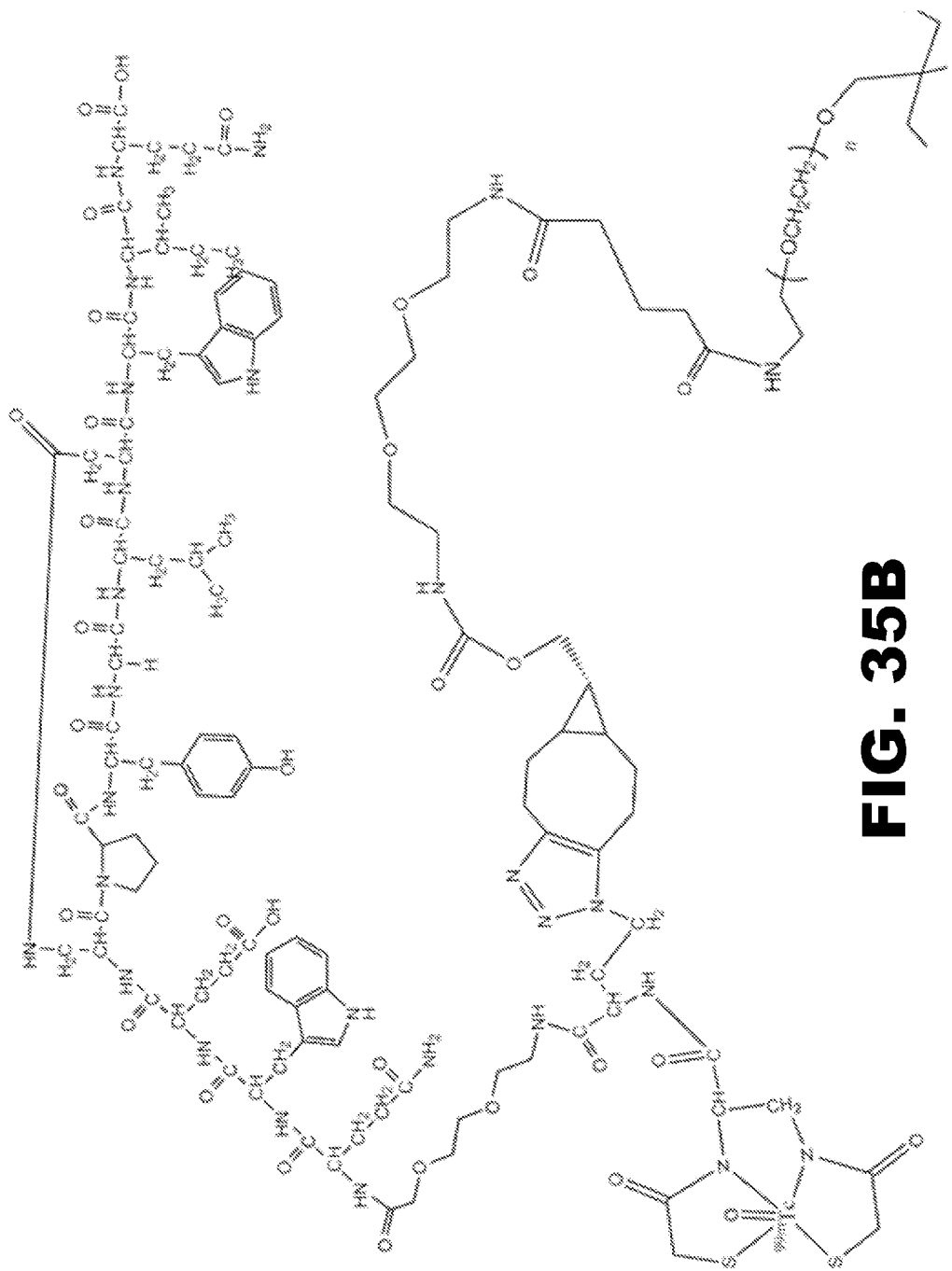
Figure 35C:
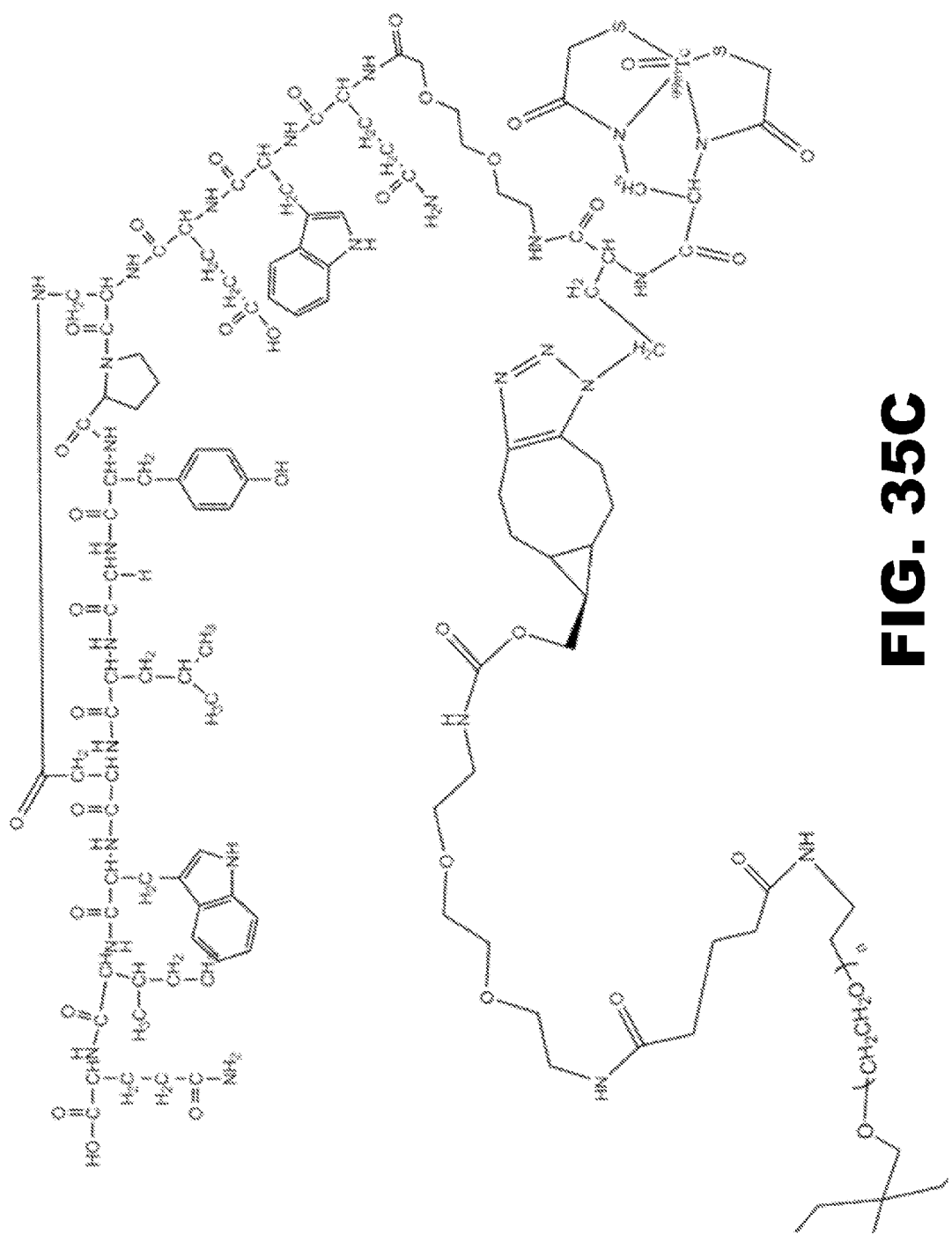
Figure 35D:
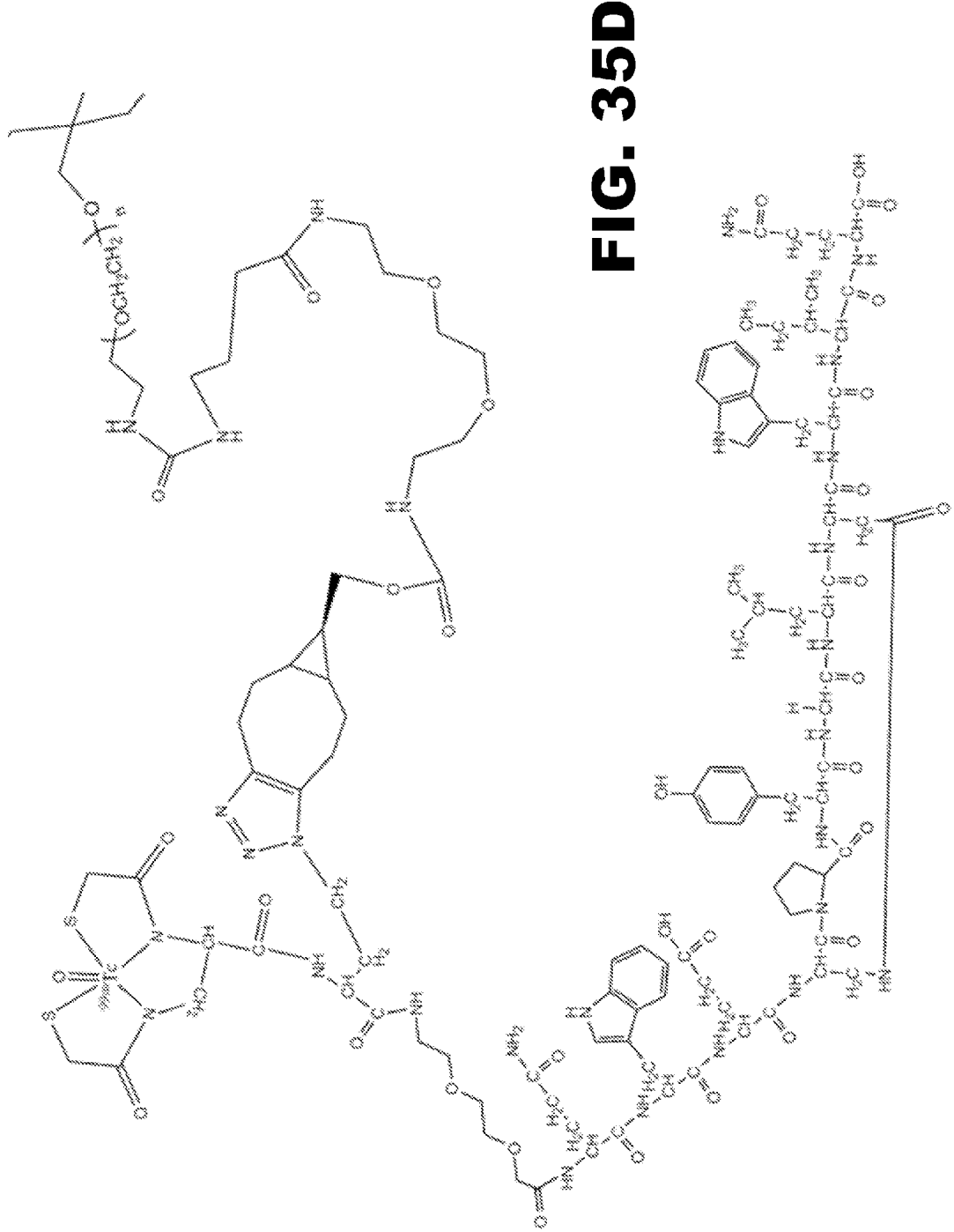
Figure 35E:
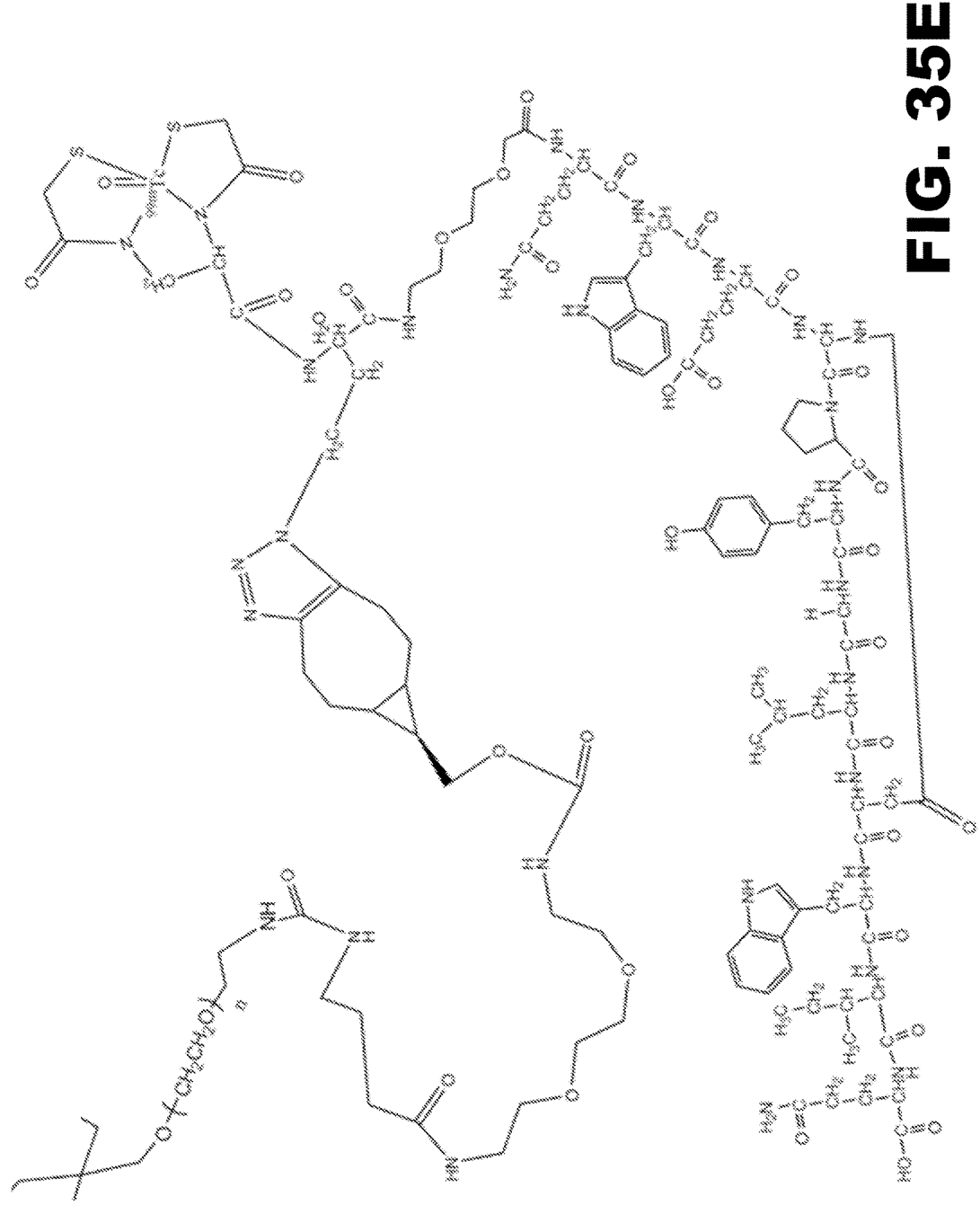

FIG. 22 depicts images showing examples of explanted LVAD pumps following exposure to $^{99m}$Tc-F4A and Nano-SPECT imaging. (A/B) Negligible binding of the probe in a control reference Heartmate 11 pump. (C/D) Minimal nano-SPECT signal found for small accretion of fibrin along the inlet stator surface. Additional signal was noted around the inlet collet but this may be residual blood artifact. (E/F) Significant thrombus accumulation originating on the stator and extending into the turbine mid-section of the pump consistent with clinically significant thrombus. Top row images are longitudinal images in line with blood flowing from the bottom to the top. The bottom images are transaxial views.

FIG. 23 depicts the structure of $^{99m}$Tc-F4A-NTA (A). $^{99m}$Tc-F4A-NTA is easily prepared in a rapid one-step radiosynthesis for in vitro and in vivo applications. This agent may be preferable for hospital and clinical applications due to ease of production in any radiopharmacy. (B,C,D,E) Depict each arm of the 4-arm tetrameric construct.

FIG. 24 depicts the structure of $^{18}$F-AlF-NOTA-F4A (A). Radiosynthesis of $^{18}$F-AlF-NOTA-F4A for in vitro and in vivo applications. This agent may be preferable for hospital and clinical applications involving tomographic imaging afforded by CT or MRI in conjunction with PET. (B,C,D,E) Depict each arm of the 4-arm tetrameric construct.

FIG. 25 depicts the structure of $^{68}$Ga-NOTA-F4A, a generator produced radioisotope for PET imaging A. (B,C,D,E) Depict each arm of the 4-arm tetrameric construct.

FIG. 26 depicts the structure of $^{64}$Cu-CB-TE2A-F4A for PET imaging (A). (B,C,D,E) Depict each arm of the 4-arm tetrameric construct.

FIG. 27 depicts the structure of Gd-DOTA-F4A for use with T1W MR imaging (A). (B,C,D,E) Depict each arm of the 4-arm tetrameric construct.

FIG. 28 depicts the structure of an optical labeled F4A for use for fluorescent or NIR imaging in vitro or in vivo (A). (B,C,D,E) Depict each arm of the 4-arm tetrameric construct.

FIG. 29 depicts the structure of $N_2S_2$-4 $PEG_{2000}$ armed modified fibrin peptide A. (B,C,D,E) Depict each arm of the 4-arm tetrameric construct.

FIG. 30 depicts the structure of $N_2S_2$-4 $PEG_{2000}$ armed modified fibrin peptide radiolabeled with $^{99m}$Tc A. (B,C,D,E) Depict each arm of the 4-arm tetrameric construct.

FIG. 31 depicts the structure of $N_3S$-4 $PEG_{2000}$ armed modified fibrin peptide A. (B,C,D,E) Depict each arm of the 4-arm tetrameric construct.

FIG. 32 depicts the structure of $N_3S$-4 $PEG_{2000}$ armed modified fibrin peptide radiolabeled with $^{99m}$Tc A. (B,C,D,E) Depict each arm of the 4-arm tetrameric construct.

FIG. 33 depicts the structure of $N_3S$-4 $PEG_{2000}$, BCN armed modified peptide radiolabeled with $^{99m}$Tc A. (B,C,D,E) Depict each arm of the 4-arm tetrameric construct.

FIG. 34 depicts the structure of NOTA-4 $PEG_{2000}$, BCN armed modified peptide radiolabeled with Al$^{18}$F A. (B,C,D,E) Depict each arm of the 4-arm tetrameric construct.

FIG. 35 depicts the structure of $N_2S_2$-4 $PEG_{2000}$, BCN armed modified peptide radiolabeled with $^{99m}$Tc A. (B,C,D,E) Depict each arm of the 4-arm tetrameric construct.

DETAILED DESCRIPTION OF THE INVENTION

The present disclosure describes homing agents comprising PEG-based multimers, such as PEG-based tetramers, linked to a diagnostic or therapeutic agent and including multiple peptide monomers or functionally analogous compounds, each of which is capable of binding to one and the same target molecule.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. Any chemical, enzymatic or staining reactions, or purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry including radiopharmaceutical chemistry described herein are also those well known and commonly used in the art. Standard techniques are used for chemical syntheses, chemical analyses, pharmaceutical preparation, formulation, delivery, diagnosis and treatment of all subjects, human and animal.

The term "subject" includes humans and other mammals that may receive diagnostic testing, or prophylactic or therapeutic treatment.

I. Peptide Constructs and Homing Agents

The present disclosure provides certain homing agents such as a peptide construct including multi-armed peptide multimers capable of specifically binding a target molecule, and labeled with a diagnostic or therapeutic agent. Alternative classes of homing molecules include peptide mimics, organic compounds, nuclear-based compounds or analogues thereof, carbohydrate based or modified compounds, and other classes of targeting binders with adequate homing specificity and binding affinity to be useful. Suitable diagnostic agents include imaging agents such as nuclear imaging agents (radionuclides or paramagnetic/superparamagnetic metals) and optical imaging agents (NIR or visible light fluorophores and dyes). The homing agents in the present disclosure can be produced using standard synthetic procedures, have minimal off target serum interactions, and clear rapidly from circulating blood predominantly through the renal elimination pathway.

A homing agent as described herein may comprise a p-armed peptide construct comprising n PEG monomers. The n monomers are covalently bound together to form a p-armed PEG multimer, wherein p is at least 3. The peptide construct further comprises p linkers, and p homing molecules, wherein each homing molecule is linked to an arm of the PEG multimer by one of the linkers. Each homing molecule is capable of selectively binding a target molecule. The peptide construct further comprises a diagnostic or therapeutic agent linked to an N-terminus of at least one of the homing molecules.

A homing molecule may be a peptide, a peptidomimetic, or any small molecule with specific binding capability with respect to a target molecule. A suitable small molecule of the invention may be a molecule that binds a target molecule. The benefits of avidity, decreased plasma protein, improved $P_K$, etc apply to all such small molecules. Non-limiting examples of suitable small molecules may include agents selected from the group consisting of an aptamer, an antibody, an antibody fragment, a double-stranded DNA sequence, modified nucleic acids, nucleic acid mimics (e.g. LNA or PNA), a ligand, a ligand fragment, a receptor, a receptor fragment, a polypeptide, a peptide, a coenzyme, a coregulator, an allosteric molecule, and an ion. Most peptides have 2 to 3 orders of magnitude lower binding affinity versus antibodies, which are by definition bivalent (for IgG) and 10-binding sites for IgM class. In comparison to the use of monoclonal antibodies as homing molecules, peptides are easier to make, and their smaller size renders them more likely to clear more rapidly from circulation. Peptides are also less likely to cause an immunologic response. In a preferred embodiment, the homing molecule is a peptide. In another preferred embodiment, the homing molecule is a peptide that binds ICAM. In an exemplary embodiment, the homing molecule is a peptide that binds fibrin. In yet another exemplary embodiment, the homing molecule is a peptide that binds fibrin, wherein the amino acid sequence of the peptide is QWECPYGLCWIQ (SEQ ID NO: 1).

A homing molecule is capable of binding a target molecule. It will be understood that the target molecule may vary, and that the homing molecule, which selectively binds a target molecule is not limited to the fibrin-binding peptide shown in FIG. 1. For example, the target molecule may be a biomarker for which a selectively binding peptide or other small molecule is known or can be generated, i.e., a peptide monomer, which exhibits target specificity and a binding constant adequate for in vivo diagnostic and therapeutic use. In an embodiment, a target molecule may be a vascularly accessible cell surface biomarker, biosignature, receptor, or carbohydrate. A target molecule may be transiently or constitutively inherent to the cell or transfected into a cell. A target molecule may be a biomarker of, but not limited to, thrombotic disease, inflammatory disease, cancer, cardiovascular disease, infectious disease, pulmonary disease, neurologic disease, renal disease, urogenital disease, or a regenerative tissue derived through cell therapy or synthesized ex vivo and subsequently implanted. Synthetic target molecules may be incorporated into homing agents, which could be used to both quantify delivery or retention efficacy in terms of amount and location. This is particularly true for cardiovascular tissues or for measuring the host response to these manipulations, such as increased rejection (inflammation) or increased angiogenesis for cell implant success with proliferation. Vascularly accessible biomarkers which may serve as a target molecule for a specifically binding homing molecule include but are not limited to biomarkers of inflammation, such as ICAM, VCAM, or a selectin; biomarkers of infection including viral, bacterial, protozoan, and fungal infection; biomarkers of angiogenesis such as an integrin, robo-4, and VEGF; biomarkers of cancer such as VLA-4, and other integrins; biomarkers of cardiovascular disease such as fibrinogen, CD40 ligand, myoglobin, ICAM, or VCAM; and biomarkers of thrombosis such as fibrin, P-selectin, D-dimer, factor VIII, thrombin, tissue factor, and c-reactive protein. A target molecule may be a cellular marker on cells of the bone marrow or microstructure of the bone marrow, such as VLA-4 for multiple myeloma and other markers associated with leukemia. Further, a target molecule may be a marker of hematologic cancer and solid tumors metastasized to the bone marrow. Bone marrow may be highly permeable to homing agents of the invention. In an embodiment, the target molecule is a biomarker of thrombosis. In an exemplary embodiment, the target molecule is fibrin. In another exemplary embodiment, the target molecule is ICAM.

Additionally, the target molecule may be a biomarker specific for neovascular sprouts, tubules, and/or microvessels. The target molecule may be a biomarker specific for integrins, VCAM, selectins, a cell adhesion receptor or a biomarker of inflammation. Non-limiting examples of biomarkers of a disease or disorder which may be a target of a homing molecule according to the present disclosure include: Integrin alpha 1/CD49a, Integrin alpha L/CD11a, Integrin alpha 1 beta 1, Integrin alpha L beta 2, Integrin alpha 11 beta 1, Integrin alpha M/CD11b, Integrin alpha 2/CD49b, Integrin alpha M beta 2, Integrin alpha 2 beta 1, Integrin alpha V/CD51, Integrin alpha 2b/CD41, Integrin alpha V beta 1, Integrin alpha 2b beta 3, Integrin alpha V beta 3, Integrin alpha 3/CD49c, Integrin alpha V beta 5, Integrin alpha 3 beta 1/VLA-3 Integrin-associated Molecules, Integrin alpha V beta 6, Integrin alpha 4/CD49d, Integrin alpha V beta 8, Integrin alpha 4 beta 1, Integrin alpha X/CD11c, Integrin alpha 4 beta 7/LPAM-1, Integrin alpha X beta 2, Integrin alpha 5/CD49e, Integrin alpha 10 beta 1, Integrin alpha 5 beta 1, Integrin alpha 11, Integrin alpha 6/CD49f, Integrin beta 1/CD29, Integrin alpha 6 beta 1, Integrin beta 2/CD18, Integrin alpha 6 beta 4, Integrin beta 3/CD61, Integrin alpha 7, Integrin beta 4/CD104, Integrin alpha 7 beta 1, Integrin beta 5, Integrin alpha 8, Integrin beta 6, Integrin alpha 9, Integrin beta 7, Integrin alpha 9 beta 1, Integrin beta 8, Integrin alpha E/CD103, Integrin Receptor Inhibitors, Integrin alpha E beta 7, alpha-Parvin, Nidogen-2, beta IG-H3, NIF, Cadherin-6/KCAD, Osteopontin/OPN, CD47, Paxillin, CD63, PINCH1, CD151, RAGE, CIB1, RIAM/APBB1IP, Cytohesin-1, Talin1, DMP-1, Talin2, EDIL3, Tenascin X, EGF-L6, TIN-Ag, EMP2, TM4SF4, FERMT3, TSPAN1, HGF, TSPAN2, IBSP/Sialoprotein II, TSPAN6, ICAP-1, TSPAN7, IGSF8/CD316, TSPAN8, ILK, TSPAN9, Melusin, TSPAN10, MEPE/OF45, TSPAN12, MFG-E8, TSPAN15, MIG2, TSPAN19, NEDD9/CASL, TSPAN3, Nidogen-1/Entactin, ALCAM/CD166, JAM-C, AMICA/JAML, JAM-4/IGSF5, ASAM, Kilon/NEGR1, BCAM, Kirrel1/NEPH1, BOC, Kirrel2/NEPH3, CD31/PECAM-1, Kirrel3/NEPH2, CDO, L1CAM, CEACAM-1/CD66a, LAMP, CEACAM-3/CD66d, MAdCAM-1, CEACAM-4, MCAM/CD146, CEACAM-5/CD66e, MDGA1, CEACAM-6/CD66c, MDGA2, CEACAM-7, MFG-E8, CEACAM-8/CD66b, NCAM-1/CD56, CHL-1/L1CAM-2, Nephrin, CLP24, Neurofascin, DSCAM, Ninjurin-1, DSCAM-L1, Ninjurin-2, EpCAM/TROP1, NrCAM, ESAM, OBCAM/OPCML, HepaCAM, OCAM/NCAM2, ICAM-1/CD54, PEAR1, ICAM-2/CD102, SALM2/LRFN1, ICAM-3/CD50, SALM3/LRFN4, ICAM-4, SALM4/LRFN3, ICAM-5, SIRP alpha/CD172a, IGSF4A/SynCAM1, TCAM-1, IGSF4B/SynCAM3, Thrombospondin-1, IGSF4C/SynCAM4, TROP-2, IGSF4D/SynCAM2, UBE2S, ISLR-2, VCAM-1/CD106, JAM-A, VSIG3, and JAM-B/VE-JAM.

According to the invention, each homing molecule is linked to an arm of the PEG multimer by a linker. As used herein a "linker" refers to a molecule or molecules that connects two separate entities to each other. Linkers may provide for optimal spacing of the two entities. The linker may vary but usually includes at least two functional groups such that the linker molecule is disposed between a homing molecule and another element such as a PEG moiety and/or a diagnostic agent such as an imaging agent and/or a therapeutic agent. A linker may be a bifunctional chemical linker, or a polymer of bifunctional chemical linkers. A linker may be a heterobifunctional linker or a homobifunctional linker. In an embodiment, a linker may be a peptide linker. A "peptide linker" includes at least two amino acid residues. Usually the peptide linker includes at least 2, 3, 4, 5, 6, 7, 8, 9 or 10 amino acid residues. For example 10 amino acid residues or less, preferably 7 amino acid residues or less, and more preferably 2 to 4 amino acid residues. In an exemplary embodiment, the peptide linker includes 3 amino acid residues. In another exemplary embodiment, the peptide linker is HHE.

A peptide linker may further include a hydrophilic moiety bound to the peptide, for example to the N-terminal amino acid. In such an embodiment, the N-terminus of the homing molecule is attached to the C-terminus of the peptide linker using a hydrophilic moiety. The hydrophilic moiety may be selected from, but not limited to, polyethylene glycol, a plasma protein, or polyethylene oxide. In an exemplary embodiment, the peptide linker further comprises a hydrophilic moiety such as polyethylene oxide.

In an alternative embodiment, a peptide linker may be substituted with a chelator. Examples of chelating agents include, but are not limited to, nitrilotriacetic acid (NTA), ininocarboxylic and polyaminopolycarboxylic reactive groups, diethylenetriaminepentaacetic acid (DTPA), 1,4,7,10-tetraazacyclododecane-1,4,7,10-tetraacetic acid (DOTA), 1,4,7-triazacyclononane-N,N',N"-triacetic acid (NOTA), and 1,4,8,11-Tetraazabicyclo[6.6.2]hexadecane-4,11-diacetic acid (TE2A). Additionally, NNNS or NNSS chelating motif may be used. NNNS or NNSS chelating motifs require amide based peptide cyclization and may be used with $^{99m}$Tc. The chelating agent can be coupled via its amino acid side chain directly to the homing molecule. Alternatively, an intervening amino acid sequence or hydrophilic moiety can be used to couple the homing molecule to the chelating agent. Exemplary chelators include NTA, DOTA, NOTA, and TE2A.

According to the invention, a p-armed peptide construct comprises n PEG monomers covalently bound together to from a p-armed PEG multimer. As used interchangeably herein, the terms "polyethylene glycol" and "PEG", refer to mixtures of condensation polymers of ethylene oxide and water, in a branched or straight chain, represented by the general formula —(O—CH$_2$—CH$_2$)$_n$—, wherein n is at least 2. For example, when PEG is about 10,000 Da, n=60 and when PEG is about 2,000 Da, n=9. The molecular weight of a PEG arm as described herein may be about 10,000 Da or less, or preferably about 5000 Da or less, or more preferably about 2500 Da or less. In an exemplary embodiment, the molecular weight of a PEG arm is about 2000 Da.

According to the invention, the homing agent comprises at least one diagnostic or therapeutic agent linked to an N-terminus of at least one homing molecule. A diagnostic agent or therapeutic agent may for example be an imaging agent, including a nuclear imaging agent or an optical imaging agent. A nuclear imaging agent may be a radionuclide or metal atom. An optical imaging agent may be a fluorophore or dye, such as for example a dye capable of emitting NIR and/or fluorescent wavelengths. As used herein, an "imaging agent" is an agent having an emission profile useful for imaging and/or therapy. Suitable imaging modalities may include, but not limited to, magnetic resonance imaging (MRI), ultrasound (US), computed tomography (CT), Positron Emission Tomography (PET), Single Photon Emission Computed Tomography (SPECT), Cerenkov luminescence imaging, and optical imaging (OI, bioluminescence and fluorescence).

A nuclear imaging agent may comprise a metal atom, or may be a radionuclide. As used herein, a "radionuclide", or a "radioactive nuclide", is an atom with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Radionuclides occur naturally, or can be produced artificially. A radionuclide having diagnostic or therapeutic value may be used as a nuclear imaging agent in the compositions of the present disclosure. The radionuclide may include, but not limited to, a gamma emitter, an alpha emitter, a beta emitter, a positron emitter, or a combination thereof, such as a gamma and beta emitter. Non-limiting examples of suitable radionuclides include technetium-99m, iodine-123 and 131, thallium-201, gallium-67 and 68, fluorine-18, fluorodeoxyglucose-18, indium-111, and copper-64. Suitable γ-emitting radionuclides include those which are useful in diagnostic imaging applications. A γ-emitting radionuclide preferably has a half-life of from 1 hour to 40 days, or 12 hours to 3 days. Suitable γ-emitting radionuclides include but are not limited to $^{67}$Ga, $^{111}$In, $^{99m}$Tc, $^{131}$I, $^{123}$I, $^{169}$Yb, $^{186}$Re, $^{125}$I, $^{201}$Tl and $^{103}$Pd. Suitable positron emitters include but are not restricted to $^{68}$Ga, $^{18}$F, $^{18}$F-FDG, $^{64}$Cu, $^{82}$Rb, and $^{13}$N. Exemplary nuclear imaging agents include $^{99m}$Tc, $^{18}$F, $^{68}$Ga, $^{64}$Cu, and Gd. Suitable α and β-emitting radionuclides include those which may be useful in therapeutic applications. Examples include $^{90}$Y, $^{131}$I, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$P, $^{142}$Pr, $^{153}$Sm $^{177}$Lu, $^{133}$Xe, $^{213}$Bi (45.6 min) and $^{212}$Pb (10.64 hr). A β-emitting radionuclide preferably has a half-life of from 2 hours to two weeks, and more preferably from about 2 hours to 100 hours. Exemplary nuclear imaging agents are $^{186}$Re, $^{188}$Re or $^{177}$Lu, which are therapeutic, emitting both beta and gamma. Alpha-emitting radionuclides may also be used, including but not limited to Bi-213 (46.5 min half-life), Pb-212 (16.64 h), and are useful for therapeutic applications. In an embodiment, a nuclear imaging agent may comprise dual function radionuclides useful for nuclear imaging and therapy.

An optical imaging agent may comprise a fluorophore or a dye capable of emitting NIR and/or fluorescent wavelengths. Suitable fluorophores or dyes include, but are not limited to, fluorescein isothiocyante (FITC), fluorescein thiosemicarbazide, rhodamine, Texas Red, CyDyes (e.g., Cy3, Cy5, Cy5.5, Cy7.5), Alexa Fluors (e.g., Alexa488, Alexa555, Alexa594; Alexa647), and near infrared (NIR) (700-900 nm) fluorescent dyes.

The imaging agent may be coupled to the homing molecule or its analogue by standard methodology known in the art. For example, radionuclide complexes may be prepared by reacting a specified amount of the selected composition with a metal salt of the selected radionuclide in the presence of a reducing agent and a transfer agent. Preferred reducing agents include, but are not limited to, dithionite, stannous ion, and ferrous ion. Preferred transfer agents include, but are not limited to, sodium gluconate, sodium tartrate, sodium citrate, and mannitol.

In another embodiment, a homing agent may comprise an imaging agent on at least one arm and a therapeutic agent on at least one other arm. In still another embodiment, a homing agent may comprise a radionuclide on at least one arm and a therapeutic agent on at least one other arm. A therapeutic agent may be derived from a broad class of compounds including but not limited to peptides, organic molecules, organo-metallo complexes, nucleic acid based compounds and their analogues, carbohydrate or carbohydrate modified compounds, as well as natural, synthetic, or synthetically modified naturally occurring compounds. Suitable therapeutic agents are known in the art and will depend on the condition or disease to be treated. For example, if the disease or condition is cancer, suitable cancer agents may be found via the National Cancer Institute at the National Institutes of Health and the FDA Approved Drug Product database. Suitable therapeutic agents for thrombosis are known in the art and may include antiplatelet agents or thrombolytics. Non-limiting examples of anti-platelet drugs include: irreversible cyclooxygenase inhibitors such as Aspirin and Triflusal (Disgren), Adenosine diphosphate (ADP) receptor inhibitors such as Clopidogrel (Plavix), Prasugrel (Effient), Ticagrelor (Brilinta), and Ticlopidine (Ticlid), Phosphodiesterase inhibitors such as Cilostazol (Pletal), Glycoprotein IIB/IIIA inhibitors (intravenous use only) such as Abciximab (ReoPro), Eptifibatide (Integrilin), and Tirofiban (Aggrastat), Adenosine reuptake inhibitors such as Dipyridamole (Persantine), and Thromboxane inhibitors such as Thromboxane synthase inhibitors, Thromboxane receptor antagonists, and Terutroban. Thrombolytic therapy may include streptokinase, anistreplase, urokinase and plasminogen activators such as alteplase, reteplase and tenecteplase. A skilled artisan would also be able to determine common therapeutic agents for infectious diseases, cardiovascular disease and inflammatory diseases.

According to the invention, a homing agent comprises a p-armed peptide construct comprising n PEG monomers covalently bound together to form a p-armed PEG multimer, wherein p is at least 3. The peptide construct further comprises p linkers, and p homing molecules. In an embodiment, p may be at least 3. For example, p may be at least 4, at least 6, at least 8 or at least 10. In an exemplary embodiment, p is 4, such that the PEG multimer is a four-armed tetramer, and each of four peptide monomers is linked to a different arm of the PEG multimer by one of four linkers.

In an embodiment, a homing agent of the invention may have an increased avidity for a target molecule relative to a monomeric peptide construct comprising one PEG monomer and one homing molecule and a decreased affinity for circulating serum peptides. Such a homing agent with a decreased affinity for serum peptides may exhibit more rapid clearance from plasma, thereby reducing background signal generated by the diagnostic agent. For example, when the target molecule is fibrin, and n is 4, the homing agent may have an increased avidity for fibrin relative to a monomeric peptide, or one peptide-PEG monomer with only one peptide monomer which is capable of selective binding to fibrin. An exemplary such homing agent is shown in FIG. 2, and comparative avidity described in the Examples.

Figure 1:
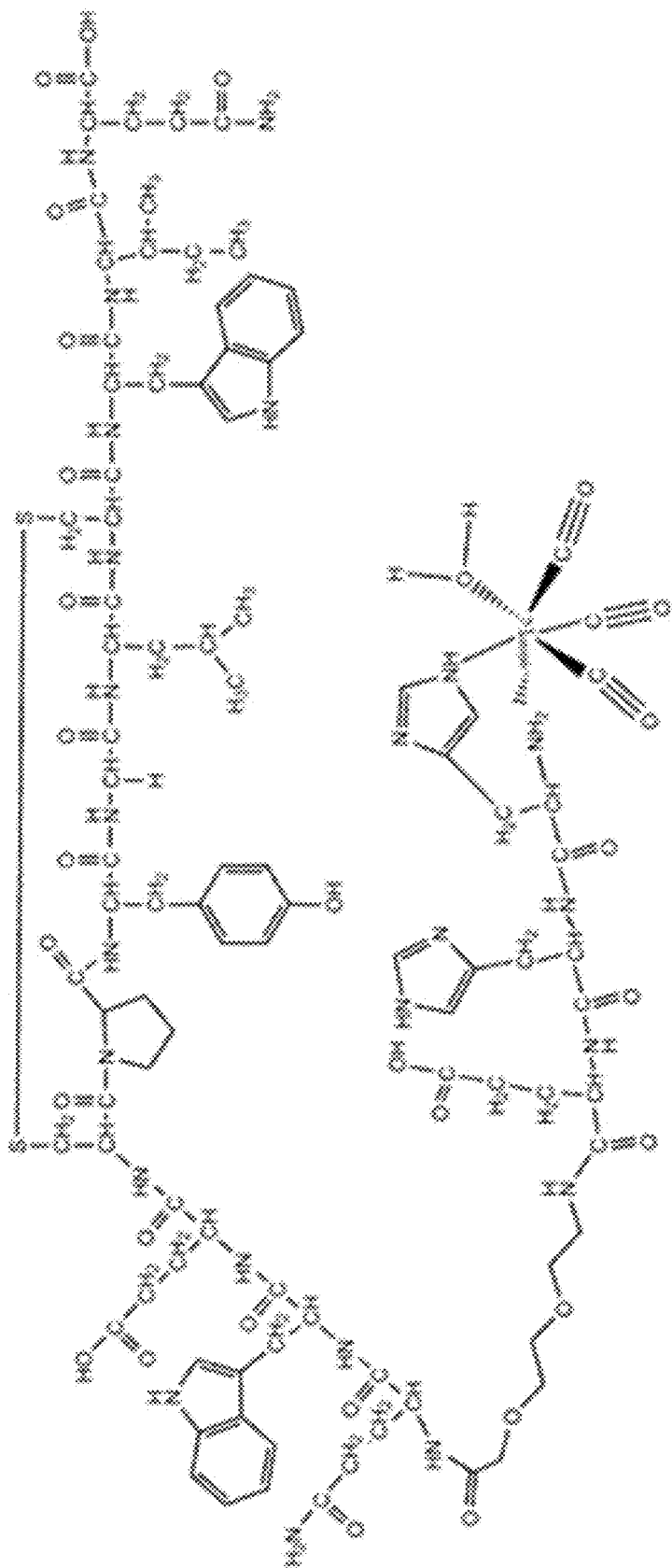
FIG. 1 depicts the chemical structure of the $^{99m}$Tc-labeled monomeric fibrin-binding peptide construct.
Figure 2A:
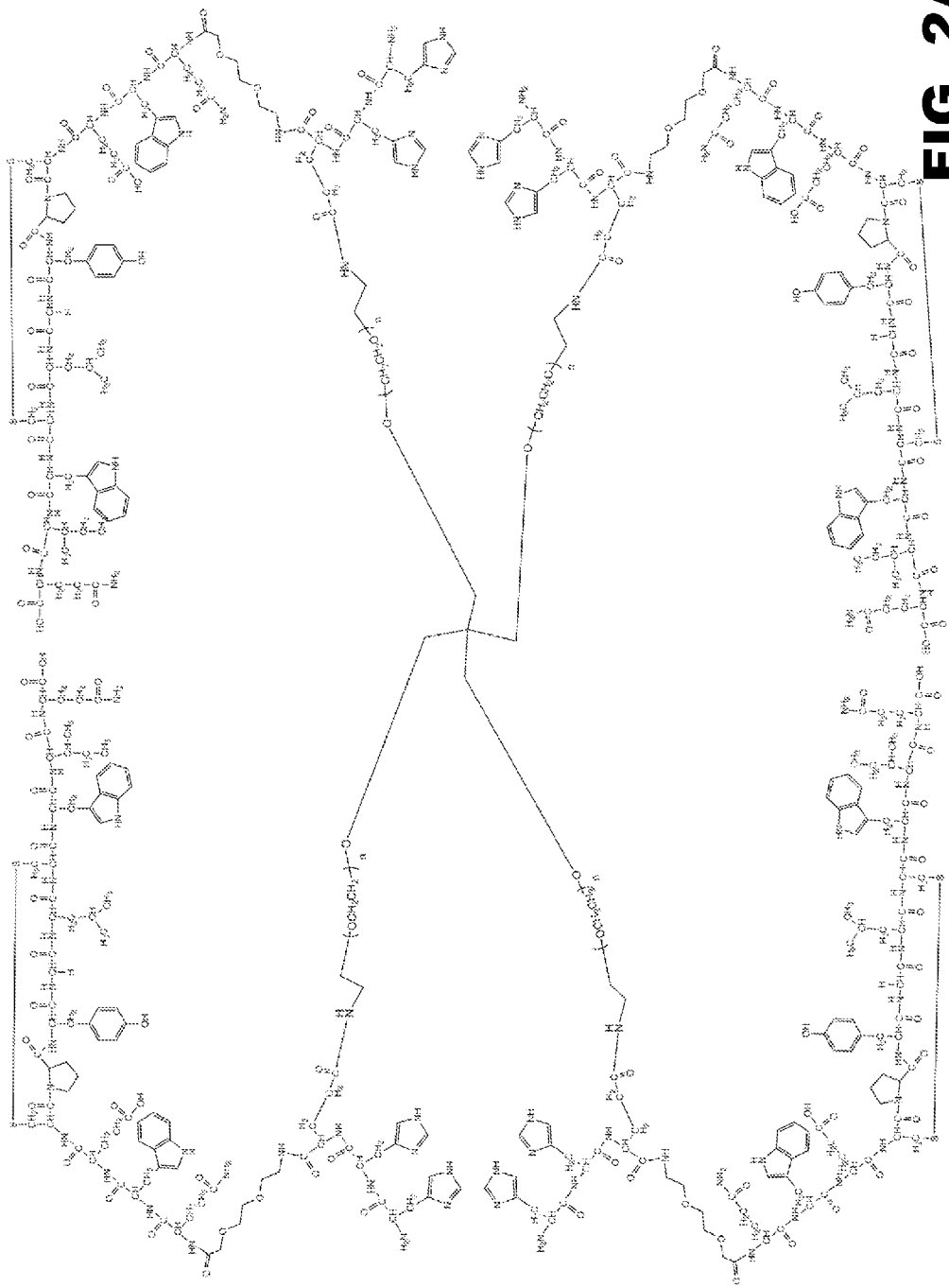
FIG. 2 depicts the chemical structure of the $^{99m}$Tc-labeled tetrameric fibrin-binding peptide construct showing four $^{99m}$Tc-labeled monomeric fibrin-binding peptide constructs linked to the four arms of 4-arm PEG, wherein n is the number of ethylene oxide repeats (A). When 4-arm PEG is PEG10K, n=60. When 4-arm PEG is PEG2K, n=9. (B,C,D, E) Depict each arm of the 4-arm tetrameric fibrin-binding construct.
Figure 2B:
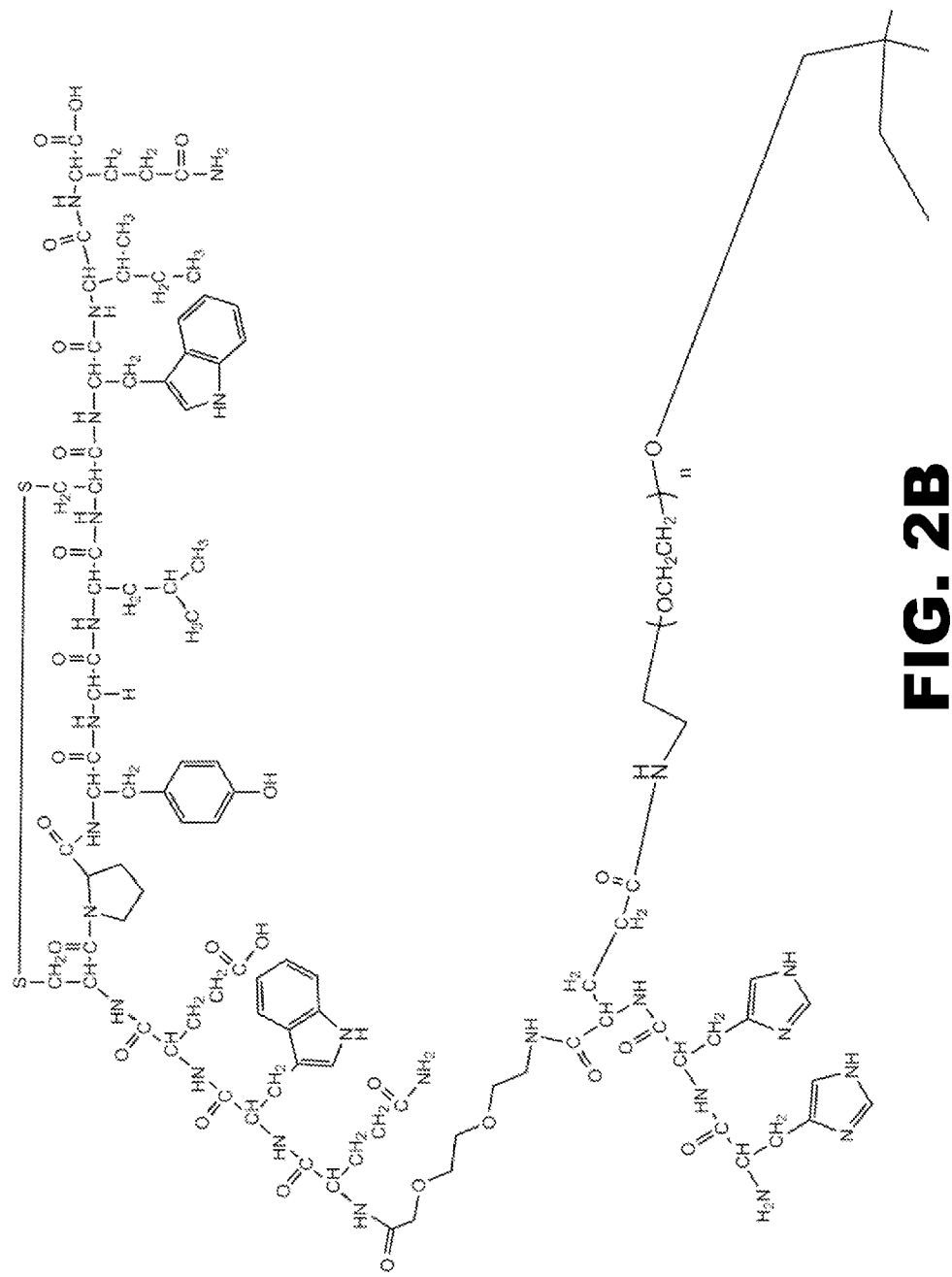
Figure 2C:
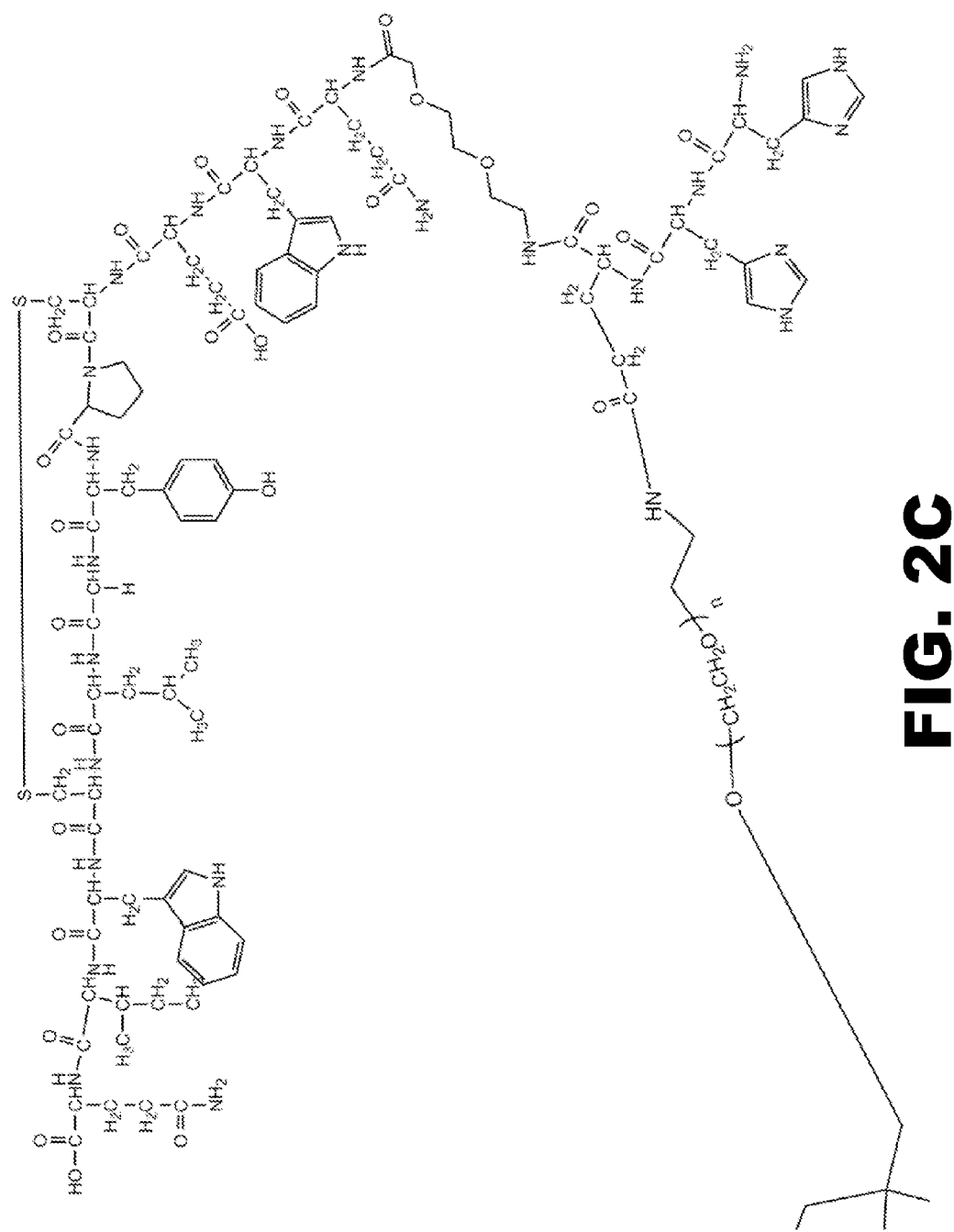
Figure 2D:
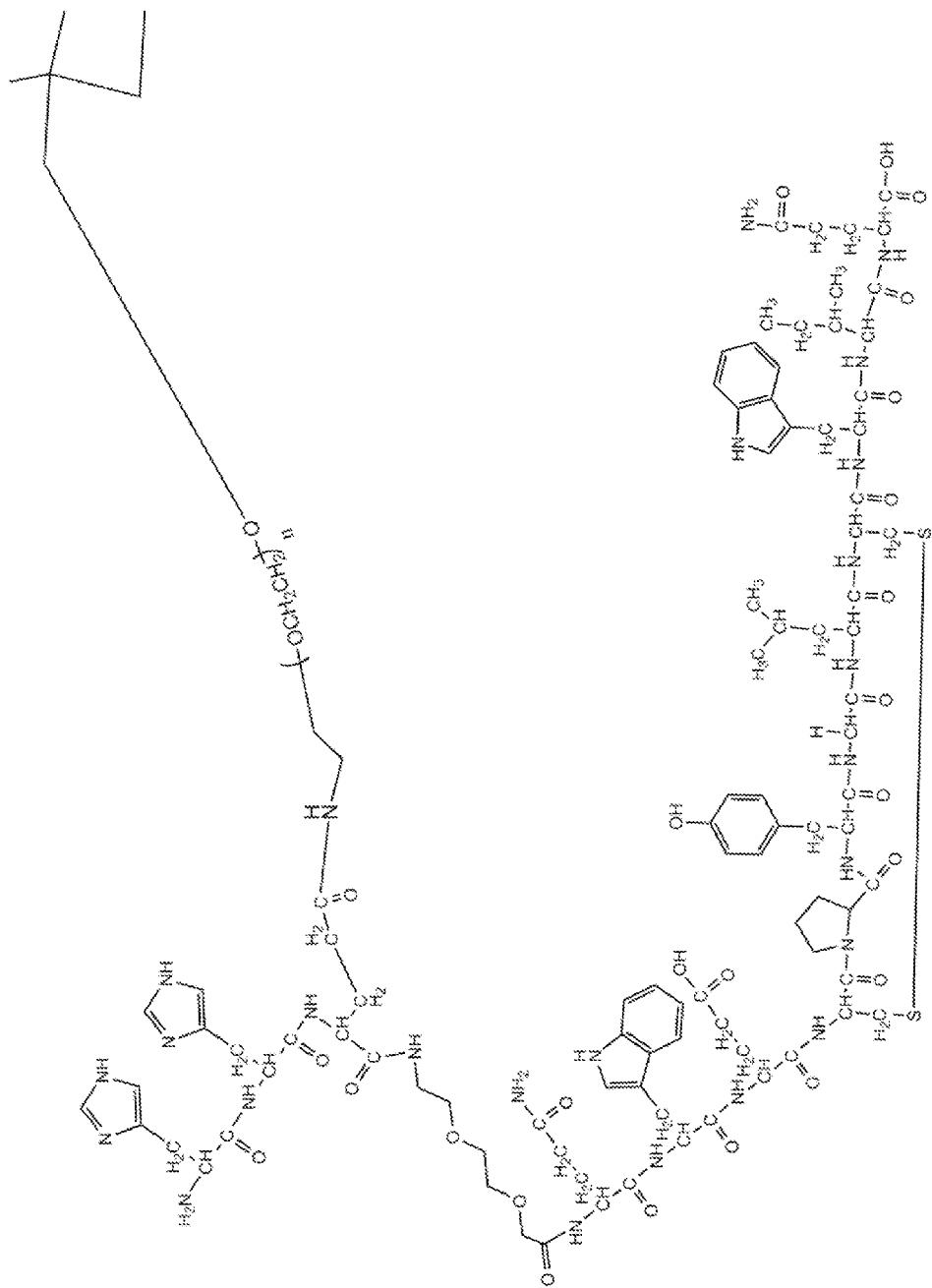
Figure 2E:
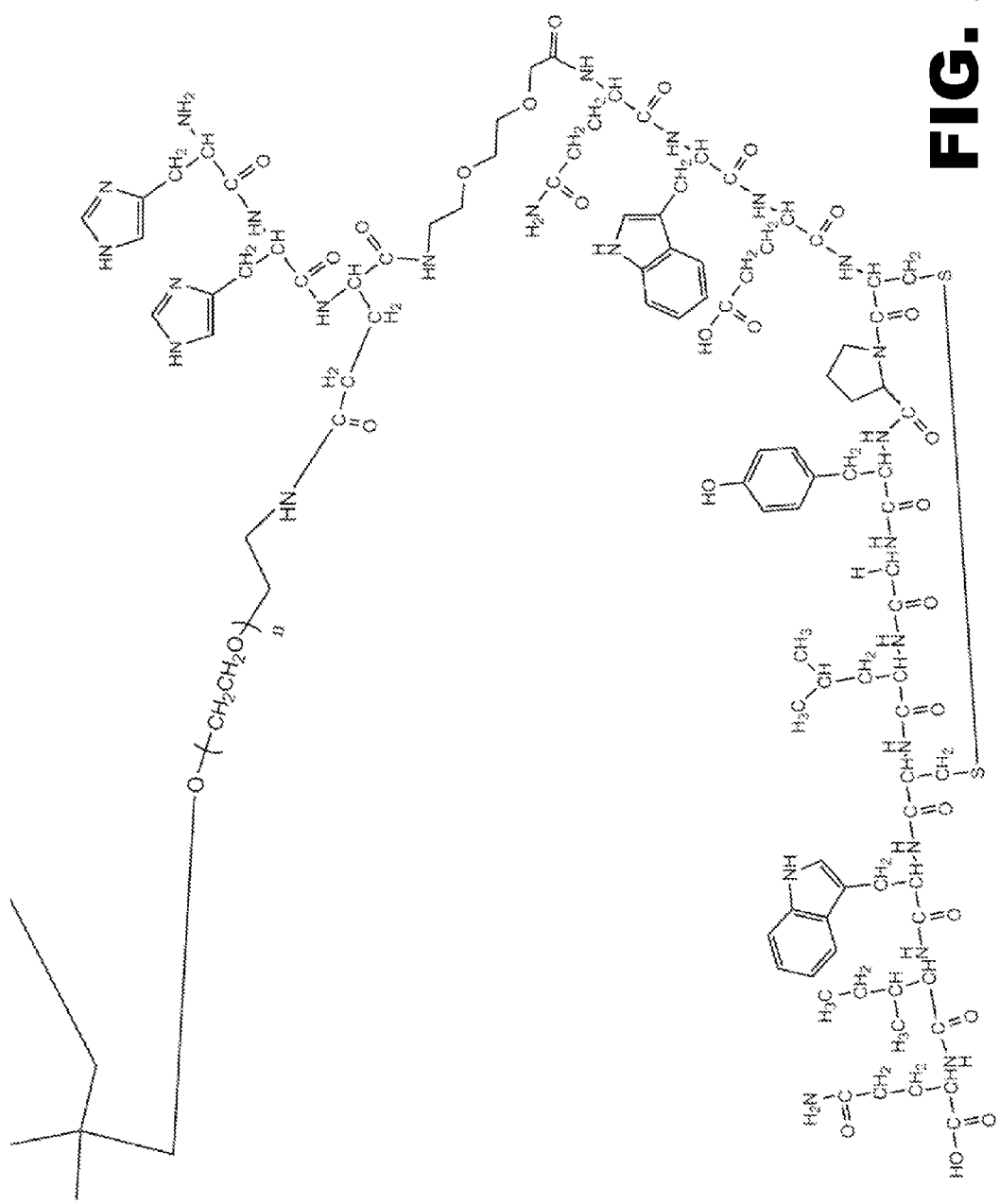

A p-armed peptide construct may be generated from a monomeric peptide construct. For example, a tetrameric peptide construct may be generated from a monomeric peptide construct. The monomeric peptide construct comprises a homing molecule capable of selectively binding a target molecule, and a peptide linker coupling the homing molecule to a diagnostic or therapeutic agent, such as but not limited to an imaging agent. For example, the N-terminus of the homing molecule is coupled to the C-terminus of the linker peptide. A non-limiting example of a monomeric peptide construct that may be used as a basis for a homing agent according to the present disclosure is shown in FIG. 1, in which the target-specific homing molecule is a fibrin-binding peptide. The amino acid sequence of the fibrin-binding homing molecule is QWECPYGLCWIQ (SEQ ID NO: 1), and the monomer is a modification of a cyclic peptide described in A. F. Kolodziej et al., Bioconjug Chem 23 (3):548-556 (2012). In an embodiment, click chemistry may be used for tetramer preparation. In another embodiment, copper free click chemistry may be used for tetramer preparation. Copper-free click chemistry may be more suitable for solution phase scale-up for commercial use. Conventional click chemistry requires the presence of a Cu(I) catalyst. Copper-free click chemistry is based on the reaction of a cyclooctyne (DBCO) moiety with an azide-labeled reaction partner, known as strain-promoted alkyne azide cycloaddition (SPAAC). Copper-free click chemistry is very fast at room temperature and does not require a cytotoxic Cu(I) catalyst. Cyclooctynes are thermostable with very narrow and specific reactivity toward azides, resulting in almost quantitative yields of stable triazoles. In an embodiment where copper free click chemistry is used for tetramer preparation, BCN (bicycle[6,1,0]non-4-yn-9-ylmethanol) may be used. For example, a monomeric peptide may be synthesized on solid phase then coupled with tetramer BCN to form a tetrameric peptide later radiolabeled with a radionuclide. Alternatively, a tetrameric peptide may be synthesized on solid phase then radiolabeled with a radionuclide. In still another example, a monomeric peptide may be synthesized on solid phase, then a tetrameric peptide may be prepared through known copper click chemistry. Finally tetrameric peptide may be conjugated with a chelator, such as 1,4,7-triazacyclononane-1,4,7-triacetic acid (NOTA), and the resulting chelator-tetramer may then be radiolabeled.

A homing agent may be for example a peptide construct having the formula of Formula I:

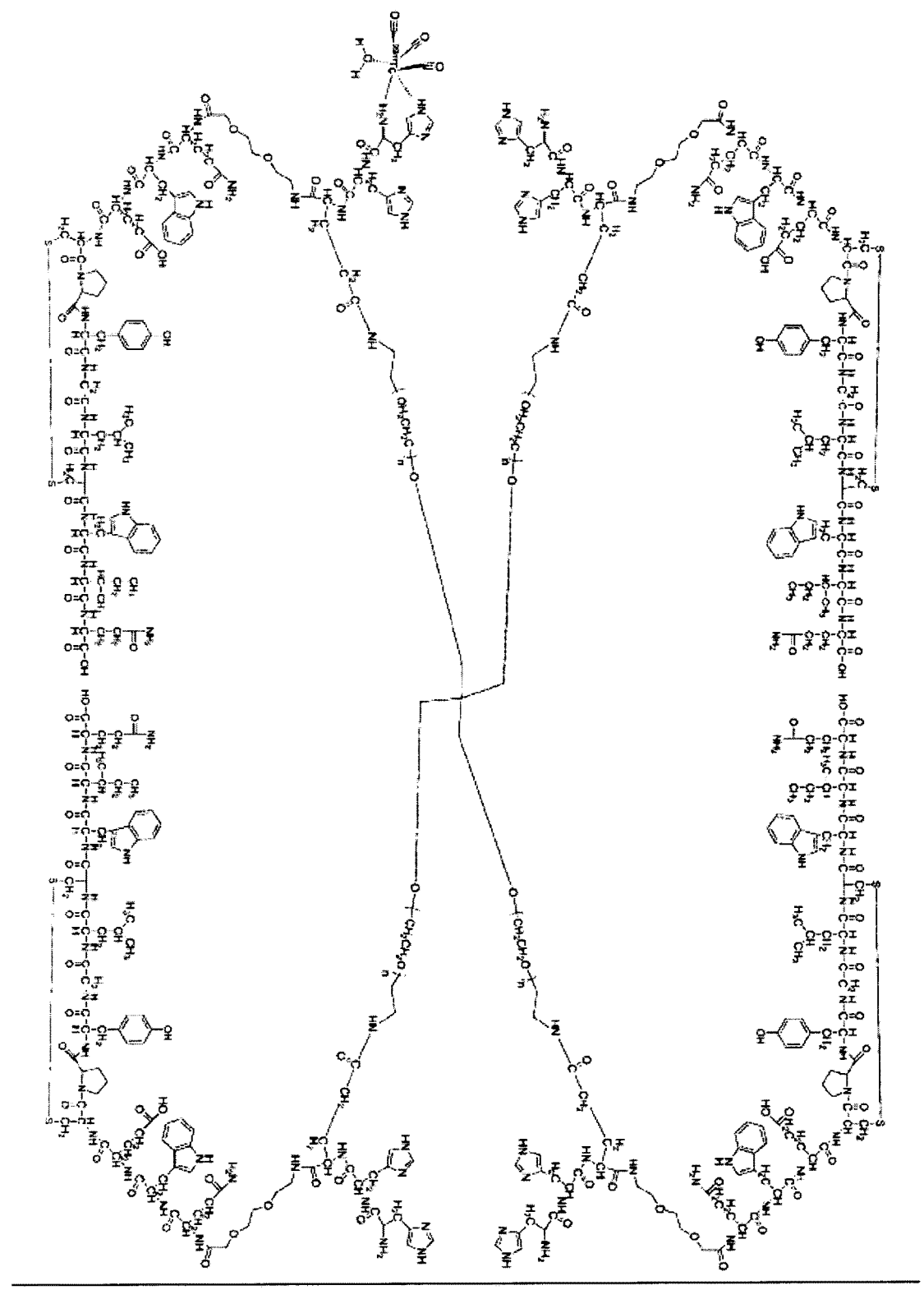

Alternatively, a homing agent may be for example have the formula of Formula II:

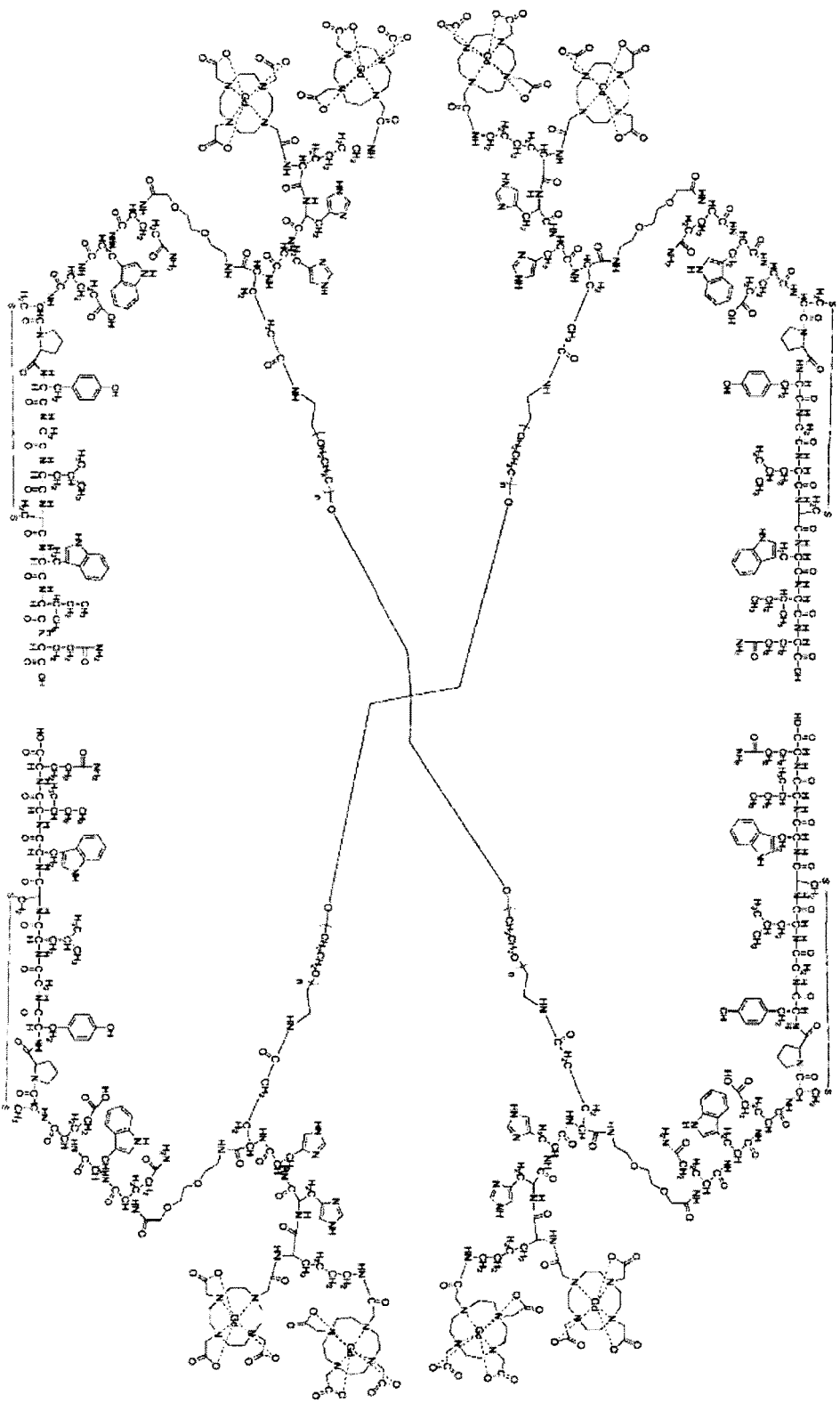

A homing agent of Formula II may be used for imaging using MRI and may increase the nuclear specific activity by increasing the number of isotopes bound per construct. Each arm of the construct has two chelating compounds bound to the construct in the hinge or linker unit between them, forming a Y-shape. The homing agent of Formula II may be used to detect clot formation using MRI.

The present disclosure also provides a radiopharmaceutical composition comprising any homing agent as described herein, together with a pharmaceutically-acceptable carrier. Pharmaceutically acceptable carriers include any commonly used pharmaceutical carrier, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans, and blood plasma. Any pharmaceutically acceptable carrier may also include pharmaceutically acceptable adjunct elements such as salts, buffers, preservatives and the like.

II. Kits

The present disclosure also provides a kit for detecting or quantifying an intradevice thrombus in a subject having an implanted mechanical circulation assist device. The kit includes an amount of a thrombus imaging agent which is any of the homing agents as described herein and comprising: homing molecules capable of selectively binding fibrin, such as but not limited to the tetrameric construct shown in Formula I, in which the nuclear imaging agent is $^{99m}$T. The kit may include an amount of a thrombus imaging agent comprising: a p-armed peptide construct comprising n PEG monomers covalently bound together to form a p-armed PEG multimer wherein p is at least 3; p linkers; and p homing molecules, wherein each homing molecule is linked to an arm of the PEG multimer by one of the linkers, the homing molecules capable of selectively binding fibrin; and an imaging agent linked to an N-terminus of at least one homing molecule. In an embodiment, the imaging agent may be a nuclear imaging agent selected from the group consisting of $^{111}$In, $^{18}$F, $^{18}$F-FDG, $^{68}$Ga, $^{64}$Cu and Gd. The kit additionally includes an amount of at least one additional reagent useful in the chemistry involved in generating and/or measuring a signal from the imaging agent. Additional reagents may include any one or more of a reducing agent, a coordinating ligand, an adjuvant, an antioxidant, a buffer, and a chelating agent.

A kit may comprise a radiopharmaceutical composition comprising a thrombus imaging agent as described herein, together with a pharmaceutically-acceptable carrier as described herein above. A kit may include for example the radiopharmaceutical composition in a first container such as a vial, and a composition capable of complexing with the imaging agent is provided in a second container. The contents of each container may be combined and mixed prior to administration to the subject. The mixture may be treated further, for example by heating as needed to enhance labeling. The radiochemical purity of the resulting composition, that is the efficiency or completeness of radionuclide sequestration by the homing agent, may be readily determined using standard methodology known to those of skill in the art, and preferably is at least 90% and more preferably at least 95% of the radioactivity.

The imaging agents of the invention and their pharmaceutically acceptable salts are useful as diagnostic and therapeutic agents as described further below.

III. Methods

In an aspect, the present disclosure provides a method for detecting intradevice thrombus in a subject having an implanted mechanical circulation assist device. The method comprises administering into the bloodstream of the subject an effective amount of a homing agent comprising: a p-armed peptide construct comprising n PEG monomers covalently bound together to form a p-armed PEG multimer wherein p is at least 3; p linkers; p homing molecules, wherein each homing molecule is linked to an arm of the PEG multimer by one of the linkers, the homing molecules capable of selectively binding fibrin; and at least one imaging agent linked to an N-terminus of at least one homing molecule; waiting a time sufficient for binding of the homing agent to thrombus to occur; and detecting a signal from the imaging agent localized at a site of thrombus. In an embodiment, the method further comprises quantifying intradevice thrombus by determining an amount of the imaging agent localized at a site of thrombus from the signal detected, wherein the amount of the imaging agent is indicative of the size of the thrombus.

(a) Thrombus Detection and Quantification

The homing agents may be prepared in a pharmaceutically acceptable carrier, as described above, and administered to an individual in an amount determined to be diagnostically and/or therapeutically effective using standard methodology known to those of average skill in the art.

The present disclosure thus also provides methods for detecting, quantifying and/or imaging intradevice thrombus in a subject having an implanted mechanical circulation assist device. The methods can be applied to any mechanical circulation assist device including but not limited to a left ventricular assist device, a right ventricular assist device, a biventricular assist device, a pulsatile flow device, a continuous flow device, a centrifugal flow device or an axial flow device.

Radiolabeled peptide constructs are prepared for example to provide a predetermined radioactive dose, which is dependent on the radionuclide selected for use. Such doses may be for example between about 0.05 mCi and about 50 mCi, preferably about 1 mCi to about 33 mCi for $^{99m}$Tc. Such a dose is administered into the bloodstream of the subject using any conventional means, for example by intravenous infusion into the bloodstream of the subject. As used with respect to radiolabeled constructs, "a diagnostically effective amount" refers to an amount of the radiolabeled construct that is sufficient to allow its detection by scintigraphic measurement. As used with respect to fluorophore-labeled constructs, "a diagnostically effective amount" refers to an amount of the fluorophore-labeled construct that is sufficient to allow its detection by optical imaging. Imaging of a site of interest in the body of the subject following administration of the labeled peptide construct may be performed following a period which is sufficient for binding of the peptide construct to fibrin to occur, for example at a site of thrombus, which may be from about 1 minute to several minutes, about one hour, or about 3-5 hours, to several hours. In an embodiment, the period may be from about 5 minutes to about 20 minutes. Radioactivity in each dose may be measured before and after administration and recorded. A suitable reference solution with a known quantity of the nuclear imaging agent, e.g. $^{99m}$Tc may also be prepared. Any conventional method of imaging for signal detection, quantification and diagnostic purposes may be utilized. For example, when the imaging agent is a radionuclide, a radiosignal may be detected using a γ-camera, serial scintigraphic images may be obtained and, for each image, counts collected. In the most basic assessment method, a Geiger counter or similar non imaging device may be used. However in practice, since radioactive blood will be flowing through the pump and the potential for fibrinous debris of a nonpathological nature to be present throughout the pump with out clinical sequelae, high resolution imaging or localized directional counting will likely be employed to assess uniformity of binding. We suspect that most clots targeted will be formed on the inlet side and be differentiated from the outlet side by higher counts. Of course the reverse is true and likely to occur as well.

The present disclosure thus encompasses a method for detecting intradevice thrombus in a subject having an implanted mechanical circulation assist device, the method comprising: a) administering into the bloodstream of the subject an effective amount of a homing agent comprising an imaging agent and a homing molecule specific for fibrin as described herein, b) waiting a time sufficient for binding of the homing agent to thrombus to occur; and c) detecting a signal from the imaging agent localized at a site of thrombus. In the method, when the imaging agent is a nuclear imaging agent, detecting the signal from the nuclear imaging agent may comprise acquiring a scintigraphic image of the device and determining the presence or absence in the image of a signal generated by the nuclear imaging agent localized at a site of thrombus. The scintigraphic image may have adequate resolution to differentiate signal generated within different compartments of the device, such as the inlet, pumping, and outlet compartments. The relative signal generated within different compartments may be used to calculate baseline fibrinous lining from clinically significant thrombus accumulation.

In another aspect, the present disclosure provides a method for quantifying intradevice thrombus in a subject having an implanted mechanical circulation assist device, the method comprising: a) administering into the bloodstream of the subject an effective amount of a homing agent comprising a nuclear imaging agent and a homing molecule specific for fibrin as described herein; b) waiting for a time sufficient for binding of the imaging agent to thrombus to occur; c) acquiring a scintigraphic image of the device; and d) determining an amount of the nuclear imaging agent localized at a site of thrombus from the scinitgraphic image, wherein the amount of nuclear imaging agent is indicative of the size of the thrombus. In an embodiment, the location of the thrombus may be determined from the scintographic image. For example, the thrombus may be located in the turbine only. Alternatively, the thrombus may be located in the stator only. Further, the thrombus may be located in the turbine and the stator.

In another aspect, the present disclosure provides a method for imaging an intradevice thrombus in a subject having an implanted mechanical circulation assist device, the method comprising: a) administering to the bloodstream of the subject an effective amount of a homing agent comprising a nuclear imaging agent and a homing molecule specific for fibrin as described herein; b) waiting for a time sufficient for binding of the imaging agent to thrombus to occur; and c) generating a scintigraphic image of the thrombus.

With respect to any of the preceding methods using a homing agent comprising an imaging agent and a homing molecule specific for fibrin, the homing agent may have an increased avidity for fibrin relative to a monomeric peptide construct comprising one PEG monomer and one homing molecule specific to fibrin, and a decreased affinity for circulating serum proteins. A homing agent with a decreased affinity for serum peptides exhibits more rapid clearance from plasma, thereby reducing background signal generated by the diagnostic (imaging) agent.

With respect to use of any of the fibrin targeted peptide constructs, kits described herein according to the related methods also described herein, an implanted mechanical circulation assist device may be a left ventricular assist device, a right ventricular assist device, a biventricular assist device, a pulsatile flow device, a continuous flow device, a centrifugal flow device or an axial flow device.

(b) Diagnostic and Therapeutic Applications

The compositions of the invention are also particularly suited for use in detecting and/or quantifying disease processes involving one or more vascularly accessible biomarkers of a disease or disorder for which a binding peptide may be obtained, as described herein above. The present disclosure thus also encompasses various methods using the peptide constructs described herein.

Accordingly, the present disclosure provides a method for detecting or modifying at least one vascularly accessible biomarker of a disease or disorder. The at least one biomarker may be constitutively or transiently present by or in a cell. The method comprises for example administering into the bloodstream of the subject an effective amount of any homing agent as described herein, wherein the at least one homing molecule is capable of specifically binding the at least one biomarker. Alternatively, the homing agent may be administered intraperitoneally, intratumorally, subcutaneously or intrabladder. The method further comprises waiting for a time sufficient for binding of the homing agent to the at least one biomarker (target molecule) to occur. An imaging signal is then obtained at a pathologic site, for example at a site of infection, inflammation or at a tumor site. The disease or disorder may be selected from a cancer, a cardiovascular disease, a pulmonary disease, an inflammatory disease, and an infectious disease. Any biomarker as described herein may be the target molecule for the homing agent.

The diagnostic or therapeutic agent may be an imaging agent. In an embodiment, the diagnostic or therapeutic agent may be a nuclear imaging agent and the imaging signal may comprise a nuclear signal. The nuclear imaging agent may have a therapeutic effect, and the method may further comprise allowing the nuclear agent to provide the therapeutic effect at the pathologic site. Alternatively, the homing agent may further comprise a therapeutic agent linked to at least one arm of the peptide construct, and the method may further comprise allowing the therapeutic agent to provide the therapeutic effect at the pathologic site. Alternatively, the diagnostic or therapeutic agent may be an optical imaging agent and the imaging signal comprise an optical signal. An optical imaging agent may be selected from an optical agent capable of emitting visible, NIR or microwave energy. The homing agent may comprise a therapeutic agent comprising a non-nuclear drug organic compound. The non-nuclear drug organic compound may be selected from, but not limited to, organometallic complexes, pharmaceutical drug classes, nucleic acid derived agents, and carbohydrate based drugs. The homing agent may comprise a therapeutic agent occupying one or more arms of the peptide construct and a detectable imaging marker on one or more arms of the peptide construct. The homing agent may comprise a homing molecule specific to an integrin or an integrin-associated molecule, such as but not limited to Integrin alpha 1/CD49a, integrin VLA-4, integrin avb3, integrin avb5, and integrin a5b1. The homing agent may comprise a homing molecule specific to a cell adhesion molecule (CAM) or an Ig superfamily CAM, such as but not limited a homing molecule specific to ALCAM/CD166, a vascular cell adhesion molecule (VCAM), or an intercellular adhesion molecule (ICAM).

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Introduction for Examples 1-11

Several thrombus specific SPECT agents have been reported, but none are likely to be effective in this application. The major issues arise from the morphological differences between intra-pump thrombus and typical intravascular thrombus combined with the high avidity required to target clot, i.e., "stick and stay", under extremely high blood flow rates (9,000 RPM, 5-6 L/min).

Figure 14:
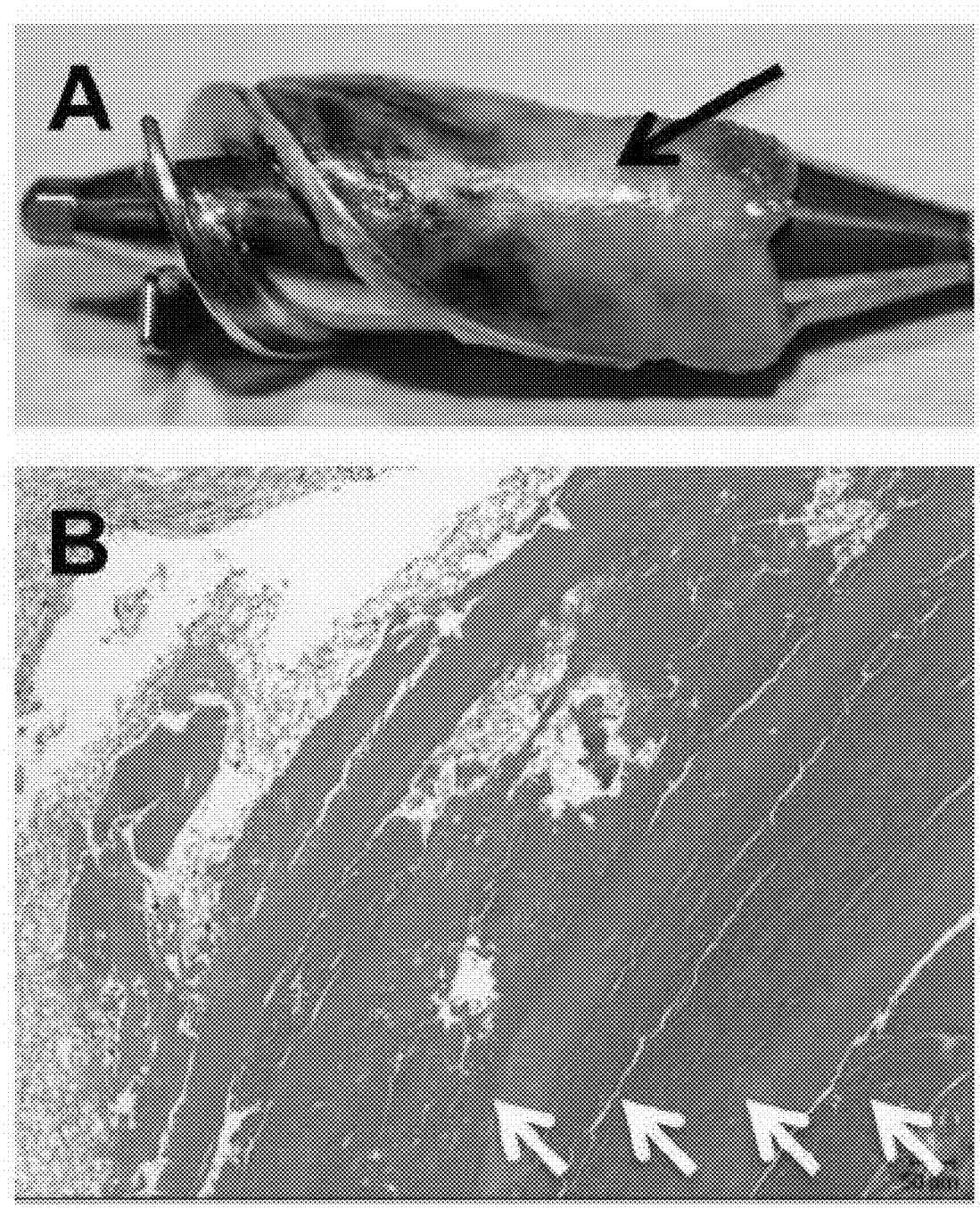
FIG. 14 depicts images of (A) intrapump thrombus showing friction wear and (B) histology of the clot of in A showing fibrin "rings of a tree".

Typically, thrombus is simplistically envisioned as densely cross-linked fibrin fibrils and platelets combined with other entrapped blood cells and proteins. Several antibodies to fibrin that have been developed with good affinity ($10^{-9}$ M) and avidity (although not as effective as $^{99m}$Tc-F4A). Antibody circulatory half-life is prolonged, lasting days, which results in high background nuclear signal in blood passing through the pump, confounding thrombus diagnosis. Moreover, under the high flow of the pump, one would anticipate that these antibodies, which can be competed off fibrin clots in vitro, will dissociate from the thrombus as circulating ligand concentrations decline and equilibrium shifts. The anti-d-dimer antibody (DD-3B6) is directed against the degradation product of fibrinogen to fibrin conversion. The serum D-dimer assay is used routinely as a clinical marker of thrombus formation, for instance in the context of suspected pulmonary embolism. However, its use as a targeted radioligand for thrombus depends upon slow wash out of residual clipped peptide within a porous clot. However, histochemistry of intrapump thrombus shows negligible porosity with layers of fibrin assembled in bands like "growth rings of a tree" (FIG. 14). In this high-flow environ, surface released d-dimer would be rapidly washed away. Anti-B knob antibodies directed to a neo-epitopes formed by the liberation of fibrinopeptides A and B were developed in the late 1980's. Access to the "A-knob" is quickly lost with the cross-linking of fibrin, but the B-knob remains transiently accessible. Subsequent, preclinical and clinical studies revealed that the B-epitope was rapidly buried within the forming thrombosis and the approach was nonviable.

Figure 15:
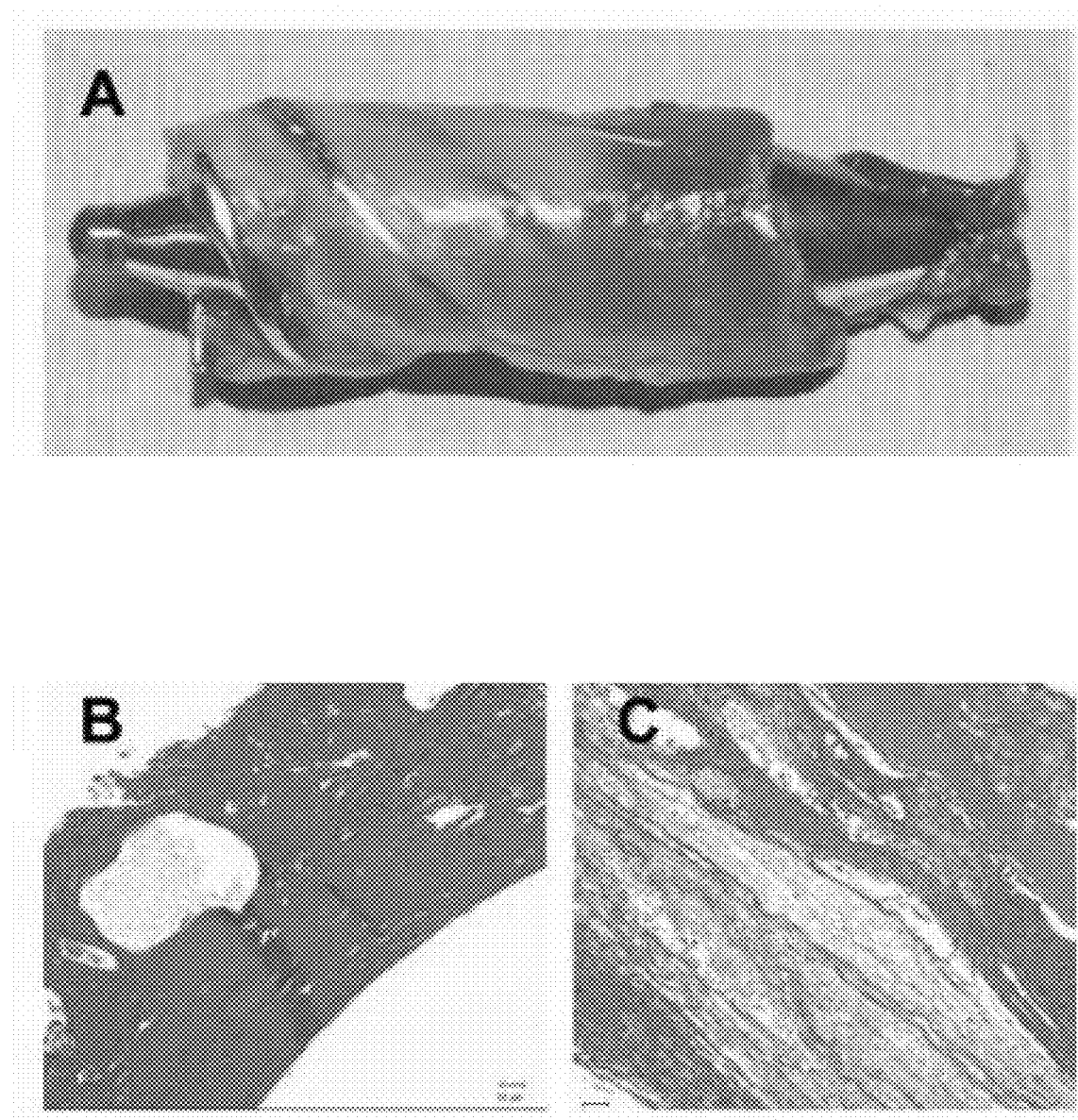
FIG. 15 depicts images of (A) intrapump thrombus is large and severely compacted near the inlet port, as shown in (B), and less dense (lighter colored) near the outflow port (C). The looser clot matrix shows a paucity of cellular components. LVAD thrombus is densely fibrin-rich with few platelets or entrapped blood cellular components.

Other thrombus specific agents target platelets, but platelet receptors are inherently difficult biomarkers for imaging. Platelets are small, and highly dysmorphic when activated. Although some are present on the surface during active clotting, the majority are found buried in the thrombus with limited accessibility. Even "fresher" LVAD thrombus has minimal platelets available for imaging (FIG. 15).

Unlike prior agents, $^{99m}$Tc-F4A is fibrin specific, with very high clot avidity, negligible serum interference, and rapid renal clearance, as described in the Examples below. $^{99m}$Tc-F4A is based on the previously published EPIX fibrin peptides (U.S. Pat. Nos. 6,652,835, 6,991,775, 7,238,341, 7,412,279). The parent peptide was originally modified with gadolinium chelates and although the contrast was acceptable for T1-weighted MR imaging, the concept failed in the clinic. Part of the decision to discontinue may relate to the delay of a day or more required for optimal readout. Given the rapid clearance expected for such a small peptide, we speculated that the marked hydrophobicity of the ligand led to significant serum protein binding. These anti-fibrin peptides were known to have low-level albumin affinity and no fibrinogen affinity. Given the abundance of albumin in plasma, the absorptive effective on peptide targeting and clearance would be amplified. Further, direct coupling of gadolinium chelates to the peptide likely diminished fibrin binding affinity. Caravan et al. have reported the development of PET and PET/MR agents specific for fibrin, but these monomeric agents have fast clearance with inadequate avidity for LVAD use. Moreover, these monomers likely retain considerable serum interference as suggested by our preliminary data for a similar monomer construct.

Figure 16:
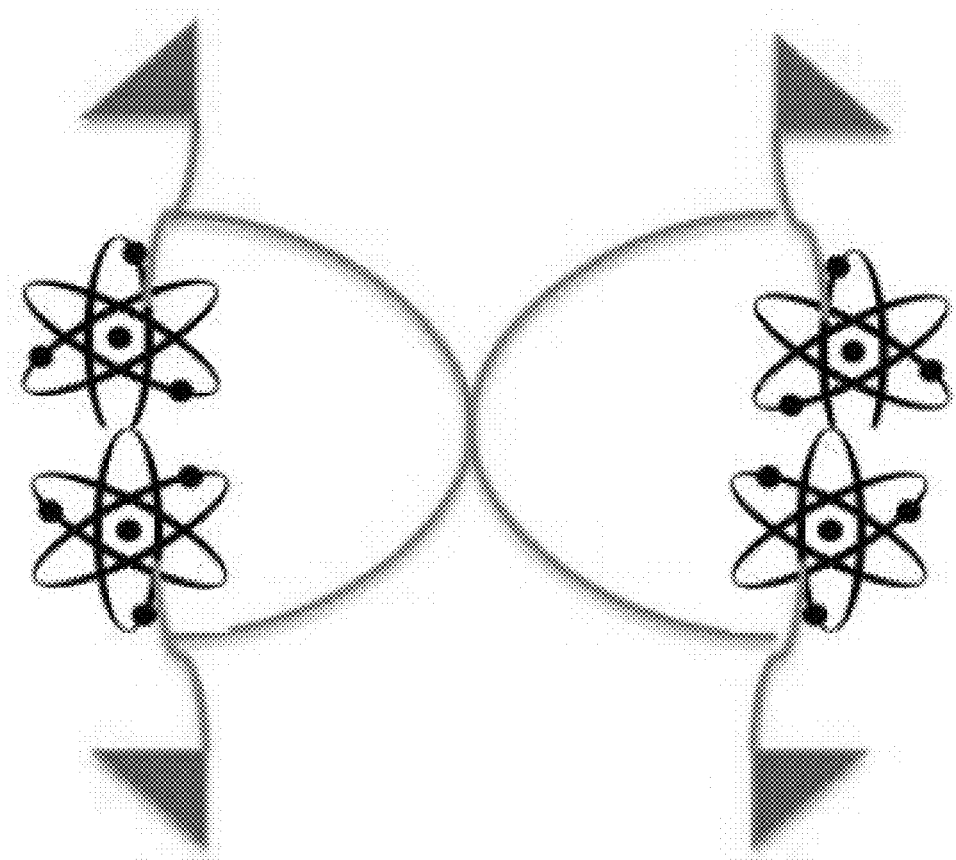
FIG. 16 depicts an illustration of a 4-arm construct with bifunctional cyclic anti-fibrin peptide (red)-$^{99m}$Tc ligands (atom) coupled through tetrametric PEG$_{2000}$ spacers.

$^{99m}$Tc-F4A utilizes a dual-armed approach with the fibrin-peptide on one arm, extended by a short linker and connecting with a high affinity $^{99m}$Tc amino-acid sequence (FIG. 16). A PEG2000 arm is attached between the homing and nuclear functional regions and the covalently bonding of 4 monomeric moieties yielded $^{99m}$Tc-F4A. This new chemistry yielded very high avidity and essentially eliminated plasma interference. Contrary to expectation, the pharmacokinetic clearance rate for the larger tetramer was faster than for the smaller anti-fibrin monomer component with rapid biodistribution into the urine and no appreciable accumulation in the liver or spleen of mice. A novel, fibrin-specific $^{99m}$Tc small tetrameric molecular imaging agent ($^{99m}$Tc-F4A) to detect, localize, and quantify LVAD thrombosis noninvasively was developed to provide direct diagnosis of LVAD thrombosis in this high-risk population. Accordingly, early diagnosis of acute LVAD clot formation would allow better INR adjustments to minimize GI bleeding and possibly thrombolysis and late direct diagnosis of clot formation will support decisions for pump exchange. Further, a $^{99m}$Tc probe used with a small, portable detector placed immediately over the LVAD will be easy for use in clinics and hospitals.

Example 1. $^{99m}$Tc-Labeled Monomeric Peptide Construct

A fibrin-binding monomeric peptide construct labeled with $^{99m}$Tc (FIG. 1) was generated. The peptide construct comprises a fibrin-binding peptide and a linker peptide coupled to $^{99m}$Tc. The amino acid sequence of the fibrin-binding peptide is QWECPYGLCWIQ (SEQ ID NO: 1). The amino acid sequence of the linker peptide is HHE. The N-terminus of the fibrin-binding peptide is attached to the C-terminus of the linker peptide using a polyethylene oxide linker.

Example 2. Synthesis of the Monomeric Fibrin-Binding Peptide Construct

The fibrin-binding peptide construct was prepared by linear Fmoc-solid phase peptide synthesis using HBTU (≥99% purity) and Fmoc-Gln(tBu)-Wang resin (0.5 mmol/g) following standard procedure described in the art. In short, the peptide construct was synthesized using a CS136 peptide synthesizer at the 0.2 mmol scale. Fmoc deprotection was performed with 20% piperidine in DMF (15 min) and the coupling of amino acids was performed with a combination of 0.1 M HBTU coupling agent and 1.0 M DIPEA in DMF (5× excess) for 4 hours. The resin was washed with DMF 3 time (30 s each) followed by deprotection with TFA/anisole/water (95/2.5/2.5) for 2 h. All amino acids were dissolved in DMF. The disulfide bond was formed on the resin. The final product was purified by HPLC and characterized by ESI-TOF mass spectrometer. ESI-TOF (positive mode): m/z [Chemical Formula: C94H126N24O26S2+2 H]+[MW+2H]+ Calcd. 1037.14 Da.; Obsd. 1037 Da. The polyethylene oxide linker was attached to the peptide using HBTU as the coupling agent, and DIPEA as base in DMF as solvent.

Example 3. Synthesis of the Tetrameric Fibrin-Binding Construct

The tetrameric nuclear agent was prepared by coupling the fibrin-binding monomeric construct to a 4-arm PEG2K (MW 2Kda), or a 4-arm PEG1 OK amine (MW 10Kda) using a solid-phase synthesis approach to generate a tetrameric construct (FIG. 2). In short, after the fibrin-binding monomer construct was synthesized (Example 1) on the resin, methoxytrityl and 2-phenylisopropyl groups were removed selectively with 1% TFA in DCM. The 4 PEG armed amine was coupled on the resin. Size exclusion column was used to isolate the final tetrameric product.

Example 4. $^{99m}$Tc Labeling of the Fibrin-Binding Monomeric and Tetrameric Constructs The monomeric peptide construct synthesized in Example 2 and the tetrameric peptide construct synthesized in Example 3 were covalently labeled using pertechnitate (Na$^{99m}$TcO$_4$). In short, 1.0 ml of Na$^{99m}$TcO$_4$ (~9 mCi) in saline was added to an IsoLink vial. The mixture was heated at 100° C. for 20 min to form the intermediate [$^{99m}$Tc(CO)$_3$(H$_2$O)$_3$]+. The mixture was allowed to cool to room temperature, and neutralized with 0.2 ml of a 1:2 mixture of 1 M phosphate buffer (pH 7.4) and 1 M HCl. The resulting solution (0.2 ml) was added to a 5 ml vial containing monomeric, tetrameric PEG2K, or tetrameric PEG10K peptide construct in 0.15 ml of physiological phosphate-buffered saline. The reaction mixture was heated at 60° C. for 30 min. After cooling to room temperature, a sample of the resulting solution was purified by size exclusion column and analyzed by TLC. The radiochemical purity of [$^{99m}$Tc(CO)$_3$(L)]+(L=monomer, tetramer PEG2K, or tetramer PEG1 OK peptide construct) was 95%.

Example 5. In Vitro Binding of the Fibrin-Binding Monomeric Construct to Acellular Clot Phantoms Clot phantoms were generated using a typical procedure wherein 100 μL of human plasma was quickly mixed with 3 unit of thrombin solution. The resulting solution was then transferred into a plastic cylinder tube. Once clots were formed, they were placed each in 4 mL 0.1 M PBS buffer, pH7.0 solution.

The fibrin-binding monomer construct labeled with $^{99m}$Tc (10 mCi/350 μg) was prepared and analyzed by TLC as described in the examples above. The construct was diluted to generate a dilution series comprising 1, 5, 10, 15, 25, and 30 μg peptide construct in a total volume of 0.5 mL 0.1 M PBS at pH 7.4.

Figure 3:
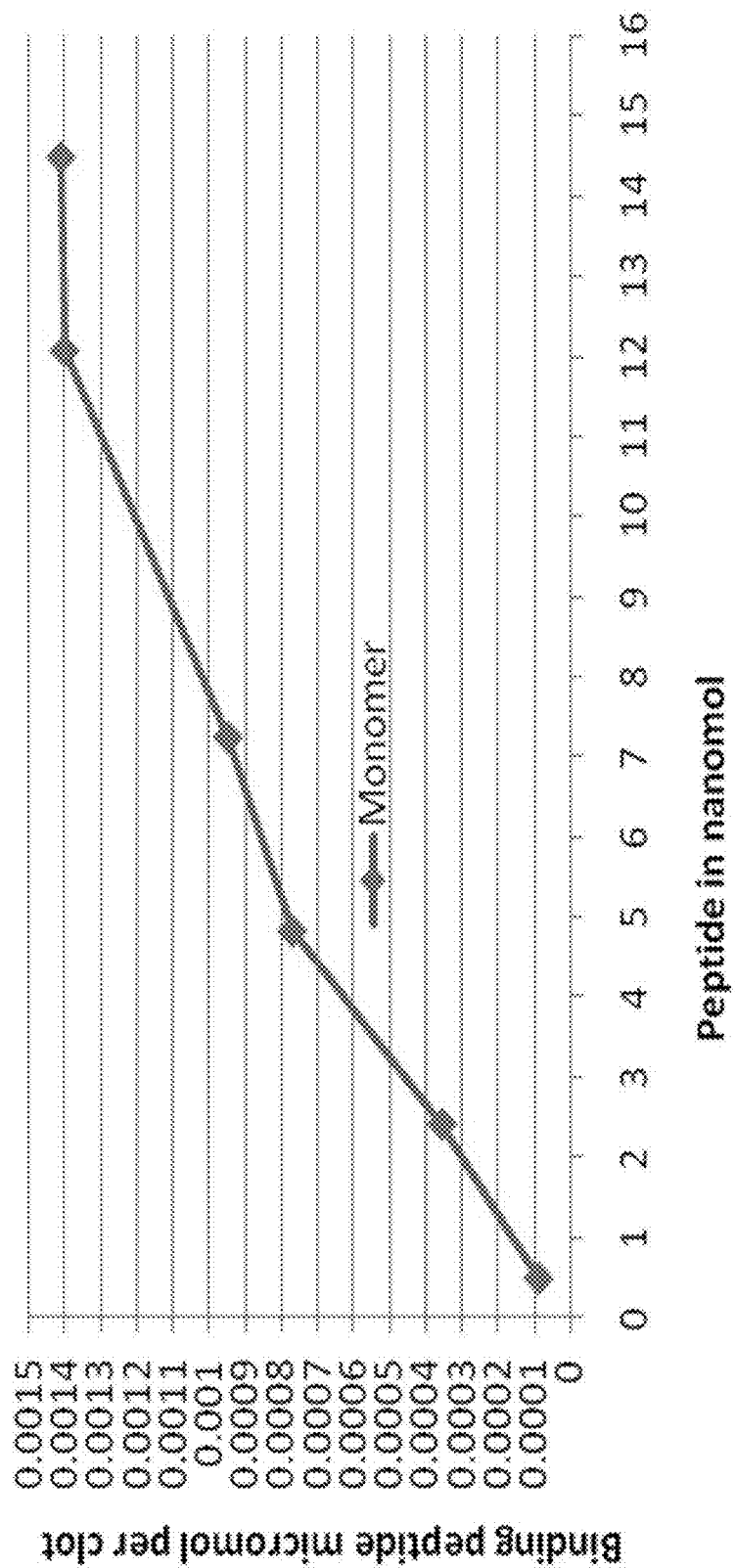
FIG. 3 depicts a Scatchard plot showing the binding of monomeric peptide construct per clot relative to the concentration of the peptide.

The monomeric construct was then combined with clot phantoms and incubated for 30 min at 37° C. in a water bath. Clot phantoms were separated from the solution by centrifugation device, and radioactivity was measured in the clot and the supernatant using a calibrated dosimeter. The experiment was repeated for three times and data were analyzed by Scatchard plot and regression analysis (FIG. 3). The IC$_{50}$ for the modified monomer was determined to be about 4.5 nM. The dissociation constant (Kd) and the number of binding sites per clot were also determined. The Kd was 4.5E-09, the binding site per clot was 8.48E+14, and the binding site per mg: 1.21E+15.

Figure 4:
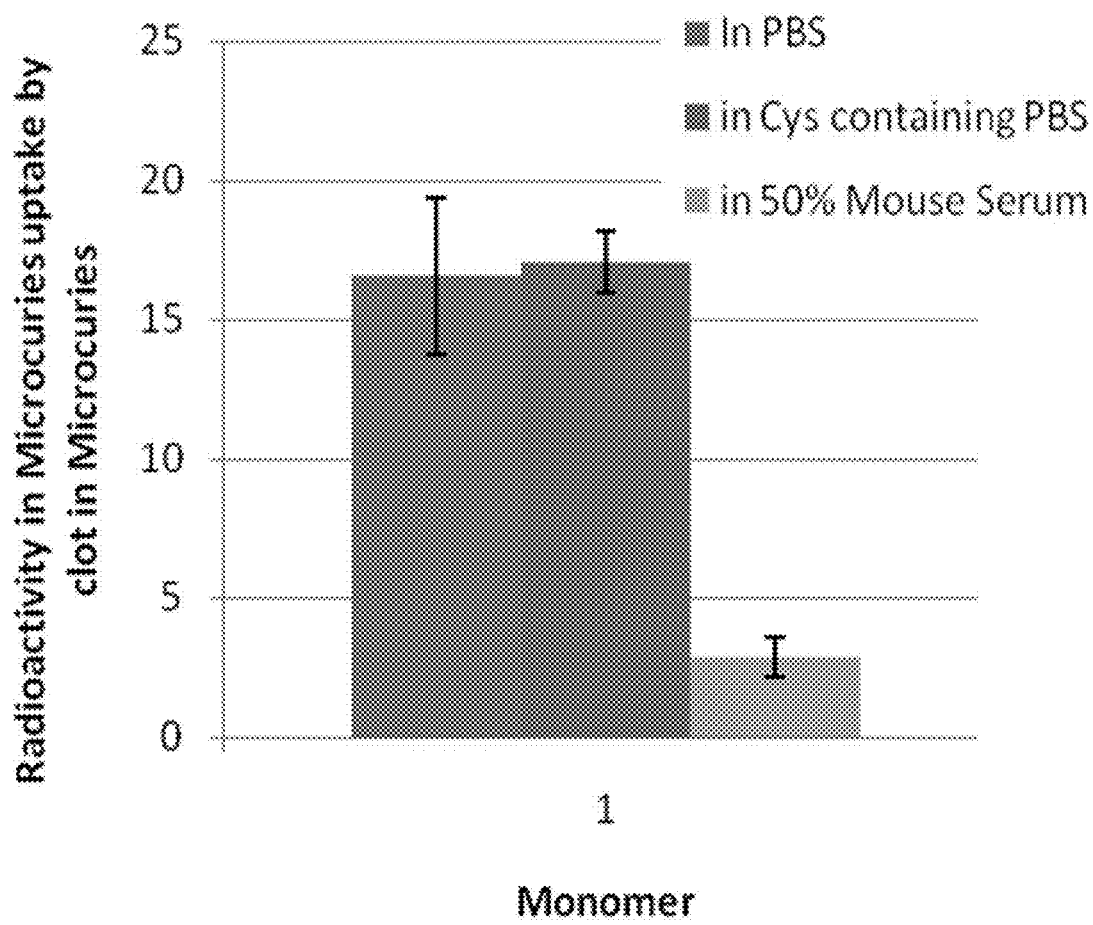
FIG. 4 depicts a bar graph showing the effects of excess cysteine and serum on the retention of $^{99m}$Tc isotope in the binding of the monomeric fibrin-binding peptide to human serum plasma clot.

In a parallel experiment, binding of the fibrin-binding monomeric construct to acellular clot phantoms in the presence of excess cysteine, or in the presence of 50% serum was also tested. For excess cysteine conditions, 0.25 mg of cysteine in 0.5 mL PBS was also combined with the monomeric construct and clot phantoms. The experiment was conducted as described above, and incubated for 120 min at 37° C. in a water bath. As shown in FIG. 4, the presence of excess cysteine did not impact the secure coupling of the 99mTc radiolabel. Cys is used to test the stability of the metal on the agent, and binding of the agent without the metal would look like lower binding. Instability and loss of the metal in the presence of serum could have accounted for the lower binding of the monomeric peptide, but the metal was stable. However, in the presence of 50% serum, the binding of the labeled peptide was greatly diminished, indicating a protein binding/interference effect. Thus the peptide binding was interfered with by off-target association with something in serum, likely albumen. This was consistent with previous reports describing the serum binding of the monomeric fibrin-binding peptide.

Example 6. In Vitro Binding of the Fibrin-Binding Tetrameric Construct to Acellular Clot Phantoms The labeled 4-arm peptide construct was prepared as described in Example 4. In a typical procedure, cationic complexes [$^{99m}$Tc(CO)3(L)]+ were prepared by reacting a tetrameric construct with the tricarbonyl intermediate [$^{99m}$Tc(CO)3(H2O)3]+ at 60° C. for 30 min. The labeled tetramer was purified and the radiochemical purity was 95%.

Figure 5:
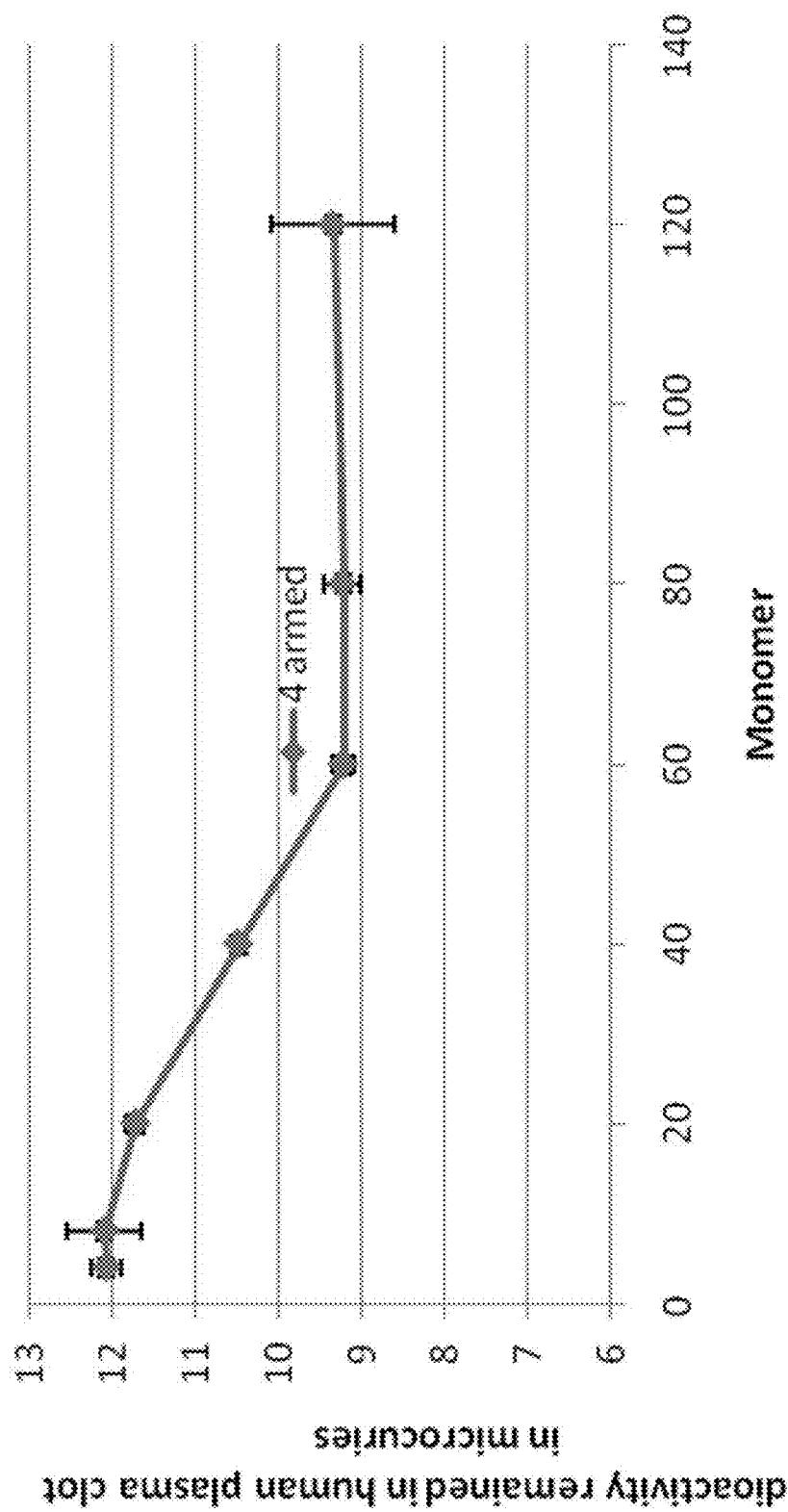
FIG. 5 depicts a graph showing the affinity of $^{99m}$Tc-labeled tetrameric fibrin-binding peptide in the presence of increasing concentrations of monomeric fibrin-binding peptide.

Binding of the 4-arm $^{99m}$Tc construct to clots was conducted in the presence of unlabeled titrated fibrin-binding monomer construct. The binding assay, and titration of monomer was as described in Example 5. The titrated binding pattern of the 4-arm $^{99m}$Tc construct in the presence of increasing concentrations of the monomer agent is shown in FIG. 5. Significant concentrations of the monomer construct were required to compete the binding of some of the 4-arm $^{99m}$Tc constructs. However, as shown in FIG. 5, further increasing concentrations of the monomer construct did not displace the binding of most of the 4-arm $^{99m}$Tc constructs bound to the clots. The almost irreversible binding of the 4-arm $^{99m}$Tc constructs to the fibrin clots indicates extraordinary avidity, far exceeding the already excellent binding affinity of the monomer alone.

Example 7. Clot Detection in HeartMate II Left Ventricular Assist Device (LVAD)

In a preliminary experiment, imaging through a mechanical circulatory device was simulated by imaging titrated amounts of the 4-arm $^{99m}$Tc construct described above through a thin titanium plate. In short, titrated amounts of the 4-arm $^{99m}$Tc construct (Table 1) were placed in a thin plastic holder in the imaging tray of the Carestream Multispectral FX Pro imager with isotope pad, and imaged using a 1 minute acquisition time (FIG. 6a). The samples were imaged again after a thin titanium plate was placed beneath the samples (FIG. 6b). Acquisition time for samples imaged through the titanium plate was increased to 5 min (FIG. 6c). Due to the diffusion of signal generated through the titanium plate by the samples comprising the 4 lowest concentrations, the samples were spaced further apart and imaged again using the same settings (FIG. 6d). FIG. 7 plots signal attenuation of the titrated samples of 4-arm $^{99m}$Tc construct.

TABLE 1

Figure 6:
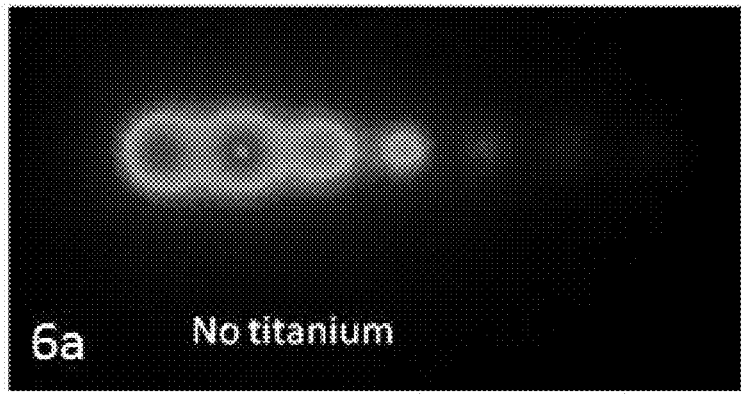
FIG. 6 depicts scintigraphy images. (a) Scintigraphy image of titrated amounts of the 4-arm $^{99m}$Tc construct using a minute acquisition time. Titrations are as described in Table 1. (b) Scintigraphy image of the titrated samples of the 4-arm $^{99m}$Tc construct in (a), through a titanium plate, using a 1 minute acquisition time. (c) Scintigraphy image of the titrated samples of the 4-arm $^{99m}$Tc construct in (a), through a titanium plate, using a 5 minute acquisition time. (d) Scintigraphy image of the titrated samples comprising the 4 lowest concentrations of the titrated samples of the 4-arm $^{99m}$Tc construct in (a), through a titanium plate, using a 5 minute acquisition time. (e and f) Scintigraphy image of a clot in a Heartmate II LVAD. The clot was labeled with the 4-arm $^{99m}$Tc construct.
Figure 6:
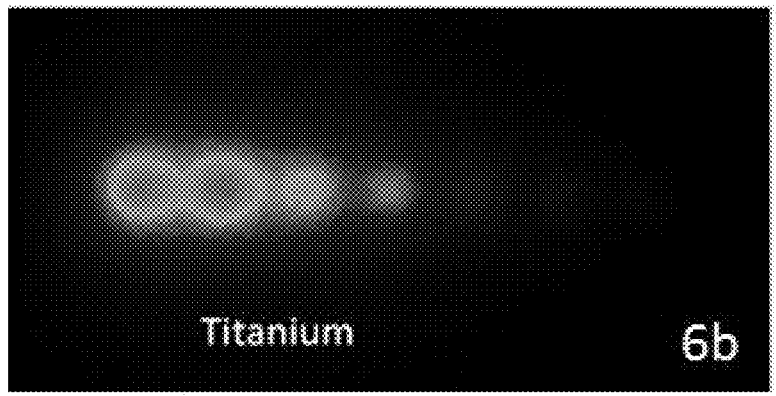
Figure 6:
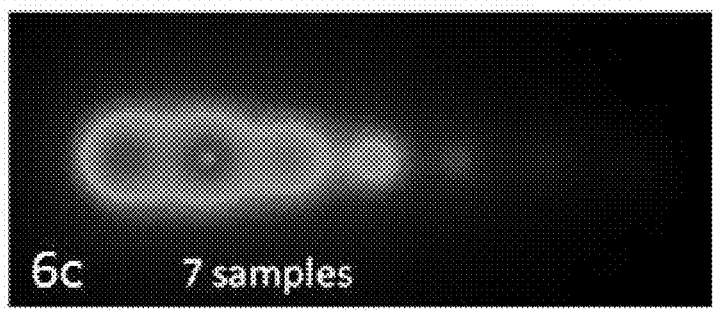
Figure 6:
Figure 6:
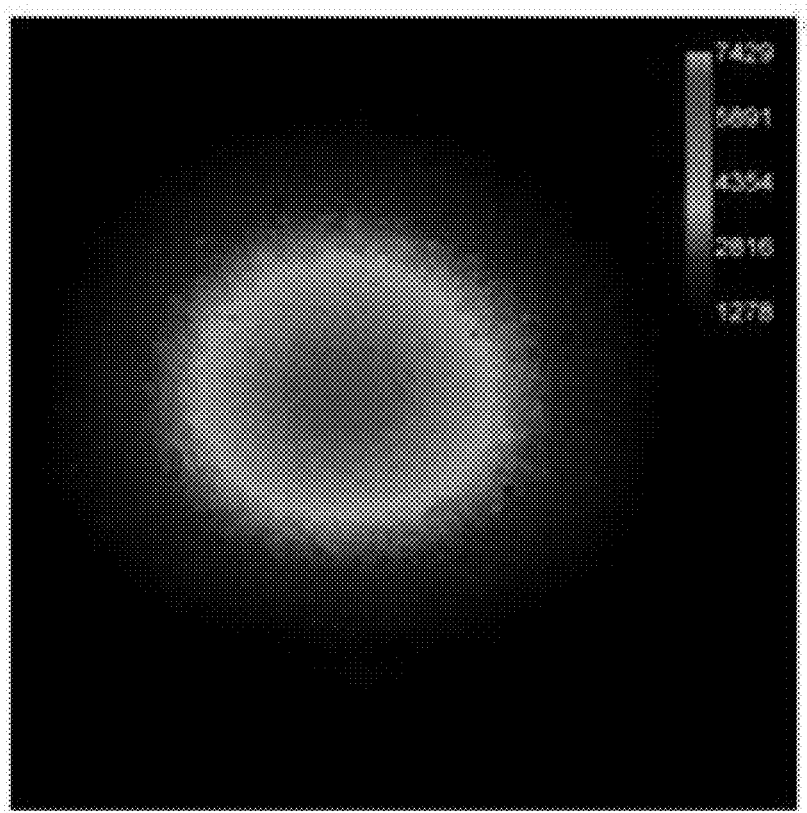
Figure 6:
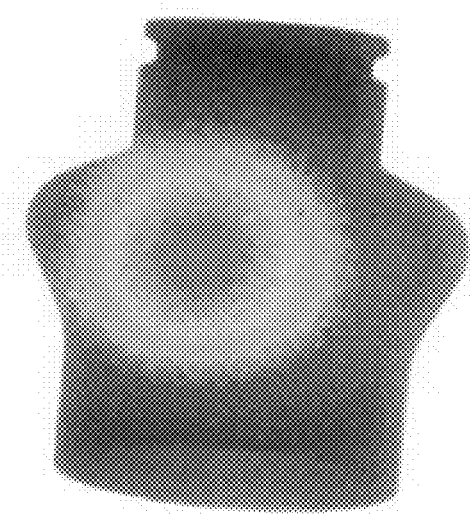
Figure 7:
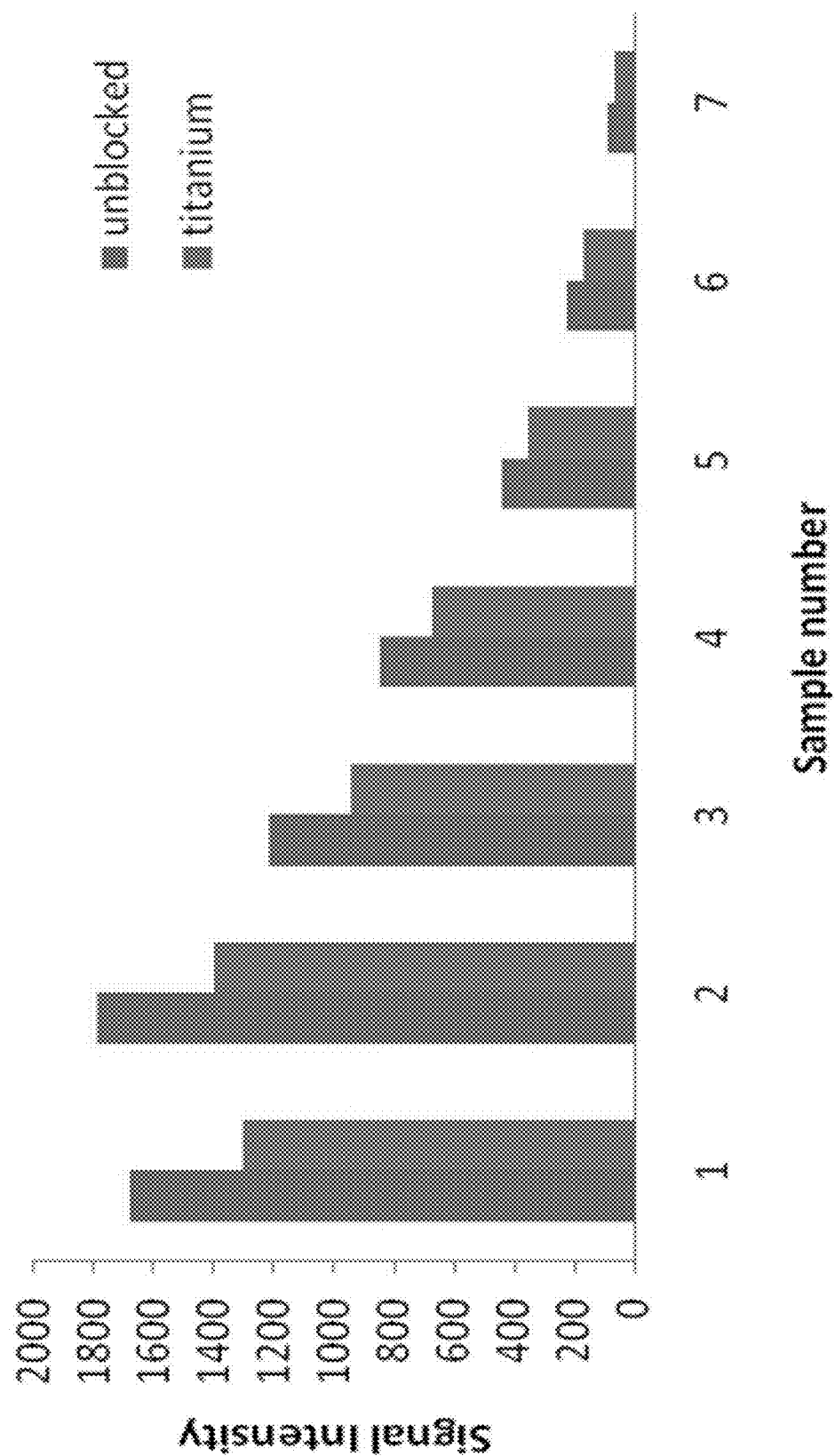
FIG. 7 depicts a bar graph showing attenuation of $^{99m}$Tc signal by titanium. Titration samples are as described in Table 1.

Radioactivities and volumes of samples used in FIG. 6 and FIG. 7

| Sample Number | 1 | 2 | 3 | 4 | 5 | 6 | 7 |
|---|---|---|---|---|---|---|---|
| Radioactivity (µCi) | 20 | 15 | 10 | 5 | 2.5 | 1.25 | 0.625 |
| Volume µL | 105 | 90 | 60 | 30 | 15 | 7.5 | 3.75 |

The 4-arm $^{99m}$Tc construct bound to a fibrin clot through a mechanical circulatory device was then performed to emulate intrapump thrombosis imaging using the 4-arm $^{99m}$Tc construct. A human plasma clot was incubated with the 4-arm $^{99m}$Tc construct (230 µCi in 4 mL PBS buffer) at 37° C. for 2 hours. The clot was then washed 5 times. The radioactivity of the clot was measured by dosimeter to be 23 to 33 µCi. The clot was placed in a Heartmate II LVAD, and imaged using an acquisition time of 5 min (FIGS. 6e and 6f).

These results show that gamma emission penetration of the titanium pump housing is very efficient. In clinical practice, it is anticipated that a simple, collimated gamma detector could be placed immediately above the pump implantation area and diagnostically significant count levels would be acquired in a less than 20 minutes, typically less than 10 minutes. Because there is no requirement for rapid counting, tomographic imaging or attenuation correction, the approach lends itself to a simple application with relatively low health cost, as compared to PET imaging for example.

Example 8. Pharmacokinetics of the Monomeric and Tetrameric Constructs

Figure 8:
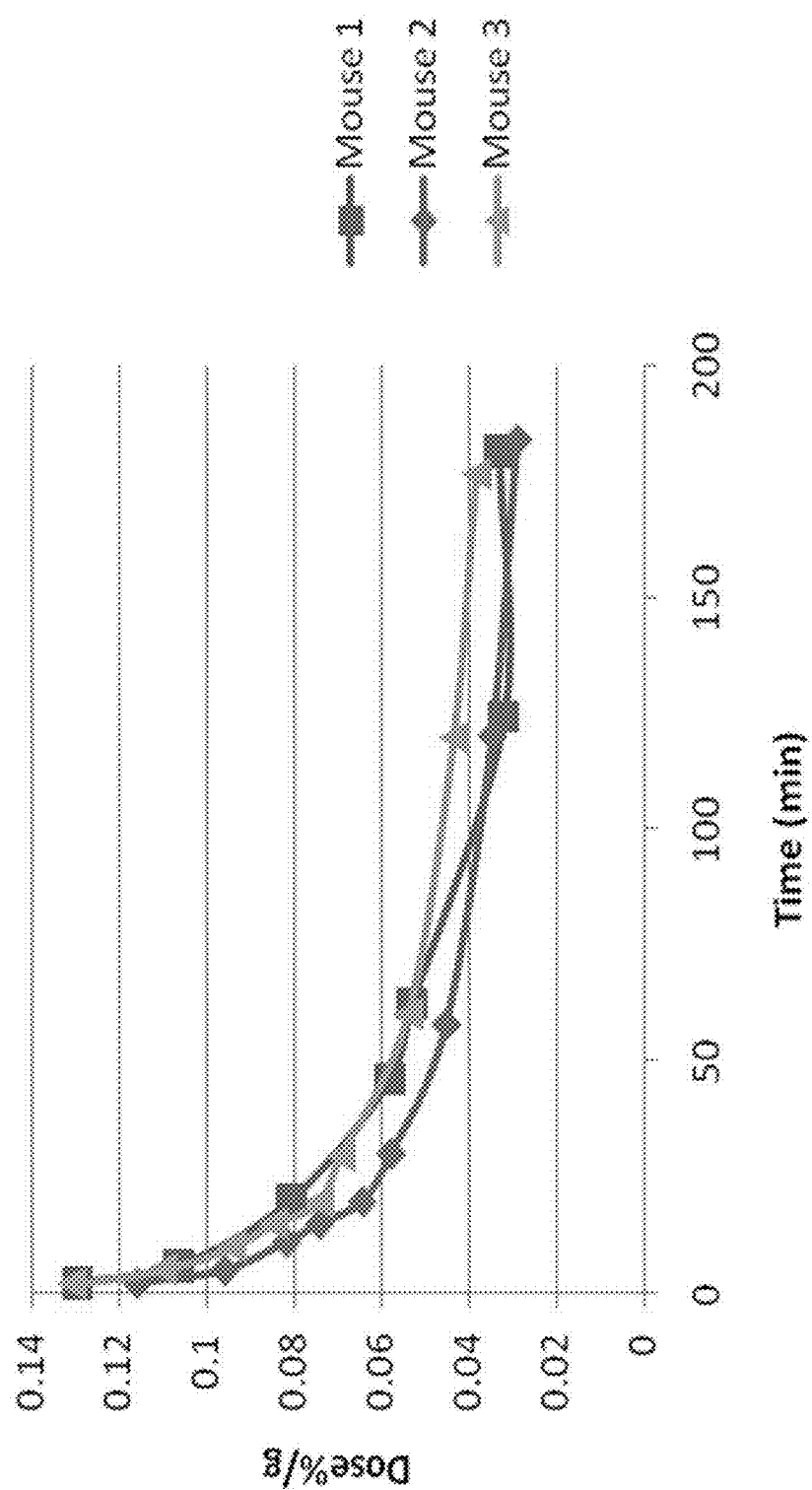
FIG. 8 depicts a graph showing the pharmacokinetics (PK) of the $^{99m}$Tc-labeled monomeric construct.
Figure 9:
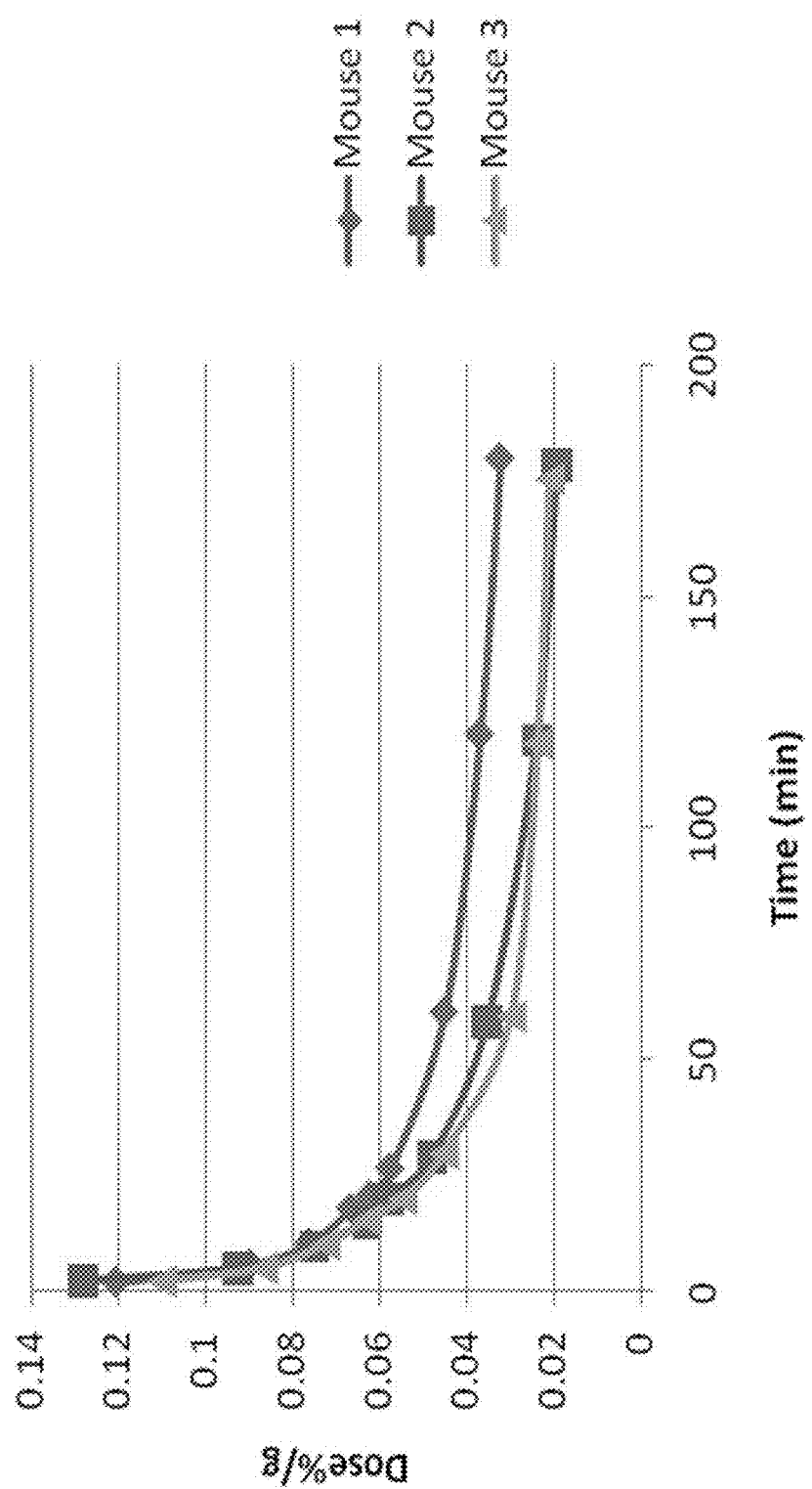
FIG. 9 depicts a graph showing the pharmacokinetics (PK) of the $^{99m}$Tc-labeled tetrameric construct.

The pharmacokinetics of the $^{99m}$Tc-monomeric (FIG. 8) and the 4-arm tetrameric (FIG. 9) constructs were studied in mice. The experiments were performed in triplicate. The monomeric construct exhibited an alpha and beta elimination rates of 8.4±1.5 min and 174.3±26.2 min, respectively. On the other hand, the 4-arm tetrameric construct exhibited an alpha and beta elimination rates of 5.0±1.9 and 124.7±41.1 min, respectively. As expected, the alpha and beta elimination rates of the monomeric construct were longer. The substantially longer distribution and clearance half-lives of the monomer most likely reflect the known protein binding effects that were overcome in the tetrameric agent.

Example 9. Biodistribution of the Monomeric and Tetrameric Constructs

Figure 10:
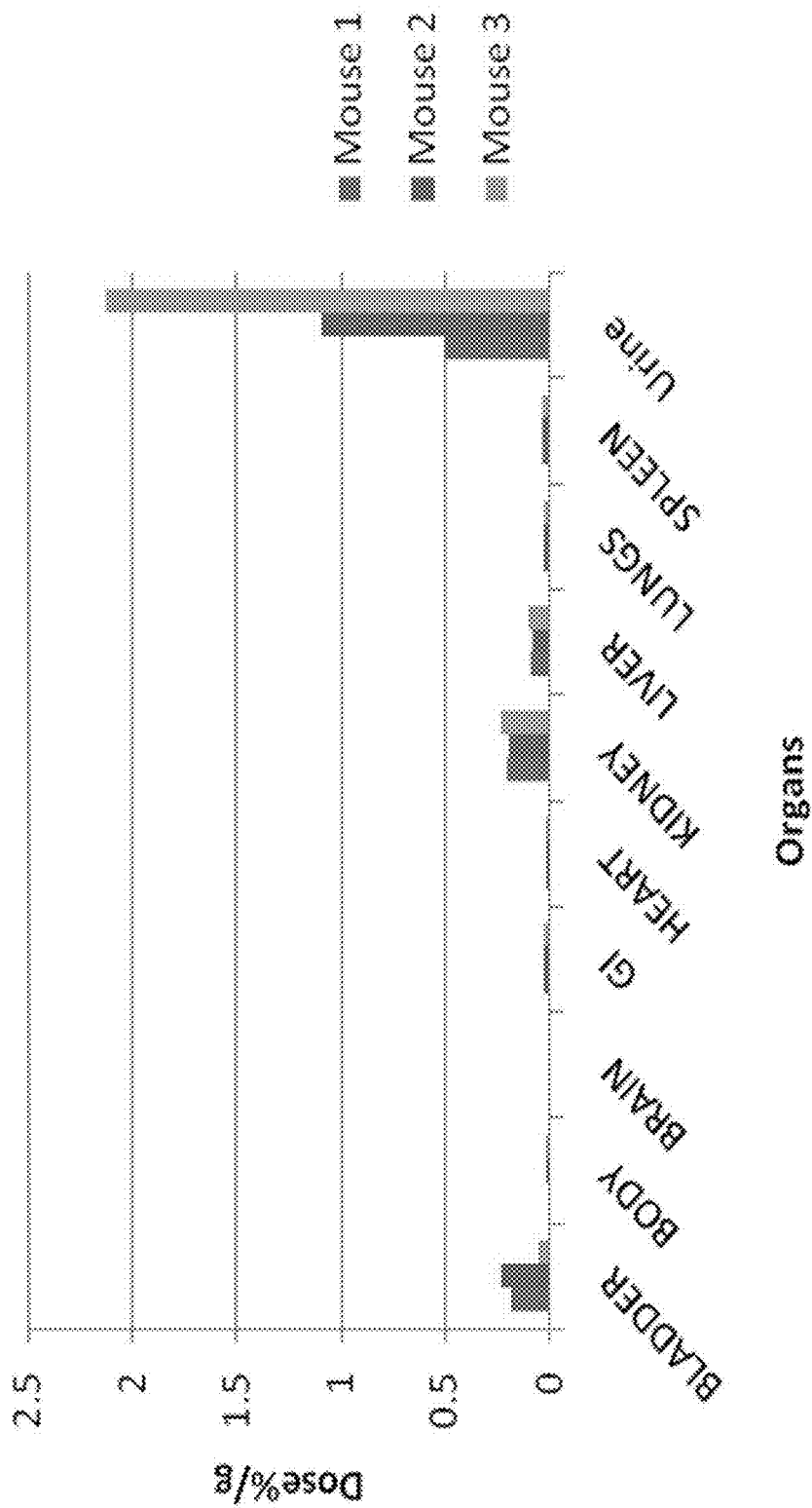
FIG. 10 depicts a bar graph showing the biodistribution of the $^{99m}$Tc-monomeric construct.
Figure 11:
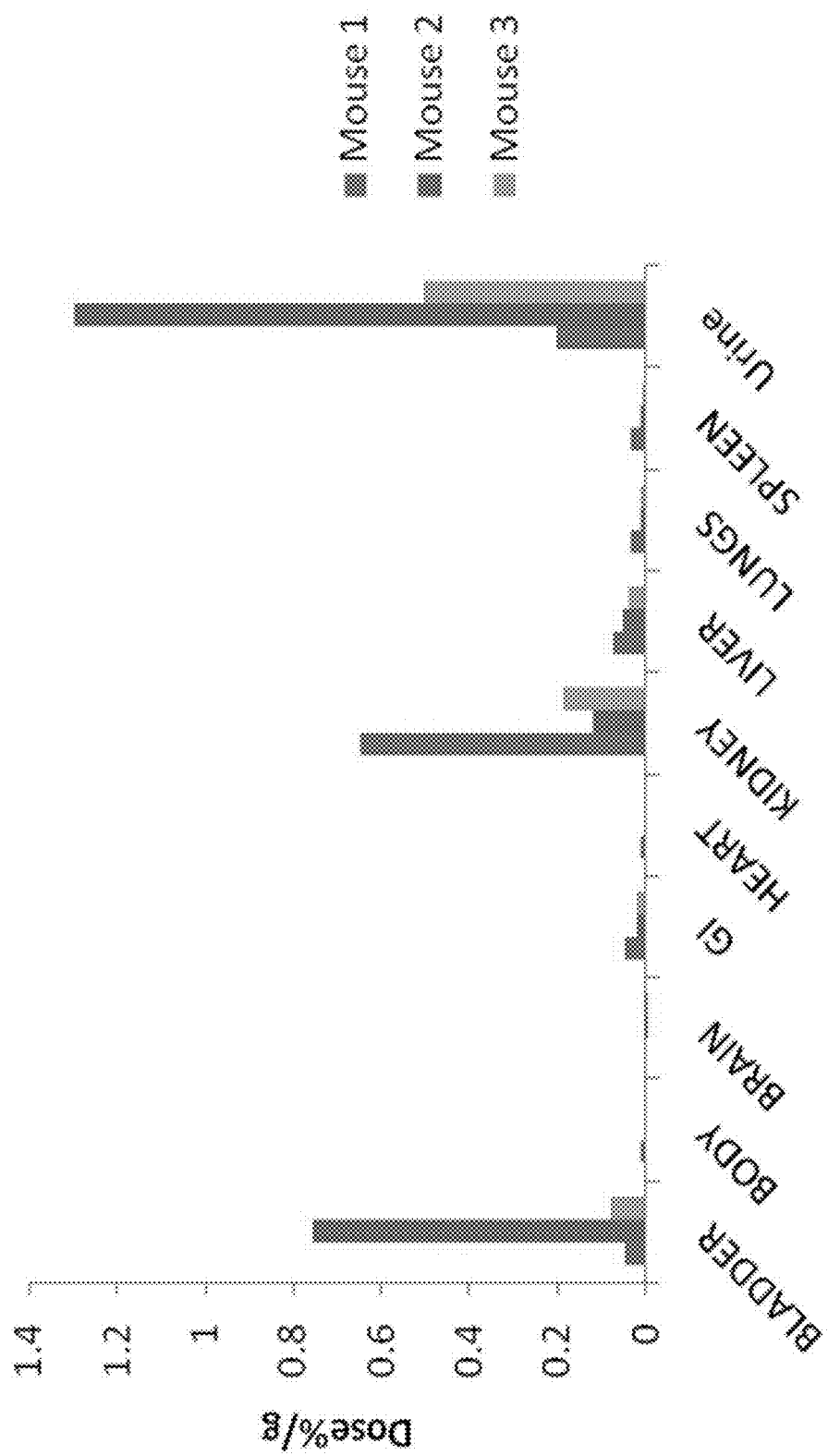
FIG. 11 depicts a bar graph showing the biodistribution of the $^{99m}$Tc-tetrameric construct.

Biodistribution studies of the $^{99m}$Tc-monomeric and the 4-arm tetrameric constructs were assessed three hours after intravenous injection. The results show that the bioelimination of both nuclear agents was through a renal mechanism, with label appearing mostly in the urine and bladder and to a lesser extent in the kidney (FIGS. 10 and 11).

The combination of rapid blood pool clearance of the $^{99m}$Tc-4-arm construct described in Example 9, and the low liver and spleen accumulation shown in this example suggest that the background noise when the construct is imaged will be minimal. In contradistinction, the background blood pool signal of the $^{99m}$Tc-monomeric construct suggests that the background noise will be substantially higher, especially considering that all of the cardiac blood output is passing through the pump, making detection of early or small thrombus more difficult, as fibrin counts are masked by label associated with circulating plasma proteins. Moreover, waiting for blood pool signal to decay further makes the procedure more time-consuming to perform on these sick patients as well as allowing the short nuclear half-life to decay further.

Example 10. In Vivo Targeting of the $^{99m}$Tc-4-Arm Construct

In vivo targeting of the $^{99m}$Tc-4-arm construct was performed in mice. A carotid thrombus was introduced using the Rose Bengal method. In short, the mice were anesthetized with an I.P. cocktail (0.1 cc/20 g), an incision was made and lidocaine was applied. The mouse skin and muscle was held back with retractors and the right carotid artery was isolated. Two sutures were threaded under the carotid artery to lift the artery and separate it from surrounding muscle. The artery was then cleaned of fat and excess muscle if necessary. An ultrasound probe was placed onto the artery.

The prepared mice were administered 60 µg/g body weight by tail vein injection of a 20 mg/ml solution of Rose Bengal dye dissolved in normal saline. The singlet oxygen was generated by the photoactivation of the dye using a HeNe laser 540 nm at 1.5 mW applied to the artery distal to the probe, and moved every 15 minutes to avoid total occlusion of the artery. Laser illumination induced clots in the vessels at the site of illumination. A reduction of blood flow rate was detected, indicating the formation of clots in the vessel.

Figure 12:
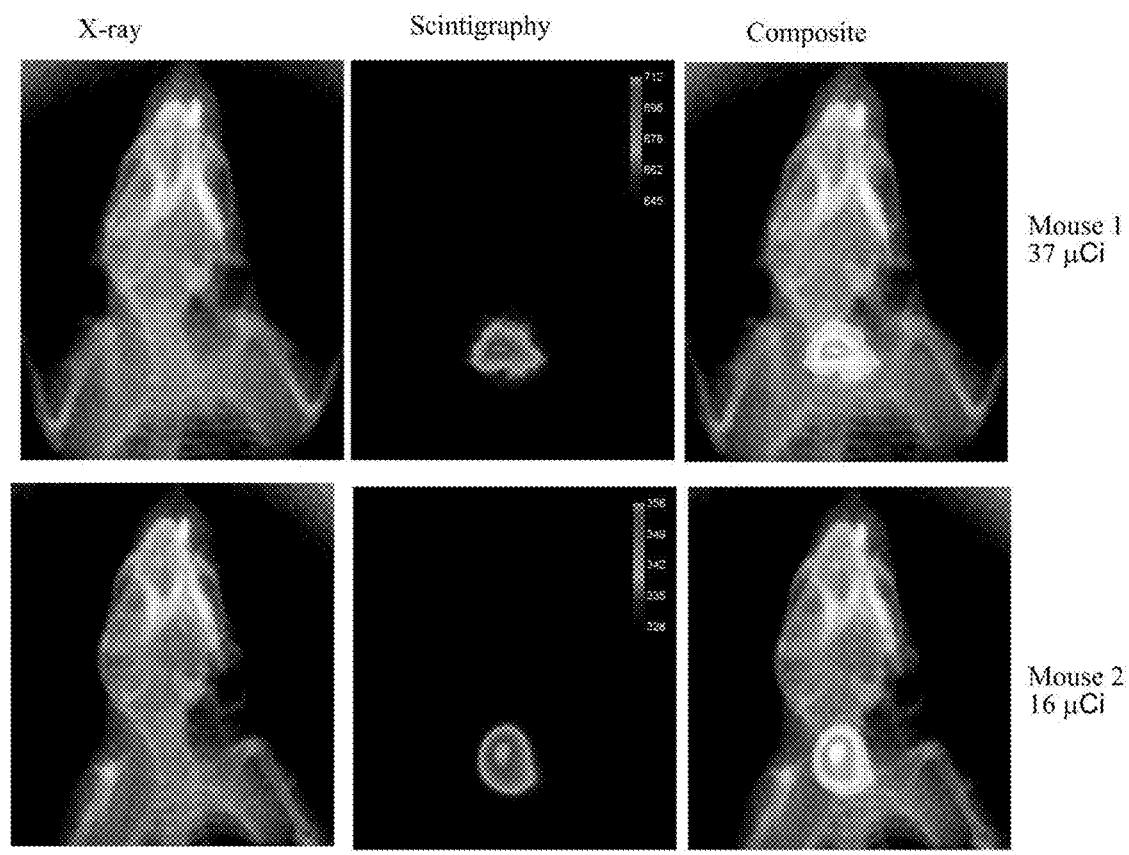
FIG. 12 depicts scintigraphy images of carotid clot targeted with the $^{99m}$Tc-tetrameric construct.
Figure 13:
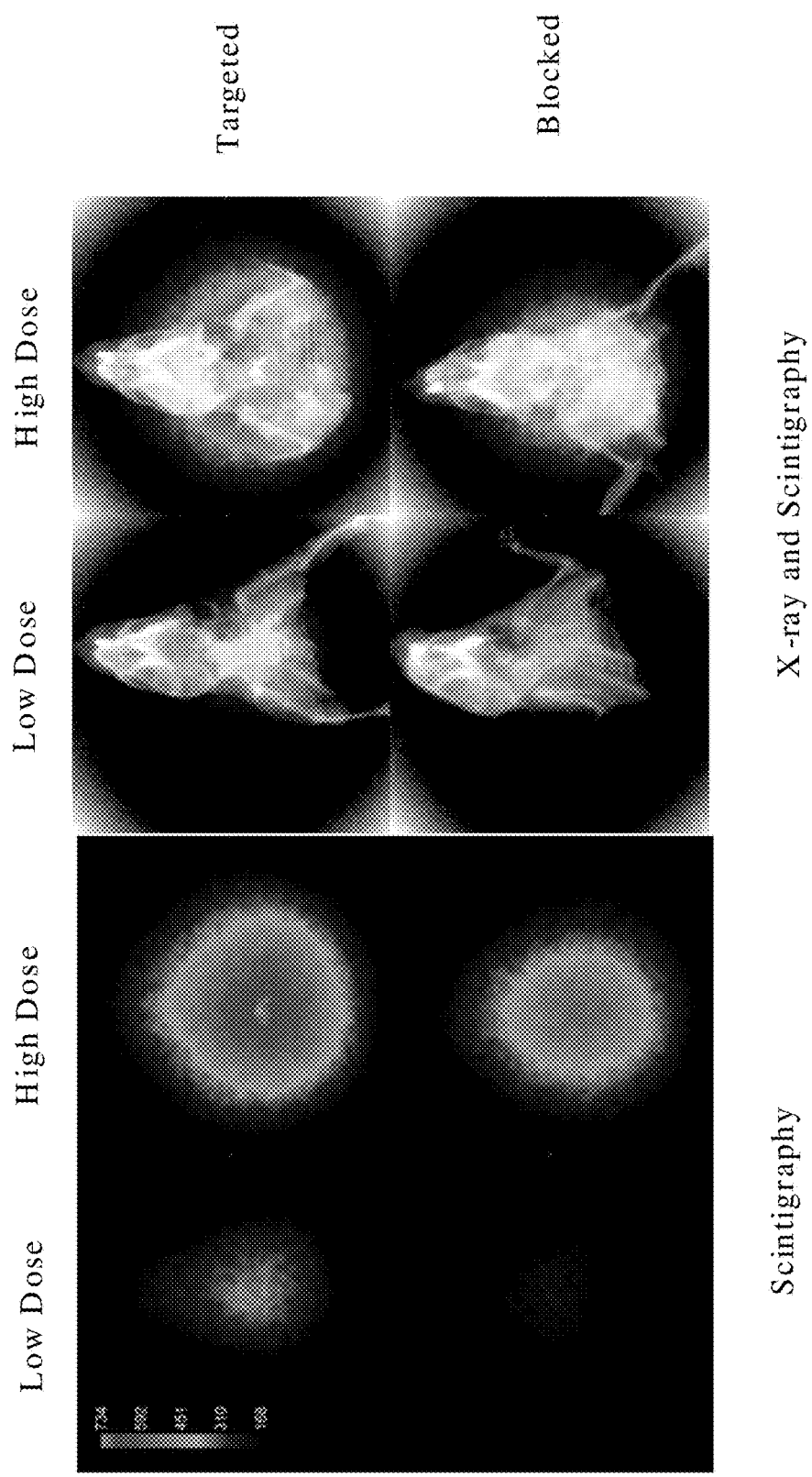
FIG. 13 depicts postmortem scintigraphy images of a blocked carotid targeted with the $^{99m}$Tc-tetrameric construct.

After clot formation, the $^{99m}$Tc-4-arm construct was administered intravenously, and allowed to circulate for 2 hours before imaging. For imaging, animals were euthanized and imaged using a nanoSPECT scanner. As shown in FIG. 12 and FIG. 13, targeting of the $^{99m}$Tc signal to the carotid clot was specific, and was obtained in every animal tested. These minute thrombi created in vivo were not uniform and much smaller than the in vitro clots studied, yet, the signal obtained in every animal tested was clear and positive.

In vivo competition assays were also performed by administering into labeled mice a competitive dosage of the unlabeled 4-arm construct. Unlabeled construct was only able to competitively reduce 30 to 50% of the signal.

Example 11. An ICAM-Targeted Tetramer for Imaging Based Diagnosis of Pathological Inflammation in Neurological Disease Although $^{99m}$Tc-F4A was conceived specifically for intraLVAD clot imaging, the general construct makes it highly suitable for any vascularly accessible target using ligands up to 4,000 daltons (e.g., small proteins). The preference is for ligands less than 2000 daltons. For peptides these may be cyclic as the fibrin example or linear, which is simpler to synthesize. Peptidomimetics and other molecules with appropriate binding selectivity and affinity maybe used.

A $^{99m}$Tc or other radiolabeled tetrameric agent homing to ICAM and appropriate control construct via a peptide specific for the receptor is synthesized analogous to methods described above and injected iv into a rodent following mild, repetitive traumatic brain injury induced by percussion or alternative means as practiced commonly by scientific practitioners of this research, three days following the initial injury. The agent is given at a suitable dose (e.g., 32 uCi) and allowed to circulate. Serial imaging of the brain performed with a nanoSPECT/CT or nanoPET/CT is performed every hour for three hours. Initial scan shows increased nuclear signal in the midbrain of the animals receiving the ICAM level with background blood born signal. Serial scans over the next two hours shows increasing signal to noise within the tissue as the background noise in circulating blood continuously decreases through renal clearance. The non-targeted control shows signal homogeneously and similar throughout the brain, proportional to regional bloodflow expectations, that decreases with successive imaging as the bioelimination continues.

The experiment above conducted using a tetrameric agent modified to deliver up to 8 gadolinium atoms per binding event to the ICAM receptor, induced by mild traumatic brain injury as described above. Following a pretreatment baseline scan set and injection of currently approved gadolinium dose for MRI (no more than 0.07 and 0.1 mmol/kg) in animals without renal disease (Creatinine clearance less than 30 ml/min/1.73 m$^2$) serial T1w MRI scans are performed over the following 3 hour time frame with the first post injection scan obtained 60 minutes post injection. Negligible MR contrast is appreciated in the circulating blood or as enhanced tissue contrast. The brain signature reveals increasing contrast in the midbrain on day 3 following injury. The signal intensity normalized by a gadolinium control reference within the imaging field of view of each acquisition shows increasing intensity overtime, which appears to plateau by 3 hours. The control agent reveals minimal change in brain tissue signal. The signal observed in the control is unorganized, diffuse versus focal, and most consistent with imaging noise.

The experiment above in the preceding paragraph which the nuclear tetrameric agent is modified to deliver an anti-inflammatory drug, such as a steroid, which is attached to one arm of the construct through an intracellular labile linker. The compound is given to animals following mild traumatic brain injury as described above. The multimeric ICAM peptide accumulates in the injured regions of the brain parenchyma via a transcytosis mechanism. The anti-inflammatory drug is delivered into the injured area and dissociated from the tetrameric construct by intracellular and or extracellular enzymes resident injured regions, such as peptidases, which were expelled by necrosing brain cells. The serial administration of this construct over the following 2 week period shows diminishing uptake of ICAM homing agent coincident with resolving behavioral subjective and other objective measures of traumatic brain injury.

The experiments above wherein the pathology is a cancerous tissue, such as breast cancer, and the ICAM-homing agent is used for detecting the inflammation associated with the lesions as well as for transporting and concentrating a chemotherapeutic agent from blood into the tumor cells themselves or into the surrounding extracellular tumor matrix, where the drug is liberated from the homing agent by peptidase excision of an appropriately designed linker. Serial imaging and drug delivery show the tumor uptake of the dual imaging and therapeutic construct decreases with time consistent with decreased tumor viability and diminishing resulting inflammation.

The experiment in the preceding paragraph wherein the radionuclide selected has both imaging and therapeutic utility, such as $^{186/188}$Re. Delivery of the therapeutic/diagnostic ICAM-targeted homing agent in a preclinical rodent model reveals the rapid uptake of construct, which results in killing of the tumor cells. Increased inflammation associated with tumor killing leads to continued Rhenium delivery with serial treatments. Eventually, destruction of the tumor through local beta emission leads to subsiding inflammation and no further or highly diminishing ICAM-mediated uptake is appreciated in the lesion, consistent with tumor radioablation.

Introduction for Examples 12-18

Heart failure annually affects over five million Americans of all ages, both sexes, and all races.[1] Patients with severe heart failure that is refractory to medical therapy have limited options including: 1) heart transplantation, but only 2,200 donor hearts are available annually, 2) a mechanical circulatory assist pump, such as a left ventricular assist device (LVAD), or 3) hospice care with death typically transpiring within 6 months.[2,3]

Surgically implantable LVADs have evolved from large pulsatile room filling instruments to small implantable continuous flow devices (FIG. 17).[4,5] The reduced size and power requirements of today's continuous-flow pumps have allowed LVADs to become a therapeutic option for patients with refractory HF, whether as a bridge-to-transplantation (BTT), long-term destination-therapy (DT), or bridge-to-recovery (BTR).[3] While LVAD placement offers considerable hope and benefit to many patients with severe HF, their successful clinical implementation requires management of well-known complications: 1) gastrointestinal bleeding (GIB) due to platelet dysfunction secondary to the high shear effects,[6] 2) bacterial infections along the percutaneous driveline to the pump, 3) intra-pump thrombosis and 4) stroke.[7,8] In terms of hospital readmissions, bleeding, infection, and thrombosis were 30%, 22%, and 14%, respectively, in one recent retrospective study.[7] While GI bleeding and infection can readily be diagnosed and medically addressed, the early diagnosis of intra-pump thrombosis remains a severe medical management barrier.[9-16]

Successful outcomes require careful management of anti-coagulation and the complex interplay between bleeding and prevention of intrapump thrombus. Today intra-pump thrombus cannot be directly diagnosed but only inferred from nonspecific evidence such as markedly elevated serum lactic dehydrogenase levels (LDH) reflecting increased erythrocyte hemolysis, variations in LVAD pump speed or power readouts, or echocardiographic Doppler estimates of inappropriate differential blood flow with varying pump speed settings. Although catastrophic LVAD pump failure due to thrombus may be acutely obvious, these suggestive markers of pump thrombosis are late findings often coincident with other clinical indicators, such as thromboembolism and stroke.[12] Early detection of intrapump thrombus may allow for intensification of anticoagulation therapies and prevention of pump thrombosis, which can only be treated by surgical pump exchange, which carries a high morbidity and mortality (50%) risk. Without a sensitive metric for early intrapump thrombus accumulation, multi-center efforts to lower anticoagulation goals to minimize bleeding complications resulted in a tripled incidence of pump thrombosis.[9]

Direct diagnosis and quantification of intrapump thrombus with imaging is very challenging. The titanium LVAD housing precludes the use of MRI, CT, or ultrasound and favors a nuclear medicine approach. The continuous flow rotor of a continuous flow LVAD, such as the Heartmate II (Thoratec Pleasanton, Calif.), spin at 8-10,000 RPM to provide adequate systemic perfusion. To bind thrombus under these high-shear and high blood flow conditions requires a probe with both high specificity and avidity. Although normal thrombus is comprised of platelets, erythrocytes, and other blood elements entrapped in a dense fibrin network, LVAD thrombus is essentially devoid of cellular components. Furthermore, long-standing pump thrombus is often a dense fibrin concretion with rings of accumulation mimicking the growth rings of a tree trunk. In addition, to recognize small clot accumulation in the pump, persistent radioactive background noise from probe retention in blood passing through the pump or its accumulation in the liver, spleen or lungs must be minimized. The objective of this project was to design and demonstrate a translatable fibrin specific $^{99m}$Tc probe that meets these stringent criteria.

Example 12. Synthesis of Monomeric (F1A) and Tetrameric (F4A) Fibrin Probes

Figure 18A:
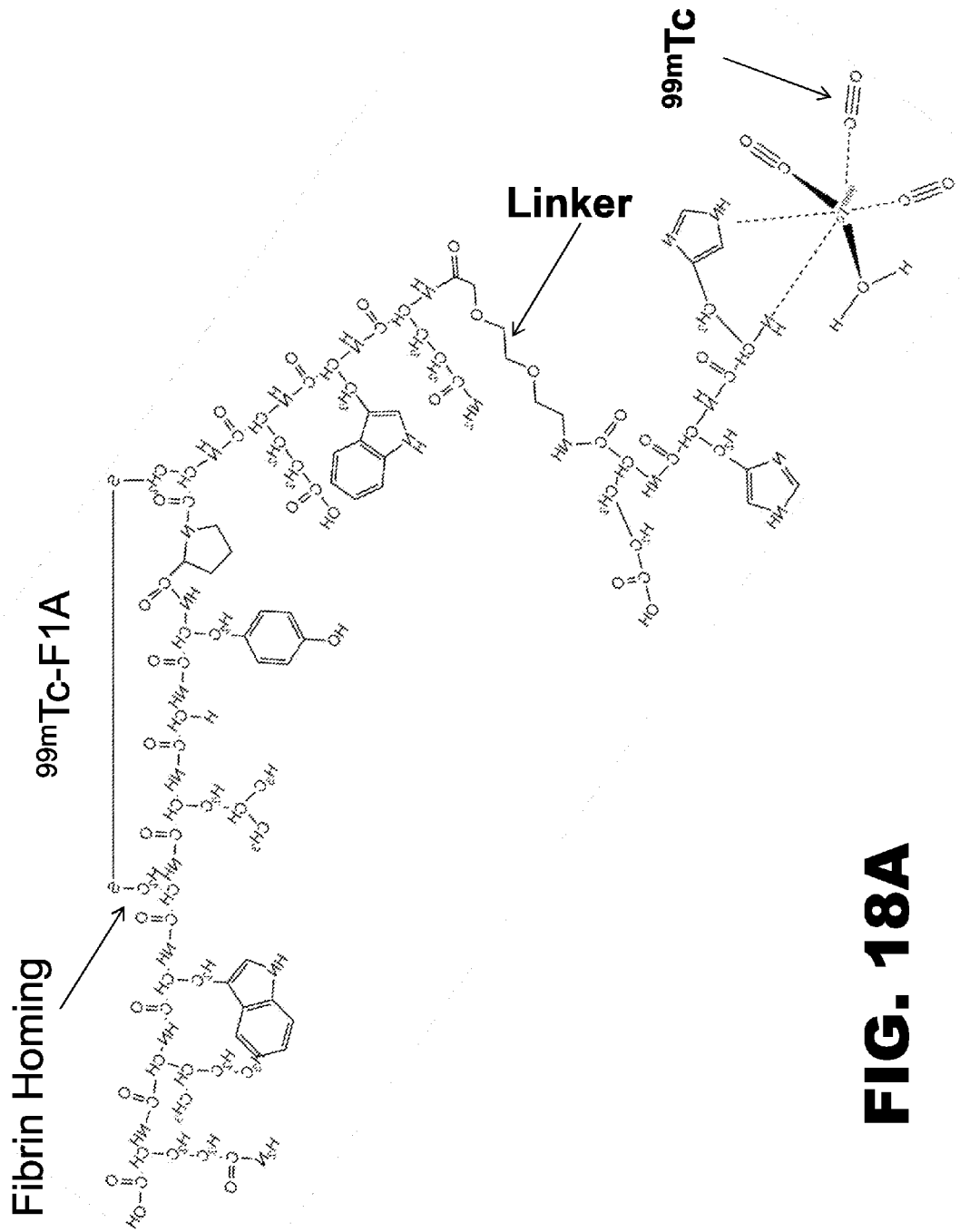
FIG. 18 depicts monomeric and tetrameric homing agent structures. (A)$^{99m}$Tc-F1A bifunctional monomer depicting cyclic homing sequence, short spacer, and $^{99m}$Tc chelating site. (B)$^{99m}$Tc-F4A is a tetramer created by the balanced cross-linking of the 4 F1A monomers with PEG$_{2000}$. Each arm of the tetramer is depicted as a monomer in (A). (C,D,E,F) Depict each arm of the 4-arm tetrameric fibrin-binding construct.
Figure 18B:
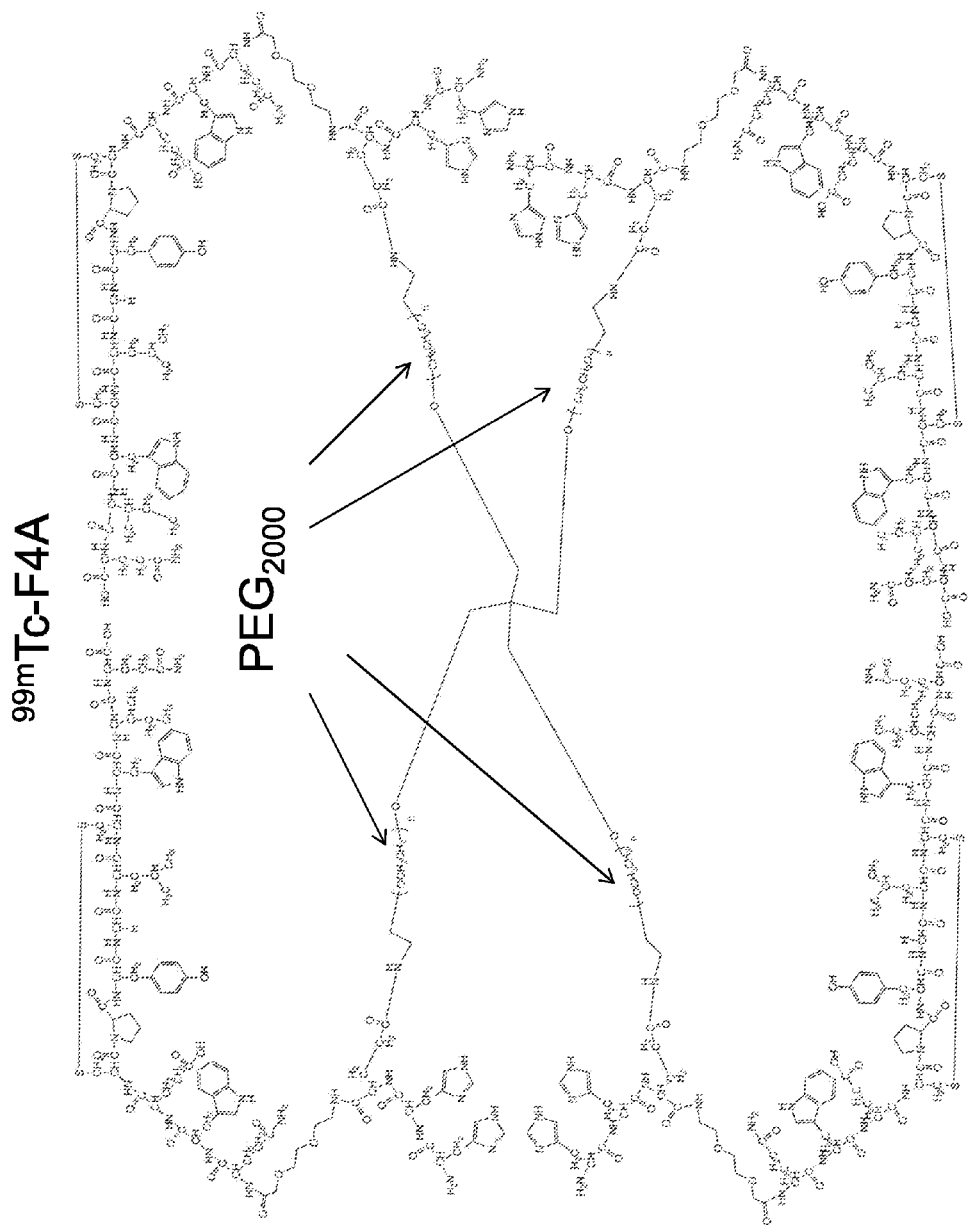
Figure 18C:
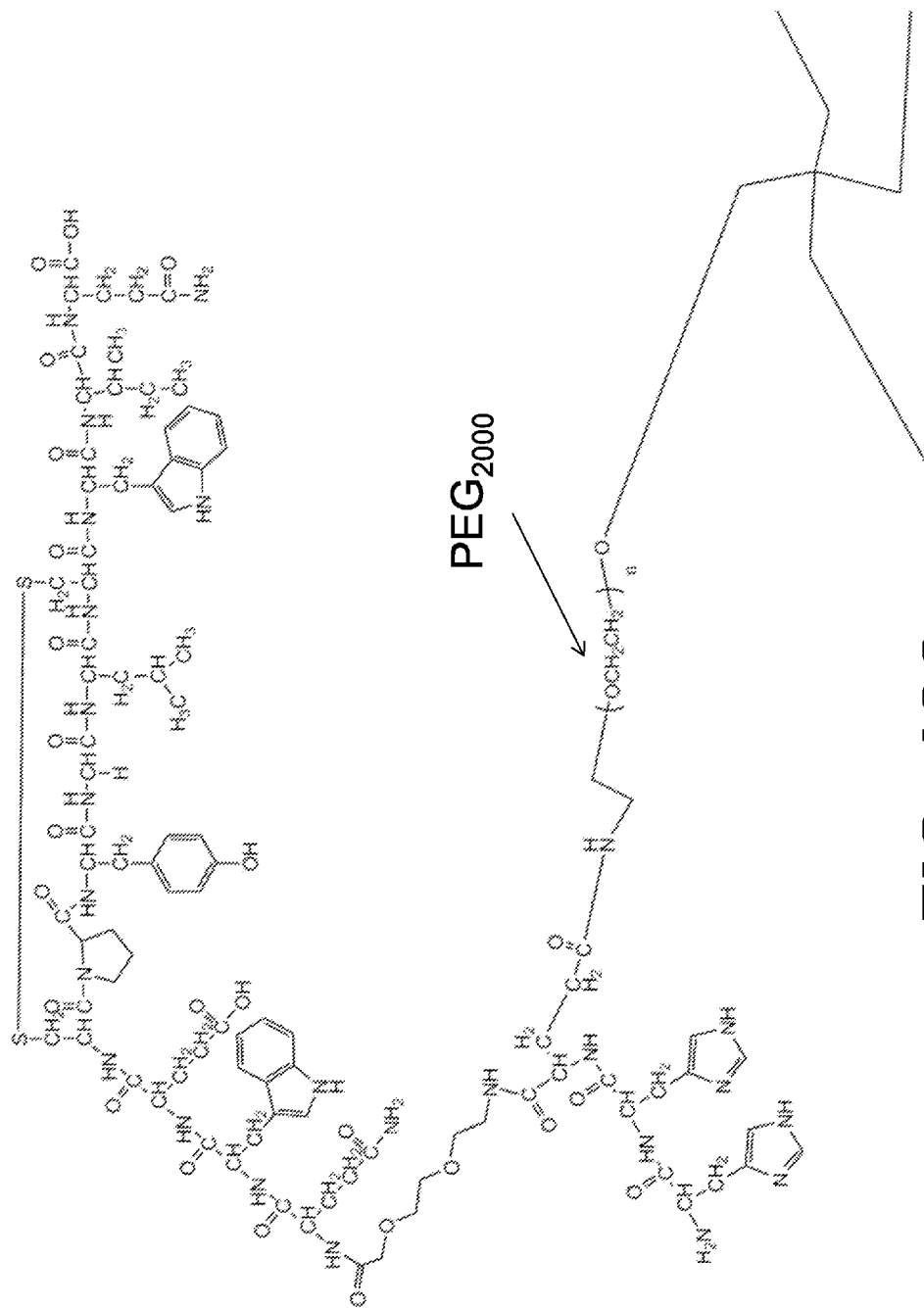
Figure 18D:
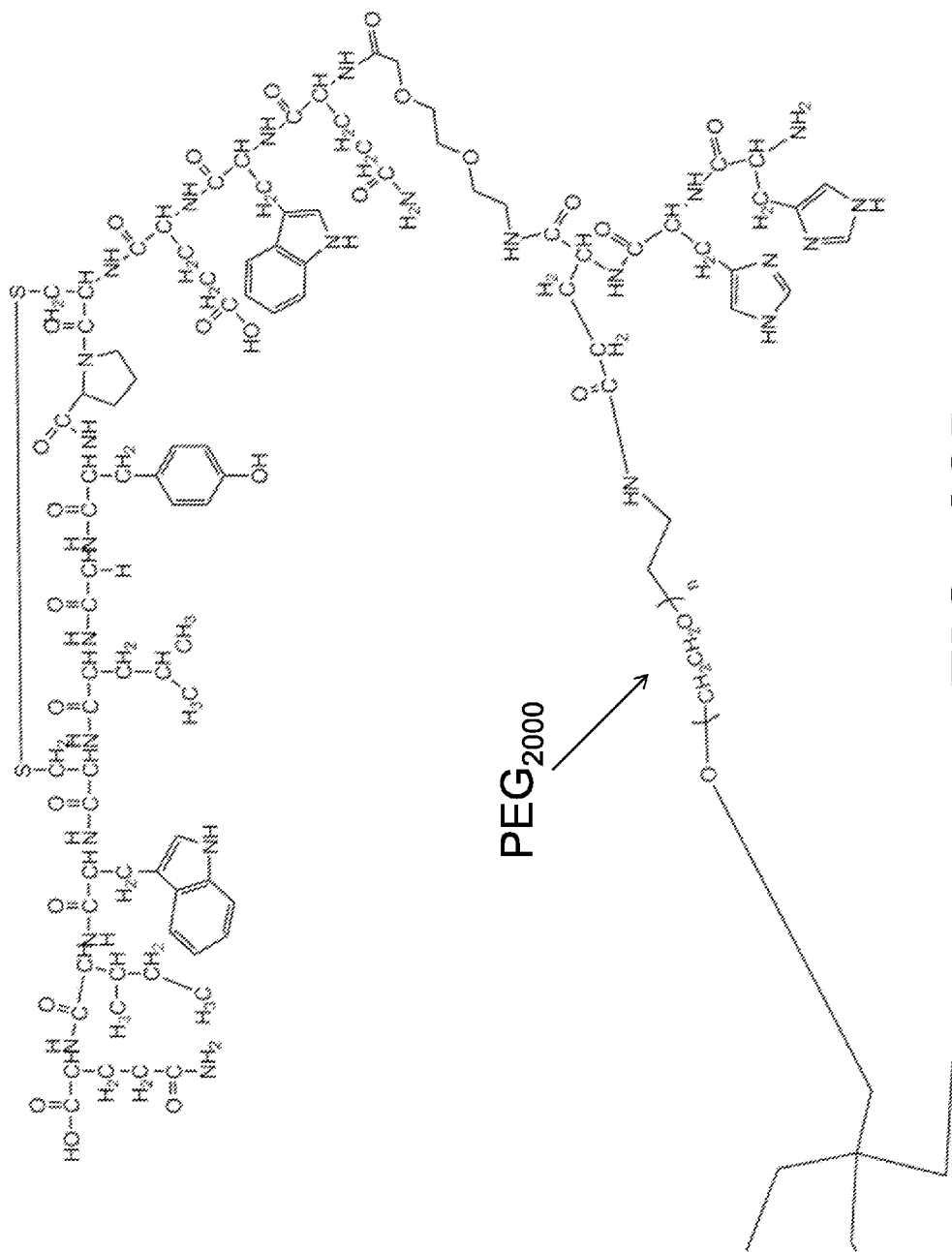
Figure 18E:
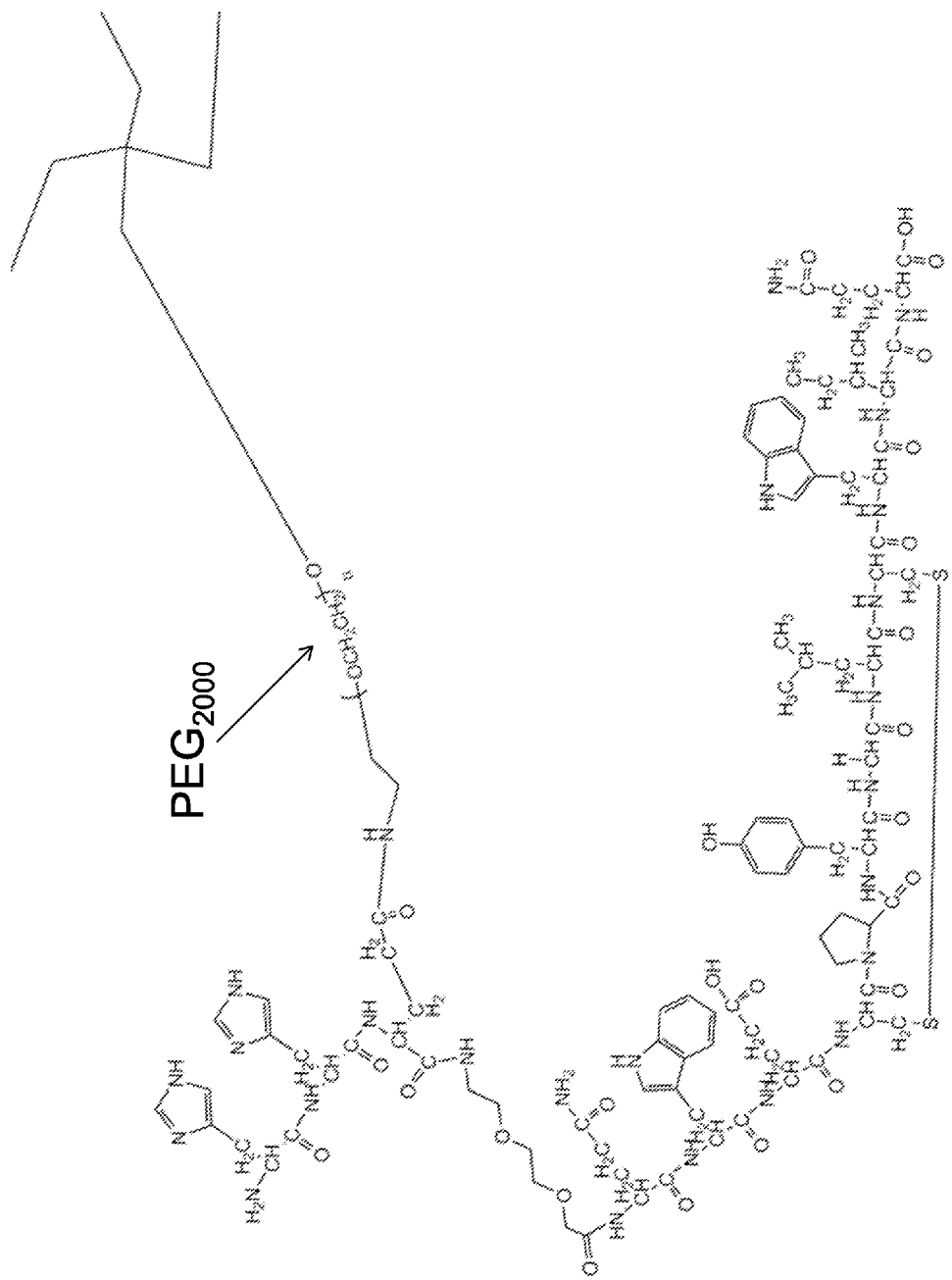

From the outset, we understood that intrapump thrombus imaging would require a very high affinity probe to bind and stay on the clot under the high-flow high-shear conditions within the device. Building upon the best peptide sequence for fibrin available,[17] which was derived by phage display techniques, a bifunctional reference monomeric unit (F1A, 1-arm) was designed and synthesized. A very close variant of the core fibrin-binding sequence was used as an MRI probe that was abandoned from further clinical development due to poor performance.[17] F1A was comprised of the fibrin-specific homing peptide (SEQ ID NO:1—QWECPYGLCWIQ) interconnected through a PEG$_2$ spacer to a technetium chelating amino acid sequence (HHE) was prepared (FIG. 18A). To achieve the higher avidity and affinity anticipated for this application, a tetramer of PEG$_{2000}$ was used to intercouple four F1A monomers into F4A (4-arm) (FIG. 18B). F1A and F4A were radiolabeled with $^{99m}$Tc using an IsoLink kit (Center for Radiopharmaceutical Sciences of PSI, ETH and USZ, Paul Scherrer Institute, Switzerland) with 90 to 95% radiochemical purity to form $^{99m}$Tc-F1A and $^{99m}$Tc-F4A, respectively.

Figure 19:
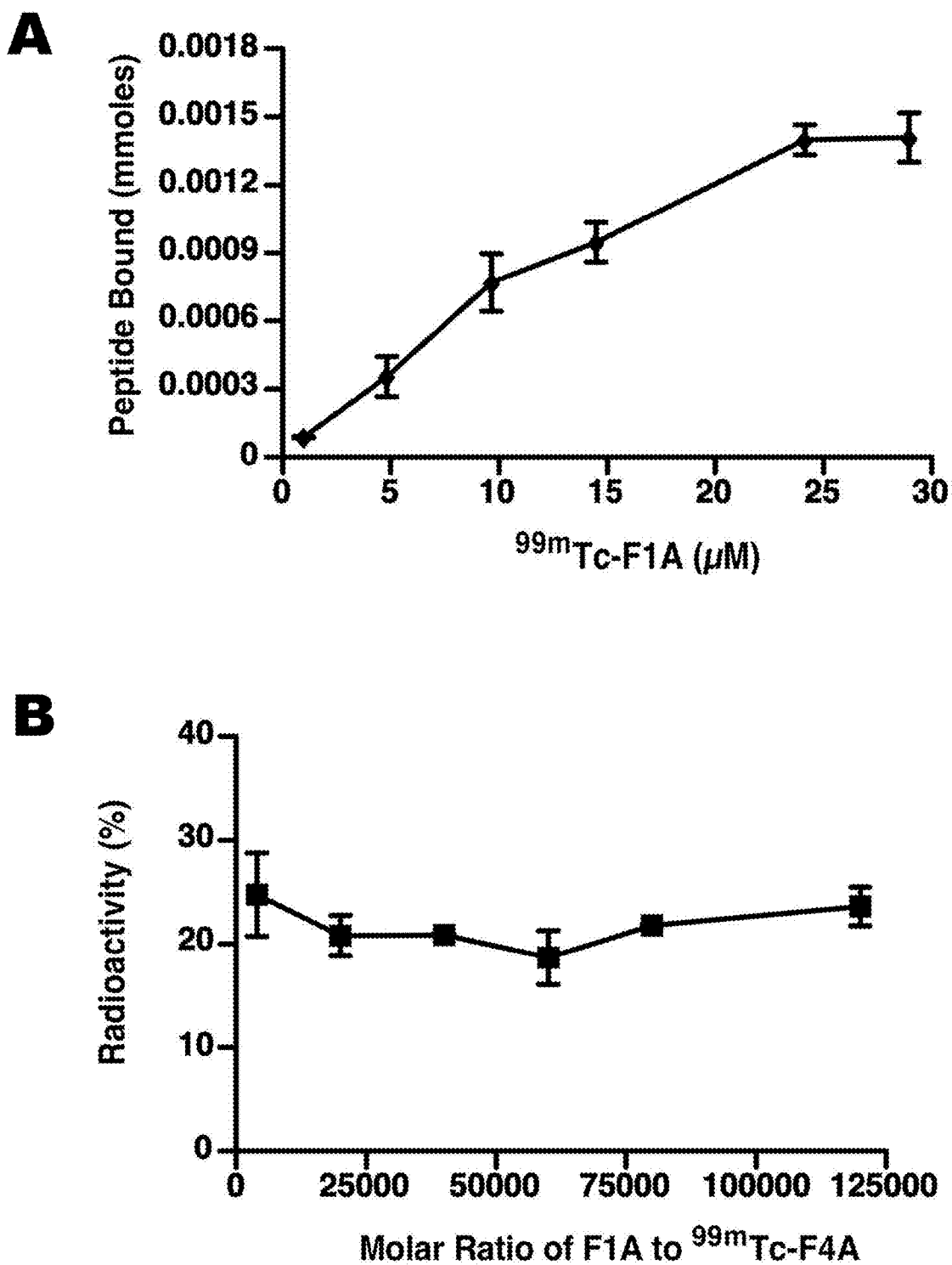
FIG. 19 depicts graph showing $^{99m}$TcF1A and $^{99m}$Tc-F4A fibrin affinity, radiolabel stability, plasma interference and nuclear signal attenuation due to titanium LVAD housing. (A) Titrated dosages of $^{99m}$Tc-F1A bound to uniform fibrin clot in PBS. The dissociation constant ((K$_d$~10.2 µM) was adjusted for decay and estimated using the Hill slope model, Y=Bmax*X$^h$/(Kd$^h$+X$^h$) three times independently (±s.e.m.). Total fibrin concentration was estimated from plasma fibrinogen (0.735 nmoles per clot). (B) The percentage of $^{99m}$Tc-F4A bound to each clot in the presence of unlabeled F1A (monomer) at molar ratios up to 120,000 to 1. $^{99m}$Tc-F1A (C) and $^{99m}$Tc-F4A (D) were bound to clots in the presence of PBS, PBS and excess cysteine to evaluate $^{99m}$Tc label stability, and in a 50:50 PBS/Plasma mixture to assess potential plasma matrix effects, presented as mean±s.e.m. Both $^{99m}$Tc-F1A and $^{99m}$Tc-F4A bound to fibrin clot phantoms well in PBS and the radio-metal was securely chelated to both probes. However, in plasma the binding of $^{99m}$Tc-F1A to clot was dramatically reduced (p<0.05, n=3/group, ANOVA) whereas $^{99m}$Tc-F4A was unaffected. (E) The attenuation of $^{99m}$Tc-F4A by titanium plate of equivalent quality and thickness (1 mm) to that used to form the housing for HeartMate II titanium was evaluated by titrating the probe radioactivity in triplicate from 20 µCi down to 0.5 µCi. The nuclear signal attenuation from titanium across phantoms was 23%±3% and was independent radioactivity level.
Figure 19:
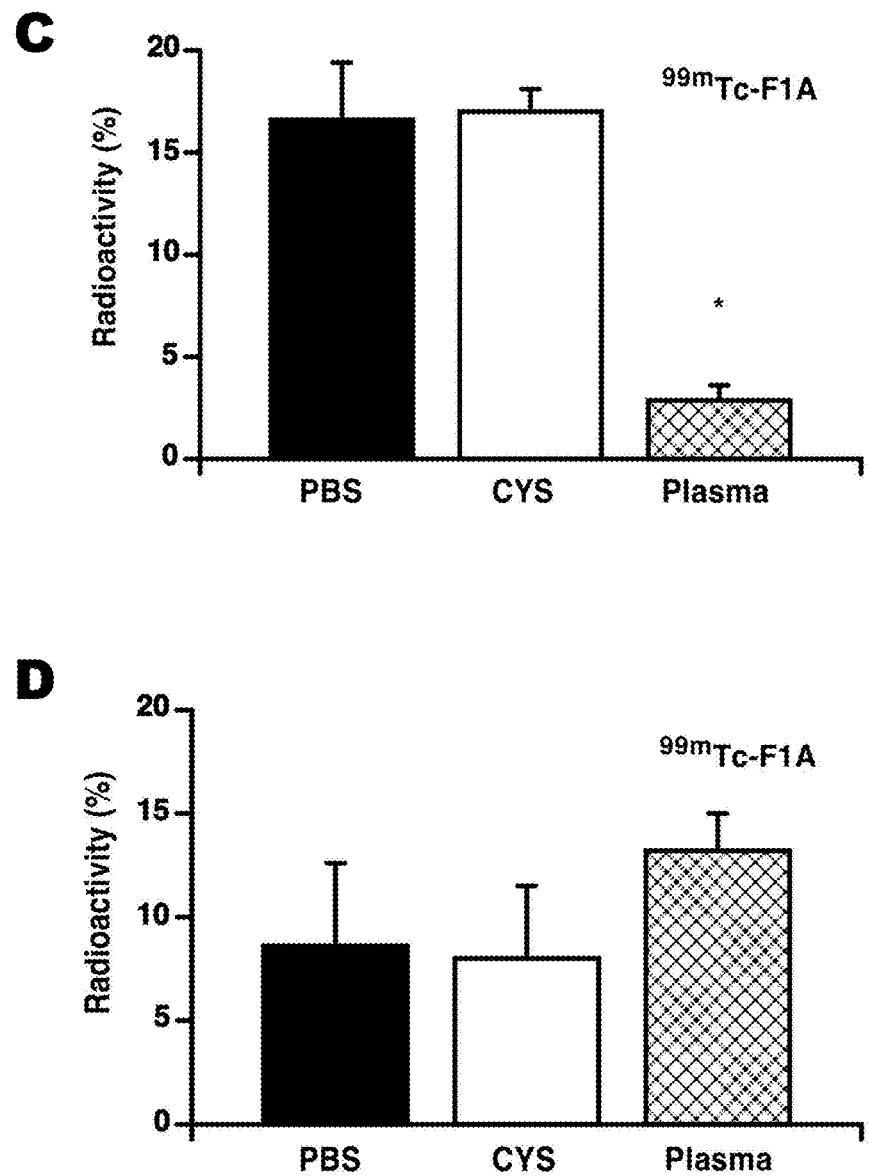

Example 13. $^{99m}$Tc-F1A and $^{99m}$Tc-F4A Fibrin Affinity, Radiolabel Stability, Plasma Interference In these experiments, the binding affinity, radio-stability, and plasma matrix effects of the $^{99m}$Tc-F1A and the new $^{99m}$Tc-F4A probes were characterized. As shown in FIG. 19A, titrated dosages of $^{99m}$Tc-F1A bound to uniform fibrin clots in PBS with good affinity (K$_d$~10.2 µM), which was consistent with the earlier report.[17] By comparison, $^{99m}$Tc-F4A bound with extraordinary affinity and avidity to analogous fibrin targets in PBS. FIG. 19B shows the percentage of $^{99m}$Tc-F4A bound to each clot, which was not displaced despite increasing the relative molar concentration of unlabeled F1A (monomer) up to a ratio of 120,000 to 1.

The radiolabel stability of the $^{99m}$Tc on the F1A and F4A probes was demonstrated when no difference in nuclear signal was detected between $^{99m}$Tc-F1A or $^{99m}$Tc-F4A in PBS versus co-incubation of these agents with excess cysteine (FIG. 19C,D). However, the binding of $^{99m}$Tc-F1A in 50:50 plasma:PBS was severely compromised (p<0.05) compared to its retained clot radioactivity using PBS alone (FIG. 19C). In contradistinction, $^{99m}$Tc-F4A experienced no plasma interference and bound the fibrin clots in PBS and plasma:PBS matrices the same (p>0.05) (FIG. 19D). Plasma interference likely arose from the hydrophobic interactions of the cyclic homing ligand with albumin and could compromise the rapid and specific binding of the probe to LVAD thrombus as well as create higher circulating background radioactivity signal.

Example 14. Nuclear Signal Attenuation Due to Titanium LVAD Housing

Figure 19E:
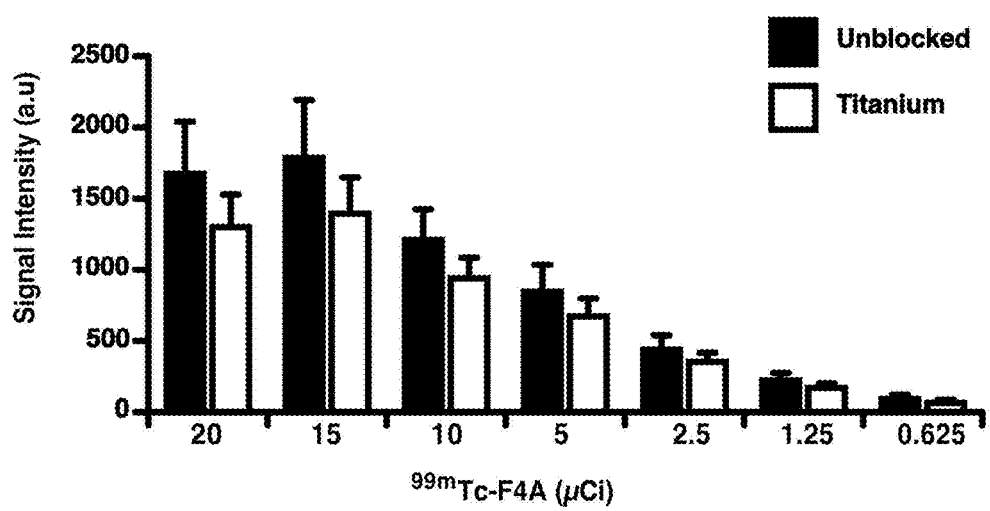

The decision to approach the intrapump thrombus diagnosis problem with a nuclear medicine solution reflected the need for the probe signal to penetrate through the titanium pump housing. The attenuation of Na$^{99m}$TcO$_4$ by a titanium plate of equivalent quality and thickness (1 mm) to that used to form the housing for HeartMate II was evaluated by titrating the isotope concentration from 20 µCi down to 0.5 µCi. Gamma scintigraphy imaging of the phantoms were for 1 min. FIG. 19E presents a histogram of the signals obtained with and without the titanium sheet shielding. Overall, the nuclear signal attenuation from the titanium shielding across phantoms was 23%±3% and attenuation effect was independent of the level of radioactivity. Clearly, the influence of signal attenuation due to the titanium housing, although present, was relatively minor and uniform, permitting both the high sensitivity and quantitative imaging of minute levels of intrapump fibrin that are required to detect early pump thrombus.

Figure 17:
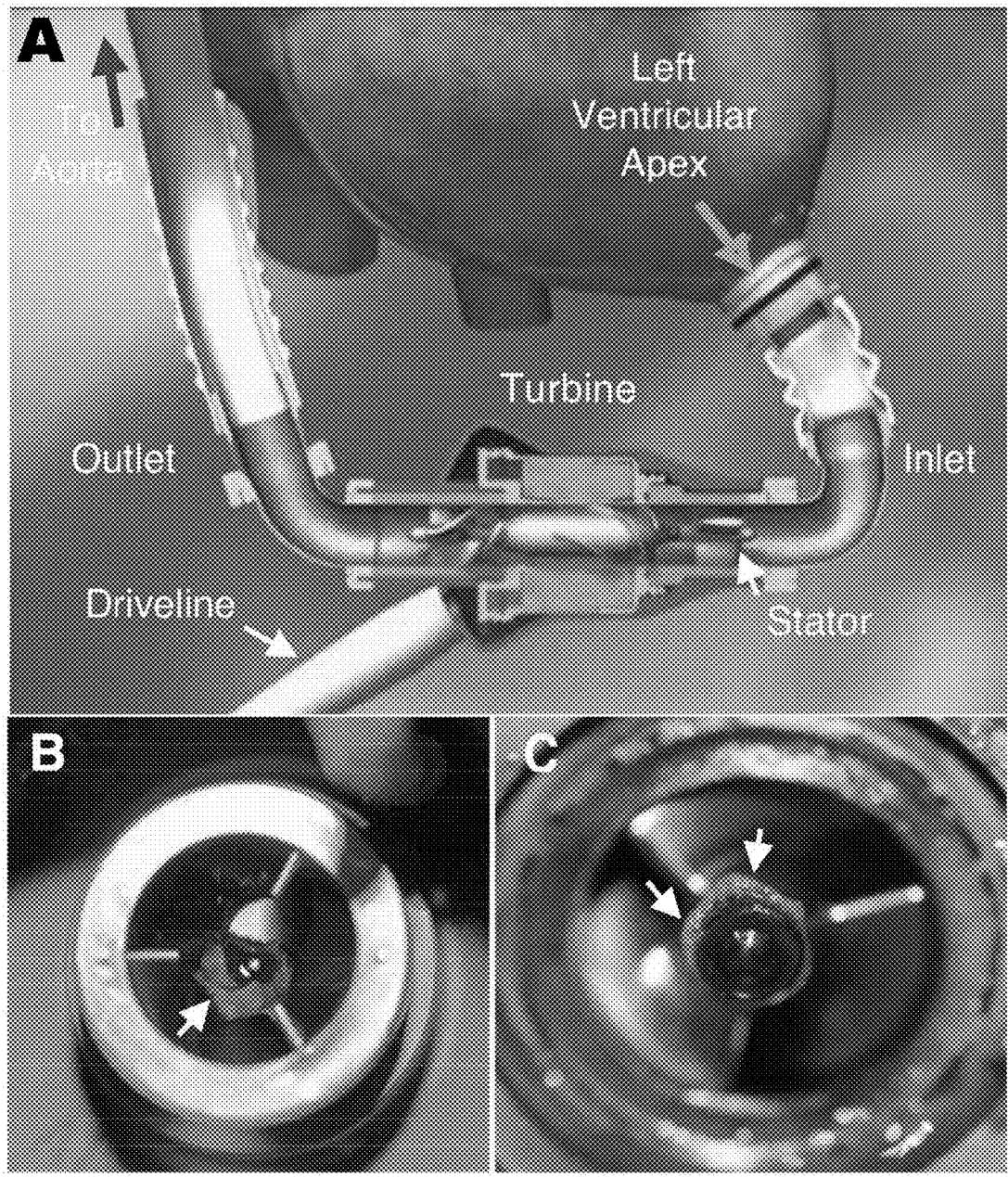
FIG. 17 depicts images of a HeartMate II left ventricular assist device. (A) Diagrammatic representation of a HeartMate II left ventricular assist device (LVAD) depicting its small size relative to the heart. Blood (red arrow) is drawn into the pump through a cannula, which penetrates the ventricular apex. Blood flows by the stator through the turbine, which rotates at up to 10,000 RPM producing blood throughput of 6 L/min. The pump is powered by an externalized driveline cable that connects to the device on the outlet side of the LVAD. Blood is returned to systemic circulation through the outlet cannula, which extends to and penetrates into the aortic arch. (B) Small residual intraLVAD thrombus on inlet stator and around bearing (C) from a patient admitted with elevated lactate dehydrogenase (LDH) (1300's) after symptomatic hemorrhagic/embolic stroke due to a suspected pump thrombosis. White arrows point to residual thrombus. LVAD Image is copyright protected by Thoratec, Inc and used as modified with permission.
Figure 20:
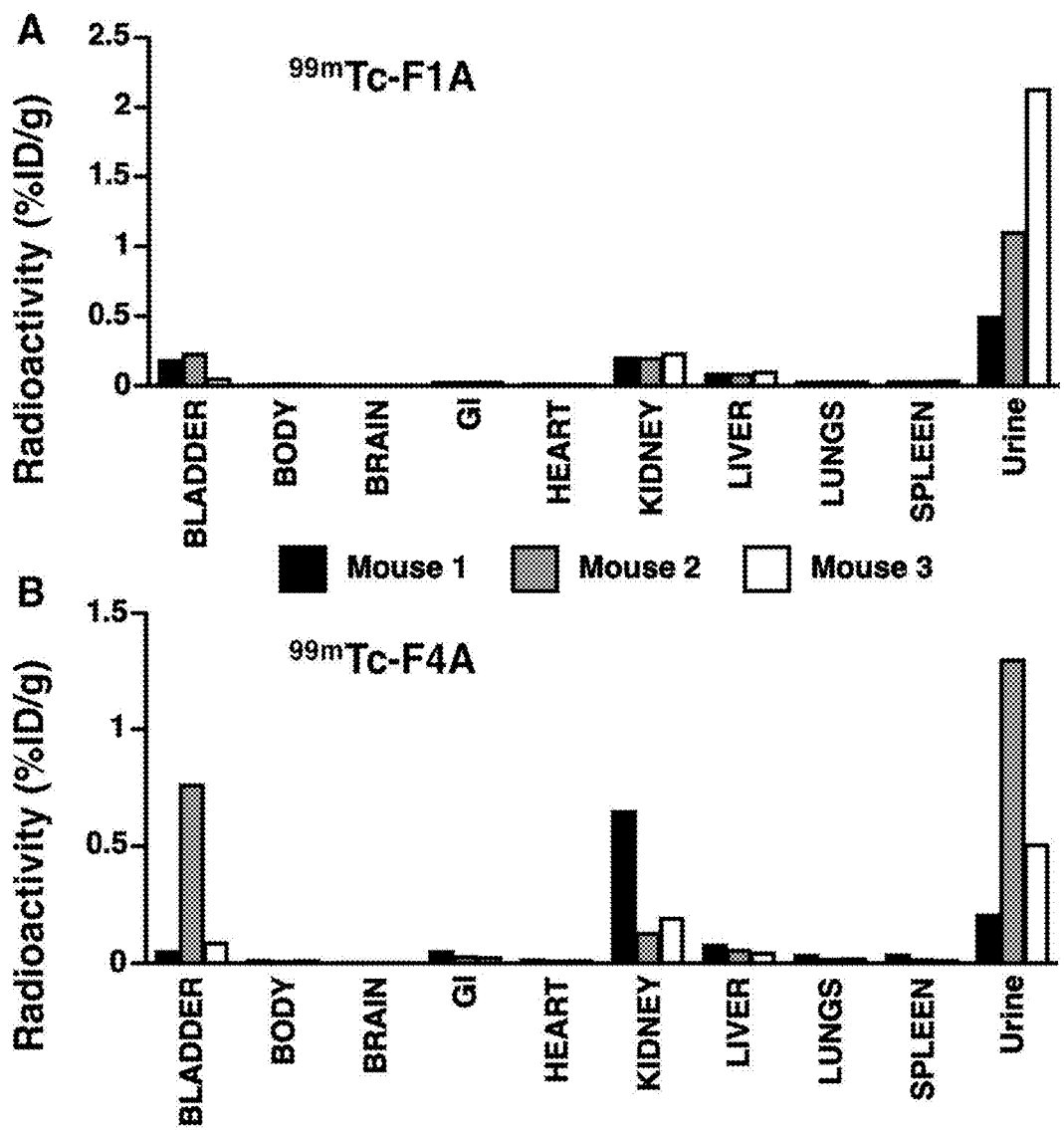
FIG. 20 depicts graphs and images showing pharmacokinetics (PK) and biodistribution (BD) of $^{99m}$Tc-F1A and $^{99m}$Tc-F4A and efficacy of $^{99m}$Tc-F4A in mice. Biodistribution of $^{99m}$Tc-F1A (A) and $^{99m}$Tc-F4A (B) in individual mice (n=3/group) 3 hours after injection of probe expressed as percent injected radioactivity per gram tissue (% ID/g). Note that the vast majority of the radiolabeled probe was excreted through the renal system for both probes. (C) The targeted binding of $^{99m}$Tc-F4A to the thrombus was robust and occurred in every animal studied. (D) Corroboration of in vivo homing specificity was supported by the competitive inhibition (4:1) of $^{99m}$Tc-F4A with co-administered F4A. ($^{99m}$Tc-F4A, ~75 µCi/animal) (E) Histogram displaying the average region of interest (ROI) signal normalized by the actual specific activity (±s.e.m.) administered iv showing significant increase in signal of the targeted $^{99m}$Tc-F4A alone versus the competitive inhibition group. (n=5 mice/group, p<0.05, t-test)
Figure 20:
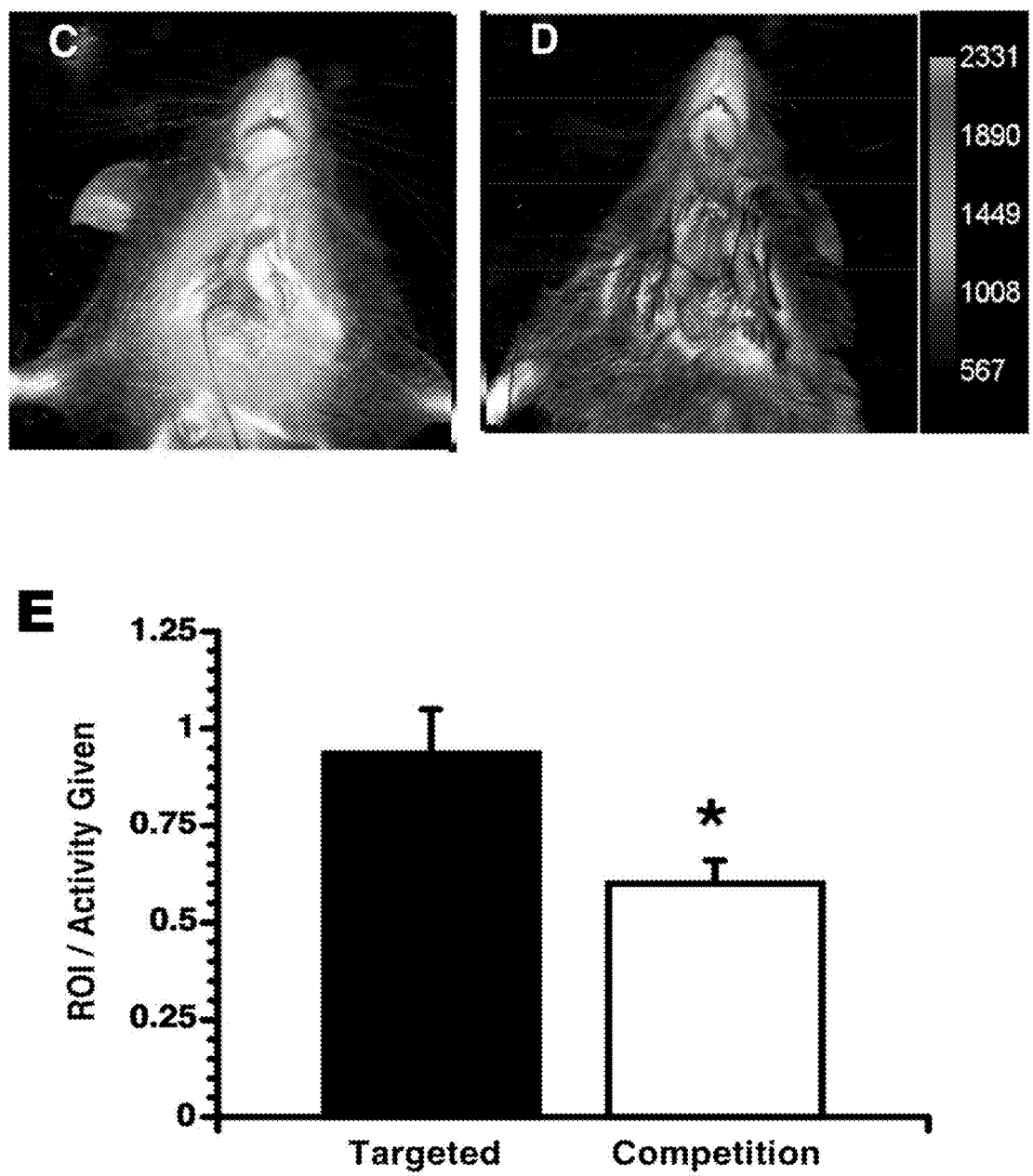

Example 15. Pharmacokinetics (PK) and Biodistribution (BD) of $^{99m}$Tc-F1A and $^{99m}$Tc-F4A in Mice As shown in FIG. 17, LVADs are positioned at the apex of the heart and some, like the HeartMate II, are positioned in the preperitoneum under the rectus muscle of the left abdomen. The sensitivity of LVAD thrombus detection in man will be dependent on the relative background nuclear signal, which can arise from prolonged persistence of the probe in blood or from accumulation of the agent in nearby organs. The pharmacokinetics (PK) and biodistribution (BD) of the reference radiolabeled $^{99m}$Tc-F1A were compared to that of the $^{99m}$Tc-F4A in mice in triplicate. Both agents closely followed a two-compartment bi-exponential PK model. The alpha distribution half-lives of $^{99m}$Tc-F4A in mice (5.0±1.9 min) was 41% faster (p=0.04) than that of $^{99m}$Tc-F1A (8.6±1.9 min). Similarly, the beta elimination half-lives of $^{99m}$Tc-F4A (124.7±41.3 min) was 50 min shorter (27%) than $^{99m}$Tc-F1A (174.2±26.2 min) (p=0.08), which were likely related to the minimal plasma interaction with $^{99m}$Tc-F4A. The organ biodistributions of both agents at the conclusion of the PK study (180 min) were very similar with neither probe accumulating in the lung, liver or spleen. Essentially, all of the $^{99m}$Tc activity was found in the kidney, bladder and urine (FIG. 20A,B). These data suggest that circulating $^{99m}$Tc-F4A blood pool background levels will decrease more rapidly than the reference monomeric probe and that nonspecific background imaging issues will be minimal.

Example 16. Efficacy of $^{99m}$Tc-F4A in Mice

The $^{99m}$Tc-F4A was evaluated in vivo for targeting efficacy and specificity to native thrombus using mouse model of carotid thrombus. Rose Bengal (tetrachloro-tetraiodo-fluorescein) was used to create singlet oxygen radicals under laser excitation to induce focal damage to the vascular endothelium and to initiate clot formation. The targeted binding of $^{99m}$Tc-F4A to the thrombus was robust and occurred in every animal studied (P=0.001 vs. contralateral vessel). As an indicator of in vivo targeting specificity, cold F4A was co-administered (4:1) and competitively inhibited $^{99m}$Tc-F4A by about one-third (p<0.05) (FIG. 20C,D,E). These data demonstrate that $^{99m}$Tc-F4A effectively, specifically and systemically targeted native carotid thrombus in vivo.

Example 17. Ex Vivo LVAD Flow Study Using a Mock Loop

Figure 21:
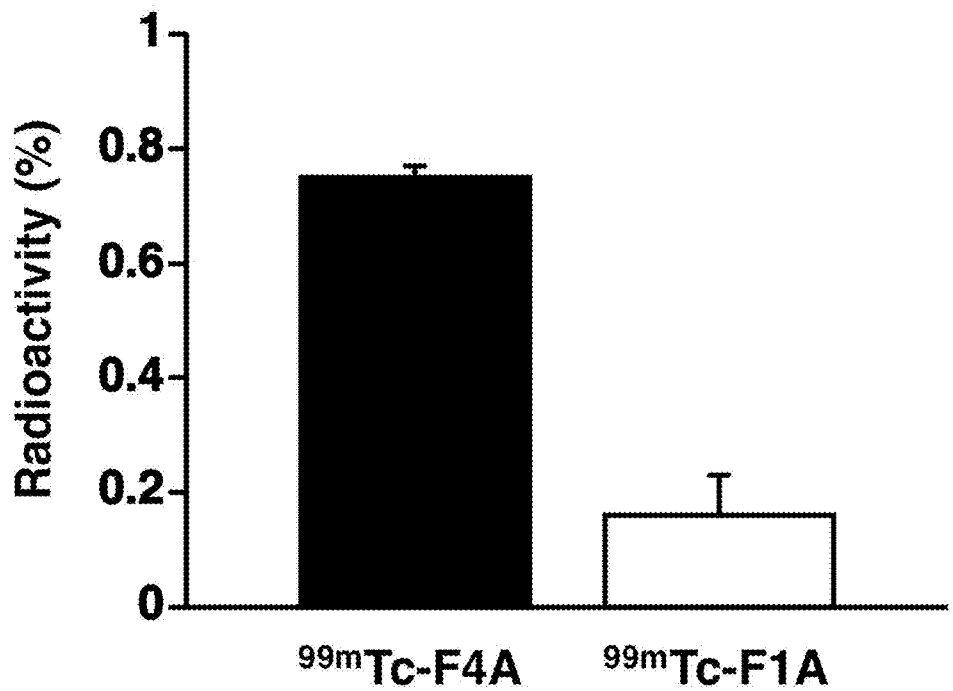
FIG. 21 depicts a graph and image of the ex vivo LVAD flow study using a mock loop. (A) Average percent radioactivity (±s.e.m.) of $^{99m}$Tc-F4A versus $^{99m}$Tc-F1A bound to uniform fibrin clots after 2 minutes of circulation in LVAD mock flow loop (B) operating at 10,000 RPM with 6 L/min flow. Circulation media was 200 ml of 50:50 Plasma:PBS.
Figure 21:
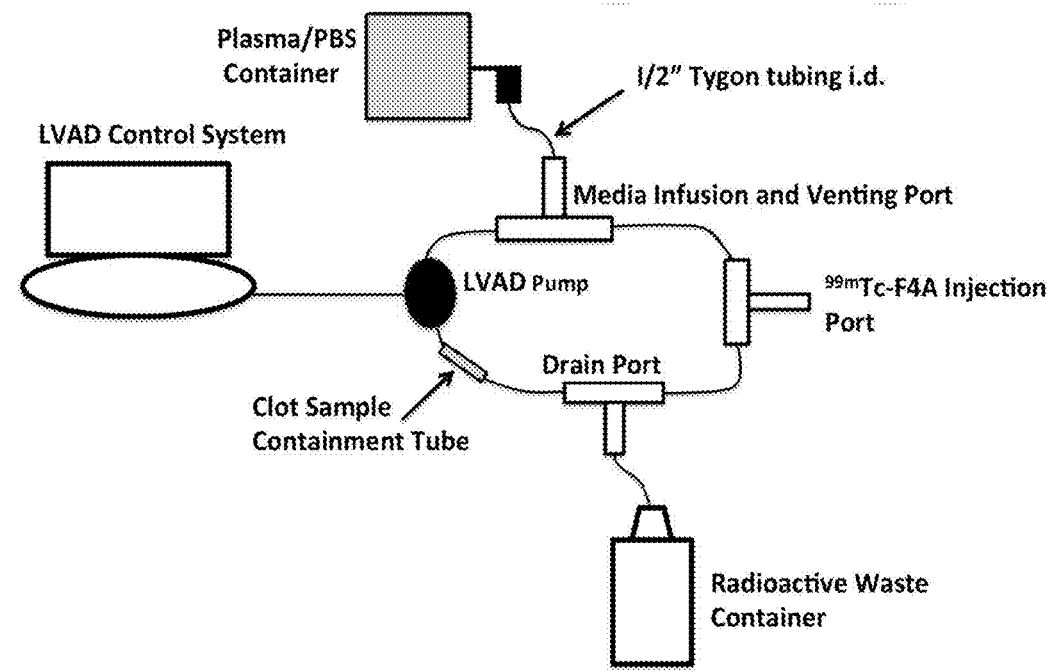

The high shear (10,000 RPM) and high flow (6 L/min) of the LVAD, which is required to pump the entire circulating blood volume of the patient every minute, places severe demands on the binding affinity and clot retention of the nuclear probe. Therefore, fibrin clot binding of the reference monomer, $^{99m}$Tc-F1A, and $^{99m}$Tc-F4A was compared in triplicate under the full flow and high shear conditions produced by a HeartMate II LVAD using a mock loop to demonstrate the effectiveness of the highly avid $^{99m}$Tc-F4A (FIG. 21B). The ½" plastic tubing circuit was filled with a 50:50 human plasma:PBS mixture (200 ml). Uniform fibrin clots were secured with a highly porous, thin gauze netting within a plastic ½" chamber immediately proximal to the LVAD inlet secured. $^{99m}$Tc-F1A or $^{99m}$Tc-F4A were injected into the mock loop and allowed to target the clots at the full flux rate for 2 minutes. After rapidly draining the radioactive plasma:PBS mix and washing the clots with PBS to remove unbound label, the percent clot radioactivity showed that the $^{99m}$Tc-F4A bound rapidly and was retained on the clot significantly better than the reference $^{99m}$Tc-F1A (p<0.01), which bound at a very low signal level (FIG. 21A). This superior fibrin binding of $^{99m}$Tc-F4A compared to the reference $^{99m}$Tc-F1A further illustrated the criticality of the PEG-based tetrameric design to increase avidity and minimize hydrophobic plasma interference.

Collectively, these results demonstrate that $^{99m}$Tc-F4A overcomes the plasma interference of the monomer, has more rapid background blood clearance, binds to the target more avidly, and is effective at targeting clot rapidly under the high-flow conditions generated by the LVAD operated at maximum output. The monomer binding ($^{99m}$Tc-F1A) was very close to background level counts, suggesting an inability "stick and stay" under the high flow shear produced by the pump. These data indicate that the previously reported peptide optimized in to the radiolabeled monomer would not be effective for effective intraLVAD clot detection and would be generally less effective for systemic detection of thrombus elsewhere in the body compared to $^{99m}$Tc-F4A.

Example 18. Ex Vivo Assessment of Intrapump Thrombosis in Explanted LVADs with $^{99m}$Tc-F4A For further proof of concept of this clot-binding contrast agent, $^{99m}$Tc-F4A binding was assessed in explanted LVADs from patients receiving heart transplants to corroborate the probe's affinity for the native intrapump fibrin deposition and to determine if high resolution imaging could spatially characterize the extent and likely medical significance of thrombus formation. FIG. 22A,B illustrates the negligible nonspecific binding of $^{99m}$Tc-F4A to a never implanted control LVAD in both longitudinal and transaxial views. A small amount of fibrin deposition along the stator was detected in a second explanted pump, which was visually confirmed as minimal translucent fibrin deposition along the inlet stator (FIG. 22C,D). Importantly, no other residual clot deposition was found within this pump as either random fibrin accumulations or film-like coatings on the inner pump wall or turbine surface. Although a small amount of signal around the inlet collet was seen on this and other pumps, this may be an artifact of incompletely flushed blood at the time of explanation. FIG. 22E,F shows a third LVAD with fibrin deposition not only on the stator but also accumulated further into the pump along the turbine spines. Whereas $^{99m}$Tc-F4A signal derived along the stator from minimal quantities of fibrin in FIG. 22C,D would likely have trivial medical impact as opposed to fibrin extending from the stator along the turbine, which would raise concern for acute thromboembolic events and possible pump replacement. If fresh clot was detected early after implantation, thrombolytic therapy may be considered, but this strategy has not been consistently successful, particularly for patients who have accumulated more matured and lytic-resistant thrombus.[15-21]

Discussion for Examples 12-18

In general, fibrin imaging has been a challenging endeavor pursued by many investigators with generally unsatisfying results. Several antibodies to fibrin were developed[22-25] with very good affinity ($10^{-9}$ M) but the circulatory half-lives on immunoglobulins created high background nuclear signal. Other clinical and preclinical antibodies were developed unsuccessfully against D-dimer, a fibrinogen degradation product, and the fibrin B-knob epitope, a fibrin epitope transiently exposed with fibrinopeptides A and B liberation.[26-33] Platelet receptors have also been pursued as imaging targets with no significant success in general, and in the context of the dense fibrin-rich acellular thrombus expected in LVADs, the effectiveness for such probes was deemed unlikely.[34-37]

In the present study, the homing sequence of $^{99m}$Tc-F4A was derived from an anti-fibrin peptide backbone that was functionalized for MRI T1-weighted thrombus imaging, but perhaps for the reasons illustrated by the reference agent, $^{99m}$Tc-F1A, it was abandoned. Other research modifications of that agent for nuclear imaging had similar μM binding affinity.[38-40] As shown for $^{99m}$Tc-F1A, these agents lacked the requisite binding avidity to fibrin and freedom from plasma interference on binding that $^{99m}$Tc-F4A demonstrated, particularly in the high-flow high-shear LVAD mock loop experiment.

LVAD utilization for both the BTT and DT indications has significantly increased over the past 10 years. During this same timeframe the cost-effectiveness of LVADs and their management have improved substantially.[41] A focused trend analysis of two newer devices implanted between 2009-2011 showed that the high total hospital costs per patient, excluding device costs, were falling as the number of treated patients increased.[42] In fact, of the two viable treatment options for severe heart failure, i.e., heart transplant versus LVAD placement, BTT therapy is now approaching the cost-effective threshold in high and medium risk HF patients.[43]

Beyond the cost of the mechanical device itself, a major cost and morbidity issue surrounding LVAD use is the predisposition for GI bleeding due to platelet dysfunction balanced against the need to anti-coagulate patients to prevent pump-related thromboembolism. Medical strategies that attempted to lower anticoagulation goals as a means to reduce GI bleeding incidence or efforts to reduce international normalized ratio (INR) targets in patients following a GI bleed were both associated with increased frequencies of pump thrombosis.[9,16] Moreover, treatment of thrombosis with GPIIbIIIa[44] or plasminogen activators therapies[18-21] in situations of suspected thrombosis has had limited benefit and often poor patient outcomes, including death by cerebral hemorrhage. $^{99m}$Tc-F4A offers the potential for early non-invasive quantitative diagnosis of fibrin accumulation to better individualize patient INR goals with their propensity for GI bleeding.

Data from the newest generation of centrifugal LVAD pumps reveals that management intrapump thrombus and thromboembolism will be continued diagnostic challenges. Furthermore, with the emergence of centrifugal pump designs, evidence suggests that the underlying biochemical mechanisms predisposing to thrombosis are different, which further reflects the multifactorial nature of this problem.[13,45] While intrapump thrombus may form de novo in the LVAD as discussed so far, it can form in compromised regions of the heart where blood has stagnated and simply become "sucked" into the pump.[46] Regardless, early diagnosis and characterization of LVAD thrombus will be invaluable for informed medical decisions and a marked advancement over clinical judgment based on nonspecific LDH and pump electrical variation.

In summary, we have developed and demonstrated a robust fibrin-specific gamma-imaging probe, $^{99m}$Tc-F4A, for diagnosis and characterization of intraLVAD thrombus. The tetrameric nuclear agent was highly detectable through the titanium pump housing and had very avid fibrin binding properties in plasma under extremely high flow and high shear conditions. $^{99m}$Tc-F4A targeted fibrin effectively in vivo with rapid blood clearance into urine and without typical probe accumulation in the liver, spleen, or lung. $^{99m}$Tc-F4A addresses the need for early diagnosis and characterization of LVAD thrombus definitively. In addition, this technology may provide a key tool to balance patient anticoagulation requirements with GI bleeding risk. Overcoming these barriers will further lower the healthcare costs, will decrease the morbidity and mortality associated with LVAD therapy, and will extend the life-saving potential of cardiac mechanical assistance to the myriad of patients, particularly younger individuals, unable to receive a timely heart transplant.

Methods for Examples 12-18

Solid Phase Synthesis Monomeric (F1A) and Tetrameric (F4A) Fibrin Probes:

In brief overview, each monomeric unit (F1A) was a bifunctional entity comprised of a fibrin-specific homing peptide (SEQ ID NO:1—QWECPYGLCWIQ) interconnected through a $PEG_2$ spacer to a technetium chelating amino acid sequence (HHE). (FIG. 17A) $PEG_{2000}$ in a tetramer was used to intercouple four F1A monomers to form F4A (FIG. 17B). The tetramer (F4A, ~10,437 kDa) was corroborated by size exclusion column chromatography.

More specifically, peptide precursors were synthesized with a CS136 peptide synthesizer at the 0.2 mmol scale. Standard solid phase Fmoc deprotection and amino acid coupling reactions were used[47]. Disulfide cyclization was carried out with TECP reduction and DTNB coupling, followed by 1% TFA deprotection while the peptide intermediate remained on solid support[48]. After assembling the peptide, the resin was washed with DMF, and then cleaved with TFA/anisole/water (95/2.5/2.5) for 2 h. The synthesis was repeated using HBTU coupling (≥99% purity) and Fmoc-Gln(tBu)-Wang resin (0.5 mmol/g). The final product was purified by HPLC and characterized by ESI-TOF mass spectrometer: ESI-TOF$^+$ (positive mode): m/z [C94H126N24O26S2+2H]$^+$ Calcd. 1036.4 Da.; Obsd. 1036.3 Da. To obtain the tetramer, 2-phenylisopropyl was selectively removed from Glu and coupled with the 4-arm-PEG amine (PSB-431, MW by MALDI 2220 Da, Creative PEGWorks). Size exclusion chromatography was used to purify the uncoupled 4-arm-PEG-amine (10,437.12 g/mol).

$^{99m}$Tc Labeling of FM and F4A:

F1A and F4A were radiolabeled with $^{99m}$Tc for gamma imaging. This was accomplished by adding Na$^{99m}$TcO$_4$ (~9 mCi; 1.0 ml) in saline to an IsoLink vial (Center for Radiopharmaceutical Sciences of PSI, ETH and USZ, Paul Scherrer Institute, Switzerland). The mixture was heated to 100° C. for 20 min to form the intermediate [$^{99m}$Tc(CO)$_3$(H$_2$O)$_3$]$^+$, then cooled to ~25° C. and neutralized with 0.2 ml of a 1:2 mixture of 1 M phosphate buffer (pH 7.4) and 1 M HCl. This solution (0.16 M) was added into a 5 ml vial containing the peptide ligand in 0.15 ml of PBS. The reaction mixture was heated at 60° C. for 30 min before cooling to ~25° C. The resulting solution was purified by size exclusion column chromatography and analyzed by radio TLC. Radiochemical purity of 90 to 95% was repeatedly achieved with a specific activity of 40 mCi/μmole or greater.

Acellular Fibrin Clot Assays of Probe Affinity, Radiolabel Stability, and Plasma Interference:

Acellular fibrin clots were used: 1) to characterize the binding affinity of $^{99m}$Tc-F1A and $^{99m}$Tc-F4A, 2) to assess the stability of $^{99m}$Tc chelation, and 3) to evaluate the extent of plasma interference of fibrin binding. Specifically, uniform clots were produced by quickly admixing 100 μl of fresh human plasma with 3 units thrombin (Sigma Chemical). The mixture was pipetted into uniform cylindrical plastic tubes. Once formed, clots were washed repeatedly in 0.1 M PBS buffer (pH 7.0) then stored in same until use at 4° C.

Fibrin Binding Affinity:

$^{99m}$Tc-F1A or $^{99m}$Tc-F4A (20 μCi) were incubated with the clot samples at 37° C. for 30 minutes with 1, 5, 10, 15, 25, and 30 μg cold monomer supplemented with 0.1 M PBS pH 7.4 to bring each test volume total to 0.5 ml. The fibrin clots were separated from unbound radioactivity by repeated centrifugation and washing then counted in a calibrated well counter (Wizard 3, Perkin Elmer). Results, adjusted for decay, were used to estimate dissociation constant ($k_d$) using the Hill slope model, Y=Bmax*X$^h$/(Kd$^h$+X$^h$) (MatLab). Total fibrin concentration was estimated from plasma fibrinogen estimated to be 0.735 nmoles per clot.

Assessment of $^{99m}$Tc-F1A and $^{99m}$Tc-F4A Radiolabel Stability and Plasma Interference:

Radiolabeled F1A and F4A were bound to clots in the presence of marked excess cysteine to evaluate the stability of the $^{99m}$Tc label in triplicate.[49] $^{99m}$Tc-F1A or $^{99m}$Tc-F4A (20 μCi) supplemented with 0.1 M PBS pH 7.4 (total volume of 0.5 ml) were incubated with fibrin clot samples at 37° C. for 30 minutes. Similarly, the 0.1 M PBS buffer diluted 50% with fresh human plasma (total volume of 0.5 ml) was used to assess potential matrix interference on radiolabeled peptide binding in triplicate. In both instances, fibrin clots were separated from unbound radioactivity by repeated centrifugation, washed, then counted in a calibrated well counter (Wizard 3, Perkin Elmer).

Gamma Signal Attenuation Due to Titanium LVAD Housing:

Na$^{99m}$TcO$_4$ was serially diluted into plastic snap-cap vials from 20 µCi to 0.5 µCi and radioactivity was evaluated using the Multispectral FX multimodal imaging system (Bruker-Biospin) with the isotope phosphor screen for planar scintigraphy using a 1.0 min acquisition time. Samples were imaged before and after placement of a 1 mm titanium sheet provided by Thoratec Corp., which corresponded to the titanium metal used to form the LVAD HeartMate II housing.

Pharmacokinetics (PK) and Biodistribution (BD) of $^{99m}$Tc-F1A and $^{99m}$Tc-F4A in Mice:

All animal research was conducted under a protocol approved by the Washington University Animal Studies Committee.

The pharmacokinetics of $^{99m}$Tc-F1A and $^{99m}$Tc-F4A were studied in triplicate in mice (male, Harlan, C57BL/6, 4-6 wks). Mice were anesthetized with ketamine (85 mg/kg)/xylazine (10 mg/kg) and maintained with 1-2% isofluorane nosecone to effect. $^{99m}$Tc-F1A or $^{99m}$Tc-F4A (16-30 µCi) were injected via tail vein and serial blood samples were obtained at 0, 2, 5, 10, 15, 20, 30, 60, 120, and 180 min via an indwelling jugular catheter. Blood samples were timed, weighed, and counted with a calibrated gamma counter (Wizard 3, Perkin Elmer). The data adjusted for decay were fit to bi-exponential models (MatLab). After 180 minutes, animals were sacrificed; tissue and fluid aliquots (bladder, brain, GI, heart, lung, liver, spleen, urine, body remains) were excised, weighed, counted, and the results adjusted for decay. Biodistribution results were expressed as % ID/g tissue or fluid.

Efficacy of $^{99m}$Tc-F4A in Mice:

In vivo targeting of $^{99m}$Tc-F4A was performed in mice (male, Harlan, C57BL/6, 4-6 wks) following the introduction a carotid thrombus using the Rose Bengal method.[50-52] Briefly, mice were administered 60 µg/g body weight by tail vein injection of a 20 mg/ml solution of Rose Bengal dye (the singlet oxygen was generated by the photoactivation of the dye). HeNe laser (540 nm 1.5 mW) was focused on a surgically exposed carotid artery distal to a Doppler cuff probe. The probe was moved every 15 min to avoid total occlusion of the artery. A target 50% to 70% reduction in flow rate due to thrombus formation was sought. After laser treatment, the mice were heparinized and $^{99m}$Tc-F4A (40 mCi/µmole) or a competition mixture of $^{99m}$Tc-F4A:F4A (1:4) was administered via tail vein injection (3 µCi/g BW, ~75 µCi/mouse). Animals were serially scanned over 2 hours to assess time to peak signal and stability of signal using a Multispectral FX as described above. Using a standardized 5-minute acquisition in all animals, the intensity values for the region of interest were reported in total photon counts and calibrated to total radioactivity. In vivo treatments were replicated 5 times per group.

Ex Vivo LVAD Flow Study Using a Mock Loop:

A LVAD (Heartmate II) driven by a computer-controlled console was inserted into a 200 ml mock flow loop comprised of ½" plastic tubing interconnecting a PBS/Fresh Plasma (50:50) reservoir, an injection port, a media drainage port, and an inline ½" plastic chamber. Uniform fibrin clots produced by mixing fibrinogen, thrombin, and calcium and aged 24 hours were secured within the inline chamber using a highly porous, single thread layer of cotton gauze. The LVAD was operated at maximum flow rate (10,000 RPM, 6 L/flow per minute). $^{99m}$Tc-F4A or $^{99m}$Tc-F1A (0.5 mCi) were injected into the loop and allowed to circulate for 2 minutes. Each treatment was repeated in triplicate. Radioactive circulating plasma/PBS was drained and replaced with PBS, which circulated for 2 minutes to remove unbound radioactivity. Clot radioactivity was counted in a calibrated gamma well counter and the results adjusted for decay.

Assessment of Intrapump Thrombosis in Explanted LVADs with $^{99m}$Tc-F4A:

To confirm the binding of $^{99m}$Tc-F4A to naturally occurring intra-LVAD thrombosis, pumps excised (with drivelines severed) from patients receiving heart transplants were studied. Explanted pumps were referenced to a control, unused HeartMate II LVAD. In each study, the control and excised LVADs received 10 ml of plasma:PBS (50:50) containing 1 mCi of $^{99m}$Tc-F4A in 0.2 ml saline. The mechanical assist devices were incubated with the nuclear probe for 2 hours with mild nutator agitation at 37° C. After treatment, each pump was washed with saline (10 ml, 3×) to remove unbound label. The pumps were imaged with single-photon emission counting tomography with Xray-CT (NanoSPECT/CT, Bioscan). Helical SPECT and CT scans were performed with 16 projections per rotation for 60 s per projection and 65 kVp, 177 µAs, respectively and reconstructed with Invivoscope software. Total photon counts were calibrated to total radioactivity of the sample.

Statistical Analysis:

Data were analyzed using studentized T-Tests or analysis of variance (SAS Inc.; Cary, N.C., USA). Data are presented as the mean±standard error of the mean unless otherwise stated. In vitro data were replicated in triplicate as independent experiments. Biodistribution and pharmacokinetic data involved 3 animals per treatment group. In vivo targeting of carotid thrombus was replicated 5 times per treatment group in randomized complete block design projected to allow a 20% difference detected with 80% power at an alpha level of 0.05. Each block consisted of a replicate animal of from the fibrin targeted and competition treatment groups. Homogeneity of variance for the in vivo carotid studies was affirmed using Bartlett's test for homogeneity of variance. All animals receiving the specified test article dosage and completing the study were included in the data analysis. NanoSPECT imaging was performed and analyzed by an investigator independent from those individuals who performed the in vivo experiment. For other in vitro and biodistribution studies, the individuals preparing the labeled materials and conducting the studies could not be blinded to the treatment groups.

Example 19. Alternative Approach to Coupling $^{99m}$Tc to F4A Using a Nitrilotriacetic Acid (NTA) Group $^{99m}$Tc can be coupled stably to the F4A using alternative methods, and one desirable approach is to substitute the chelator NTA (Sigma Aldrich) for the bis-histidine amino acids used to couple the metal through a tricarboxylic acid linkage. NTA is activated by 1-ethyl-3-[3-(dimethylamino) propyl]carbodiimide (EDC) and N-hydroxysulfono-succinimide (NHS) and conjugated with the anti-fibrin peptide via the short bridge previously described for F4A. This new monomer is purified by a semi-preparative HPLC and characterized by analytical HPLC and mass spectrometry (ESI-TOF MS). The monomers are assembled into the 4-arm construct as previously described in Example 3.

The analog F4A-NTA is radiolabeled with $^{99m}$Tc in a simple one-step synthesis. Na$^{99m}$TcO4 in saline (1 mL 370 MBq) is added to a mixture of F4A-NTA (e.g., 20 mg) and SnCL2 (e.g., 0.4 mg) at room temperature for 10 min for chelation. The crude mixture is purified by centrifugation using a 7000 MWCO filter. The fractions containing $^{99m}$Tc-F4A-NTA (FIG. 23) are collected and reconstituted in phosphate-buffered saline (PBS, 1×, pH 7.4), which is sterile filtered through a 0.22-µm Millipore filter into sterile vials for in vitro and in vivo experiments.

Example 20. PET-Labeled F4As for Use with PET-CT and PET-MR Imaging

1. Radiosynthesis of $^{18}$F-AlF-NOTA-F4A:

A major obstacle for the clinical translation of $^{18}$F-labeled peptides has been the laborious multistep radiosynthesis required. However, alternative strategies for peptide-based positron emission tomography (PET) probes have emerged and are applicable to ThromboScint. In particular the chelation reaction between Al$^{18}$F (AlF) and a macrocyclic chelator-functionalized F4A can be envisioned as a simple one-step $^{18}$F labeling strategy allowing fibrin imaging in the coronary, pulmonary, cerebral, peripheral vascular and other vascular beds with rapid, highly sensitive tomographic imaging available in the clinic today, either PET CT or PET MR.

Radiofluorination strategies involving the NOTA-AlF chelation chemistry can be accomplished in water. From a biological perspective, these one-step and water-compatible reactions are ideal for incorporation of $^{18}$F-fluoride into biologically active ligands, especially biomacromolecules that loose bioactivity except when solubilized in water. In overview, each fibrin-monomer arm is functionalized with a macrocyclic chelator, 1,4,7-triazacyclononane-1,4,7-triacetic acid (NOTA) through the short bridge group and the four monomer arms are chemically combined into the F4A analogue (NOTA-F4A). NOTA-F4A is then radiofluorinated via Al$^{18}$F intermediate to synthesize $^{18}$F-AlF-NOTA-F4A.

Preparation of NOTA or TE2A-Peptide:

The chelator, NOTA or TE2A is purchased from Macrocyclics and is activated by 1-ethyl-3-[3-(dimethylamino)propyl]carbodiimide (EDC) and N-hydroxysulfono-succinimide (NHS) to conjugate with peptides through the short bridge, as previously described. The NOTA or TE2A-peptide conjugate chemically linked to produce the tetramer and purified by a semi-preparative HPLC and characterized by analytical HPLC and mass spectrometry (ESI-TOF MS).

Radiochemistry:

The $^{18}$F labeling reaction is shown in FIG. 24. A QMA Sep-Pak Light cartridge (Waters, Milford, Mass., USA) fixed with 30 mCi (1.1 GBq) of $^{18}$F-fluoride is washed with 2.5 ml of metal-free water. $^{18}$F is then eluted from the cartridge with 400 pl of 0.4 M KHCO3, from which a 200-pl fraction is taken. The pH of the solution is adjusted to 4 with metal-free glacial acetic acid. AlCl3 (2 mM, 3 pl) in 0.1 M sodium acetate buffer (pH 4) and 5 pl of NOTA-peptide [60 mg/ml in dimethyl sulfoxide (DMSO)] are added to the reaction solution sequentially. The reaction mixture is incubated at 100° C. for 15 m in. After dilution with 1 ml of metal-free water, the crude mixture is purified with semi-preparative HPLC. The fractions containing $^{18}$F-AlF-NOTA-peptide are collected and combined. The solvent is removed using a rotary evaporator. The product is reconstituted in phosphate-buffered saline (PBS, 1×, pH 7.4) and passed through a 0.22-pm Millipore filter into a sterile vial for in vitro and in vivo experiments.

2. Radiosynthesis of $^{68}$Ga-NOTA-F4A, a Generator Produced Radioisotope for PET Imaging.

Radiochemistry-$^{68}$Ga-Tetramer: NOTA-F4A (100 µg) in 1400 µl of 1 M 4-(2-hydroxyethyl)-1-piperazineethanesulfonic acid (HEPES, pH=6.5) solution is combined in a 2.0 mL vial with 111 MBq of $^{68}$GaCl3 in 0.6 N HCl. The reaction mixture is shaken and incubated at 75 °C for 0.5 h. Then, 2 µL of 5 M methylendiaminetetraacetic acid (EDTA) is added to the reaction mixture and allowed to incubate for another 5 min (EDTA is used to remove free $^{68}$Ga from the $^{68}$Ga-labeled tetramer). Purification of $^{68}$Ga-labeled conjugate is carried via centrifugation through a MWCO 7500 sieve. The product is analyzed by radio-HPLC to determine the radiochemical purity of the product. The product is reconstituted in phosphate-buffered saline (PBS, 1×, pH 7.4) and passed through a 0.22-µm Millipore filter into a sterile vial for in vitro and in vivo experiments (FIG. 25).

3. Radiosynthesis of $^{64}$Cu-CB-TE2A-F4A for PET Imaging.

CB-TE2A (M-220) is purchased from macrocyclics. TE2A is coupled to N-terminus of the monomer on solid phase synthesis and the 4 monomer arms are combined as previously described. The Cu-CB-TE2A complex has remarkable kinetic inertness towards acid decomplexation, with a half-life of almost a week in 5 M HCl, even at 90°. $^{64}$Cu is produced on the CS-15 biomedical cyclotron at Washington University School of Medicine using reported methods and is widely available.

Preparation of TE2A-Peptide Monomer:

The chelator TE2A (Macrocyclic) is activated by 1-ethyl-3-[3-(dimethylamino)propyl]carbodiimide (EDC) and N-hydroxysulfono-succinimide (NHS) and conjugated with peptides. The TE2A-peptide monomer conjugate are combined to produce the tetramer as described previously and purified by semi-preparative HPLC and characterized by analytical HPLC and mass spectrometry (ESI-TOF MS).

Radiochemistry-Cu-64:

$^{64}$Cu (0.5-2 mCi) in 0.1 M NH4OAc buffer (pH 8.0, 100 pL) is added to 800 pg of TE2A-Tetramer in 0.1 M NH4OAc buffer (pH 8.0, 100 pL) or simple distilled water. The reaction mixture is incubated at 25° C. for 10 min, then 100 pg of DTPA is added to the reaction mixture for an additional 20 min at 30° C. The radi ochemical yield is checked with instant thin layer chromatography (ITLC, saline). The $^{64}$Cu-labeled TE2A-Tetramer is purified by centrifugation through a MWCO 7500 seive to remove free $^{64}$Cu-DTPA complexes. Radiochemical purity is determined by high-performance liquid chromatography. The product is reconstituted in phosphate-buffered saline (PBS, 1×, pH 7.4) and passed through a 0.22-pm Millipore filter into a sterile vial for in vitro and in vivo experiments (FIG. 26).

4. Gadolinium-Labeled F4As for Use with T1W MR Imaging.

Although ThromboScint ($^{99m}$Tc-F4A) was conceived specifically intraLVAD clot nuclear imaging, the construct is highly amenable to T1W MRI imaging with Gadolinium, or similarly with CEST or paracest agents.

Preparation of DOTA-Tetramer Peptide:

The chelator DOTA is purchased from Macrocyclics. It is activated by 1-ethyl-3-[3-(dimethylamino)propyl]carbodiimide (EDC) and N-hydroxysulfono-succinimide (NHS) and conjugated with monomer peptide backbone through the short bridge. The DOTA-peptide conjugates are chemically combined into the tetramer and purified by semi-preparative HPLC and characterized by analytical HPLC and mass spectrometry (ESI-TOF MS).

Chemistry-Gd-DOTA-F4A:

8 mg GdCl$_3$ in 0.5 mL 0.01 M HCl is added to 30 mg of DOTA-F4A in 0.1 M NH4OAc buffer (pH 6.0, 5 mL) or simple distilled water. The reaction mixture is incubated at 25° C. for 10 min, then 50 mg of DOTA is added and the reaction mixture further incubated for 20 min at 30° C. Gd-coupled DOTA-F4A is purified by centrifugation using MWCO 7500 device to remove free Gd-DOTA complexes. Purity is determined by high-performance liquid chromatography. The final product is reconstituted in phosphate-buffered saline (PBS, 1×, pH 7.4) and passed through a 0.22-μm Millipore filter into a sterile vial for in vitro and in vivo experiments (FIG. 27).

Example 21. Optical-Labeled F4As for Use Fluorescent or NIR Imaging In Vitro and In Vivo Optical imaging is highly desirable today and most peptide optical conjugates have marked nonspecific binding interference to blood borne proteins or nonspecific cells. Optical-labeled F4A is anticipated to improve the binding to targets with less nonspecific adhesion and for in vivo, rapid background elimination. Near infrared (NIR) fluorescent imaging takes advantage of transparency of biological tissues at particular range of wavelengths. The method is nondestructive, and allows one to monitor the distribution of various labeled molecules in live organisms. Sulfo-Cy7 NHS ester is a common reagent that allows facile preparation of Cy7-labeled biomolecules, such as peptides and proteins.

Chemical Synthesis:

Both tetramer and Sulfo-Cy7 NHS ester is dissolved in PBS buffer at a 10:1 ratio of dye to peptide. The reaction proceeds at RT for one hour and the product is purified with semipreparative HPLC then characterized by LC-MS (FIG. 28).

Example 22. Synthesis of $N_2S_2$ Coupled Amide Bond Cyclized Tetramer

The goal of the present study was to prepare a stable cyclized peptide in a thiol containing environment as a potential radiopharmaceutical with better commercial properties for clinical use. We proposed amide based side chain cyclization for our $N_2S_2$ containing antifibrin or ICAM1 tetramer. $N_2S_2$ tetramer peptide was synthesized on solid phase then radiolabeled with Tc-99m.

1. Synthesis of Modified Peptide Monomer:

The peptides were synthesized based on Fmoc/tBu solid phase method, an orthogonal protecting group strategy using the base labile N-Fmoc group for protection of the α-amino function, acid labile side chain protecting groups and acid labile linkers that constitute the C-terminal amino acid protecting group. They were synthesized on CS136 peptide synthesizer at the 0.2 mmol scale. Fmoc deprotection was achieved by 20% piperidine in DMF for 15 min; Coupling of AAs combined with 0.1 M coupling agent HBTU and 1.0 M DIPEA in DMF (5× excess) for 4 hours; The resin was washed with DMF for 3 time 30 s following deprotection; Cleavage: 95/2.5/2.5 TFA/anisole/water for 2 h. All amino acids were dissolved in DMF. This synthesis was repeated using HBTU (≥99% purity), using Fmoc-Gln(tBu)-Wang resin (0.5 mmol/g). Instead of cyclization of peptide via Cys-Cys, we cyclized peptide by side chain to side chain amide bond via Fmoc-Asp(O-2-PhiPr)-OH and Fmoc-Dpr (ivDde)-OH. The final product was characterized by ESI-TOF mass spectrometer. The final product was characterized by ESI-TOF mass spectrometer. ESI-TOF (positive mode): m/z [Chemical Formula: $[C90H124N22O27S2+2\ H]^+$ $[MW+2H]^+$ Calcd. 1005.42 Da.

2. Synthesis of $N_2S_2$-4 PEG 2 k Armed Modified Peptide:

The peptides were synthesized on CS136 peptide synthesizer at the 0.2 mmole scale. First monomer was synthesized on the resin, then selectively cleaved off O-2-Phi Pr and ivDde group with 1% TFA in DCM, cyclized via amide bond. Later Dmab group was removed selectively with 2% hydrazine in DMF. The 4 PEG armed amine was coupled onto the resin. Fmoc-Dpr(ivDde)-OH and N-succinimidyl S-acetylthioacetate couple onto N-terminus, treated with hydroxylamine to expose the labile sulfhydryl group when needed for further reactions. Size exclusion column was used to purify the final product, any unreacted monomer or impurity size less than 7 K will be retained on the column and discarded. The structure of the final product is depicted in FIG. 29.

3. Tc-99m Radiolabeling:

Technetium in pertechnetate ion, obtained by the elution of the Moly generator, has the most stable $Tc^{7+}$ oxidation state and it will be reduced to lower oxidation states by reducing agent to make it readily react with chelating agents. Stannous chloride ($SnCl_2 \cdot 2H_2O$) is the most common reducing agent in Tc radiopharmaceuticals. 10 microliter of 1 mg/mL $SnCl_2$ in 0.1 M HCl, 40 microliter of 0.5 M ammonium acetate ($NH_4OAc$) pH 5.2, 100 microliter of 0.2 M sodium tartrate (pH 9.2), 100 microliter Tc-99m solution (10 mCi/37 MBq), and 10-50 microliter peptide 1 mg/mL in aqueous solution were added into reaction vial and incubated at room temperature for 20 min to form labeled peptide. Then it was purified to a single product by Waters HPC on a C-18 reverse phase analytical column using 20-30 min gradient of 16-30 acetonitrile in 20 mM HCl aqueous solution at a flow rate of 1 mL/min. The purified peptide was purged with nitrogen or Ar gas for 20 min to remove acetonitrile and the pH was adjusted to 7.4. The structure of the product is depicted in FIG. 30.

Example 23. Synthesis of $N_3S$ Coupled Amide Bond Cyclized Tetramer

The goal of the present study was to prepare a stable cyclized peptide in a thiol containing environment as a potential renal radiopharmaceutical. We proposed amide based side chain cyclization for our $N_3S$ containing antifibrin or ICAM1 tetramer. $N_3S$ tetramer peptide was synthesized on solid phase then radiolabeled with Tc-99m.

1. Synthesis of Modified Peptide Monomer:

The peptides were synthesized based on Fmoc/tBu solid phase method, an orthogonal protecting group strategy using the base labile N-Fmoc group for protection of the α-amino function, acid labile side chain protecting groups and acid labile linkers that constitute the C-terminal amino acid protecting group. They were synthesized on CS136 peptide synthesizer at the 0.2 mmol scale. Fmoc deprotection was achieved by 20% piperidine in DMF for 15 min; Coupling of AAs combined with 0.1 M coupling agent HBTU and 1.0 M DIPEA in DMF (5× excess) for 4 hours; The resin was washed with DMF for 3 time 30 s following deprotection; Cleavage: 95/2.5/2.5 TFA/anisole/water for 2 h. All amino acids were dissolved in DMF. This synthesis was repeated using HBTU (≥99% purity), using Fmoc-Gln(tBu)-Wang resin (0.5 mmol/g). Instead of cyclization of peptide via Cys-Cys, we cyclized peptide by side chain to side chain amide bond via Fmoc-Asp(O-2-PhiPr)-OH and Fmoc-Dpr (ivDde)-OH. The final product was characterized by ESI-TOF mass spectrometer. The final product was characterized by ESI-TOF mass spectrometer. ESI-TOF (positive mode): m/z [Chemical Formula: $[C89H125N23O26S+2H]^+$ $[MW+2H]^+$ Calcd. 982.9 Da.

2. Synthesis of N₃S-4 PEG 2 k Armed Modified Peptide:

The peptides were synthesized on CS136 peptide synthesizer at the 0.2 mmole scale. First monomer was synthesized on the resin, then selectively cleaved off O-2-Phi Pr and ivDde group with 1% TFA in DCM, cyclized via amide bond. Later Dmab group was removed selectively with 2% hydrazine in DMF. The 4 PEG armed amine was coupled onto the resin. Fmoc-Dpr(ivDde)-OH and Fmoc-Cys(tBu)-OH couple onto N-terminus. Size exclusion column was used to purify the final product, any unreacted monomer or impurity size less than 9 KDa will be retained on the column and discarded. The structure of the final product is depicted in FIG. 31.

3. Tc-99m Radiolabeling:

Technetium in pertechnetate ion, obtained by the elution of the Moly generator, has the most stable $Tc^{7+}$ oxidation state and it will be reduced to lower oxidation states by reducing agent to make it readily react with chelating agents. Stannous chloride ($SnCl_2.2H_2O$) is the most common reducing agent in Tc radiopharmaceuticals. 10 microliter of 1 mg/mL $SnCl_2$ in 0.1 M HCl, 40 microliter of 0.5 M ammonium acetate ($NH_4OAc$) pH 5.2, 100 microliter of 0.2 M sodium tartrate (pH 9.2), 100 microliter Tc-99m solution (10 mCi/37 MBq), and 10-50 microliter peptide 1 mg/mL in aqueous solution were added into reaction vial and incubated at room temperature for 20 min to form labeled peptide. Then it was purified to a single product by Waters HPC on a C-18 reverse phase analytical column using 20-30 min gradient of 16-30 acetonitrile in 20 mM HCl aqueous solution at a flow rate of 1 mL/min. The purified peptide was purged with nitrogen or Ar gas for 20 min to remove acetonitrile and the pH was adjusted to 7.4. The structure of the product is depicted in FIG. 32.

Example 24. Synthesis of N₃S Coupled, Amide Bond Cyclized, Copper Free Click Tetramer The goal of the present study was to prepare a stable cyclized peptide in a thiol containing environment and to synthesize tetramer in solution phase as a potential radiopharmaceutical with improved commercial scale-up and yield properties. We proposed amide based side chain cyclization for our N₃S containing antifibrin or ICAM1 tetramer using copper free click chemistry for tetramer preparation. N₃S monomer peptide was synthesized on solid phase then coupled with tetramer BCN to form antifibrin tetramer later radiolabeled with Tc-99m.

1. Synthesis of Modified Peptide Monomer:

The peptides were synthesized based on Fmoc/tBu solid phase method, an orthogonal protecting group strategy using the base labile N-Fmoc group for protection of the α-amino function, acid labile side chain protecting groups and acid labile linkers that constitute the C-terminal amino acid protecting group. They were synthesized on CS136 peptide synthesizer at the 0.2 mmol scale. Fmoc deprotection was achieved by 20% piperidine in DMF for 15 min; Coupling of AAs combined with 0.1 M coupling agent HBTU and 1.0 M DIPEA in DMF (5× excess) for 4 hours; The resin was washed with DMF for 3 time 30 s following deprotection; Cleavage: 95/2.5/2.5 TFA/anisole/water for 2 h. All amino acids were dissolved in DMF. This synthesis was repeated using HBTU (≥99% purity), using Fmoc-Gln(tBu)-Wang resin (0.5 mmol/g). Instead of cyclization of peptide via Cys-Cys, we cyclized peptide by side chain to side chain amide bond via Fmoc-Asp(O-2-PhiPr)-OH and Fmoc-Dpr(ivDde)-OH. The final product was characterized by ESI-TOF mass spectrometer. The final product was characterized by ESI-TOF mass spectrometer. ESI-TOF (positive mode): m/z [Chemical Formula: [C88H123N25O25S+2H]⁺ [MW+2H]⁺ Calcd. 981.9 Da.

2. Synthesis of N₃S-4 PEG 2 k Armed Modified Peptide:

The peptides were synthesized on CS136 peptide synthesizer at the 0.2 mmole scale. First monomer was synthesized on the resin. After Fmoc-Ado-OH, Fmoc-Azh-OH was conjugated, then selectively cleaved off O-2-Phi Pr and ivDde group with 1% TFA in DCM, cyclized via amide bond. Fmoc-Dpr(ivDde)-OH and Fmoc-Cys(tBu)-OH couple onto N-terminus. After the peptide cleaved from the resin and purified by HPLC, then 4PEG armed BCN was coupled with the monomer to form tetramer in solution. Size exclusion column was used to purify the final product, any unreacted monomer or impurity size less than 9 KDa will be retained on the column and discarded. The structure of the final product is depicted in FIG. 33.

3. Tc-99m Radiolabeling:

Technetium in pertechnetate ion, obtained by the elution of the Moly generator, has the most stable $Tc^{7+}$ oxidation state and it will be reduced to lower oxidation states by reducing agent to make it readily react with chelating agents. Stannous chloride ($SnCl_2.2H_2O$) is the most common reducing agent in Tc radiopharmaceuticals. 10 microliter of 1 mg/mL $SnCl_2$ in 0.1 M HCl, 40 microliter of 0.5 M ammonium acetate ($NH_4OAc$) pH 5.2, 100 microliter of 0.2 M sodium tartrate (pH 9.2), 100 microliter Tc-99m solution (10 mCi/37 MBq), and 10-50 microliter peptide 1 mg/mL in aqueous solution were added into reaction vial and incubated at room temperature for 20 min to form labeled peptide. Then it was purified to a single product by Waters HPC on a C-18 reverse phase analytical column using 20-30 min gradient of 16-30 acetonitrile in 20 mM HCl aqueous solution at a flow rate of 1 mL/min. The purified peptide was purged with nitrogen or Ar gas for 20 min to remove acetonitrile and the pH was adjusted to 7.4.

Example 25. Synthesis of NOTA (for NaF Via Aluminum or Galium or Copper) Coupled, Amide Bond Cyclized Tetramer In order to make cyclized peptide stable in thiol containing environment, we proposed amide based side chain cyclization for our NOTA containing tetramer. The peptide monomer was synthesized on solid phase, then tetramer was prepared through known copper click chemistry. Finally tetramer cyclic peptide was first conjugated with a macrocyclic chelator, 1,4,7-triazacyclononane-1,4,7-triacetic acid (NOTA), and the resulting bioconjugate NOTA-tetramer was then radiofluorinated via Al18F intermediate to synthesize 18F-AlF-NOTA-tetramer.

1. Synthesis of Modified Fibrin Peptide Monomer:

The peptides were synthesized based on Fmoc/tBu solid phase method, an orthogonal protecting group strategy using the base labile N-Fmoc group for protection of the α-amino function, acid labile side chain protecting groups and acid labile linkers that constitute the C-terminal amino acid protecting group. They were synthesized on CS136 peptide synthesizer at the 0.2 mmol scale. Fmoc deprotection was achieved by 20% piperidine in DMF for 15 min; Coupling of AAs combined with 0.1 M coupling agent HBTU and 1.0 M DIPEA in DMF (5× excess) for 4 hours; The resin was washed with DMF for 3 time 30 s following deprotection; Cleavage: 95/2.5/2.5 TFA/anisole/water for 2 h. All amino acids were dissolved in DMF. This synthesis was repeated using HBTU (≥99% purity), using Fmoc-Gln(tBu)-Wang resin (0.5 mmol/g). Instead of cyclization of peptide via Cys-Cys, we cyclized peptide by side chain to side chain amide bond via Fmoc-Asp(O-2-PhiPr)-OH and Fmoc-Dpr (ivDde)-OH. The final product was characterized by ESI-TOF mass spectrometer. The final product was characterized by ESI-TOF mass spectrometer. ESI-TOF (positive mode): m/z [Chemical Formula: [C94H131N25O28S+2H] [MW+2H]$^+$ Calcd. 1029.98 Da.

2. Synthesis 4 PEG 2 k Armed Modified Peptide:

The peptides were synthesized on CS136 peptide synthesizer at the 0.2 mmole scale. First monomer was synthesized on the resin. After Fmoc-Ado-OH, Fmoc-Azh-OH was conjugated, then selectively cleaved off O-2-Phi Pr and ivDde group with 1% TFA in DCM, cyclized via amide bond. Then cleave the monomer and purified it. Finally the 4PEG armed BCN was coupled with purified monomer. Size exclusion column was used to purify the final product, any unreacted monomer or impurity size less than 10 KDa will be retained on the column and discarded. The structure of the final product is depicted in FIG. 34.

Example 26. Synthesis of $N_2S_2$ Coupled, Amide Bond Cyclized, BCN Tetramer The goal of the present study was to prepare a stable cyclized peptide in thiol containing environment and to synthesize tetramer in solution phase as a potential radiopharmaceutical with better commercial scale-up properties and higher yield. We proposed amide based side chain cyclization for our $N_2S_2$ containing antifibrin or ICAM1 tetramer using copper free click chemistry for tetramer preparation. $N_2S_2$ monomer peptide was synthesized on solid phase then coupled with tetramer BCN to form antifibrin tetramer later radiolabeled with Tc-99m.

1. Synthesis of Modified Fibrin Peptide Monomer:

The peptides were synthesized based on Fmoc/tBu solid phase method, an orthogonal protecting group strategy using the base labile N-Fmoc group for protection of the α-amino function, acid labile side chain protecting groups and acid labile linkers that constitute the C-terminal amino acid protecting group. They were synthesized on CS136 peptide synthesizer at the 0.2 mmol scale. Fmoc deprotection was achieved by 20% piperidine in DMF for 15 min; Coupling of AAs combined with 0.1 M coupling agent HBTU and 1.0 M DIPEA in DMF (5× excess) for 4 hours; The resin was washed with DMF for 3 time 30 s following deprotection; Cleavage: 95/2.5/2.5 TFA/anisole/water for 2 h. All amino acids were dissolved in DMF. This synthesis was repeated using HBTU (≥99% purity), using Fmoc-Gln(tBu)-Wang resin (0.5 mmol/g). Instead of cyclization of peptide via Cys-Cys, we cyclized peptide by side chain to side chain amide bond via Fmoc-Asp(O-2-PhiPr)-OH and Fmoc-Dpr (ivDde)-OH. The final product was characterized by ESI-TOF mass spectrometer. The final product was characterized by ESI-TOF mass spectrometer. ESI-TOF (positive mode): m/z [Chemical Formula: [C89H122N24O26S2+2 H]+ [MW+2H]+ Calcd. 1004.42 Da.

2. Synthesis $N_2S_2$-4 PEG 2 k Armed Modified Peptide:

The peptides were synthesized on CS136 peptide synthesizer at the 0.2 mmole scale. First monomer was synthesized on the resin. After Fmoc-Ado-OH, Fmoc-Azh-OH was conjugated, then selectively cleaved off O-2-Phi Pr and ivDde group with 1% TFA in DCM, cyclized via amide bond. Fmoc-Dpr(ivDde)-OH and N-succinimidyl S-acetylthioacetate couple onto N-terminus, treated with hydroxylamine to expose the labile sulfhydryl group when needed for further reactions. After the peptide cleaved from the resin and purified by HPLC, then 4 PEG armed BCN was coupled with the monomer to form tetramer in solution. Size exclusion column was used to purify the final product, any unreacted monomer or impurity size less than 10 K will be retained on the column and discarded. The structure of the final product is depicted in FIG. 35.

3. Tc-99m Radiolabeling:

Technetium in pertechnetate ion, obtained by the elution of the Moly generator, has the most stable $Tc^{7+}$ oxidation state and it will be reduced to lower oxidation states by reducing agent to make it readily react with chelating agents. Stannous chloride ($SnCl_2.2H_2O$) is the most common reducing agent in Tc radiopharmaceuticals. 10 microliter of 1 mg/mL $SnCl_2$ in 0.1 M HCl, 40 microliter of 0.5 M ammonium acetate ($NH_4OAc$) pH 5.2, 100 microliter of 0.2 M sodium tartrate (pH 9.2), 100 microliter Tc-99m solution (10 mCi/37 MBq), and 10-50 microliter peptide 1 mg/mL in aqueous solution were added into reaction vial and incubated at room temperature for 20 min to form labeled peptide. Then it was purified to a single product by Waters HPC on a C-18 reverse phase analytical column using 20-30 min gradient of 16-30 acetonitrile in 20 mM HCl aqueous solution at a flow rate of 1 mL/min. The purified peptide was purged with nitrogen or Ar gas for 20 min to remove acetonitrile and the pH was adjusted to 7.4.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

REFERENCES FOR THE EXAMPLES

1. Go, A. S., et al. Heart disease and stroke statistics—2014 update: a report from the american heart association. *Circulation* 129, e28-e292 (2014).
2. Taylor, D. O., et al. Registry of the International Society for Heart and Lung Transplantation: Twenty-sixth Official Adult Heart Transplant Report-2009. *J Heart Lung Transplant* 28, 1007-1022 (2009).
3. Yancy, C. W., et al. 2013 ACCF/AHA guideline for the management of heart failure: a report of the American College of Cardiology Foundation/American Heart Association Task Force on Practice Guidelines. *J Am Coll Cardiol* 62, e147-239 (2013).
4. DeBakey, M. E. Left ventricular bypass pump for cardiac assistance. Clinical experience. *Am J Cardiol* 27, 3-11 (1971).
5. Sheikh, F. H. & Russell, S. D. HeartMate(R) II continuous-flow left ventricular assist system. *Expert Rev Med Devices* 8, 11-21 (2011).
6. Crow, S., et al. Acquired von Willebrand syndrome in continuous-flow ventricular assist device recipients. *Ann Thorac Surg* 90, 1263-1269; discussion 1269 (2010).
7. Hasin, T., et al. Readmissions after implantation of axial flow left ventricular assist device. *J Am Coll Cardiol* 61, 153-163 (2013).
8. Yuan, N., et al. The spectrum of complications following left ventricular assist device placement. *J Card Surg* 27, 630-638 (2012).
9. Starling, R. C., et al. Unexpected abrupt increase in left ventricular assist device thrombosis. *N Engl J Med* 370, 33-40 (2014).
10. Shah, S., Mehra, M. R., Couper, G. S. & Desai, A. S. Continuous flow left ventricular assist device related aortic root thrombosis complicated by left main coronary artery occlusion. *J Heart Lung Transplant* 33, 119-120 (2014).
11. Birschmann, I., et al. Ambient hemolysis and activation of coagulation is different between HeartMate II and HeartWare left ventricular assist devices. *J Heart Lung Transplant* 33, 80-87 (2014).
12. Cowger, J. A., et al. Hemolysis: A harbinger of adverse outcome after left ventricular assist device implant. *J Heart Lung Transplant* 33, 35-43 (2014).
13. Najjar, S. S., et al. An analysis of pump thrombus events in patients in the HeartWare ADVANCE bridge to transplant and continued access protocol trial. *J Heart Lung Transplant* 33, 23-34 (2014).
14. Kirklin, J. K., et al. Interagency Registry for Mechanically Assisted Circulatory Support (INTERMACS) analysis of pump thrombosis in the HeartMate 11 left ventricular assist device. *J Heart Lung Transplant* 33, 12-22 (2014).
15. Mehra, M. R., Stewart, G. C. & Uber, P. A. The vexing problem of thrombosis in long-term mechanical circulatory support. *J Heart Lung Transplant* 33, 1-11 (2014).
16. Stulak, J. M., et al. Gastrointestinal bleeding and subsequent risk of thromboembolic events during support with a left ventricular assist device. *J Heart Lung Transplant* 33, 60-64 (2014).
17. Kolodziej, A. F., et al. Fibrin specific peptides derived by phage display: characterization of peptides and conjugates for imaging. *Bioconjug Chem* 23, 548-556 (2012).
18. Rothenburger, M., et al. Treatment of thrombus formation associated with the MicroMed DeBakey VAD using recombinant tissue plasminogen activator. *Circulation* 106 (13 SUPPL.), 1189-1192 (2002).
19. Delgado III, R., et al. Direct thrombolytic therapy for intraventricular thrombosis in patients with the Jarvik 2000 left ventricular assist device. *J Heart Lung Transplant* 24, 231-233 (2005).
20. Kiernan, M. S., Pham, D. T., Denofrio, D. & Kapur, N. K. Management of HeartWare left ventricular assist device thrombosis using intracavitary thrombolytics. The *Journal of thoracic and cardiovascular surgery* 142, 712-714 (2011).
21. Tang, G. H. L., Kim, M. C., Pinney, S. P. & Anyanwu, A. C. Failed repeated thrombolysis requiring left ventricular assist device pump exchange. *Catheter Cardiovasc Interv* 81, 1072-1074 (2013).
22. Edgell, T., McEnvoy, F., Webbon, P. & Gaffney, P. Monoclonal antibodies to human fibrin: interaction with other animal fibrins. *Thromb Haemost* 75, 595-599 (1996).
23. Raut, S. & Gaffney, P. J. Evaluation of the fibrin binding profile of two anti-fibrin monoclonal antibodies. *Thromb Haemost* 76, 56-64 (1996).
24. Tymkewycz, P., Creighton Kempsford, L. & Gaffney, P. Generation and partial characterization of five monoclonal antibodies with high affinities for fibrin. *Blood Coagul Fibrinolysis* 4, 211-221 (1993).
25. Kudryk, B. J. & Bini, A. Monoclonal antibody designated T2G1 reacts with human fibrin beta-chain but not with the corresponding chain from mouse fibrin. *Arterioscler Thromb Vasc Biol* 20, 1848-1849 (2000).
26. Angelides, S., et al. Detection of malignant tumors using Tc-99m labeled Fab' fragments from a monoclonal antibody with specificity for D-dimer of cross-linked fibrin. *Clinical nuclear medicine* 21, 242-244 (1996).
27. Bautovich, G., et al. Detection of deep venous thrombi and pulmonary embolus with technetium-99m-DD-3B6/22 anti-fibrin monoclonal antibody Fab' fragment. *J Nucl Med* 35, 195-203 (1994).
28. Morris, T. A. SPECT imaging of pulmonary emboli with radiolabeled thrombus-specific imaging agents. *Seminars in nuclear medicine* 40, 474-479 (2010).
29. Morris, T. A., et al. Pulmonary Emboli Imaging with 99mTc-labelled Anti-D-dimer (DI-80B3) Fab' Followed by SPECT. *Heart Lung Circ* 20, 503-511 (2011).
30. Kudryk, B., Rohoza, A., Ahadi, M., Chin, J. & Wiebe, M. E. Specificity of a monoclonal antibody for the NH2-terminal region of fibrin. *Molecular immunology* 21, 89-94 (1984).
31. Rosebrough, S. F., et al. Thrombus imaging with indium-111 and iodine-131-labeled fibrin-specific monoclonal antibody and its F(ab')2 and Fab fragments. *J Nucl Med* 29, 1212-1222 (1988).
32. Knight, L. C., et al. Tc-99m antifibrin Fab' fragments for imaging venous thrombi: evaluation in a canine model. *Radiology* 173, 163-169 (1989).
33. Rosebrough, S. F., et al. Thrombus imaging: a comparison of radiolabeled GC4 and T2G1s fibrin-specific monoclonal antibodies. *J Nucl Med* 31, 1048-1054 (1990).
34. Bates, S. M., et al. Imaging characteristics of a novel technetium Tc 99m-labeled platelet glycoprotein IIb/IIIa receptor antagonist in patients with acute deep vein thrombosis or a history of deep vein thrombosis. *Arch Intern Med* 163, 452-456 (2003).
35. Heidt, T., et al. Activated platelets in carotid artery thrombosis in mice can be selectively targeted with a radiolabeled single-chain antibody. *PLoS ONE* 6(2011).
36. Klink, A., et al. Magnetic resonance molecular imaging of thrombosis in an arachidonic acid mouse model using an activated platelet targeted probe. *Arterioscler Thromb Vasc Biol* 30, 403-410 (2010).
37. Von Zur Muhlen, C., et al. Magnetic resonance imaging contrast agent targeted toward activated platelets allows in vivo detection of thrombosis and monitoring of thrombolysis. *Circulation* 118, 258-267 (2008).
38. Ciesienski, K. L., et al. Fibrin-targeted PET probes for the detection of thrombi. *Mol Pharm* 10, 1100-1110 (2013).
39. Uppal, R., et al. Molecular imaging of fibrin in a breast cancer xenograft mouse model. *Invest Radiol* 47, 553-558 (2012).
40. Uppal, R., et al. Bimodal thrombus imaging: simultaneous PET/MR imaging with a fibrin-targeted dual PET/MR probe—feasibility study in rat model. *Radiology* 258, 812-820 (2011).
41. Kirklin, J. K., et al. The Fourth INTERMACS Annual Report: 4,000 implants and counting. *J Heart Lung Transplant* 31, 117-126 (2012).
42. Mishra, V., et al. Hospital costs fell as numbers of LVADs were increasing:
experiences from Oslo University Hospital. *J Cardiothorac Surg* 7, 76 (2012).
43. Alba, A. C., et al. Cost-effectiveness of ventricular assist device therapy as a bridge to transplantation compared with nonbridged cardiac recipients. *Circulation* 127, 2424-2435 (2013).
44. Tellor, B. R., Smith, J. R., Prasad, S. M., Joseph, S. M. & Silvestry, S. C. The use of eptifibatide for suspected pump thrombus or thrombosis in patients with left ventricular assist devices. *J Heart Lung Transplant* 33, 94-101 (2014).

45. Popov, A. F., et al. Clinical experience with heartware left ventricular assist device in patients with end-stage heart failure. *Ann Thorac Surg* 93, 810-815 (2012).
46. May-Newman, K., et al. Thromboembolism is linked to intraventricular flow stasis in a patient supported with a left ventricle assist device. *ASAIO Journal* 59, 452-455 (2013).
47. Albericio, F. *Solid-Phase Synthesis: A Practical Guide*, (CRC Press, Boca Raton, Fla., 2000).
48. Annis, I., Chen, L. & Barany, G. Novel solid-phase reagents for facile formation of intramolecular disulfide bridges in peptides under mild conditions. *J Am Chem Soc* 120, 7226-7238 (1998).
49. Bigott-Hennkens, H. M., et al. Labeling, stability and biodistribution studies of 99mTc-cyclized Tyr3-octreotate derivatives. *Nucl Med Biol* 38, 549-555 (2011).
50. Vicente, C., He, L., Pavão, M. & Tollefsen, D. Antithrombotic activity of dermatan sulfate in heparin cofactor II-deficient mice. *Blood* 104, 3965-3970 (2004).
51. Mousa, S. In vivo models for the evaluation of antithrombotics and thrombolytics. *Methods Mol Biol.* 663, 29-107 (2010).
52. Westrick, R., Winn, M. & Eitzman, D. Murine models of vascular thrombosis. *Arterioscler Thromb Vasc Biol* 27, 2079-2093 (2007).

What is claimed is:

1. A p-armed multimer, each arm of the multimer comprising:
   a polymer comprising n PEG monomers, wherein n is at least 2;
   a linker comprising His-His-Glu; and
   a homing molecule selected from the group consisting of an antibody, an aptamer, and a peptide, wherein the homing molecule binds a biomarker of thrombosis,
   wherein the homing molecule is linked to the C-terminus of the linker, and the polymer is linked via an amino acid side chain of the linker; and
   wherein p is at least 3, and each arm of the multimer is bound to the other arms of the multimer via an end of the polymer not attached to the linker;
   wherein the p-armed multimer further comprises at least one diagnostic and/or therapeutic agent attached to an N-terminus of the linker of that arm, wherein the at least one diagnostic agent or therapeutic agent is a radioisotope of technetium or a radioisotope of rhenium.

2. A p-armed multimer of claim 1, wherein the biomarker of thrombosis is selected from the group consisting of fibrin and ICAM.

3. A p-armed multimer of claim 1, wherein the radionuclide is selected from the group consisting of $^{99m}$Tc, $^{186}$Re, and $^{188}$Re.

4. A p-armed multimer of claim 1, comprising a diagnostic agent on at least one arm and a therapeutic agent on at least one other arm.

5. A radiopharmaceutical composition comprising a p-armed multimer of claim 1, together with a pharmaceutically-acceptable carrier.

6. A method for detecting intradevice thrombus in a subject having an implanted mechanical circulation assist device, the method comprising:
   (a) administering into the bloodstream of the subject an effective amount of the p-armed multimer of claim 1;
   (b) allowing the p-armed multimer to bind thrombus; and
   (c) detecting a signal from the radioisotope of the p-armed multimer localized at a site of thrombus.

7. The method of claim 6, wherein the method further comprises quantifying intradevice thrombus by: (d) determining the amount of p-armed multimer localized at a site of thrombus from the signal detected, wherein the amount of p-armed multimer is indicative of the size of the thrombus.

8. A p-armed multimer of claim 1, wherein the homing molecule is attached to the C-terminus of the linker via a hydrophilic moiety.

9. A p-armed multimer of claim 1, wherein n is 2 to 60.

10. A p-armed multimer, each arm of the multimer comprising:
    a polymer comprising n PEG monomers, wherein n is at least 2;
    a linker comprising His-His-Glu; and
    a homing molecule that is an antibody, wherein the homing molecule binds a target molecule;
    wherein the homing molecule is linked to the C-terminus of the linker, and the polymer is linked via an amino acid side chain of the linker; and
    wherein p is at least 3, and each arm of the multimer is bound to the other arms of the multimer via an end of the polymer not attached to the linker;
    wherein the p-armed multimer further comprises at least one diagnostic and/or therapeutic agent attached to an N-terminus of the linker of that arm, wherein the at least one diagnostic agent or therapeutic agent is a radioisotope of technetium or a radioisotope of rhenium.

11. A p-armed multimer of claim 10, wherein the target molecule is a biomarker of thrombosis.

12. A p-armed multimer of claim 10, wherein the target molecule is selected from the group consisting of fibrin and ICAM.

13. A p-armed multimer of claim 10, wherein n is 2 to 60.

14. A p-armed multimer of claim 10, wherein the N-terminus of the homing molecule is attached to the C-terminus of the linker using a hydrophilic moiety.

15. A p-armed multimer, each arm of the multimer comprising:
- a polymer comprising n PEG monomers, wherein n is at least 2;
- a linker comprising His-His-Glu; and
- a homing molecule comprising SEQ ID NO: 1;

wherein the homing molecule is linked to the C-terminus of the linker, and the polymer is linked via an amino acid side chain of the linker; and wherein p is at least 3, and each arm of the multimer is bound to the other arms of the multimer via an end of the polymer not attached to the linker;

wherein the p-armed multimer further comprises at least one diagnostic and/or therapeutic agent attached to an N-terminus of the linker of that arm, wherein the at least one diagnostic agent or therapeutic agent is a radioisotope of technetium or a radioisotope of rhenium.

16. A p-armed multimer of claim 15, wherein the homing molecule is attached to the C-terminus of the linker via a hydrophilic moiety.

17. A p-armed multimer of claim 15, wherein n is 2 to 60.

* * * * *

UNITED STATES PATENT AND TRADEMARK OFFICE
CERTIFICATE OF CORRECTION

PATENT NO. : 9,849,201 B2
APPLICATION NO. : 14/270061
DATED : December 26, 2017
INVENTOR(S) : Gregory M. Lanza, Samuel A. Achilefu and Grace Hufang Cui It is certified that error appears in the above-identified patent and that said Letters Patent is hereby corrected as shown below:

On the Title Page

Item (72) Inventor "Samuel A. Achilefu, St. Louis, MO (US)" should be -- Samuel I. Achilefu, St. Louis, MO (US) --

Signed and Sealed this
Thirteenth Day of August, 2024

Katherine Kelly Vidal
*Director of the United States Patent and Trademark Office*